US012807688B2

(12) United States Patent
Nijjar et al.

(10) Patent No.: US 12,807,688 B2
(45) Date of Patent: *Nov. 24, 2026

(54) ANTIBODIES RECOGNIZING TAU

(71) Applicant: Prothena Biosciences Limited, Dublin (IE)

(72) Inventors: Tarlochan S. Nijjar, Orinda, CA (US); Robin Barbour, Walnut Creek, CA (US); Philip James Dolan, III, Foster City, CA (US); Yue Liu, Foster City, CA (US); Svetlana Alexander, Sunnyvale, CA (US); Mark E. Renz, Millbrae, CA (US)

(73) Assignee: Prothena Biosciences Limited, Dublin (IE)

( * ) Notice: Subject to any disclaimer, the term of this patent is extended or adjusted under 35 U.S.C. 154(b) by 381 days.

This patent is subject to a terminal disclaimer.

(21) Appl. No.: 18/422,712

(22) Filed: Jan. 25, 2024

(65) Prior Publication Data

US 2024/0209073 A1 Jun. 27, 2024

Related U.S. Application Data

(63) Continuation of application No. 17/181,997, filed on Feb. 22, 2021, now Pat. No. 11,926,659, which is a continuation of application No. 16/808,209, filed on Mar. 3, 2020, now Pat. No. 10,961,302.

(60) Provisional application No. 62/838,159, filed on Apr. 24, 2019, provisional application No. 62/813,137, filed on Mar. 3, 2019, provisional application No. 62/813,126, filed on Mar. 3, 2019.

(51) Int. Cl.

| | |
|---|---|
| ***C07K 16/18*** | (2006.01) |
| ***A61K 9/00*** | (2006.01) |
| ***A61K 45/06*** | (2006.01) |
| ***C12N 15/63*** | (2006.01) |

(52) U.S. Cl.

CPC ............ *C07K 16/18* (2013.01); *A61K 9/0019* (2013.01); *C12N 15/63* (2013.01); *A61K 45/06* (2013.01); *C07K 2317/565* (2013.01)

(58) Field of Classification Search

None

See application file for complete search history.

(56) References Cited

U.S. PATENT DOCUMENTS 4,634,664 A 1/1987 Oestberg
4,634,666 A 1/1987 Engleman et al.
(Continued)

FOREIGN PATENT DOCUMENTS

CN 106749658 A 5/2017
GB 2220211 1/1990
(Continued)

OTHER PUBLICATIONS

"WHO-INN: International nonproprietary names (INN) for biological and biotechnological substances (a review)," 2014, retrieved on Aug. 15, 2022, retrieved from URL<https://cdn.who.int/media/docs/default-source/international-nonproprietary-names-(inn)/biorev2014.pdf?sfvrsn=8cbc13e0_7&download-true>, 81 pages.
(Continued)

*Primary Examiner* — Aurora M Fontainhas
(74) *Attorney, Agent, or Firm* — Fish & Richardson P.C.

(57) ABSTRACT

The invention provides antibodies that specifically bind tau. The antibodies inhibit or delay tau-associated pathologies and associated symptomatic deterioration.

25 Claims, 21 Drawing Sheets

Specification includes a Sequence Listing.

(56) References Cited

U.S. PATENT DOCUMENTS 5,057,540 A 10/1991 Kensil et al.
5,194,594 A 3/1993 Khawli et al.
5,208,036 A 5/1993 Eppstein et al.
5,225,539 A 7/1993 Winter
5,264,618 A 11/1993 Felgner
5,279,833 A 1/1994 Rose
5,283,185 A 2/1994 Epand et al.
5,304,489 A 4/1994 Rosen
5,530,101 A 6/1996 Queen et al.
5,545,806 A 8/1996 Lonberg et al.
5,565,332 A 10/1996 Hoogenboom et al.
5,569,825 A 10/1996 Lonberg et al.
5,585,089 A 12/1996 Queen et al.
5,624,821 A 4/1997 Winter et al.
5,625,126 A 4/1997 Lonberg et al.
5,633,425 A 5/1997 Lonberg et al.
5,643,576 A 7/1997 Johnston
5,661,016 A 8/1997 Lonberg et al.
5,733,743 A 3/1998 Johnson et al.
5,736,142 A 4/1998 Sette et al.
5,741,957 A 4/1998 Deboer et al.
5,770,429 A 6/1998 Lonberg et al.
5,786,464 A 7/1998 Seed et al.
5,789,650 A 8/1998 Lonberg et al.
5,814,318 A 9/1998 Lonberg et al.
5,834,597 A 11/1998 Tso et al.
5,837,242 A 11/1998 Holliger et al.
5,849,992 A 12/1998 Meade et al.
5,858,657 A 1/1999 Winter et al.
5,859,205 A 1/1999 Adair et al.
5,871,907 A 2/1999 Winter et al.
5,874,299 A 2/1999 Lonberg et al.
5,877,218 A 3/1999 Herzig et al.
5,877,397 A 3/1999 Lonberg et al.
5,888,809 A 3/1999 Allison
6,063,598 A 5/2000 Enenkel et al.
6,114,148 A 9/2000 Seed et al.
6,407,213 B1 6/2002 Carter et al.
6,624,821 B1 9/2003 Shin et al.
6,881,557 B2 4/2005 Foote
7,442,516 B2 10/2008 Ohno et al.
7,569,339 B2 8/2009 Kaufmann et al.
8,012,936 B2 9/2011 Sigurdsson et al.
8,455,622 B2 6/2013 Carter et al.
8,778,343 B2 7/2014 Kayed
8,926,974 B2 1/2015 Griswold-Prenner et al.
8,987,419 B2 3/2015 Barghorn et al.
9,051,367 B2 6/2015 Griswold-Prenner et al.
9,321,841 B2 4/2016 Jones et al.
9,605,054 B2 3/2017 Brady et al.
10,196,439 B2 2/2019 Pedersen et al.
10,253,100 B2 4/2019 Igawa et al.
10,301,379 B2 5/2019 Wadia et al.
10,478,142 B2 11/2019 Pedersen et al.
10,501,531 B2 12/2019 Seubert et al.
10,711,058 B2 7/2020 Adolfsson et al.
10,752,679 B2 8/2020 Seubert et al.
10,766,953 B2 9/2020 Mercken et al.
10,829,547 B2 11/2020 Roberts et al.
10,836,817 B2 11/2020 Adolfsson et al.
10,889,638 B2 1/2021 Barbour et al.
10,906,964 B2 2/2021 Barbour et al.
2005/0009150 A1 1/2005 Basi et al.
2005/0114912 A1 5/2005 Botas et al.
2005/0132424 A1 6/2005 Lowe et al.
2007/0042359 A1 2/2007 Throsby et al.
2008/0050383 A1 2/2008 Sigurdsson et al.
2008/0076145 A1 3/2008 Cummings et al.
2009/0028851 A1 1/2009 Stuhmer et al.
2010/0022026 A1 1/2010 Rump et al.
2010/0216703 A1 8/2010 Akassoglou et al.
2010/0267927 A1 10/2010 Garrett et al.
2010/0316564 A1 12/2010 Sigurdsson
2011/0053264 A1 3/2011 Kashmiri et al.
2011/0206702 A1 8/2011 Polakis et al.
2012/0023911 A1 2/2012 Liu et al.
2012/0100152 A1 4/2012 Roberts et al.
2012/0142602 A1 6/2012 Brady et al.
2012/0149880 A1 6/2012 Cheung et al.
2012/0204275 A1 8/2012 Schenk et al.
2012/0288507 A1 11/2012 Qian et al.
2012/0301473 A1 11/2012 Binder et al.
2012/0308480 A1 12/2012 Smith et al.
2013/0189289 A1 7/2013 Inoue et al.
2013/0209453 A1 8/2013 Black et al.
2013/0295021 A1 11/2013 Chen et al.
2014/0056901 A1 2/2014 Agadjanyan et al.
2014/0086921 A1 3/2014 Griswold-Prenner et al.
2014/0171373 A1 6/2014 Ashe et al.
2014/0294731 A1 10/2014 Pfeifer et al.
2015/0050215 A1 2/2015 Novak et al.
2015/0050270 A1 2/2015 Sanofi
2015/0056721 A1 2/2015 Siman
2015/0166661 A1 6/2015 Chen et al.
2015/0175682 A1 6/2015 Pfeifer et al.
2015/0196663 A1 7/2015 Shusta et al.
2015/0253341 A1 9/2015 McAvoy et al.
2015/0266947 A1 9/2015 Sierks et al.
2016/0031976 A1 2/2016 Seubert et al.
2016/0289309 A1 10/2016 Griswold-Prenner et al.
2016/0376341 A1 12/2016 Adolfsson et al.
2016/0376351 A1 12/2016 Adolfsson et al.
2017/0355756 A1 12/2017 Julien et al.
2018/0209994 A1 7/2018 Lannfelt et al.
2018/0371066 A1 12/2018 West et al.
2019/0322728 A1 10/2019 Seubert et al.
2019/0330314 A1 10/2019 Barbour et al.
2019/0330316 A1 10/2019 Barbour et al.
2020/0030445 A1 1/2020 John et al.
2020/0123239 A1 4/2020 Seubert et al.
2020/0131255 A1 4/2020 Kerchner et al.
2020/0181245 A1 6/2020 Masliah et al.
2021/0023216 A1 1/2021 Angstenberger et al.
2021/0032319 A1 2/2021 Seubert et al.
2021/0130449 A1 5/2021 Barbour et al.

FOREIGN PATENT DOCUMENTS

JP 2010511388 4/2010
JP 2011501655 1/2011
JP 2014530597 11/2014
JP 2015520685 7/2015
JP 2015530971 10/2015
KR 10-2012-0024952 A 3/2012
WO WO 9110741 7/1991
WO WO 9117271 11/1991
WO WO 9201047 1/1992
WO WO 9220791 11/1992
WO WO 9312227 6/1993
WO WO 9412629 6/1994
WO WO 9507707 3/1995
WO WO 199615452 5/1996
WO WO 9634625 11/1996
WO WO 9823635 6/1998
WO WO 9840100 9/1998
WO WO 2000072880 12/2000
WO WO 03057838 7/2003
WO WO 2004050884 6/2004
WO WO 2005019442 3/2005
WO WO 2008012142 1/2008
WO WO 2008081008 7/2008
WO WO 2008103472 8/2008
WO WO 2008107388 9/2008
WO WO 2009027471 3/2009
WO WO 2011053565 5/2011
WO WO 2011154321 12/2011
WO WO 2012049570 4/2012
WO WO 2013004717 1/2013
WO WO 2013007839 1/2013
WO WO 2013028810 2/2013
WO WO 2014006000 1/2014
WO WO 2014008404 1/2014
WO WO 2014165271 10/2014
WO WO 2016079597 5/2016

(56) References Cited

FOREIGN PATENT DOCUMENTS

| | | |
|---|---|---|
| WO | WO 2016137950 | 9/2016 |
| WO | WO 2015200806 | 12/2016 |
| WO | WO 2016196726 | 12/2016 |
| WO | WO 2017005732 | 1/2017 |
| WO | WO 2017062672 | 4/2017 |
| WO | WO 2017091512 | 6/2017 |
| WO | WO 2017191559 | 11/2017 |
| WO | WO 2017191560 | 11/2017 |
| WO | WO 2017191561 | 11/2017 |
| WO | WO 2018106781 | 6/2018 |
| WO | WO 2018152359 | 8/2018 |
| WO | WO 2018156250 | 8/2018 |
| WO | WO 2018178077 | 10/2018 |
| WO | WO 2018204546 | 11/2018 |
| WO | WO 2018231254 | 12/2018 |
| WO | WO 2019094595 | 5/2019 |
| WO | WO 2019110571 | 6/2019 |
| WO | WO 2019186276 | 10/2019 |
| WO | WO 2019207159 | 10/2019 |
| WO | WO 2020096608 | 5/2020 |
| WO | WO 2020097561 | 5/2020 |
| WO | WO 2020106598 | 5/2020 |
| WO | WO 2020163817 | 8/2020 |
| WO | WO 2020180819 | 9/2020 |
| WO | WO 2020193520 | 10/2020 |
| WO | WO 2021010712 | 1/2021 |

OTHER PUBLICATIONS

Agadjanyan et al., “Humanized monoclonal antibody armanezumab specific to N-terminus of pathological tau: characterization and therapeutic potency,” Molecular Neurodegeneration, 2017, 12:33.

Alexander et al., “Development of High Potency Universal DR-Restricted Helper Epitopes by Modification of High Affinity DR-Blocking Peptides,” Immunity, Dec. 1994, 1:751-761.

Almagro, et al., “Humanization of antibodies”, Frontiers in Bioscience, 13, 1619-1633, (Jan. 1, 2008).

Altshuler et al., “Generation of Recombinant Antibodies and Methods for Increasing Their Affinity,” Advances in biological chemistry, 2010, 50:229-250, 79 pages (with English translation).

Andreadis et al., “Structure and novel exons of the human .tau. Gene,” Biochemistry, 1992, 31:10626-1063.

Atwal et al., “A Therapeutic Antibody Targeting BACE1 Inhibits Amyloid-β Production in Vivo,” Sci. Translation Med., May 2011, 84(3):1-12.

Bacskai et al., “Imaging of amyloid-β deposits in brains of living mice permits direct observation of clearance of plaques with immunotherapy,” Nature Medicine, vol. 7, No. 3, pp. 369-372, (Mar. 2001).

Banner et al., “Mapping the conformational space accessible to BACE2 using surface mutants and cocrystals with Fab fragments, Fynomers and Xaperones,” Acta. Crystallogr. D. Biol. Crystallogr., 2013, 69(Pt6): 1124-1137.

Bertschinger et al., “Selection of single domain binding proteins by covalent DNA display,” Feb. 2007, Protein Eng. Des. Sel. 20:57-68.

Bett et al., “Packaging Capacity and Stability of Human Adenovirus Type 5 Vectors,” J. Virol., 1993, 67:5911-5921.

Boris-Lawrie et al., “Recent advances in retrovirus vector technology,” Cur. Opin. Genet. Develop., Feb. 1993, 3:102-109.

Brack et al., “A bispecific HER2-targeting FynomAb with superior antitumor activity and novel mode of action,” Mol. Cancer Ther., 2014, 13:2030-2039.

Castillo-Carranza et al., “Tau aggregates as immunotherapeutic targets,” Frontiers in Bioscience, Scholar, Jan. 1, 2013, 5:426-438.

Chen et al., “Enhancement and destruction of antibody function by somatic mutation: unequal occurrence is controlled by V gene combinatorial associations,” the EMBO Journal, 1995, 14(12):2784-2794.

Chicz et al., “Specificity and promiscuity among naturally processed peptides bound to HLA-DR alleles,” J. Exp. Med., Jul. 1993, 178(1):27-47.

Chothia et al., “Canonical structures for the hypervariable regions of immunoglobulins,” Journal of Molecular Biology, Aug. 1987, 196(4):901-917.

Chothia et al., “Conformations of immunoglobulin hypervariable regions,” Nature, Dec. 1989, 342:878-883.

Co et al., “Chimeric and humanized antibodies with specificity for the CD33 antigen,” J. Immunol., Feb. 1992, 148(4): 1149-1154.

Croft et al., “Novel monoclonal antibodies targeting the microtubule-binding domain of human tau, ” PLoS ONE, Apr. 2018, 13(4).

Deshpande et al., “The RCSB Protein Data Bank: a redesigned query system and relational database based on the mmCIF schema,” Nucleic Acids Res., Jan. 2005, 33: D233-D237.

Dhanda et al., “Development of a strategy and computational application to select candidate protein analogues with reduced HLA binding and immunogenicity,” Immunology, 2018, 153(1):118-132.

Dubel “Molecular Engineering I: Humanization,” Handbook of Therapeutic Antibodies, 2007, Chapter 6, pp. 119-144.

Dubensky et al., “Sindbis virus DNA-based expression vectors: utility for in vitro and in vivo gene transfer,” J. Virol., Jan. 1996, 70(1):508-519.

Edelman et al., “The Covalent Structure of an Entire γ G Immunoglobulin Molecule,” Proc. Natl. Acad. USA, May 1969, 63(1)78-85.

EP 18795047 Extended European Search Report mailed Feb. 2, 2021.

European Supplementarty Search Report in European Application No. 14778358.2, dated Nov. 8, 2016.

Extended European Search Report in European Appln No. 20766551.4, dated Oct. 28, 2022, 11 pages.

Extended European Search Report in European Appln. No. EP 19213368, dated Jun. 24, 2020.

Falk et al., “Pool sequencing of natural HLA-DR, DQ, and DP ligands reveals detailed peptide motifs, constraints of processing, and general rules,” Immunogenetics, 1994, 39:230-242.

Florenzano et al., “Extracellular truncated tau causes early presynaptic dysfunction associated with Alzheimer’s disease and other tauopathies,” Oncotarget, Apr. 2017, 8(29): 64745-64778.

Foote et al., “Antibody framework residues affecting the conformation of the hypervariable loops,” Journal of Molecular Biology, Mar. 1992, 224(2):487-499.

Friden et al., “Anti-transferrin receptor antibody and antibody-drug conjugates cross the blood-brain barrier,” Proc. Natl. Acad Sci. USA, Jun. 1991, 88(11):4771-4775.

Friden et al., “Blood-Brain Barrier Penetration and in Vivo Activity of an NGF Conjugate,” Science, Jan. 1993, 259(5093):373-377.

Gershoni et al., “Epitope Mapping, The First Step in Developing Epitope-Based Vaccines,” Biodrugs, 21:(3), p. 145-156. (2007).

Ghoshal et al., “Tau Conformational Changes Correspond to Impairments of Episodic Memory in Mild Cognitive Impairment and Alzheimer’s Disease,” Experimental Neurology, Jun. 2002, 177:475-493.

Goedert et al., “Cloning and sequencing of the cDNA encoding an isoform of microtubule-associated protein tau containing four tandem repeats: differential expression of tau protein mRNAs in human brain,” EMBO J., 1989, 8:393-399.

Goedert et al., “Multiple isoforms of human microtubule-associated protein tau: sequences and localization in neurofibrillary tangles of Alzheimer’s disease,” Neuron, Oct. 1989, 3:519-526.

Goedert et al., “Cloning and sequencing of the cDNA encoding a core protein of the paired helical filament of Alzheimer disease: Identification as the microtubule-associated protein tau” Proc. Natl. Acad. Sci. USA, vol. 85, pp. 4051-4055, (Jun. 1998).

Gonzales et al., “SDR grafting of a murine antibody using multiple human germline templates to minimize its immunogenicity,” Jul. 2004, Mol. Immunol., 41: 863.

Grabulovski et al., “A novel, non-immunogenic Fyn SH3-derived binding protein with tumor vascular targeting properties,” Feb. 2007, J. Biol. Chem. 282:3196-3204.

Hammer et al., “Promiscuous and allele-specific anchors in HLA-DR-binding peptides,” Cell, Jul. 1993, 74:197-203.

(56) References Cited

OTHER PUBLICATIONS

Hasegawa et al., "Characterization of Two distinct Monoclonal Antibodies to Paired Helical Filaments: Further Evidence for Fetal-Type Phosphorylation of the T in Paired Helical Filaments", Journal of Neurochemistry, 1993, 60(6).
Hazra et al., "Linking radiosilver to monoclonal antibodies reduced by ascorbic acid. Comparison of results with stable silver using gravimetric technique and silver 110-M using radiotracer technique," 1994, Cell Biophys, 24-25:1-7.
Hinton et al., "Engineered human IgG antibodies with longer serum half-lives in primates," Feb. 2004, J. Biol. Chem. 279:6213-6216.
IEDB [online], "Deimmunication Tool," Dec. 8, 2018, retrieved on Feb. 21, 2024, retrieved from URL<http://web.archive.org/web/20181208045007/http://tools.iedb.org/deimmunization/>, 1 page.
Imbimbo et al., "Initial failures of anti-tau antibodies in Alzheimer's disease are reminiscent of the amyloid-β story," Neural Regeneration Research, Apr. 25, 2022, 18(1):117-118.
Itner et al., "Parkinsonism and impaired axonal transport in a mouse model of frontotemporal dementia," Oct. 2008, Proc. Natl. Acad. Sci. USA, 105(41):15997-6002.
Iwahashi et al., "CDR substitutions of a humanized monoclonal antibody (CC49): contributions of individual CDRs to antigen binding and immunogenicity," Mol. Immunol., Oct. 1999, 36:1079-1091.
Jack et al., "Hypothetical model of dynamic biomarkers of the Alzheimer's pathological cascade," Lancet Neurol, Jan. 2010, 9:119-28.
Jicha et al., "Sequence Requirements for Formation of Conformational Variants of Tau Similar to Those Found in Alzheimer's Disease," Journal of Neuroscience Research, Dec. 1999, 55:713-723.
Jones et al., "The INNs and outs of antibody nonproprietary names," Oct. 2015, mAbs, retrieved from URL<http://dx.doi.org/10.1080/19420862.2015.1114320>.
Junghans et al., "Anti-Tac-H, a Humanized Antibody to the Interleukin 2 Receptor with New Features for Immunotherapy in Malignant and Immune Disorders," Cancer Res., Mar. 1990, 50(5): 1495-1502.
Kanyo et al., "Antibody binding defines a structure for an epitope that participates in the PrPC-->PrPSc conformational change," Nov. 1999, J. Mol. Biol. 293: 855-863.
Kawahara et al., "The Novel Monoclonal Antibody 9F5 Reveals Expression of a Fragment of GPNMB/Osteoactivin Processed by Furin-like Protease(s) in a Subpopulation of Microglia in Neonatal Rat Brain," GLIA, vol. 64, No. 11, pp. 1938-1961, (Nov. 2016).
Khlistunova et al., "Inhibition of tau aggregation in cell models of tauopathy," Dec. 2007, Current Alzheimer Research, 4:544-546.
Kontsekova et al., "First-in-man tau vaccine targeting structural determinants essential for pathological tau-tau interaction reduces tau oligomerisation and neurofibrillary degeneration in an Alzheimer's disease model," Alzheimer's Research & Therapy, 6:44, (2014).
Kostelny et al., "Formation of a bispecific antibody by the use of leucine zippers," Journal of Immunology, Mar. 1992, 148(5):1547-1553.
Kussie et al., "A Single Engineered Amino Acid Substitution Changes Antibody Fine Specificity," J Immunol, 1994, 152(1):146-52.
Ladner, "Mapping the Epitopes of Antibodies," Biotechnology and Genetic Engineering Reviews, vol. 24, 1-30, (2007).
Lazar et al., "A molecular immunology approach to antibody humanization and functional optimization", Molecular Immunology, 44:1986-1998 (2007).
Lazar et al., "Engineered antibody Fc variants with enhanced effector function," Mar. 2005, Proc. Natl. Acad. Sci. USA 103:4005.
Lee et al., "The microtubule binding domain of tau protein," Jun. 1989, Neuron, 2:1615-1624.
Lefranc et al., "IMGT unique numbering for immunoglobulin and T cell receptor constant domains and lg superfamily C-like domains," Dev. Comp. Immunol., 2005, 29(3):185-203.
Leger et al., "Antibody Drug Discovery Chapter 1: Humanization of Antibodies", Molecular medicine and Medicinal Chemistry, Jan. 2011, pp. 1-23.
Lewis, et al., "Neurofibrillary tangles, amyotrophy and progressive motor disturbance in mice expressing mutant (P301L) tau protein," Aug. 2000, Nat Genet. 25:402-405.
Liu, et al., "N-terminal glutamate to pyroglutamate conversion in vivo for human IgG2 antibodies," J. Biol. Chem., Apr. 2011, 286: 11211-11217.
Martin et al., "Structural families in loops of homologous proteins: automatic classification, modelling and application to antibodies," Nov. 1996, J. Mol. Biol. 263:800-15.
McGee et al., "The encapsulation of a model protein in poly (D, L lactide-co-glycolide) microparticles of various sizes: an evaluation of process reproducibility," 1997, J. Microenncapsul, 14(2):197-210.
Morris "Epitope Mapping of Protein Antigens by Competition ELISA," The Protein Protocols Handbook, Walker ed., Jan. 1996, pp. 595-600.
Neuberger, "Generating high-avidity human Mabs in mice," Nat. Biotechnol. Jul. 1996, 14:826.
Oddo et al., "Reduction of Soluble Aβ and Tau, but Not Soluble Aβ Alone, Ameliorates Cognitive Decline in Transgenic Mice with Plaques and Tangles," The Journal of Biological Chemistry, vol. 281, No. 51, pp. 39413-39423 (Dec. 22, 2016).
Oestberg et al., "Human X (mouse X human) hybridomas stably producing human antibodies," 1983, Hybridoma, 2:361-367.
Office Action in Japanese Appln. No. 2021-552257, mailed on Feb. 27, 2024, 13 pages (with English translation).
Ohe et al., "Construction of a novel bovine papillomavirus vector without detectable transforming activity suitable for gene transfer," Human Gene Therapy, Mar. 1995, 6:325-333.
Padlan, "A possible procedure for reducing the immunogenicity of antibody variable domains while preserving their ligand-binding properties," Mal. Immunol. Apr.-May 1991, 28:489.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol., Sep. 2002, 169(6):3076.
PCT/IB2017/052543 International Report on Patentability issued Nov. 6, 2018.
PCT/IB2017/052544 International Report on Patentability issued Nov. 6, 2018.
PCT/IB2017/052544 Search Report and Written Opinion mailed Jul. 31, 2017.
PCT/IB2017/052545 International Report on Patentability issued Nov. 6, 2018.
PCT/IB2017/052545 Search Report and Written Opinion mailed Aug. 1, 2017.
PCT/US2014/025044 International Preliminary Report on Patentability dated Sep. 15, 2014.
PCT/US2014/025044 International Search Report and Written Opinion mailed Nov. 3, 2014.
PCT/US2014/025044 Invitation to Pay Additional Fees and, Where Applicable, Protest Fee mailed Aug. 15, 2014.
PCT/US2018/030739 International Preliminary Report on Patentability mailed Nov. 5, 2019.
PCT/US2018/030739 International Search Report and Written Opinion mailed Nov. 5, 2018.
PCT/US2018/059895 International Preliminary Report on Patentability mailed May 11, 2021.
PCT/US2018/059895 International Search Report and Written Opinion mailed Apr. 12, 2019.
PCT/US2019/060616 International Search Report and Written Opinion mailed Mar. 20, 2020.
PCT/US2020/017357 International Search Report and Written Opinion mailed Jun. 17, 2020.
PCT/US2020/017357 Invitation to Pay Additional Fees mailed Apr. 23, 2020.
PCT/US2020/020704 Invitation to Pay Additional Fees mailed Jun. 3, 2020.
PCT/US2020/020704 Search Report and Written Opinion mailed Aug. 4, 2020.
Pedersen et al., "Tau immunotherapy for Alzheimer's disease," Trends in Molecular Medicine, vol. 21, No. 6, pp. 394-402, (Jun. 2015).

(56) References Cited

OTHER PUBLICATIONS

Piechotta et al., "Structural and functional analyses of pyroglutamate-amyloid-β-specific antibodies as a basis for Alzheimer immunotherapy," Jul. 2017, J Biol Chem 292: 12713-12724.
Pietersz et al., "Novel synthesis and in vitro characterization of disulfide-linked ricin-monoclonal antibody conjugates devoid of galactose binding activity," Aug. 1988, Cancer Res. 48(16):4469-4476.
Polito et al., "The conjugate Rituximab/saporin-S6 completely inhibits clonogenic growth of CD20-expressing cells and produces a synergistic toxic effect with Fludarabine," Jul. 2004, Leukemia 18:1215-1222.
Poorkaj et al., "Tau is a candidate gene for chromosome 17 frontotemporal dementia," Annals of Neurology, 1998, 43(6):815-825.
Powilleit et al., "Exploiting the Yeast L-A Viral Capsid for the In Vivo Assembly of Chimeric VLPs as Platform in Vaccine Development and Foreign Protein Expression," PLoS ONE, May 2007, 2(5):e415.
Queen et al., "Cell-Type Specific Regulation of a K Immunoglobulin Gene by Promoter and Enhancer Elements," Immunol. Rev., Feb. 1986, 89(1):49-68.
Rosseels et al., "Tau Monoclonal Antibody Generation Based on Humanized Yeast Models," Journal of Biological Chemistry, vol. 290, No. 7, pp. 4059-4074, (Dec. 24, 2014).
Schlatter et al., "Generation, characterization and structural data of chymase binding proteins based on the human Fyn kinase SH3 domain," Jul.-Aug. 2012, MAbs. 4:497-508.
Sinigaglia et al., "A malaria T-cell epitope recognized in association with most mouse and human MHC class II molecules," Nature, Dec. 1988, 336:778-780.
Songsivilai et al., "Bispecific antibody: a tool for diagnosis and treatment of disease," Clin. Exp. Immunol., Mar. 1990, 79(3):315-321.
Southwood et al., "Several Common HLA-DR Types Share Largely Overlapping Peptide Binding Repertoires," J. Immunology, Apr. 1998, 160:3363-3373.
Stoute et al., "A Preliminary Evaluation of a Recombinant Circumsporozoite Protein Vaccine against Plasmodium falciparum Malaria," N. Engl. J. Med., 1997, 336:86-91.
Strang et al., "Generation and characterization of new monoclonal antibodies targeting the PHFI and AT8 epitopes on human tau," Acta Neuropathologica Communications, 5:58, (2017).
Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, Feb. 2000, 164(3):1432-1441.
Thorpe et al., "The preparation and cytotoxic properties of antibody-toxin conjugates," 1982, Immunol. Rev., 62:119-58.
Vajdos et al., "Comprehensive functional maps of the antigen-binding site of an anti-ErbB2 antibody obtained with shotgun scanning mutagenesis," J. of Mal. Biol., Jul. 2002, 320: 415-428.
Vigo-Pelfrey et al., "Elevation of microtubule-associated protein tau in the cerebrospinal fluid of patients with Alzheimer's disease", Neurology, 45:788-793 (Apr. 1995).
Wang et al., "Two-stage PCR protocol allowing introduction of multiple mutations, deletions and insertions using QuikChange Site-Directed Mutagenesis," BioTechniques, Apr. 1999, 26:680-682.
Wedemayer et al., "Structural insights into the evolution of an antibody combining site," Jun. 1997, Science 276: 1665-1669.
Witzig, "Radioimmunotherapy for patients with relapsed B-cell non-Hodgkin lymphoma," Aug. 2001, Cancer Chemother Pharmacol., 48 Suppl 1:S91-S95.
Wu et al., "Simultaneous Humanization and Affinity Optimization of Monoclonal Antibodies", Methods of Molecular Biology, vol. 207: Recombinant Antibodies for Cancer Therapy: Methods and Protocols, Edited by M. Weischof and J. Krauss @ Humana Press Inc., Tolowa NJ, pp. 197-212 (Jan. 1, 2003).
Wu et al., Generation and Characterization of a Dual Variable Domain Immunoglobulin (DVD-Ig™) Molecule, In: Antibody Engineering, Springer Berlin Heidelberg (2010).
Xiao et al., "High efficiency, long-term clinical expression of cottontail rabbit papillomavirus (CRPV) DNA in rabbit skin following particle-mediated DNA transfer," Jul. 1996, Nucleic Acids. Res. 24:2630-2622.
Yanamandra et al., "Anti-Tau Antibodies that Block Tau Aggregate Seeding In Vitro Markedly Decrease Pathology and Improve Cognition in Vivo," Neuron, 80, 402-414 (Oct. 15, 2013).
Yu et al., "Boosting brain uptake of a therapeutic antibody by reducing its affinity for a transcytosis target," May 2011, Sci. Trans. Med. 3, 84ra44.
Zhou et al., "Adeno-associated virus 2-mediated high efficiency gene transfer into immature and mature subsets of hematopoietic progenitor cells in human umbilical cord blood," J. Exp. Med., Jun. 1994, 179:1867-75.
Funk et al., "Distinct therapeutic mechanisms of tau antibodies: promoting microglial clearance versus blocking neuronal uptake," Journal of Biological Chemistry, Aug. 28, 2015, 290(35):21652-62.
Imbimbo et al., "Initial failures of anti-tau antibodies in Alzheimer's disease are reminiscent of the amyloid-β story," Neural regeneration research, Jan. 2023, 18(1):117-8.
Ksiezak-Reding et al., "Recognition of tau epitopes by anti-neurofilament antibodies that bind to Alzheimer neurofibrillary tangles," Proceedings of the National Academy of Sciences, May 1987, 84(10):3410-4.

Fig. 2

```
                 ------------------+-------------------+-------------------+-------------------+--
                                  10                  20                  30                  40
                 ------------------+-------------------+-------------------+-------------------+--
mouse3D6VH       E V Q L Q Q S G A D L V R P G A L V K L S C K A S G F N I K D Y Y L H W V R Q R    40
IGHV1-69-2*01    E V Q L V Q S G A E V K K P G A T V K I S C K V S G Y T F T D Y Y M H W V Q Q A    40
2RCS VH hFrwk    Q V Q L Q Q S G A E L V K P G A S V K L S C T A S G F N I K D T Y M H W V K Q R    40
hu3D6 VHvb1      Q V Q L Q Q S G A E L V K P G A S V K L S C T A S G F N I K D Y Y L H W V K Q R    40
hu3D6 VHvb2      E V Q L V Q S G A E V V K P G A S V K I S C K A S G F N I K D Y Y L H W V R Q R    40
hu3D6 VHvb3      E V Q L V Q S G A E V V K P G A T V K I S C K A S G F N I K D Y Y L H W V R Q R    40
hu3D6 VHvb4      E V Q L V Q S G A E V V K P G A T V K I S C K A S G F T I K D Y Y L H W V R Q R    40
hu3D6 VHvb5      E V Q L V Q S G A E V V K P G A T V K I S C K A S G F T I K D Y Y L H W V R Q R    40
hu3D6 VHvb6      E V Q L V Q S G A E V V K P G A T V K I S C K A S G F T I K D Y Y L H W V R Q R    40
hu3D6 VHvb7      E V Q L V Q S G A E V V K P G A T V K I S C K A S G F T I K D Y Y L H W V R Q R    40

                 ------------------+-------------------+-------------------+-------------------+--
                                  50                  60                  70                  80
                 ------------------+-------------------+-------------------+-------------------+--
mouse3D6VH       P E Q G L E W I G W I D P E N G D T V Y D P K F Q G K A T I T A D T S S N T A Y    80
IGHV1-69-2*01    P G K G L E W M G L V D P E D G E T I Y A E K F Q G R V T I T A D T S T D T A Y    80
2RCS VH hFrwk    P E Q G L E W I G R I D P A N G N T K Y D P K F Q G K A T I T A D T S S N T A Y    80
hu3D6 VHvb1      P E Q G L E W I G W I D P E N G D T V Y D P K F Q G K A T I T A D T S S N T A Y    80
hu3D6 VHvb2      P G K G L E W I G W I D P E N G D T V Y D P K F Q G R A T I T A D T S T D T A Y    80
hu3D6 VHvb3      P G K G L E W I G W I D P E N G D T I Y D P K F Q G R A T I T A D T S T D T A Y    80
hu3D6 VHvb4      P G K G L E W I G W I D P E N G D T I Y D P K F Q G R V T I T A D T S T D T A Y    80
hu3D6 VHvb5      P G K G L E W I G W I D P E D G E T I Y D P K F Q G R V T I T A D T S T D T A Y    80
hu3D6 VHvb6      P G K G L E W I G W I D P E D G E T V Y D P K F Q G R V T I T A D T S T D T A Y    80
hu3D6 VHvb7      P G K G L E W I G W I D P E D G E T V Y D P K F Q G R V T I T A D T S T D T A Y    80

                 ------------------+-------------------+-------------------+---------
                                  90                 100                 110
                 ------------------+-------------------+-------------------+---------
mouse3D6VH       L Q L G S L T S E D T A V Y F C S T L D - - F W G Q G T T L T V S S               112
IGHV1-69-2*01    M E L S S L R S E D T A V Y Y C A T - Q - - H W G Q G T L V T V S S               111
2RCS VH hFrwk    L Q L S S L T S E D T A V Y Y C A S Y Y G I Y W G Q G T T L T V S S               114
hu3D6 VHvb1      L Q L S S L T S E D T A V Y F C S T L D - - F W G Q G T T L T V S S               112
hu3D6 VHvb2      L E L S S L T S E D T A V Y F C S T L D - - F W G Q G T L V T V S S               112
hu3D6 VHvb3      M E L S S L R S E D T A V Y Y C S T L D - - F W G Q G T L V T V S S               112
hu3D6 VHvb4      M E L S S L R S E D T A V Y Y C S T L D - - F W G Q G T L V T V S S               112
hu3D6 VHvb5      M E L S S L R S E D T A V Y Y C S T L D - - F W G Q G T L V T V S S               112
hu3D6 VHvb6      M E L S S L R S E D T A V Y F C S T L D - - F W G Q G T L V T V S S               112
hu3D6 VHvb7      M E L S S L R S E D T A V Y Y C S T L D - - F W G Q G T L V T V S S               112
```

Fig. 3

```
                    ------------------+-------------------+-------------------+-------------------+-
                                     10                  20                  30                  40
                    ------------------+-------------------+-------------------+-------------------+-
mouse3D6VL          D V V M T Q T P L T L S V T I G Q P A S I S C K S S Q S L L D S D G K T Y L N W      40
ARX71335_VL_hFrwk   D V V M T Q T P L T L S V T I G Q P A S I S C K S S Q S L L Y S N G K T Y L N W      40
IGKV2-30*02         D V V M T Q S P L S L P V T L G Q P A S I S C R S S Q S L V H S D G N T Y L N W      40
hu3D6VLvb1          D V V M T Q T P L T L S V T I G Q P A S I S C K S S Q S L L D S D G K T Y L N W      40
hu3D6VLvb2          D V V M T Q S P L S L S V T L G Q P A S I S C K S S Q S L L D S D G K T Y L N W      40
hu3D6VLvb3          D V V M T Q S P L S L S V T L G E P A S I S C R S S Q S L L D S D G K T Y L N W      40

                    ------------------+-------------------+-------------------+-------------------+-
                                     50                  60                  70                  80
                    ------------------+-------------------+-------------------+-------------------+-
mouse3D6VL          L L Q R P G Q S P K R L I Y L V S K L D S G V P D R F T G S G S G T D F T L K I      80
ARX71335_VL_hFrwk   L L Q R P G Q S P K R L I Y L V S K L D S G V P D R F S G S G S G T D F T L K I      80
IGKV2-30*02         F Q Q R P G Q S P R R L I Y K V S N R D S G V P D R F S G S G S G T D F T L K I      80
hu3D6VLvb1          L L Q R P G Q S P K R L I Y L V S K L D S G V P D R F S G S G S G T D F T L K I      80
hu3D6VLvb2          L L Q R P G Q S P K R L I Y L V S K L D S G V P D R F S G S G S G T D F T L K I      80
hu3D6VLvb3          L Q Q R P G Q S P R R L I Y L V S K L D S G V P D R F S G S G S G T D F T L K I      80

                    ------------------+-------------------+-------------------+-----
                                     90                 100                 110
                    ------------------+-------------------+-------------------+-----
mouse3D6VL          S R V E A E D L G V Y Y C W Q G T H F P Y T F G G G T K L E I K                    112
ARX71335_VL_hFrwk   S R V E A E D L G V H Y C E Q G T H F P L T F G A G T K L E L K                    112
IGKV2-30*02         S R V E A E D V G V Y Y C M Q G T H W P Y T F G Q G T K L E I K                    112
hu3D6VLvb1          S R V E A E D L G V H Y C W Q G T H F P Y T F G A G T K L E L K                    112
hu3D6VLvb2          S R V E A E D V G V Y Y C W Q G T H F P Y T F G A G T K L E I K                    112
hu3D6VLvb3          S R V E A E D V G V Y Y C W Q G T H F P Y T F G Q G T K L E I K                    112
```

| Name | $k_a (M^{-1} s^{-1})$ | $k_d (s^{-1})$ | $k_D$ (nM) |
|---|---|---|---|
| 3D6 | $2.58 \times 10^6$ | $1.19 \times 10^{-3}$ | 0.46 |
| 1H8 | $5.07 \times 10^5$ | $5.61 \times 10^{-3}$ | 11.1 |
| 3H9 | $4.71 \times 10^5$ | $1.41 \times 10^{-3}$ | 3.0 |
| 5G8 | $3.75 \times 10^5$ | $2.54 \times 10^{-3}$ | 6.78 |
| 6D2 | $3.83 \times 10^5$ | $3.18 \times 10^{-3}$ | 8.29 |
| 7G6 | $5.76 \times 10^5$ | $3.32 \times 10^{-3}$ | 5.77 |
| 8A4 | $5.99 \times 10^5$ | $2.27 \times 10^{-3}$ | 3.8 |

Figure 9A

```
                ------------------+-------------------+-------------------+-------------------+-
                                 10                  20                  30                  40
                ------------------+-------------------+-------------------+-------------------+-
Murine 3D6VH    E V Q L Q Q S G A D L V R P G A L V K L S C K A S G F N I K D Y Y L H W V R Q R    40
IGHV1-69-2*01   . . . . V . . . . E V K K . . . T . . I . . . V . . Y T F T . . . M . . . Q . A    40
2RCS VH hFrwk   Q . . . . . . . . E . . K . . . S . . . . . T . . . . . . . . T . M . . . K . .    40
hu3D6 VHvb1     Q . . . . . . . . E . . K . . . S . . . . . T . . . . . . . . . . . . . . K . .    40
hu3D6 VHvb2     . . . . V . . . . E V . K . . . S . . I . . . . . . . . . . . . . . . . . . . .    40
hu3D6 VHvb3     . . . . V . . . . E V . K . . . T . . I . . . . . . . . . . . . . . . . . . . .    40
hu3D6 VHvb4     . . . . V . . . . E V . K . . . T . . I . . . . . . . T . . . . . . . . . . . .    40
hu3D6 VHvb5     . . . . V . . . . E V . K . . . T . . I . . . . . . . T . . . . . . . . . . . .    40
hu3D6 VHvb6     . . . . V . . . . E V . K . . . T . . I . . . . . . . T . . . . . . . . . . . .    40
hu3D6 VHvb7     . . . . V . . . . E V . K . . . T . . I . . . . . . . T . . . . . . . . . . . .    40
hu3D6VHv1bA11   . . . . V . . . . E V . K . . . T . . I . . . . . . . . . . . . . . . . . . . .    40
h3D6 VHvb8      . . . . V . . . . E V . K . . . T . . I . . . . . . . . . . . . . . . . . . . .    40
h3D6 VHvb9      . . . . V . . . . E V . K . . . T . . I . . . . . . . . . . . . . . . . . . . .    40

                ------------------+-------------------+-------------------+-------------------+-
                                 50                  60                  70                  80
                ------------------+-------------------+-------------------+-------------------+-
Murine 3D6VH    P E Q G L E W I G W I D P E N G D T V Y D P K F Q G K A T I T A D T S S N T A Y    80
IGHV1-69-2*01   . G K . . . . M . L V . . . D . E . I . A E . . . . R V . . . . . . . . T D . . .    80
2RCS VH hFrwk   . . . . . . . . . R . . . A . . N . K . . . . . . . . . . . . . . . . . . . . .    80
hu3D6 VHvb1     . . . . . . . . . . . . . . . . . . . . . . . . . . . . . . . . . . . . . . . .    80
hu3D6 VHvb2     . G K . . . . . . . . . . . . . . . . . . . . . . . R . . . . . . . . T D . . .    80
hu3D6 VHvb3     . G K . . . . . . . . . . . . . . . I . . . . . . . R . . . . . . . . T D . . .    80
hu3D6 VHvb4     . G K . . . . . . . . . . . . . . . I . . . . . . . R V . . . . . . . T D . . .    80
hu3D6 VHvb5     . G K . . . . . . . . . . . D . E . I . . . . . . . R V . . . . . . . T D . . .    80
hu3D6 VHvb6     . G K . . . . . . . . . . . D . E . . . . . . . . . R V . . . . . . . T D . . .    80
hu3D6 VHvb7     . G K . . . . . . . . . . . D . E . . . . . . . . . R V . . . . . . . T D . . .    80
hu3D6VHv1bA11   . G . . . . . . . . . . . . . . . . . . . . . . . . R . . . . . . . . T D . . .    80
h3D6 VHvb8      . G . . . . . . . . . . . . . . . . . . E . . . . . R . . . . . . . . T D . . .    80
h3D6 VHvb9      . G . . . . . . . . . . . . . . . . . . E . . . . . R . . . . . . . . T D . . .    80
```

Figure 9B

```
                 ------------------+--------------------+-    ------------------+-----
                                  90                  100                      110
                 ------------------+--------------------+-    ------------------+-----
Murine 3D6VH     L Q L G S L T S E D T A V Y F C S T L D - - F W G Q G T T L T V S S    112
IGHV1-69-2*01    M E . S . . R . . . . . . . Y . A . - Q - - H . . . . . L V . . . .    111
2RCS VH hFrwk    . . . S . . . . . . . . . . Y . A S Y Y G I Y . . . . . . . . . . .    114
hu3D6 VHvb1      . . . S . . . . . . . . . . . . . . . . - - . . . . . . . . . . . .    112
hu3D6 VHvb2      . E . S . . . . . . . . . . . . . . . . - - . . . . . . L V . . . .    112
hu3D6 VHvb3      M E . S . . R . . . . . . . Y . . . . . - - . . . . . . L V . . . .    112
hu3D6 VHvb4      M E . S . . R . . . . . . . Y . . . . . - - . . . . . . L V . . . .    112
hu3D6 VHvb5      M E . S . . R . . . . . . . Y . . . . . - - . . . . . . L V . . . .    112
hu3D6 VHvb6      M E . S . . R . . . . . . . . . . . . . - - . . . . . . L V . . . .    112
hu3D6 VHvb7      M E . S . . R . . . . . . . Y . . . . . - - . . . . . . L V . . . .    112
hu3D6VHv1bA11    . . . . . . . . . . . . . . . . . . . . - - . . . . . . L V . . . .    112
h3D6 VHvb8       . . . . . . . . . . . . . . . . . . . . - - . . . . . . L V . . . .    112
h3D6 VHvb9       M E . . . V R . . . . . . . . . . . . . - - . . . . . . L V . . . .    112
```

Figure 10A

```
                                     ----------------+----------------+----------------+--
                                                    10               20               30
                                     ----------------+----------------+----------------+--
hu3D6VLv2                            D V V M T Q S P L S L P V T L G Q P A S I S C K S S Q S L L    30
hu3D6VLv2 L37Q                       . . . . . . . . . . . . . . . . . . . . . . . . . . . . . .    30
hu3D6VLv2 L50G                       . . . . . . . . . . . . . . . . . . . . . . . . . . . . . .    30
hu3D6VLv2 S52G                       . . . . . . . . . . . . . . . . . . . . . . . . . . . . . .    30
hu3D6VLv2 L54G                       . . . . . . . . . . . . . . . . . . . . . . . . . . . . . .    30
hu3D6VLv2 L54D                       . . . . . . . . . . . . . . . . . . . . . . . . . . . . . .    30
hu3D6VLv2 L54K                       . . . . . . . . . . . . . . . . . . . . . . . . . . . . . .    30
hu3D6VLv2 L54R                       . . . . . . . . . . . . . . . . . . . . . . . . . . . . . .    30
hu3D6VLv2 L54T                       . . . . . . . . . . . . . . . . . . . . . . . . . . . . . .    30
hu3D6VLv2 L37Q_L50G                  . . . . . . . . . . . . . . . . . . . . . . . . . . . . . .    30
hu3D6VLv2 L37Q_L50D                  . . . . . . . . . . . . . . . . . . . . . . . . . . . . . .    30
hu3D6VLv2 L37Q_S52G                  . . . . . . . . . . . . . . . . . . . . . . . . . . . . . .    30
hu3D6VLv2 L37Q_L54G                  . . . . . . . . . . . . . . . . . . . . . . . . . . . . . .    30
hu3D6VLv2 L37Q_L54R                  . . . . . . . . . . . . . . . . . . . . . . . . . . . . . .    30
hu3D6VLv2 L37Q_L54T                  . . . . . . . . . . . . . . . . . . . . . . . . . . . . . .    30
hu3D6VLv2 L37Q_L54D                  . . . . . . . . . . . . . . . . . . . . . . . . . . . . . .    30
hu3D6VLv2 L37Q_L54E                  . . . . . . . . . . . . . . . . . . . . . . . . . . . . . .    30
hu3D6VLv2 L37Q_L50G_L54R             . . . . . . . . . . . . . . . . . . . . . . . . . . . . . .    30
hu3D6VLv2 L37Q_L50G_L54G             . . . . . . . . . . . . . . . . . . . . . . . . . . . . . .    30
hu3D6VLv2 L37Q_L50D_L54R             . . . . . . . . . . . . . . . . . . . . . . . . . . . . . .    30
hu3D6VLv2 L37Q_L50E_L54R             . . . . . . . . . . . . . . . . . . . . . . . . . . . . . .    30
hu3D6VLv2 L37Q_L50D_L54G             . . . . . . . . . . . . . . . . . . . . . . . . . . . . . .    30
hu3D6VLv2 L37Q_S52G_L54D             . . . . . . . . . . . . . . . . . . . . . . . . . . . . . .    30
hu3D6VLv2 L37Q_S52G_L54G             . . . . . . . . . . . . . . . . . . . . . . . . . . . . . .    30
hu3D6VLv2 L37Q_S52G_L54T             . . . . . . . . . . . . . . . . . . . . . . . . . . . . . .    30
hu3D6VLv2 L37Q_S52G_L54R             . . . . . . . . . . . . . . . . . . . . . . . . . . . . . .    30
hu3D6VLv2 L37Q_L50D_L54G_G100Q       . . . . . . . . . . . . . . . . . . . . . . . . . . . . . .    30
hu3D6VLv2 L37Q_L50D_L54R_G100Q       . . . . . . . . . . . . . . . . . . . . . . . . . . . . . .    30
hu3D6VLv2 L37Q_L50G_L54G_G100Q       . . . . . . . . . . . . . . . . . . . . . . . . . . . . . .    30
hu3D6VLv2 L37Q_L50G_L54R_G100Q       . . . . . . . . . . . . . . . . . . . . . . . . . . . . . .    30
hu3D6VLv2 L37Q_L50V_L54D_G100Q       . . . . . . . . . . . . . . . . . . . . . . . . . . . . . .    30
hu3D6VLv2 L37Q_S52G_L54D_G100Q       . . . . . . . . . . . . . . . . . . . . . . . . . . . . . .    30
hu3D6VLv2 L37Q_S52G_L54R_G100Q       . . . . . . . . . . . . . . . . . . . . . . . . . . . . . .    30
```

Figure 10B

```
                                                40                  50                  60
hu3D6VLv2                          D S D G K T Y L N W L L Q R P G Q S P R R L I Y L V S K L D   60
hu3D6VLv2 L37Q                     . . . . . . . . . . . Q . . . . . . . . . . . . . . . . . .   60
hu3D6VLv2 L50G                     . . . . . . . . . . . . . . . . . . . . . . . . G . . . . .   60
hu3D6VLv2 S52G                     . . . . . . . . . . . . . . . . . . . . . . . . . . G . . .   60
hu3D6VLv2 L54G                     . . . . . . . . . . . . . . . . . . . . . . . . . . . . G .   60
hu3D6VLv2 L54D                     . . . . . . . . . . . . . . . . . . . . . . . . . . . . D .   60
hu3D6VLv2 L54K                     . . . . . . . . . . . . . . . . . . . . . . . . . . . . K .   60
hu3D6VLv2 L54R                     . . . . . . . . . . . . . . . . . . . . . . . . . . . . R .   60
hu3D6VLv2 L54T                     . . . . . . . . . . . . . . . . . . . . . . . . . . . . T .   60
hu3D6VLv2 L37Q_L50G                . . . . . . . . . . . Q . . . . . . . . . . . . G . . . . .   60
hu3D6VLv2 L37Q_L50D                . . . . . . . . . . . Q . . . . . . . . . . . . D . . . . .   60
hu3D6VLv2 L37Q_S52G                . . . . . . . . . . . Q . . . . . . . . . . . . . . G . . .   60
hu3D6VLv2 L37Q_L54G                . . . . . . . . . . . Q . . . . . . . . . . . . . . . . G .   60
hu3D6VLv2 L37Q_L54R                . . . . . . . . . . . Q . . . . . . . . . . . . . . . . R .   60
hu3D6VLv2 L37Q_L54T                . . . . . . . . . . . Q . . . . . . . . . . . . . . . . T .   60
hu3D6VLv2 L37Q_L54D                . . . . . . . . . . . Q . . . . . . . . . . . . . . . . D .   60
hu3D6VLv2 L37Q_L54E                . . . . . . . . . . . Q . . . . . . . . . . . . . . . . E .   60
hu3D6VLv2 L37Q_L50G_L54R           . . . . . . . . . . . Q . . . . . . . . . . . . G . . . R .   60
hu3D6VLv2 L37Q_L50G_L54G           . . . . . . . . . . . Q . . . . . . . . . . . . G . . . G .   60
hu3D6VLv2 L37Q_L50D_L54R           . . . . . . . . . . . Q . . . . . . . . . . . . D . . . R .   60
hu3D6VLv2 L37Q_L50E_L54R           . . . . . . . . . . . Q . . . . . . . . . . . . E . . . R .   60
hu3D6VLv2 L37Q_L50D_L54G           . . . . . . . . . . . Q . . . . . . . . . . . . D . . . G .   60
hu3D6VLv2 L37Q_S52G_L54D           . . . . . . . . . . . Q . . . . . . . . . . . . . . G . D .   60
hu3D6VLv2 L37Q_S52G_L54G           . . . . . . . . . . . Q . . . . . . . . . . . . . . G . G .   60
hu3D6VLv2 L37Q_S52G_L54T           . . . . . . . . . . . Q . . . . . . . . . . . . . . G . T .   60
hu3D6VLv2 L37Q_S52G_L54R           . . . . . . . . . . . Q . . . . . . . . . . . . . . G . R .   60
hu3D6VLv2 L37Q_L50D_L54G_G100Q     . . . . . . . . . . . Q . . . . . . . . . . . . D . . . G .   60
hu3D6VLv2 L37Q_L50D_L54R_G100Q     . . . . . . . . . . . Q . . . . . . . . . . . . D . . . R .   60
hu3D6VLv2 L37Q_L50G_L54G_G100Q     . . . . . . . . . . . Q . . . . . . . . . . . . G . . . G .   60
hu3D6VLv2 L37Q_L50G_L54R_G100Q     . . . . . . . . . . . Q . . . . . . . . . . . . G . . . R .   60
hu3D6VLv2 L37Q_L50V_L54D_G100Q     . . . . . . . . . . . Q . . . . . . . . . . . . V . . . D .   60
hu3D6VLv2 L37Q_S52G_L54D_G100Q     . . . . . . . . . . . Q . . . . . . . . . . . . . . G . D .   60
hu3D6VLv2 L37Q_S52G_L54R_G100Q     . . . . . . . . . . . Q . . . . . . . . . . . . . . G . R .   60
```

Figure 10C

```
                                                70        80        90
hu3D6VLv2                               SGVPDRFSGSGSGTDFTLKISRVEAEDVGV   90
hu3D6VLv2 L37Q                          ..............................   90
hu3D6VLv2 L50G                          ..............................   90
hu3D6VLv2 S52G                          ..............................   90
hu3D6VLv2 L54G                          ..............................   90
hu3D6VLv2 L54D                          ..............................   90
hu3D6VLv2 L54K                          ..............................   90
hu3D6VLv2 L54R                          ..............................   90
hu3D6VLv2 L54T                          ..............................   90
hu3D6VLv2 L37Q_L50G                     ..............................   90
hu3D6VLv2 L37Q_L50D                     ..............................   90
hu3D6VLv2 L37Q_S52G                     ..............................   90
hu3D6VLv2 L37Q_L54G                     ..............................   90
hu3D6VLv2 L37Q_L54R                     ..............................   90
hu3D6VLv2 L37Q_L54T                     ..............................   90
hu3D6VLv2 L37Q_L54D                     ..............................   90
hu3D6VLv2 L37Q_L54E                     ..............................   90
hu3D6VLv2 L37Q_L50G_L54R                ..............................   90
hu3D6VLv2 L37Q_L50G_L54G                ..............................   90
hu3D6VLv2 L37Q_L50D_L54R                ..............................   90
hu3D6VLv2 L37Q_L50E_L54R                ..............................   90
hu3D6VLv2 L37Q_L50D_L54G                ..............................   90
hu3D6VLv2 L37Q_S52G_L54D                ..............................   90
hu3D6VLv2 L37Q_S52G_L54G                ..............................   90
hu3D6VLv2 L37Q_S52G_L54T                ..............................   90
hu3D6VLv2 L37Q_S52G_L54R                ..............................   90
hu3D6VLv2 L37Q_L50D_L54G_G100Q          ..............................   90
hu3D6VLv2 L37Q_L50D_L54R_G100Q          ..............................   90
hu3D6VLv2 L37Q_L50G_L54G_G100Q          ..............................   90
hu3D6VLv2 L37Q_L50G_L54R_G100Q          ..............................   90
hu3D6VLv2 L37Q_L50V_L54D_G100Q          ..............................   90
hu3D6VLv2 L37Q_S52G_L54D_G100Q          ..............................   90
hu3D6VLv2 L37Q_S52G_L54R_G100Q          ..............................   90
```

Figure 10D

```
                                       100               110
                              ---------+-----------------+---
hu3D6VLv2                     Y Y C W Q G T H F P Y T F G G G T K L E I K    112
hu3D6VLv2 L37Q                . . . . . . . . . . . . . . . . . . . . . .    112
hu3D6VLv2 L50G                . . . . . . . . . . . . . . . . . . . . . .    112
hu3D6VLv2 S52G                . . . . . . . . . . . . . . . . . . . . . .    112
hu3D6VLv2 L54G                . . . . . . . . . . . . . . . . . . . . . .    112
hu3D6VLv2 L54D                . . . . . . . . . . . . . . . . . . . . . .    112
hu3D6VLv2 L54K                . . . . . . . . . . . . . . . . . . . . . .    112
hu3D6VLv2 L54R                . . . . . . . . . . . . . . . . . . . . . .    112
hu3D6VLv2 L54T                . . . . . . . . . . . . . . . . . . . . . .    112
hu3D6VLv2 L37Q_L50G           . . . . . . . . . . . . . . . . . . . . . .    112
hu3D6VLv2 L37Q_L50D           . . . . . . . . . . . . . . . . . . . . . .    112
hu3D6VLv2 L37Q_S52G           . . . . . . . . . . . . . . . . . . . . . .    112
hu3D6VLv2 L37Q_L54G           . . . . . . . . . . . . . . . . . . . . . .    112
hu3D6VLv2 L37Q_L54R           . . . . . . . . . . . . . . . . . . . . . .    112
hu3D6VLv2 L37Q_L54T           . . . . . . . . . . . . . . . . . . . . . .    112
hu3D6VLv2 L37Q_L54D           . . . . . . . . . . . . . . . . . . . . . .    112
hu3D6VLv2 L37Q_L54E           . . . . . . . . . . . . . . . . . . . . . .    112
hu3D6VLv2 L37Q_L50G_L54R      . . . . . . . . . . . . . . . . . . . . . .    112
hu3D6VLv2 L37Q_L50G_L54G      . . . . . . . . . . . . . . . . . . . . . .    112
hu3D6VLv2 L37Q_L50D_L54R      . . . . . . . . . . . . . . . . . . . . . .    112
hu3D6VLv2 L37Q_L50E_L54R      . . . . . . . . . . . . . . . . . . . . . .    112
hu3D6VLv2 L37Q_L50D_L54G      . . . . . . . . . . . . . . . . . . . . . .    112
hu3D6VLv2 L37Q_S52G_L54D      . . . . . . . . . . . . . . . . . . . . . .    112
hu3D6VLv2 L37Q_S52G_L54G      . . . . . . . . . . . . . . . . . . . . . .    112
hu3D6VLv2 L37Q_S52G_L54T      . . . . . . . . . . . . . . . . . . . . . .    112
hu3D6VLv2 L37Q_S52G_L54R      . . . . . . . . . . . . . . . . . . . . . .    112
hu3D6VLv2 L37Q_L50D_L54G_G100Q . . . . . . . . . . . . . . Q . . . . . . .    112
hu3D6VLv2 L37Q_L50D_L54R_G100Q . . . . . . . . . . . . . . Q . . . . . . .    112
hu3D6VLv2 L37Q_L50G_L54G_G100Q . . . . . . . . . . . . . . Q . . . . . . .    112
hu3D6VLv2 L37Q_L50G_L54R_G100Q . . . . . . . . . . . . . . Q . . . . . . .    112
hu3D6VLv2 L37Q_L50V_L54D_G100Q . . . . . . . . . . . . . . Q . . . . . . .    112
hu3D6VLv2 L37Q_S52G_L54D_G100Q . . . . . . . . . . . . . . Q . . . . . . .    112
hu3D6VLv2 L37Q_S52G_L54R_G100Q . . . . . . . . . . . . . . Q . . . . . . .    112
```

Normal Healthy Control
1 ug/mL

Alzheimer's disease
0.1 ug/mL

Alzheimer's disease
1 ug/mL

ANTIBODIES RECOGNIZING TAU

CROSS REFERENCE TO RELATED APPLICATIONS

The present application is a continuation of U.S. patent application Ser. No. 17/181,997, filed on Feb. 22, 2021, which is a continuation of U.S. patent application Ser. No. 16/808,209, filed Mar. 3, 2020 (issued as U.S. Pat. No. 10,961,302), which claims priority to: U.S. Provisional Patent Application No. 62/813,126, filed Mar. 3, 2019, U.S. Provisional Patent Application No. 62/813,137, filed Mar. 3, 2019, and U.S. Provisional Patent Application No. 62/838,159, filed Apr. 24, 2019, each of which is incorporated by reference in its entirety for all purposes.

REFERENCE TO A SEQUENCE LISTING

This application contains a Sequence Listing that has been submitted electronically as an XML file named 50887-0030003_SL_ST26.xml. The XML file, created on Jan. 24, 2024, is 185,505 bytes in size. The material in the XML file is hereby incorporated by reference in its entirety.

BACKGROUND OF THE INVENTION

Tau is a well-known human protein that can exist in phosphorylated forms (see, e.g., Goedert, Proc. Natl. Acad. Sci. U.S.A. 85:4051-4055(1988); Goedert, EMBO J. 8:393-399(1989); Lee, Neuron 2:1615-1624(1989); Goedert, Neuron 3:519-526(1989); Andreadis, Biochemistry 31:10626-10633(1992). Tau has been reported to have a role in stabilizing microtubules, particularly in the central nervous system. Total tau (t-tau, i.e., phosphorylated and unphosphorylated forms) and phospho-tau (p-tau, i.e., phosphorylated tau) are released by the brain in response to neuronal injury and neurodegeneration and have been reported to occur at increased levels in the CSF of Alzheimer's patients relative to the general population (Jack et al., Lancet Neurol 9: 119-28 (2010)).

Tau is the principal constituent of neurofibrillary tangles, which together with plaques are a hallmark characteristic of Alzheimer's disease. The tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Hyperphosphorylated tau has also been reported to interfere with microtubule assembly, which may promote neuronal network breakdown.

Tau inclusions are part of the defining neurophathology of several neurodegenerative diseases including Alzheimer's disease, frontotemporal lobar degeneration, progressive supranuclear palsy and Pick's disease.

BRIEF SUMMARY OF THE CLAIMED INVENTION

In one aspect, the invention provides an isolated antibody specifically binding to human tau, comprising a mature heavy chain variable region comprising CDR-H1 comprising SEQ ID NO:8, CDR-H2 comprising SEQ ID NO:9 or SEQ ID NO:149, and CDR-H3 comprising SEQ ID NO:10, wherein the heavy chain variable region is at least 90% identical to SEQ ID NO:18; and a mature light chain variable region comprising CDR-L1 comprising SEQ ID NO:12, CDR-L2 comprising SEQ ID NO: 150, 151, 153, 156, 158, 159, 160, 163, 165, 166, 167, 168, 169, 170, 171, 172, 173 or 174, and CDR-L3 comprising SEQ ID NO:14, wherein the light chain variable region is at least 90% identical to SEQ ID NO:122.

In some antibodies, at least one of positions H12, H13, H17, H24, H40, H43, H48, H66, H67, H76, H80, H81, and H91 can be occupied by V, K, T, A, R, Q, I, R, A, D, L, Q, and F, respectively, and at least one of positions L2, L12, L15, L37, L39, L45, L60 and L100 can be occupied by V, P, L, Q, R, R, D and Q respectively.

In some antibodies, CDR-L2 comprises SEQ ID NO: 150, 151, 163, 167, 168, or 169. In some antibodies, the heavy chain variable region comprises SEQ ID NO:18 and the light chain variable region comprises SEQ ID NO: 110, 121, 122 or 123.

In some antibodies, the light chain variable region comprises SEQ ID NO:110. In some antibodies, the light chain variable region comprises SEQ ID NO:121. In some antibodies, the light chain variable region comprises SEQ ID NO:122. In some antibodies, the light chain variable region comprises SEQ ID NO:123.

In some antibodies, the heavy chain variable region comprises SEQ ID NO:146 and the light chain variable region comprises SEQ ID NO: 94 or 122. In some antibodies, the light chain variable region comprises SEQ ID NO:94. In some antibodies, the light chain variable region comprises SEQ ID NO:122.

In some antibodies, the heavy chain variable region comprises SEQ ID NO:18 or 146 and the light chain variable region comprises SEQ ID NO:122.

In another aspect, the invention provides an antibody specifically binding to human tau, comprising a mature heavy chain variable region comprising CDRs H1, H2 and H3 comprising SEQ ID NOs:8, 9, and 10, respectively except that position H28 can be occupied by N or T, H54 can be occupied by N or D, H56 can be occupied by D or E, position H58 occupied by V or I, and position H60 can be occupied by D or E, and a mature light chain variable region comprising CDRs L1, L2 and L3 comprising SEQ ID NOs:12, 13, and 14 respectively, except that position L24 can be occupied by K or R, position L50 can be occupied by L, E. D, G, or V, position L52 can be occupied by S or G, and position L54 can be occupied by L, D, G, N, E, Q, K, R, T, V, or S, wherein at least one of the following positions is occupied by the amino acid as specified: H1 is occupied by Q, H5 is occupied by Q, H11 is occupied by L, H20 is occupied by L, H23 is occupied by T, H38 is occupied by K, H75 is occupied by S, H56 is occupied by E, H58 is occupied by I, H60 is occupied by E, H82c is occupied by V, L10 is occupied by T, L17 is occupied by E, L24 is occupied by R, L37 is occupied by Q, L47 is occupied by G, N, D, E, P, T, S, or A, L48 is occupied by G or D, L49 is occupied by E, L50 is occupied by E, D, G, or V, L52 is occupied by G, L54 is occupied by D, G, N. E, Q, K, R, T, V, or S, L83 is occupied by L, L86 is occupied by H, L100 is occupied by Q, L106 is occupied by L.

In another aspect, the invention provides an isolated monoclonal antibody that binds human tau comprising three light chain CDRs and three heavy chain CDRs of monoclonal antibody 3D6, wherein 3D6 is a mouse antibody characterized by a heavy chain variable region having an amino acid sequence comprising SEQ ID NO:7 and a light chain variable region having an amino acid sequence comprising SEQ ID NO:11, except that position H27 can be occupied by F or Y, position H28 can be occupied by N or T, position H29 can be occupied by I or F, position H30 can be occupied by K or T, position H51 can be occupied by I or V, position H54 can be occupied by N or D, position H60 can be occupied by D, A, or E, position H61 can be occupied by P or E, position H102 can be occupied by F or Y, position L50 can be occupied by L, E. D, G, or V, position L52 can be occupied by S or G, and position L54 can be occupied by L, D, G, N, E, Q, K, R, T, V, or S, wherein at least one of the following positions is occupied by the amino acid as specified: L37 is occupied by Q, L47 is occupied by G, N, D, E, P, T, S, or A, L48 is occupied by G or D, L49 is occupied by E, L50 is occupied by E, D, G, or V, L52 is occupied by G, L54 is occupied by D, G, N. E, Q, K, R, T, V, or S, L100 is occupied by Q, H60 is occupied by E, H82c is occupied by V.

In some antibodies, CDR-H1 has an amino acid sequence comprising SEQ ID NO:86. In some antibodies, CDR-H2 has an amino acid sequence comprising SEQ ID NO:87, SEQ ID NO:88, SEQ ID NO:92, or SEQ ID NO:149. In some antibodies, CDR-L2 has an amino acid sequence comprising any of SEQ ID NOs:150-175. In some antibodies, CDR-L1 has an amino acid sequence comprising SEQ ID NO:89. In some antibodies, CDR-H1 has an amino acid sequence comprising SEQ ID NO:86 and CDR-H2 has an amino acid sequence comprising SEQ ID NO:87. In some antibodies, CDR-H1 has an amino acid sequence comprising SEQ ID NO:86 and CDR-H2 has an amino acid sequence comprising SEQ ID NO:88. In some antibodies, CDR-H1 has an amino acid sequence comprising SEQ ID NO:86 and CDR-H2 has an amino acid sequence comprising SEQ ID NO:92. In some antibodies, CDR-H1 has an amino acid sequence comprising SEQ ID NO:42, SEQ ID NO:58, SEQ ID NO:59, or SEQ ID NO:60. In some antibodies, CDR-H2 has an amino acid sequence comprising SEQ ID NO:43, SEQ ID NO:61, SEQ ID NO:62, SEQ ID NO:63, SEQ ID NO:64, or SEQ ID NO:149. In some antibodies, CDR-H3 has an amino acid sequence comprising SEQ ID NO:65. In some antibodies, CDR-L2 has an amino acid sequence comprising any of SEQ ID NOs:150-175.

Some antibodies are a humanized antibody, veneered antibody, or chimeric antibody.

Some antibodies comprise a humanized mature heavy chain variable region having an amino acid sequence at least 95% identical to any one of SEQ ID NOs:76-80 and SEQ ID NOs:90-91, and a humanized mature light chain variable region having an amino acid sequence at least 90% identical to any one of SEQ ID NOs:83-85.

Some antibodies comprise a humanized mature heavy chain variable region having an amino acid sequence at least 95% identical to any one of SEQ ID NO:18 and SEQ ID NOs:146-148, and a humanized mature light chain variable region having an amino acid sequence at least 90% identical to any one of SEQ ID NOs:93-145.

In some antibodies, at least one of the following positions in the VH region is occupied by the amino acid as specified: H93 is occupied by S and H94 is occupied by T. In some antibodies, positions H93 and H94 are occupied by S and T, respectively. In some antibodies position H91 in the VH region is occupied by F.

In some antibodies, at least one of the following positions in the VH region is occupied by the amino acid as specified: H1 is occupied by E, H5 is occupied by V, H11 is occupied by V, H20 is occupied I, H23 is occupied by K, H38 is occupied by R, H42 is occupied by G, H43 is occupied by K, H66 is occupied by R, H75 is occupied by T, H76 is occupied by D, H81 is occupied by E, H108 is occupied by L, H109 is occupied by V. In some antibodies, positions H1, H5, H11, H20, H23, H38, H42, H43, H66, H75, H76, H81, H108, and H109 in the VH region are occupied by E, V, V, I, K, R, G, K, R, T, D, E, L, and V, respectively.

In some antibodies, at least one of the following positions in the VH region is occupied by the amino acid as specified: H17 is occupied by T, H80 is occupied by M, H83 is occupied by R. In some antibodies, positions H17, H80, and H83 in the VH region are occupied by T, M, and R, respectively.

In some antibodies, position H58 in the VH region is occupied by I.

In some antibodies, at least one of the following positions in the VH region is occupied by the amino acid as specified: H28 is occupied by T, H67 is occupied by V. In some antibodies, positions H28 and H67 in the VH region are occupied by T and V, respectively.

In some antibodies, at least one of the following positions in the VH region is occupied by the amino acid as specified: H54 is occupied by D, H56 is occupied by E. In some antibodies, positions H54 and H56 in the VH region are occupied by D and E, respectively.

In some antibodies, at least one of the following positions in the VH region is occupied by the amino acid as specified: H1 is occupied by Q or E, H5 is occupied by Q or V, H11 is occupied by L or V, H17 is occupied by S or T, H20 is occupied by L or I, H23 is occupied by T or K, H28 is occupied by N or T, H38 is occupied by K or R, H42 is occupied by E or G, H43 is occupied by Q or K, H54 is occupied by N or D, H56 is occupied by D or E, H58 is occupied by V or I, H60 is occupied by D or E, H66 is occupied by K or R, H67 is occupied by A or V, H75 is occupied by S or T, H76 is occupied by N or D, H80 is occupied by L or M, H81 is occupied by Q or E, H82c is occupied by L or V, H83 is occupied by T or R, H91 is occupied by F or Y, H93 is occupied by S, H94 is occupied by T, H108 is occupied by T or L, H109 is occupied by L or V.

In some antibodies, at least one of the following positions in the VH region is occupied by the amino acid as specified: H10 is occupied by E or D, H12 is occupied by K or V, H13 is occupied by K or R, H17 is occupied by T, L or S, H24 is occupied by V or A, H27 is occupied by F or Y, H28 is occupied by N or T, H29 is occupied by I or F, H30 is occupied by K or T, H38 is occupied by Q or R, H40 is occupied by A or R, H42 is occupied by G or E, H43 is occupied by K or Q, H48 is occupied by M or I, H51 is occupied by V or I, H54 is occupied by N or D, H60 is occupied by D, A, or E, H61 is occupied by P or E, H66 is occupied by R or K, H67 is occupied by V or A, H76 is occupied by D or N, H80 is occupied by M or L, H81 is occupied by E or Q, H82a is occupied by S or G, H82c is occupied by L or V, H83 is occupied by T or R, H91 is occupied by Y or F, H93 is occupied by A or S, H102 is occupied by F or Y, H108 is occupied by T or L, H109 is occupied by L or V.

In some antibodies, positions H91, H93, and H94 in the VH region are occupied by F, S, and T, respectively.

In some antibodies, positions H1, H5, H11, H20, H23, H38, H42, H43, H66, H75, H76, H81, H91, H93, H94, H108, and H109 in the VH region are occupied by E, V, V, I, K, R, G, K, R, T, D, E, F, S, T, L, and V, respectively. In some antibodies, positions H1, H5, H11, H17, H20, H23, H38, H42, H43, H58, H66, H75, H76, H80, H81, H83, H93, H94, H108, and H109 in the VH region are occupied by E, V, V, T, I, K, R, G, K, I, R, T, D, M, E, R, S, T, L, and V, respectively. In some antibodies, positions H1, H5, H11, H17, H20, H23, H28, H38, H42, H43, H58, H66, H67, H75, H76, H80, H81, H83, H93, H94, H108, and H109 in the VH region are occupied by E, V, V, T, I, K, T, R, G, K, I, R, V, T, D, M, E, R, S, T, L, and V, respectively. In some antibodies, positions H1, H5, H11, H17, H20, H23, H28, H38, H42, H43, H54, H56, H58, H66, H67, H75, H76, H80, H81, H83, H93, H94, H108, and H109 in the VH region are occupied by E, V, V, T, I, K, T, R, G, K, D, E, I, R, V, T, D, M, E, R, S, T, L, and V, respectively.

In some antibodies, positions H1, H5, H11, H17, H20, H23, H28, H38, H42, H43, H54, H56, H66, H67, H75, H76, H80, H81, H83, H91, H93, H94, H108, and H109 in the VH region are occupied by E, V, V, T, I, K, T, R, G, K, D, E, R, V, T, D, M, E, R, F, S, T, L, and V, respectively. In some antibodies, positions H1, H5, H11, H17, H20, H23, H28, H38, H42, H43, H54, H56, H66, H67, H75, H76, H80, H81, H83, H93, H94, H108, and H109 in the VH region are occupied by E, V, V, T, I, K, T, R, G, K, D, E, R, V, T, D, M, E, R, S, T, L, and V, respectively.

In some antibodies, position H60 is occupied by E. In some antibodies, position H82C is occupied by V. In some antibodies, positions H60, H80, H81, H82c, and H83 are occupied by E, M, E, V, and R, respectively.

In some antibodies, at least one of the following positions in the VL region is occupied by the amino acid as specified: L7 is occupied by S, L10 is occupied by S, L15 is occupied by L, L83 is occupied by V, L86 is occupied by Y, and L106 is occupied by I. In some antibodies, positions L7, L10, L15, L83, L86, and L106 are occupied by S, S, L, V, Y, and Y, respectively.

In some antibodies, at least one of the following positions in the VL region is occupied by the amino acid as specified: L7 is T or S, L10 is T or S, L15 is I or L, L17 is Q or E, L24 is K or R, L37 is L or Q, L45 is K or R, L47 is L, G, N, D, E, P, T, S, or A, L48 is I, G, or D, L49 is Y or E, L50 is L, E, D, G, or V, L52 is S or G, L54 is L, D, G, N, E, Q, K, R, T, V, or S, L83 is L or V, L86 is H or Y, L100 is A or Q, L106 is L or I.

In some antibodies, at least one of the following positions in the VL region is occupied by the amino acid as specified: L2 is V or I, L7 is S or T, L12 is P or S, L15 is L or I, L36 is L, L37 is L or Q, L45 is R or K, L47 is L, G, N, D, E, P, T, S, or A, L48 is I, G, or D, L49 is Y or E, L50 is L, E, D, G, or V, L52 is S or G, L54 is L, D, G, N, E, Q, K, R, T, V, L60 is D or S, L100 is G or Q.

In some antibodies, positions L7, L10, L15, L83, L86, and L106 in the VL region are occupied by S, S, L, V, Y, and I, respectively. In some antibodies, positions L7, L10, L15, L17, L24, L37, L45, L83, L86, L100, and L106 in the VL region are occupied by S, S, L, E, R, Q, R, V, Y, Q, and I, respectively.

In some antibodies, position L54 is occupied by D. In some antibodies, position L54 is occupied by G. In some antibodies, position L54 is occupied by N. In some antibodies, position L54 is occupied by E. In some antibodies, position L50 is occupied by E. In some antibodies, position L54 is occupied by Q. In some antibodies, position L50 is occupied by D. In some antibodies, position L54 is occupied by K. In some antibodies, position L54 is occupied by R In some antibodies, position L54 is occupied by T. In some antibodies, position L50 is occupied by G. In some antibodies, position L48 is occupied by G. In some antibodies, position L48 is occupied by D. In some antibodies, position L47 is occupied by G. In some antibodies, position L49 is occupied by E. In some antibodies, position L54 is occupied by V. In some antibodies, position L54 is occupied by S.

In some antibodies, position L52 is occupied by G. In some antibodies, position L47 is occupied by N. In some antibodies, position L47 is occupied by D. In some antibodies, position L47 is occupied by E. In some antibodies, position L47 is occupied by P. In some antibodies, position L47 is occupied by T. In some antibodies, position L47 is occupied by S. In some antibodies, position L47 is occupied by A. In some antibodies, position L50 is occupied by V.

In some antibodies, positions L37, L50, and L54 are occupied by Q, G, and R, respectively. In some antibodies, positions L37, L50, and L54 are occupied by Q, G, and G, respectively. In some antibodies, positions L37, L52, and L54 are occupied by Q, G, and G, respectively. In some antibodies, positions L37, L52, and L54 are occupied by Q, G, and R, respectively. In some antibodies, positions L37, L52, and L54 are occupied by Q, G, and T, respectively. In some antibodies, positions L37, L52, and L54 are occupied by Q, G, and D, respectively. In some antibodies, L37 and L54 are occupied Q and R, respectively.

In some antibodies, positions L37 and L54 are occupied by Q and G, respectively. In some antibodies, positions L37 and L54 are occupied by Q and D, respectively. In some antibodies, positions L37 and L50 are occupied by Q and G, respectively. In some antibodies, positions L37 and L50 are occupied by Q and D, respectively. In some antibodies, positions L37 and L54 are occupied by Q and T, respectively. In some antibodies, positions L37 and L52 are occupied by Q and G, respectively. In some antibodies, positions L37 and L54 are occupied by Q and E, respectively. In some antibodies, positions L37, L50, and L54 are occupied by Q, D, and G, respectively. In some antibodies, positions L37, L50, and L54 are occupied by Q, D, and R, respectively.

In some antibodies, positions L37, L50, and L54 are occupied by Q, E, and G, respectively. In some antibodies, positions L37, L50, and L54 are occupied by Q, E, and R, respectively. In some antibodies, positions L37, L50, L54, and L100 are occupied by Q, G, R, and Q, respectively. In some antibodies, positions L37, L50, L54, and L100 are occupied by Q, G, G, and Q, respectively. In some antibodies, positions L37, L52, L54, and L100 are occupied by Q, G, R, and Q, respectively. In some antibodies, positions L37, L52, L54, and L100 are occupied by Q, G, D, and Q, respectively. In some antibodies, positions L37, L50, L54, and L100 are occupied by Q, D, G, and Q, respectively. In some antibodies, positions L37, L50, L54, and L100 are occupied by Q, D, R, and Q, respectively.

In some antibodies, positions L37, L50, L54, and L100 are occupied by Q, V, D, and Q, respectively. In some antibodies, position L37 is occupied by Q. In some antibodies, position L100 is occupied by Q.

In some antibodies, the mature heavy chain variable region has an amino acid sequence of any one of SEQ ID NOs:76-80 and SEQ ID NOs:90-91 and the mature light chain variable region has an amino acid sequence of any one of SEQ ID NO:83-85. In some antibodies, the mature heavy chain variable region has an amino acid sequence of any one of SEQ ID NO:18 and SEQ ID NOs:146-148 and the mature light chain variable region has an amino acid sequence of any one of SEQ ID NOs:93-145.

In some antibodies, the mature heavy chain variable region has an amino acid sequence of SEQ ID NO:76 and the mature light chain variable region has an amino acid sequence of SEQ ID NO:83. In some antibodies, the mature heavy chain variable region has an amino acid sequence of SEQ ID NO:76 and the mature light chain variable region has an amino acid sequence of SEQ ID NO:84. In some antibodies, the mature heavy chain variable region has an amino acid sequence of SEQ ID NO:76 and the mature light chain variable region has an amino acid sequence of SEQ ID NO:85.

In some antibodies, the mature heavy chain variable region has an amino acid sequence of SEQ ID NO:77 and the mature light chain variable region has an amino acid sequence of SEQ ID NO:83. In some antibodies, the mature heavy chain variable region has an amino acid sequence of SEQ ID NO:77 and the mature light chain variable region has an amino acid sequence of SEQ ID NO:84. In some antibodies, the mature heavy chain variable region has an amino acid sequence of SEQ ID NO:77 and the mature light chain variable region has an amino acid sequence of SEQ ID NO:85.

In some antibodies, the mature heavy chain variable region has an amino acid sequence of SEQ ID NO:78 and the mature light chain variable region has an amino acid sequence of SEQ ID NO:83. In some antibodies, the mature heavy chain variable region has an amino acid sequence of SEQ ID NO:78 and the mature light chain variable region has an amino acid sequence of SEQ ID NO:84. In some antibodies, the mature heavy chain variable region has an amino acid sequence of SEQ ID NO:78 and the mature light chain variable region has an amino acid sequence of SEQ ID NO:85.

In some antibodies, the mature heavy chain variable region has an amino acid sequence of SEQ ID NO:79 and the mature light chain variable region has an amino acid sequence of SEQ ID NO:83. In some antibodies, the mature heavy chain variable region has an amino acid sequence of SEQ ID NO:79 and the mature light chain variable region has an amino acid sequence of SEQ ID NO:84. In some antibodies, the mature heavy chain variable region has an amino acid sequence of SEQ ID NO:79 and the mature light chain variable region has an amino acid sequence of SEQ ID NO:85.

In some antibodies, the mature heavy chain variable region has an amino acid sequence of SEQ ID NO:80 and the mature light chain variable region has an amino acid sequence of SEQ ID NO:83. In some antibodies, he mature heavy chain variable region has an amino acid sequence of SEQ ID NO:80 and the mature light chain variable region has an amino acid sequence of SEQ ID NO:84. In some antibodies, the mature heavy chain variable region has an amino acid sequence of SEQ ID NO:80 and the mature light chain variable region has an amino acid sequence of SEQ ID NO:85.

In some antibodies, the mature heavy chain variable region has an amino acid sequence of SEQ ID NO:90 and the mature light chain variable region has an amino acid sequence of SEQ ID NO:83. In some antibodies, the mature heavy chain variable region has an amino acid sequence of SEQ ID NO:90 and the mature light chain variable region has an amino acid sequence of SEQ ID NO:84. In some antibodies, the mature heavy chain variable region has an amino acid sequence of SEQ ID NO:90 and the mature light chain variable region has an amino acid sequence of SEQ ID NO:85.

In some antibodies, the mature heavy chain variable region has an amino acid sequence of SEQ ID NO:91 and the mature light chain variable region has an amino acid sequence of SEQ ID NO:83. In some antibodies, the mature heavy chain variable region has an amino acid sequence of SEQ ID NO:91 and the mature light chain variable region has an amino acid sequence of SEQ ID NO:84. In some antibodies, the mature heavy chain variable region has an amino acid sequence of SEQ ID NO:91 and the mature light chain variable region has an amino acid sequence of SEQ ID NO:85.

In some antibodies, the mature heavy chain variable region has an amino acid sequence of SEQ ID NO:18 and the mature light chain variable region has an amino acid sequence of SEQ ID NO:122. In some antibodies, the mature heavy chain variable region has an amino acid sequence of SEQ ID NO:18 and the mature light chain variable region has an amino acid sequence of SEQ ID NO:123.

In some antibodies, the mature heavy chain variable region has an amino acid sequence of SEQ ID NO:146 and the mature light chain variable region has an amino acid sequence of SEQ ID NO: 122.

In some antibodies, the mature heavy chain variable region has an amino acid sequence of SEQ ID NO:18 and the mature light chain variable region has an amino acid sequence of SEQ ID NO:121. In some antibodies, the mature heavy chain variable region has an amino acid sequence of SEQ ID NO:18 and the mature light chain variable region has an amino acid sequence of SEQ ID NO:110.

In some antibodies, the mature heavy chain variable region has an amino acid sequence of SEQ ID NO:146 and the mature light chain variable region has an amino acid sequence of SEQ ID NO:94.

In some antibodies, the mature heavy chain variable region has an amino acid sequence of SEQ ID NO:18 and the mature light chain variable region has an amino acid sequence of SEQ ID NO:103.

For example, the antibody can be a chimeric, veneered, or humanized antibody.

The antibody can be an intact chimeric, veneered or humanized antibody or a binding fragment, single-chain antibody Fab fragment, Fab'2 fragment, or single chain Fv. Some of the antibodies have a human IgG1 isotype, while others may have a human IgG2 or IgG4 isotype. Some antibodies have the mature light chain variable region fused to a light chain constant region and the mature heavy chain variable region fused to a heavy chain constant region. The heavy chain constant region of some antibodies is a mutant form of a natural human heavy chain constant region which has reduced binding to a Fcγ receptor relative to the natural human heavy chain constant region.

In some antibodies, the heavy chain constant region has an amino acid sequence of SEQ ID NO:176. In some antibodies, the mature heavy chain variable region fused to a heavy chain constant region has an amino acid sequence of SEQ ID NO:178. Some antibodies further comprise a signal peptide fused to the mature heavy and/or light chain variable region. In some antibodies, the heavy chain has an amino acid sequence of SEQ ID NO:180. In some antibodies, the light chain constant region has an amino acid sequence of SEQ ID NO:177. In some antibodies, the mature light chain variable region is fused to a light chain constant region has an amino acid sequence of SEQ ID NO: 179. In some antibodies, the light chain has an amino acid sequence of SEQ ID NO:181. In some antibodies, the heavy chain has an amino acid sequence of SEQ ID NO:178 and the light chain has an amino acid sequence of SEQ ID NO:179. In some antibodies, the heavy chain has an amino acid sequence of SEQ ID NO:180 and the light chain has an amino acid sequence of SEQ ID NO:181.

Some antibodies may have at least one mutation in the constant region, such as a mutation that reduces complement fixation or activation by the constant region, for example, a mutation at one or more of positions 241, 264, 265, 270, 296, 297, 318, 320, 322, 329 and 331 by EU numbering. Some antibodies have an alanine at positions 318, 320 and 322. Some antibodies can be at least 95% w/w pure. The antibody can be conjugated to a therapeutic, cytotoxic, cytostatic, neurotrophic, or neuroprotective agent.

In another aspect, the invention provides a pharmaceutical composition comprising any of the antibodies disclosed herein and a pharmaceutically-acceptable carrier.

In another aspect, the invention provides a nucleic acid encoding the heavy chain and/or light chain of any of the antibodies disclosed herein, a recombinant expression vector comprising the nucleic acid and a host cell transformed with the recombinant expression vector.

In some nucleic acids, the heavy chain is encoded by a sequence comprising SEQ ID NO:182 and the light chain is encoded by a sequence comprising SEQ ID NO:183.

Methods of producing antibodies, such as a humanized, chimeric or veneered antibody, for example humanized, chimeric or veneered forms of 3D6, are also provided. In such methods, cells transformed with nucleic acids encoding the heavy and light chains of the antibody are cultured so that the cells secrete the antibody. The antibody can then be purified from the cell culture media.

Cell lines producing any of the antibodies disclosed herein can be produced by introducing a vector encoding heavy and light chains of the antibody and a selectable marker into cells, propagating the cells under conditions to select for cells having increased copy number of the vector, isolating single cells from the selected cells; and banking cells cloned from a single cell selected based on yield of antibody.

In another aspect, the invention comprises a vector comprising a nucleic acid encoding a mature heavy chain variable region and a mature light chain variable region operably linked to one or more regulatory sequences to effect expression in a mammalian cell of any of the antibodies disclosed herein. In some vectors, the expressed antibody is a scFv or an Fab fragment. In some vectors, the one or more regulatory sequences include one or more of a promoter, enhancer, ribosome binding site, and transcription termination signal. In some vectors, the nucleic acid further encodes signal peptides fused to the mature heavy and light chain variable regions. In some vectors, the nucleic acid is codon-optimized for expression in a host cell. In some vectors, the one or more regulatory sequences include a eukaryotic promoter. In some vectors, the nucleic acid further encodes a selectable gene.

In yet another aspect, the invention provides methods of expressing an antibody in a mammalian cell comprising incorporating the nucleic acids disclosed herein into the genome of a transgenic animal, whereby the antibody is expressed.

In yet another aspect, the invention provides first and second vectors respectively comprising nucleic acids encoding a mature heavy chain variable region and a mature light chain variable region, each operably linked to one or more regulatory sequences to effect expression of any of the antibodies disclosed herein, and a host cell comprising the nucleic acids. In some first and second vectors, the nucleic acids respectively further encodes a heavy chain constant region fused to the mature heavy chain variable region and a light chain constant region fused to the mature light chain variable region. In some first and second vectors, the heavy chain constant region has the sequence of SEQ ID NO:176 with or without the C-terminal lysine and the light chain constant region has the sequence of SEQ ID NO:177.

In yet another aspect, the invention provides methods of expressing an antibody in a mammalian cell comprising incorporating any of the nucleic acids disclosed herein into the genome of a transgenic animal, whereby the antibody is expressed.

Methods of producing antibodies, such as a humanized, chimeric, or veneered antibody, are also provided. In such methods, cells transformed with nucleic acids encoding the heavy and light chains of the antibody of any of the antibodies disclosed herein are cultured so that the cells secrete the antibody. The antibody can then be purified from the cell culture media.

Cell lines producing any of the antibodies disclosed herein can be produced by introducing a vector encoding heavy and light chains of the antibody of claim 1 and a selectable marker into cells, propagating the cells under conditions to select for cells having increased copy number of the vector, isolating single cells from the selected cells, and banking cells cloned from a single cell selected based on yield of antibody.

Some cells can be propagated under selective conditions and screened for cell lines naturally expressing and secreting at least 100 mg/L/$10^6$ cells/24 hours. Single cells can be isolated from the selected cells. Cells cloned from a single cell can then be banked. Single cells can be selected based on desirable properties, such as the yield of the antibody. Exemplary cell lines are cell lines expressing 3D6 or humanized versions of 3D6.

The invention also provides methods of inhibiting or reducing aggregation of tau in a subject having or at risk of developing a tau-mediated amyloidosis, comprising administering to the subject an effective regime of an antibody disclosed herein, thereby inhibiting or reducing aggregation of tau in the subject. Exemplary antibodies include humanized versions of 3D6.

Also provided are methods of treating or effecting prophylaxis of a tau-related disease in a subject, comprising administering an effective regime of an antibody disclosed herein and thereby treating or effecting prophylaxis of the disease. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). In some methods, the tau-related disease is Alzheimer's disease. In some methods the patient is an ApoE4 carrier.

Also provided are methods of reducing aberrant transmission of tau comprising administering an effective regime of an antibody disclosed herein and thereby reducing transmission of tau.

Also provided are methods of inducing phagocytosis of tau comprising administering an effective regime of an antibody disclosed herein and thereby inducing phagocytosis of tau.

Also provided are methods of inhibiting tau aggregation or deposition comprising administering an effective regime of an antibody disclosed herein thereby inhibiting tau aggregation or deposition.

Also provided are methods of inhibiting formation of tau tangles comprising administering an effective regime of an antibody disclosed herein.

The invention also provides a method of detecting tau protein deposits in a subject having or at risk of a disease associated with tau aggregation or deposition comprising administering to a subject an antibody disclosed herein, and detecting the antibody bound to tau in the subject. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). In some embodiments, the antibody is administered by intravenous injection into the body of the subject. In some embodiments, the antibody is administered directly to the brain of the subject by intracranial injection or by drilling a hole through the skull of the subject. In some embodiments, the antibody is labeled. In some embodiments, the antibody is labeled with a fluorescent label, a paramagnetic label, or a radioactive label. In some embodiments, the radioactive label is detected using positron emission tomography (PET) or single-photon emission computed tomography (SPECT).

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of the antibody bound to tau in the subject, administering the treatment to the subject, measuring a second level of tau protein deposits in the in subject after treatment by administering to a subject the antibody, and detecting the antibody bound to tau in the subject, wherein a decrease in the level of tau protein deposits indicates a positive response to treatment.

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of antibody bound to tau in the subject, administering the treatment to the subject, measuring a second level of tau protein deposits in the in subject after treatment by administering to a subject the antibody, and detecting a second amount of antibody bound to tau in the subject, wherein no change in the level of tau protein deposits or a small increase in tau protein deposits indicates a positive response to treatment.

In another aspect, the invention provides methods of producing an antibody that specifically binds to human tau at an epitope within a motif of the formula KXXSXXNX(K/H)H (SEQ ID NO:191) or KIGSLDNITH (SEQ ID NO:194) comprising immunizing an animal with human tau or a fragment thereof to produce antibodies and screening for an antibody of the produced antibodies that specifically binds within the motif. In another aspect, the invention provides methods of producing an antibody that specifically binds to a peptide consisting of residues KXXSXXNX(K/H)H (SEQ ID NO:191) or KIGSLDNITH (SEQ ID NO:194) comprising immunizing an animal with human tau or a fragment thereof to produce antibodies and screening for an antibody of the produced antibodies that specifically binds to the peptide. In another aspect, the invention provides methods of producing an antibody that specifically binds to an epitope comprising KXXSXXNX(K/H)H (SEQ ID NO:191) comprising immunizing an animal with tau or a fragment thereof, and screening for antibodies that specifically bind to the epitope.

In some methods, the animal is immunized with 383 amino acid human tau (4R0N). In some methods, the human tau contains a P301S mutation. In some methods, the human tau is recombinant N-terminally His-tagged.

In some methods, the screening determines specific binding between the antibodies and one or more peptides of up to 15 amino acids comprising KIGSTENLKH (SEQ ID NO:188), KCGSKDNIKH (SEQ ID NO:192), KCGSLGNIHH (SEQ ID NO:193) respectively or any other consensus motif represented by KXXSXXNX(K/H)H (SEQ ID NO:191). In some methods, the one or more peptides comprise KIGSTENLKH (SEQ ID NO:188) or KCGSKDNIKH (SEQ ID NO:192) or KCGSLGNIHH (SEQ ID NO:193) respectively. In some methods, the animal is immunized with a tau fragment of up to 15 amino acids comprising KXXSXXNX(K/H)H (SEQ ID NO:191), linked to a carrier. In some methods, the peptide is KIGSTENLKH (SEQ ID NO:188) or KCGSKDNIKH (SEQ ID NO:192) or KCGSLGNIHH (SEQ ID NO: 193).

BRIEF DESCRIPTION OF THE DRAWINGS

FIG. 2 depicts an alignment of heavy chain variable regions of the mouse 3D6 antibody (SEQ ID NO:7) and humanized versions of the 3D6 antibody (hu3D6VHvb1, hu3D6VHvb2, hu3D6VHvb3, hu3D6VHvb4, hu3D6VHvb5, hu3D6VHvb6, and hu3D6VHvb7) with human germline heavy chain variable region sequence IGHV1-69-2*01 (SEQ ID NO:25) and with human acceptor heavy chain variable region sequence 2RCS VH hFrwk (SEQ ID NO:75). hu3D6VHvb1 is SEQ ID NO:76, hu3D6VHvb2 is SEQ ID NO:77, hu3D6VHvb3 is SEQ ID NO:78, hu3D6VHvb4 is SEQ ID NO:79, hu3D6VHvb5 is SEQ ID NO:80, hu3D6VHvb6 is SEQ ID NO:90, and hu3D6VHvb7 is SEQ ID NO:91. The CDRs as defined by Kabat/Chothia Composite are in boldface.

FIG. 3 depicts an alignment of light chain variable regions of the mouse 3D6 antibody (SEQ ID NO:11) and humanized versions of the 3D6 antibody (hu3D6VLvb1, hu3D6VLvb2, and hu3D6VLvb3) with human germline light chain variable region sequence IGKV2-30*02 (SEQ ID NO:27) and with human acceptor ARX71335_VL_hFrwk (SEQ ID NO:82). hu3D6VLvb1 is SEQ ID NO:83, hu3D6VLvb2 is SEQ ID NO:84, and hu3D6VLvb3 is SEQ ID NO:85. The CDRs as defined by Kabat are in boldface.

FIGS. 9A and 9B show alignments of the heavy chain variable region of murine 3D6 (SEQ ID NO:7) and of humanized versions of the 3D6 antibody (hu3D6VHvb1, hu3D6VHvb2, hu3D6VHvb3, hu3D6VHvb4, hu3D6VHvb5, hu3D6VHvb6, hu3D6VHvb7, hu3D6VHv1bA11, h3D6VHvb8, and h3D6VHvb9) with human germline heavy chain variable region sequence IGHV1-69-2*01 (SEQ ID NO:25) and with human acceptor heavy chain variable region sequence 2RCS VH hFrwk (SEQ ID NO:75). hu3D6VHvb1 is SEQ ID NO:76, hu3D6VHvb2 is SEQ ID NO:77, hu3D6VHvb3 is SEQ ID NO:78, hu3D6VHvb4 is SEQ ID NO:79, hu3D6VHvb5 is SEQ ID NO:80, hu3D6VHvb6 is SEQ ID NO:90, hu3D6VHvb7 is SEQ ID NO:91, hu3D6VHv1bA11 is SEQ ID NO:18, h3D6VHvb8 is SEQ ID NO:146, and h3D6VHvb9 is SEQ ID NO:148. Residues identical to those of the heavy chain variable region of murine 3D6 (SEQ ID NO:7) are noted with a "." The CDRs as defined by Kabat/Chothia Composite are in boldface.

FIGS. 10A, 10B, 10C, and 10D show alignments of the light chain variable region of humanized versions of the 3D6 antibody: hu3D6VLv2 (SEQ ID NO:21), hu3D6VLv2 L37Q (SEQ ID NO:143), hu3D6VLv2 L50G (SEQ ID NO:103), hu3D6VLv2 S52G (SEQ ID NO:110), hu3D6VLv2 L54G (SEQ ID NO:94), hu3D6VLv2 L54D (SEQ ID NO:93), hu3D6VLv2 L54K (SEQ ID NO:100), hu3D6VLv2 L54R (SEQ ID NO:101), hu3D6VLv2 L54T (SEQ ID NO:102), hu3D6VLv2 L37Q_L50G (SEQ ID NO:128), hu3D6VLv2 L37Q_L50D (SEQ ID NO:129), hu3D6VLv2 L37Q_S52G (SEQ ID NO:131), hu3D6VLv2 L37Q_L54G (SEQ ID NO:126), hu3D6VLv2 L37Q_L54R (SEQ ID NO:125), hu3D6VLv2 L37Q_L54T (SEQ ID NO:130), hu3D6VLv2 L37Q_L54D (SEQ ID NO:127), hu3D6VLv2 L37Q_L54E (SEQ ID NO:145), hu3D6VLv2 L37Q_L50G_L54R (SEQ ID NO:119), hu3D6VLv2 L37Q_L50G_L54G (SEQ ID NO:120), hu3D6VLv2 L37Q_L50D_L54R (SEQ ID NO:133), hu3D6VLv2 L37Q_L50D_L54G (SEQ ID NO:132), hu3D6VLv2 L37Q_S52G_L54D (SEQ ID NO:124), hu3D6VLv2 L37Q_S52G_L54G (SEQ ID NO:121), hu3D6VLv2 L37Q_S52G_L54T (SEQ ID NO:123), hu3D6VLv2 L37Q_S52G_L54R (SEQ ID NO:122), hu3D6VLv2 L37Q_L50D_L54G_G100Q (SEQ ID NO:140), hu3D6VLv2 L37Q_L50D_L54R_G100Q (SEQ ID NO:141), hu3D6VLv2 L37Q_L50G_L54G_G100Q (SEQ ID NO:137), hu3D6VLv2 L37Q_L50G_L54R_G100Q (SEQ ID NO:136), hu3D6VLv2 L37Q_L50V_L54D_G100Q (SEQ ID NO:142), hu3D6VLv2 L37Q_S52G_L54D_G100Q (SEQ ID NO:139), and hu3D6VLv2 L37Q_S52G_L54R_G100Q (SEQ ID NO:138). Residues identical to those of the light chain variable region of hu3D6VLv2 (SEQ ID NO:21) are noted with a "." The CDRs as defined by Kabat are in boldface.

FIG. 12A shows a plot of substitution effect, and FIG. 12B shows an alignment of portions of the tau microtubule binding repeats with important residues for binding 3D6 highlighted. aa 255-271 are SEQ ID NO:184, aa 286-302 are SEQ ID NO:185, aa 317-333 are SEQ ID NO:186, and aa 349-365 are SEQ ID NO:187.

BRIEF DESCRIPTION OF THE SEQUENCES

Figure 1:
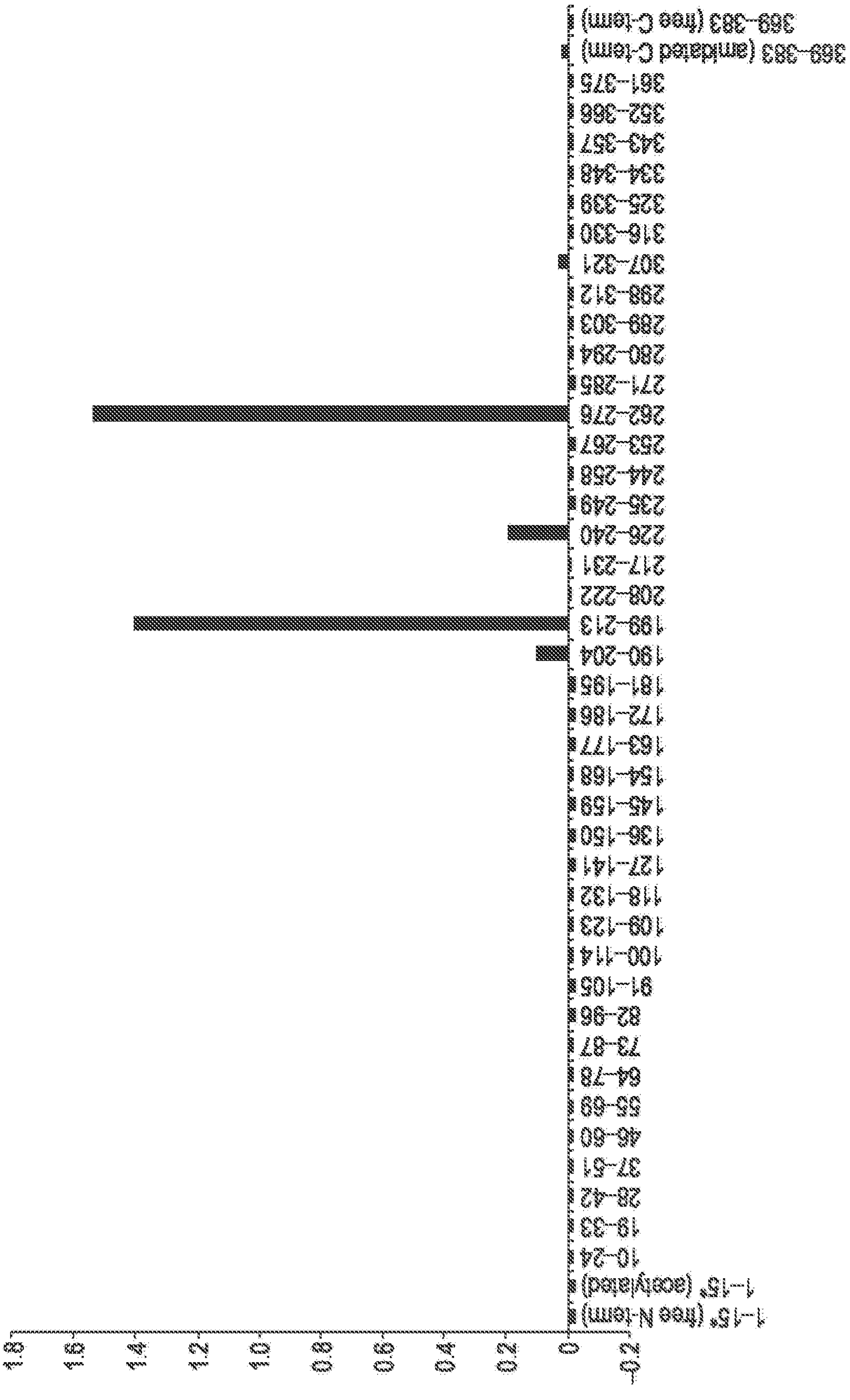
FIG. 1 depicts the results of experiments designed to map the epitope(s) bound by the murine 3D6 monoclonal antibody.

SEQ ID NO:1 sets forth the amino acid sequence of an isoform of human tau (Swiss-Prot P10636-8).

SEQ ID NO:2 sets forth the amino acid sequence of an isoform of human tau (Swiss-Prot P10636-7).

SEQ ID NO:3 sets forth the amino acid sequence of an isoform of human tau (Swiss-Prot P10636-6), (4R0N human tau).

SEQ ID NO:4 sets forth the amino acid sequence of an isoform of human tau (Swiss-Prot P10636-5)

SEQ ID NO:5 sets forth the amino acid sequence of an isoform of human tau (Swiss-Prot P10636-4).

SEQ ID NO:6 sets forth the amino acid sequence of an isoform of human tau (Swiss-Prot P10636-2).

SEQ ID NO:7 sets forth the amino acid sequence of the heavy chain variable region of the mouse 3D6 antibody.

SEQ ID NO:8 sets forth the amino acid sequence of Kabat/Chothia composite CDR-H1 of the mouse 3D6 antibody.

SEQ ID NO:9 sets forth the amino acid sequence of Kabat CDR-H2 of the mouse 3D6 antibody.

SEQ ID NO:10 sets forth the amino acid sequence of Kabat CDR-H3 of the mouse 3D6 antibody.

SEQ ID NO:11 sets forth the amino acid sequence of the light chain variable region of the mouse 3D6 antibody and of the mouse 6A10 antibody.

SEQ ID NO:12 sets forth the amino acid sequence of Kabat CDR-L1 of the mouse 3D6 antibody and of the mouse 6A10 antibody.

SEQ ID NO:13 sets forth the amino acid sequence of Kabat CDR-L2 of the mouse 3D6 antibody and of the mouse 6A10 antibody.

SEQ ID NO:14 sets forth the amino acid sequence of Kabat CDR-L3 of the mouse 3D6 antibody and of the mouse 6A10 antibody.

SEQ ID NO:15 sets forth the amino acid sequence of heavy chain variable region of the humanized 3D6 antibody hu3D6VHv1.

SEQ ID NO:16 sets forth the amino acid sequence of heavy chain variable region of the humanized 3D6 antibody hu3D6VHv2.

SEQ ID NO:17 sets forth the amino acid sequence of heavy chain variable region of the humanized 3D6 antibody hu3D6VHv1b.

SEQ ID NO:18 sets forth the amino acid sequence of heavy chain variable region of the humanized 3D6 antibody hu3D6VHv1bA11.

SEQ ID NO:19 sets forth the amino acid sequence of heavy chain variable region of the humanized 3D6 antibody hu3D6VHv5:

SEQ ID NO:20 sets forth the amino acid sequence of the light chain variable region of the humanized 3D6 antibody hu3D6VLv1.

SEQ ID NO:21 sets forth the amino acid sequence of the light chain variable region of the humanized 3D6 antibody hu3D6VLv2.

SEQ ID NO:22 sets forth the amino acid sequence of the light chain variable region of the humanized 3D6 antibody hu3D6VLv3.

SEQ ID NO:23 sets forth the amino acid sequence of the light chain variable region of the humanized 3D6 antibody hu3D6VLv4.

SEQ ID NO:24 sets forth the amino acid sequence of the heavy chain variable acceptor Acc. #BAC01986.1.

SEQ ID NO:25 sets forth the amino acid sequence of the heavy chain variable acceptor Acc. #IMGT #IGHV1-69-2*01.

SEQ ID NO:26 sets forth the amino acid sequence of the heavy chain variable acceptor Acc. #IMGT #IGKJ1*01.

SEQ ID NO:27 sets forth the amino acid sequence of the light chain variable acceptor Acc. #IMGT #IGKV2-30*02

SEQ ID NO:28 sets forth the amino acid sequence of the light chain variable acceptor Acc. #IMGT #IGKJ2*01.

SEQ ID NO:29 sets forth the amino acid sequence of the light chain variable acceptor Acc. #AAZ09048.1.

SEQ ID NO:30 sets forth a nucleic acid sequence encoding the heavy chain variable region of the mouse 3D6 antibody.

SEQ ID NO:31 sets forth a nucleic acid sequence encoding the light chain variable region of the mouse 3D6 antibody.

SEQ ID NO:32 sets forth the amino acid sequence of Kabat CDR-H1 of the mouse 3D6 antibody.

SEQ ID NO:33 sets forth the amino acid sequence of Chothia CDR-H1 of the mouse 3D6 antibody.

SEQ ID NO:34 sets forth the amino acid sequence of Chothia CDR-H2 of the mouse 3D6 antibody.

SEQ ID NO:35 sets forth the amino acid sequence of AbM CDR-H2 of the mouse 3D6 antibody.

SEQ ID NO:36 sets forth the amino acid sequence of Contact CDR-L1 of the mouse 3D6 antibody.

SEQ ID NO:37 sets forth the amino acid sequence of Contact CDR-L2 of the mouse 3D6 antibody.

SEQ ID NO:38 sets forth the amino acid sequence of Contact CDR-L3 of the mouse 3D6 antibody.

SEQ ID NO:39 sets forth the amino acid sequence of Contact CDR-H1 of the mouse 3D6 antibody.

SEQ ID NO:40 sets forth the amino acid sequence of Contact CDR-H2 of the mouse 3D6 antibody.

SEQ ID NO:41 sets forth the amino acid sequence of Contact CDR-H3 of the mouse 3D6 antibody.

SEQ ID NO:42 sets forth the amino acid sequence of an alternate Kabat-Chothia Composite CDR-H1 of a humanized 3D6 antibody (as in hu3D6VHv5, hu3D6VHv1bA11B6G2, hu3D6VHv1bA11B6H3, hu3D6VHv1e, and hu3D6VHv1f).

SEQ ID NO:43 sets forth the amino acid sequence of an alternate Kabat CDR-H2 of a humanized 3D6 antibody (as in hu3D6VHv5 and hu3D6VHv1bA11B6H3).

SEQ ID NO:44 sets forth the consensus amino acid sequence among the heavy chain variable regions of the mouse 3D6 and selected humanized 3D6 antibodies (VHv1, VHv2, VHv1b, VHv1bA11, and VHv5) (labeled "Majority' in FIG. 2 of PCT/IB2017/052544.

SEQ ID NO:45 sets forth the consensus amino acid sequence between the light chain variable regions of the mouse 3D6 and selected humanized 3D6 antibodies (labeled "Majority' in FIG. 3 of PCT/IB2017/052544).

SEQ ID NO:46 sets forth the amino acid sequence of heavy chain variable region of the humanized 3D6 antibody hu3D6VHv1bA11B6G2.

SEQ ID NO:47 sets forth the amino acid sequence of heavy chain variable region of the humanized 3D6 antibody hu3D6VHv1bA11B6H3.

SEQ ID NO:48 sets forth the amino acid sequence of heavy chain variable region of the humanized 3D6 antibody hu3D6VHv1c.

SEQ ID NO:49 sets forth the amino acid sequence of heavy chain variable region of the humanized 3D6 antibody hu3D6VHv1d.

SEQ ID NO:50 sets forth the amino acid sequence of heavy chain variable region of the humanized 3D6 antibody hu3D6VHv1e.

SEQ ID NO:51 sets forth the amino acid sequence of heavy chain variable region of the humanized 3D6 antibody hu3D6VHv1f.

SEQ ID NO:52 sets forth the amino acid sequence of heavy chain variable region of the humanized 3D6 antibody hu3D6VHv3.

SEQ ID NO:53 sets forth the amino acid sequence of heavy chain variable region of the humanized 3D6 antibody hu3D6VHv3b.

SEQ ID NO:54 sets forth the amino acid sequence of heavy chain variable region of the humanized 3D6 antibody hu3D6VHv3c.

SEQ ID NO:55 sets forth the amino acid sequence of heavy chain variable region of the humanized 3D6 antibody hu3D6VHv4.

SEQ ID NO:56 sets forth the amino acid sequence of heavy chain variable region of the humanized 3D6 antibody hu3D6VHv4b.

SEQ ID NO:57 sets forth the amino acid sequence of heavy chain variable region of the humanized 3D6 antibody hu3D6VHv4c.

SEQ ID NO:58 sets forth the amino acid sequence of an alternate Kabat-Chothia Composite CDR-H1 of a humanized 3D6 antibody (as in hu3D6VH1c).

SEQ ID NO:59 sets forth the amino acid sequence of an alternate Kabat-Chothia Composite CDR-H1 of a humanized 3D6 antibody (as in hu3D6VHv1d, hu3D6VHv3c, and hu3D6VHv4c).

SEQ ID NO:60 sets forth the amino acid sequence of an alternate Kabat-Chothia Composite CDR-H1 of a humanized 3D6 antibody (as in hu3D6VHv3b and hu3D6VHv4b).

SEQ ID NO:61 sets forth the amino acid sequence of an alternate Kabat CDR-H2 of a humanized 3D6 antibody (as in hu3D6VHv1bA11B6G2).

SEQ ID NO:62 sets forth the amino acid sequence of an alternate Kabat CDR-H2 of a humanized 3D6 antibody (as in hu3D6VHv1c, hu3D6VHv3b, AND hu3D6VHv4b.

SEQ ID NO:63 sets forth the amino acid sequence of an alternate Kabat CDR-H2 of a humanized 3D6 antibody (as in hu3D6VHv1d, hu3D6VHv1f, hu3D6VHv3c, and hu3D6VHv4c).

SEQ ID NO:64 sets forth the amino acid sequence of an alternate Kabat CDR-H2 of a humanized 3D6 antibody (as in hu3D6VHv1e).

SEQ ID NO:65 sets forth the amino acid sequence of an alternate Kabat CDR-H3 of a humanized 3D6 antibody (as in hu3D6VHv1f).

SEQ ID NO:66 sets forth the amino acid sequence of the heavy chain variable region of the mouse 6A10 antibody.

SEQ ID NO:67 sets forth the amino acid sequence of Kabat/Chothia composite CDR-H1 of the mouse 6A10 antibody.

SEQ ID NO:68 sets forth the amino acid sequence of Kabat CDR-H2 of the mouse 6A10 antibody.

SEQ ID NO:69 sets forth the amino acid sequence of Kabat CDR-H3 of the mouse 6A10 antibody.

SEQ ID NO:70 sets for the amino acid sequence of the VH region of mouse antibody (pdb code 1CR9) used as a structure template for heavy chain humanization.

Figure 4A:
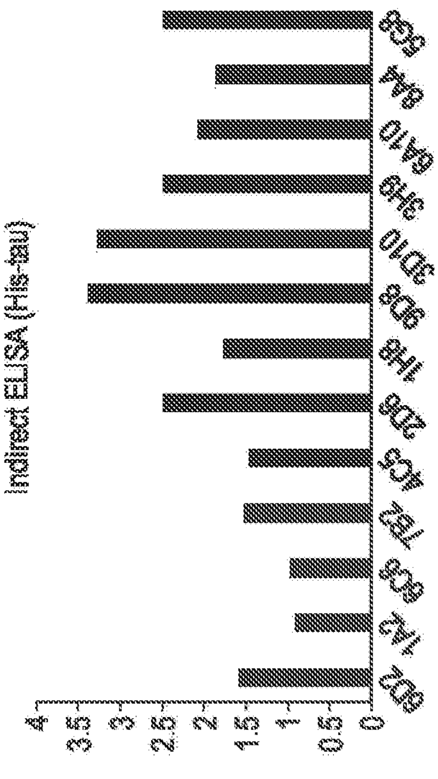
FIGS. 4A, 4B, and 4C depict results of ELISA screening assays for selected mouse monoclonal anti-tau antibodies.
Figure 4B:
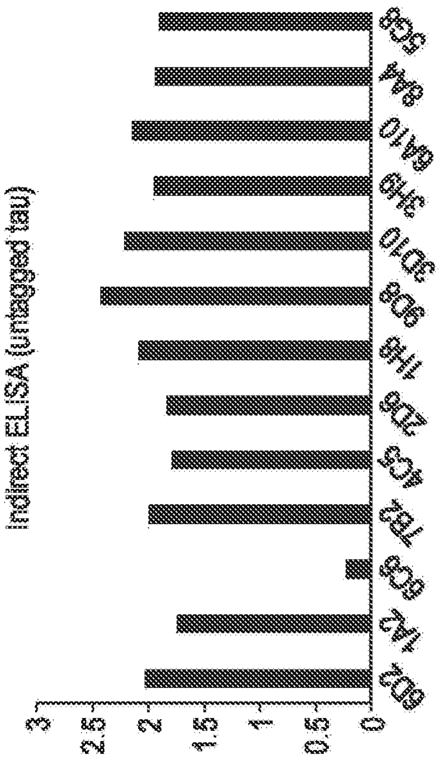

SEQ ID NO:71 sets forth the consensus amino acid sequence among the heavy chain variable regions of the selected humanized 3D6 antibodies (VHv1, VHv1b, VHv1bA11, VHv1bA11B6G2, VHv1bA11B6H3, VHv1c, VHv1d, VHv1e, VHv1f, VHv2, VHv3, VHv3b, VHv3c, VHv4, VHv4b, VHv4c, and VHv5) (labeled "Majority' in FIGS. 4A and 4B of PCT/IB2017/052544).

SEQ ID NO:72 sets forth the amino acid sequence of the heavy chain of a chimeric 3D6 antibody.

SEQ ID NO:73 sets forth the amino acid sequence of the light chain of a chimeric 3D6 antibody.

SEQ ID NO:74 sets forth the amino acid sequence of heavy chain variable structural model Acc. #5MYX-VH_mSt.

SEQ ID NO:75 sets forth the amino acid sequence of heavy chain variable acceptor Acc. #2RCS-VH_huFrwk.

SEQ ID NO:76 sets forth the amino acid sequence of heavy chain variable region of the humanized 3D6 antibody hu3D6VHvb1.

SEQ ID NO:77 sets forth the amino acid sequence of heavy chain variable region of the humanized 3D6 antibody hu3D6VHvb2.

SEQ ID NO:78 sets forth the amino acid sequence of heavy chain variable region of the humanized 3D6 antibody hu3D6VHvb3.

SEQ ID NO:79 sets forth the amino acid sequence of heavy chain variable region of the humanized 3D6 antibody hu3D6VHvb4.

SEQ ID NO:80 sets forth the amino acid sequence of heavy chain variable region of the humanized 3D6 antibody hu3D6VHvb5.

SEQ ID NO:81 sets forth the amino acid sequence of light chain variable structural model Acc. #5MYX-VL_mSt.

SEQ ID NO:82 sets forth the amino acid sequence of light chain variable acceptor Acc. #ARX71335-VL_huFrwk.

SEQ ID NO:83 sets forth the amino acid sequence of light chain variable region of the humanized 3D6 antibody hu3D6VLvb1.

SEQ ID NO:84 sets forth the amino acid sequence of light chain variable region of the humanized 3D6 antibody hu3D6VLvb2.

SEQ ID NO:85 sets forth the amino acid sequence of light chain variable region of the humanized 3D6 antibody hu3D6VLvb3.

SEQ ID NO:86 sets forth the amino acid sequence of an alternate Kabat-Chothia Composite CDR-H1 of a humanized 3D6 antibody (as in hu3D6VHvb4 and hu3D6VHvb5).

SEQ ID NO:87 sets forth the amino acid sequence of an alternate Kabat CDR-H2 of a humanized 3D6 antibody (as in hu3D6VHvb3 and hu3D6VHvb4).

SEQ ID NO:88 sets forth the amino acid sequence of an alternate Kabat CDR-H2 of a humanized 3D6 antibody (as in hu3D6VHvb5).

SEQ ID NO:89 sets forth the amino acid sequence of an alternate Kabat CDR-L1 of a humanized 3D6 antibody (as in hu3D6VLvb3).

SEQ ID NO:90 sets forth the amino acid sequence of heavy chain variable region of the humanized 3D6 antibody hu3D6VHvb6.

SEQ ID NO:91 sets forth the amino acid sequence of heavy chain variable region of the humanized 3D6 antibody hu3D6VHvb7.

SEQ ID NO:92 sets forth the amino acid sequence of an alternate Kabat CDR-H2 of a humanized 3D6 antibody (as in hu3D6VHvb6 and hu3D6VHvb7).

SEQ ID NO:93 sets forth the amino acid sequence of light chain variable region of a hu3D6VLv2 variant L54D.

SEQ ID NO:94 sets forth the amino acid sequence of light chain variable region of a hu3D6VLv2 variant L54G.

SEQ ID NO:95 sets forth the amino acid sequence of light chain variable region of a hu3D6VLv2 variant L45N.

SEQ ID NO:96 sets forth the amino acid sequence of light chain variable region of a hu3D6VLv2 variant L54E.

SEQ ID NO:97 sets forth the amino acid sequence of light chain variable region of a hu3D6VLv2 variant L50E.

SEQ ID NO:98 sets forth the amino acid sequence of light chain variable region of a hu3D6VLv2 variant L54Q.

SEQ ID NO:99 sets forth the amino acid sequence of light chain variable region of a hu3D6VLv2 variant L50D.

SEQ ID NO:100 sets forth the amino acid sequence of light chain variable region of a hu3D6VLv2 variant L54K.

SEQ ID NO:101 sets forth the amino acid sequence of light chain variable region of a hu3D6VLv2 variant L54R.

SEQ ID NO:102 sets forth the amino acid sequence of light chain variable region of a hu3D6VLv2 variant L54T.

SEQ ID NO:103 sets forth the amino acid sequence of light chain variable region of a hu3D6VLv2 variant L50G.

SEQ ID NO:104 sets forth the amino acid sequence of light chain variable region of a hu3D6VLv2 variant I48G.

SEQ ID NO:105 sets forth the amino acid sequence of light chain variable region of a hu3D6VLv2 variant I48D.

SEQ ID NO:106 sets forth the amino acid sequence of light chain variable region of a hu3D6VLv2 variant L47G.

SEQ ID NO:107 sets forth the amino acid sequence of light chain variable region of a hu3D6VLv2 variant Y49E.

SEQ ID NO:108 sets forth the amino acid sequence of light chain variable region of a hu3D6VLv2 variant L54V.

SEQ ID NO:109 sets forth the amino acid sequence of light chain variable region of a hu3D6VLv2 variant L54S.

SEQ ID NO:110 sets forth the amino acid sequence of light chain variable region of a hu3D6VLv2 variant S52G.

SEQ ID NO:111 sets forth the amino acid sequence of light chain variable region of a hu3D6VLv2 variant L47N.

SEQ ID NO:112 sets forth the amino acid sequence of light chain variable region of a hu3D6VLv2 variant L47D.

SEQ ID NO:113 sets forth the amino acid sequence of light chain variable region of a hu3D6VLv2 variant L47E.

SEQ ID NO:114 sets forth the amino acid sequence of light chain variable region of a hu3D6VLv2 variant L47P.

SEQ ID NO:115 sets forth the amino acid sequence of light chain variable region of a hu3D6VLv2 variant L47T.

SEQ ID NO:116 sets forth the amino acid sequence of light chain variable region of a hu3D6VLv2 variant L47S.

SEQ ID NO:117 sets forth the amino acid sequence of light chain variable region of a hu3D6VLv2 variant L47A.

SEQ ID NO:118 sets forth the amino acid sequence of light chain variable region of a hu3D6VLv2 variant L50V.

SEQ ID NO: 119 sets forth the amino acid sequence of light chain variable region of a hu3D6VLv2 variant L37Q_L50G_L54R.

SEQ ID NO:120 sets forth the amino acid sequence of light chain variable region of a hu3D6VLv2 variant L37Q_L50G_L54G.

SEQ ID NO: 121 sets forth the amino acid sequence of light chain variable region of a hu3D6VLv2 variant L37Q_S52G_L54G.

SEQ ID NO:122 sets forth the amino acid sequence of light chain variable region of a hu3D6VLv2 variant L37Q_S52G_L54R.

SEQ ID NO: 123 sets forth the amino acid sequence of light chain variable region of a hu3D6VLv2 variant L37Q_S52G_L54T.

SEQ ID NO:124 sets forth the amino acid sequence of light chain variable region of a hu3D6VLv2 variant L37Q_S52G_L54D.

SEQ ID NO:125 sets forth the amino acid sequence of light chain variable region of a hu3D6VLv2 variant L37Q_L54R.

SEQ ID NO:126 sets forth the amino acid sequence of light chain variable region of a hu3D6VLv2 variant L37_L54G.

SEQ ID NO: 127 sets forth the amino acid sequence of light chain variable region of a hu3D6VLv2 variant L37Q_L54D.

SEQ ID NO: 128 sets forth the amino acid sequence of light chain variable region of a hu3D6VLv2 variant L37Q_L50G.

SEQ ID NO:129 sets forth the amino acid sequence of light chain variable region of a hu3D6VLv2 variant L37Q_L50D.

SEQ ID NO: 130 sets forth the amino acid sequence of light chain variable region of a hu3D6VLv2 variant L37Q_L54T.

SEQ ID NO:131 sets forth the amino acid sequence of light chain variable region of a hu3D6VLv2 variant L37Q_S52G.

SEQ ID NO:132 sets forth the amino acid sequence of light chain variable region of a hu3D6VLv2 variant L37Q_L50D_L54G.

SEQ ID NO:133 sets forth the amino acid sequence of light chain variable region of a hu3D6VLv2 variant L37Q_L50D_L54R.

SEQ ID NO:134 sets forth the amino acid sequence of light chain variable region of a hu3D6VLv2 variant L37Q_L50E_L54G.

SEQ ID NO: 135 sets forth the amino acid sequence of light chain variable region of a hu3D6VLv2 variant L37Q_L50E_L54R.

SEQ ID NO:136 sets forth the amino acid sequence of light chain variable region of a hu3D6VLv2 variant L37Q_L50G_L54R_G100Q.

SEQ ID NO:137 sets forth the amino acid sequence of light chain variable region of a hu3D6VLv2 variant L37Q_L50G_L54G_G100Q.

SEQ ID NO:138 sets forth the amino acid sequence of light chain variable region of a hu3D6VLv2 variant L37Q_S52G_L54R_G100Q.

SEQ ID NO: 139 sets forth the amino acid sequence of light chain variable region of a hu3D6VLv2 variant L37Q_S52G_L54D_G100Q.

SEQ ID NO: 140 sets forth the amino acid sequence of light chain variable region of a Hu3D6VLv2 variant L37Q_L50D_L54G_G100Q.

SEQ ID NO:141 sets forth the amino acid sequence of light chain variable region of a Hu3D6VLv2 variant L37Q_L50D_L54R_G100Q.

SEQ ID NO: 142 sets forth the amino acid sequence of light chain variable region of a Hu3D6VLv2 variant L37Q_L50V_L54D_G100Q.

SEQ ID NO: 143 sets forth the amino acid sequence of light chain variable region of a Hu3D6VLv2 variant L37Q.

SEQ ID NO:144 sets forth the amino acid sequence of light chain variable region of a Hu3D6VLv2 variant G100Q.

SEQ ID NO:145 sets forth the amino acid sequence of light chain variable region of a Hu3D6VLv2 variant L37Q_L54E.

SEQ ID NO:146 sets forth the amino acid sequence of heavy chain variable region of a hu3D6VHv1bA11 variant D60E, also known as h3D6VHvb8.

SEQ ID NO: 147 sets forth the amino acid sequence of heavy chain variable region of a hu3D6VHv1bA11 variant L82cV.

SEQ ID NO: 148 sets forth the amino acid sequence of heavy chain variable region of a hu3D6VHv1bA11 variant D60E_L80M_Q81E_L82cV_T83R, also known as h3D6VHvb9.

SEQ ID NO:149 sets forth the amino acid sequence of an alternate Kabat CDR-H2 of a humanized 3D6 antibody (as in h3D6VHvb8 and in h3D6VHvb9).

SEQ ID NO:150 sets forth the amino acid sequence of an alternate Kabat CDR-L2 of a humanized 3D6 antibody (as in hu3D6VLv2 L54D and in hu3D6VLv2 L37Q_L54D).

SEQ ID NO:151 sets forth the amino acid sequence of an alternate Kabat CDR-L2 of a humanized 3D6 antibody (as in hu3D6VLv2 L54G and in hu3D6VLv2 L37Q_L54G).

SEQ ID NO:152 sets forth the amino acid sequence of an alternate Kabat CDR-L2 of a humanized 3D6 antibody (as in hu3D6VLv2 L54N).

SEQ ID NO:153 sets forth the amino acid sequence of an alternate Kabat CDR-L2 of a humanized 3D6 antibody (as in hu3D6VLv2 L54E and in hu3D6VLv2 L37Q_L54E).

SEQ ID NO:154 sets forth the amino acid sequence of an alternate Kabat CDR-L2 of a humanized 3D6 antibody (as in hu3D6VLv2 L50E).

SEQ ID NO:155 sets forth the amino acid sequence of an alternate Kabat CDR-L2 of a humanized 3D6 antibody (as in hu3D6VLv2 L54Q).

SEQ ID NO:156 sets forth the amino acid sequence of an alternate Kabat CDR-L2 of a humanized 3D6 antibody (as in hu3D6VLv2 L50D and in hu3D6VLv2 L37Q_L50D).

SEQ ID NO:157 sets forth the amino acid sequence of an alternate Kabat CDR-L2 of a humanized 3D6 antibody (as in hu3D6VLv2 L54K).

SEQ ID NO:158 sets forth the amino acid sequence of an alternate Kabat CDR-L2 of a humanized 3D6 antibody (as in hu3D6VLv2 L54R and in hu3D6VLv2 L37Q_L54R).

SEQ ID NO:159 sets forth the amino acid sequence of an alternate Kabat CDR-L2 of a humanized 3D6 antibody (as in hu3D6VLv2 L54T and in hu3D6VLv2 L37Q_L54T).

SEQ ID NO:160 sets forth the amino acid sequence of an alternate Kabat CDR-L2 of a humanized 3D6 antibody (as in hu3D6VLv2 L50G and in hu3D6VLv2 L37Q_L50G).

SEQ ID NO:161 sets forth the amino acid sequence of an alternate Kabat CDR-L2 of a humanized 3D6 antibody (as in hu3D6VLv2 L54V).

SEQ ID NO:162 sets forth the amino acid sequence of an alternate Kabat CDR-L2 of a humanized 3D6 antibody (as in hu3D6VLv2 L54S).

SEQ ID NO:163 sets forth the amino acid sequence of an alternate Kabat CDR-L2 of a humanized 3D6 antibody (as in hu3D6VLv2 S52G and in hu3D6VLv2 L37Q_S52G).

SEQ ID NO:164 sets forth the amino acid sequence of an alternate Kabat CDR-L2 of a humanized 3D6 antibody (as in hu3D6VLv2 L50V).

SEQ ID NO:165 sets forth the amino acid sequence of an alternate Kabat CDR-L2 of a humanized 3D6 antibody (as in hu3D6VLv2 L37Q_L50G_L54R and hu3D6VLv2 L37Q_L50G_L54R_G100Q).

SEQ ID NO:166 sets forth the amino acid sequence of an alternate Kabat CDR-L2 of a humanized 3D6 antibody (as in hu3D6VLv2 L37Q_L50G_L54G and in and in hu3D6VLv2 L37Q_L50G_L54G_G100Q).

SEQ ID NO:167 sets forth the amino acid sequence of an alternate Kabat CDR-L2 of a humanized 3D6 antibody (as in hu3D6VLv2 L37Q_S52G_L54G).

SEQ ID NO:168 sets forth the amino acid sequence of an alternate Kabat CDR-L2 of a humanized 3D6 antibody (as in hu3D6VLv2 L37Q_S52G_L54R and in and in hu3D6VLv2 L37Q_S52G_L54R_G100Q).

SEQ ID NO:169 sets forth the amino acid sequence of an alternate Kabat CDR-L2 of a humanized 3D6 antibody (as in hu3D6VLv2 L37Q_S52G_L54T).

SEQ ID NO:170 sets forth the amino acid sequence of an alternate Kabat CDR-L2 of a humanized 3D6 antibody (as in hu3D6VLv2 L37Q_S52G_L54D and in hu3D6VLv2 L37Q_S52G_L54D_G100Q).

SEQ ID NO:171 sets forth the amino acid sequence of an alternate Kabat CDR-L2 of a humanized 3D6 antibody (as in hu3D6VLv2 L37Q_L50D_L54G and in hu3D6VLv2 L37Q_L50D_L54G_G100Q).

SEQ ID NO:172 sets forth the amino acid sequence of an alternate Kabat CDR-L2 of a humanized 3D6 antibody (as in hu3D6VLv2 L37Q_L50D_L54R and in hu3D6VLv2 L37Q_L50D_L54R_G100Q).

SEQ ID NO:173 sets forth the amino acid sequence of an alternate Kabat CDR-L2 of a humanized 3D6 antibody (as in hu3D6VLv2 L37Q_L50E_L54G).

SEQ ID NO:174 sets forth the amino acid sequence of an alternate Kabat CDR-L2 of a humanized 3D6 antibody (as in hu3D6VLv2 L37Q_L50E_L54R).

SEQ ID NO:175 sets forth the amino acid sequence of an alternate Kabat CDR-L2 of a humanized 3D6 antibody (as in hu3D6VLv2 L37Q_L50V_L54D_G100Q).

SEQ ID NO: 176 sets forth the amino acid sequence of a heavy chain constant region (IgG1: allotype G1m17,1).

SEQ ID NO: 177 sets forth the amino acid sequence of a light chain constant region (kappa).

SEQ ID NO:178 sets forth the amino acid sequence of a mature heavy chain of a 3D6 humanized variant (hu3D6VHv1bA11 IgG1 G1m17 allotype).

SEQ ID NO:179 sets forth the amino acid sequence of a mature light chain of a 3D6 humanized variant (hu3D6VLv2 variant L37Q_S52G_L54R, L2-DIM4 kappa).

SEQ ID NO:180 sets forth the amino acid sequence of a heavy chain of a 3D6 humanized variant (hu3D6VHv1bA11 IgG1 G1m17 allotype) with bovine alpha-lactalbumin signal peptide at the N-terminus.

SEQ ID NO:181 sets forth the amino acid sequence of a light chain of a 3D6 humanized variant (hu3D6VLv2 variant L37Q_S52G_L54R, L2-DIM4 kappa) with bovine alpha-lactalbumin signal peptide at the N-terminus.

SEQ ID NO:182 sets forth the nucleotide sequence encoding a heavy chain of a 3D6 humanized variant (hu3D6VHv1bA11 IgG1 G1m17 allotype) with bovine alpha-lactalbumin signal peptide at the N-terminus.

SEQ ID NO:183 sets forth the nucleotide sequence encoding a light chain of a 3D6 humanized variant (hu3D6VLv2 variant L37Q_S52G_L54R, L2-DIM4 kappa) with bovine alpha-lactalbumin signal peptide at the N-terminus.

SEQ ID NO:184 sets forth the amino acid sequence of a region of tau microtubule binding repeat 1 (amino acid residues 255-271 of SEQ ID NO:1).

SEQ ID NO: 185 sets forth the amino acid sequence of a region of tau microtubule binding repeat 2 (amino acid residues 286-302 of SEQ ID NO:1).

SEQ ID NO:186 sets forth the amino acid sequence of a region of tau microtubule binding repeat 3 (amino acid residues 317-333 of SEQ ID NO:1).

SEQ ID NO:187 sets forth the amino acid sequence of a region of tau microtubule binding repeat 4 (amino acid residues 349-365 of SEQ ID NO:1).

SEQ ID NO: 188 sets forth the amino acid sequence of a core motif of tau in MBTR 1 bound by 3D6.

SEQ ID NO: 189 sets forth the amino acid sequence of tau sequence N-terminal to core motif of tau in MBTR 1 bound by 3D6.

SEQ ID NO: 190 sets forth the amino acid sequence of tau sequence C-terminal to core motif of tau in MBTR 1 bound by 3D6.

SEQ ID NO: 191 sets forth the amino acid sequence of epitope of 3D6.

SEQ ID NO:192 sets forth the amino acid sequence of a core motif of tau in MBTR 2 bound by 3D6.

SEQ ID NO:193 sets forth the amino acid sequence of a core motif of tau in MBTR 3 bound by 3D6.

SEQ ID NO:194 sets forth the amino acid sequence of a core motif of tau in MBTR 4 bound by 3D6.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity and/or avidity of at least $10^6$, $10^7$, $10^8$, $10^9$, $10^{10}$, $10^{11}$, or $10^{12}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one “light” (about 25 kDa) and one “heavy” chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 . . . H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3. When the application discloses a VL sequence with R as the C-terminal residue, the R can alternatively be considered as being the N-terminal residue of the light chain constant region. Thus, the application should also be understood as disclosing the VL sequence without the C-terminal R.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, M D, 1987 and 1991), the Chothia definition (Chothia & Lesk, J. Mol. Biol. 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target including separate heavy chains, light chains Fab, Fab', F(ab')2, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.,* 79:315-321 (1990); Kostelny et al., *J. Immunol.,* 148:1547-53 (1992)). In some bispecific antibodies, the two different heavy/light chain pairs include a humanized 3D6 heavy chain/light chain pair and a heavy chain/light chain pair specific for a different epitope on tau than that bound by 3D6.

In some bispecific antibodies, one heavy chain/light chain pair is a humanized 3D6 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include tau-related disease-affected regions, or at least not known or suspect to include diseased regions of a given type. Control samples can be obtained from individuals not afflicted with the tau-related disease. Alternatively, control samples can be obtained from patients afflicted with the tau-related disease. Such samples can be obtained at the same time as a biological sample thought to comprise the tau-related disease or on a different occasion. A biological sample and a control sample can both be obtained from the same tissue. Preferably, control samples consist essentially or entirely of normal, healthy regions and can be used in comparison to a biological sample thought to comprise tau-related disease-affected regions. Preferably, the tissue in the control sample is the same type as the tissue in the biological sample. Preferably, the tau-related disease-affected cells thought to be in the biological sample arise from the same cell type (e.g., neurons or glia) as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

The term "positive response to treatment" refers to a more favorable response in an individual patient or average response in a population of patients relative to an average response in a control population not receiving treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class.

Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients. When the disclosure refers to a feature comprising specified elements, the disclosure should alternative be understood as referring to the feature consisting essentially of or consisting of the specified elements.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

Statistical significance means $p \leq 0.05$.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that bind to tau. Some antibodies specifically bind to an epitope or epitopes within the microtubule binding region (MTBR) region of human tau defined by approximately residues 244 to 372 of SEQ ID NO:1. Because the MTBR region contains sequence repeats, a single antibody can bind at multiple repeated sites within this region. Some antibodies specifically bind to an epitope of KXXSXXNX(K/H)H (SEQ ID NO:191). Some antibodies bind within residues 199-213 and/or 262-276 of SEQ ID NO:3 (corresponding to residues 257-271 or 320-334, respectively, of SEQ ID NO:1). Some antibodies bind within residues 259-268 and/or 290-299 and/or 321-330 and/or 353-362 of SEQ ID NO:1. In some antibodies, binding to the MTBR 4 region at residues 353-362 is weaker than binding to MTBRs 1, 2 and 3. Some antibodies bind to tau irrespective of phosphorylation state. Some antibodies of the invention serve to inhibit or delay tau-associated pathologies and associated symptomatic deterioration. Although an understanding of mechanism is not required for practice of the invention, a reduction in toxicity may occur as a result of the antibody inducing phagocytosis of tau, inhibiting tau from inter or intramolecular aggregation, or from binding to other molecules, by stabilizing a non-toxic conformation, by inhibiting intercellular or intracellular transmission of pathogenic tau forms, by blockade of tau phosphorylation, by preventing binding of tau to cells, or by inducing proteolytic cleavage of tau, among other mechanisms. The antibodies of the invention or agents that induce such antibodies can be used in methods of treating or effecting prophylaxis of Alzheimer's and other diseases associated with tau.

II. Target Molecules

Unless otherwise apparent from the context, reference to tau means a natural human form of tau including all isoforms irrespective of whether posttranslational modification (e.g., phosphorylation, glycation, or acetylation) is present. There are six major isoforms (splice variants) of tau occurring in the human brain. The longest of these variants has 441 amino acids, of which the initial met residue is cleaved. Residues are numbered according to the 441 isoform. Thus, for example, reference to a phosphorylation at position 404 means position 404 of the 441 isoform, or corresponding position of any other isoform when maximally aligned with the 441 isoform. The amino acid sequences of the isoforms and Swiss-Prot numbers are indicated below.

```
P10636-8
                                                      (SEQ ID NO: 1)
        10         20         30         40         50         60
MAEPRQEFEV MEDHAGTYGL GDRKDQGGYT MHQDQEGDTD AGLKESPLQT PTEDGSEEPG

        70         80         90        100        110        120
SETSDAKSTP TAEDVTAPLV DEGAPGKQAA AQPHTEIPEG TTAEEAGIGD TPSLEDEAAG

       130        140        150        160        170        180
HVTQARMVSK SKDGTGSDDK KAKGADGKTK IATPRGAAPP GQKGQANATR IPAKTPPAPK

       190        200        210        220        230        240
TPPSSGEPPK SGDRSGYSSP GSPGTPGSRS RTPSLPTPPT REPKKVAVVR TPPKSPSSAK

       250        260        270        280        290        300
SRLQTAPVPM PDLKNVKSKI GSTENLKHQP GGGKVQIINK KLDLSNVQSK CGSKDNIKHV

       310        320        330        340        350        360
PGGGSVQIVY KPVDLSKVTS KCGSLGNIHH KPGGGQVEVK SEKLDFKDRV QSKIGSLDNI

       370        380        390        400        410        420
THVPGGGNKK IETHKLTFRE NAKAKTDHGA EIVYKSPVVS GDTSPRHLSN VSSTGSIDMV
```

-continued

```
       430        440
DSPQLATLAD EVSASLAKQG L

P10636-7
                                                   (SEQ ID NO: 2)
        10         20         30         40         50         60
MAEPRQEFEV MEDHAGTYGL GDRKDQGGYT MHQDQEGDTD AGLKESPLQT PTEDGSEEPG

        70         80         90        100        110        120
SETSDAKSTP TAEAEEAGIG DTPSLEDEAA GHVTQARMVS KSKDGTGSDD KKAKGADGKT

       130        140        150        160        170        180
KIATPRGAAP PGQKGQANAT RIPAKTPPAP KTPPSSGEPP KSGDRSGYSS PGSPGTPGSR

       190        200        210        220        230        240
SRTPSLPTPP TREPKKVAVV RTPPKSPSSA KSRLQTAPVP MPDLKNVKSK IGSTENLKHQ

       250        260        270        280        290        300
PGGGKVQIIN KKLDLSNVQS KCGSKDNIKH VPGGGSVQIV YKPVDLSKVT SKCGSLGNIH

       310        320        330        340        350        360
HKPGGGQVEV KSEKLDFKDR VQSKIGSLDN ITHVPGGGNK KIETHKLTFR ENAKAKTDHG

       370        380        390        400        410
AEIVYKSPVV SGDTSPRHLS NVSSTGSIDM VDSPQLATLA DEVSASLAKQ GL

P10636-6 (4R0N human tau)
                                                   (SEQ ID NO: 3)
        10         20         30         40         50         60
MAEPRQEFEV MEDHAGTYGL GDRKDQGGYT MHQDQEGDTD AGLKAEEAGI GDTPSLEDEA

        70         80         90        100        110        120
AGHVTQARMV SKSKDGTGSD DKKAKGADGK TKIATPRGAA PPGQKGQANA TRIPAKTPPA

       130        140        150        160        170        180
PKTPPSSGEP PKSGDRSGYS SPGSPGTPGS RSRTPSLPTP PTREPKKVAV VRTPPKSPSS

       190        200        210        220        230        240
AKSRLQTAPV PMPDLKNVKS KIGSTENLKH QPGGGKVQII NKKLDLSNVQ SKCGSKDNIK

       250        260        270        280        290        300
HVPGGGSVQI VYKPVDLSKV TSKCGSLGNI HHKPGGGQVE VKSEKLDFKD RVQSKIGSLD

       310        320        330        340        350        360
NITHVPGGGN KKIETHKLTF RENAKAKTDH GAEIVYKSPV VSGDTSPRHL SNVSSTGSID

       370        380
MVDSPQLATL ADEVSASLAK QGL

P10636-5
                                                   (SEQ ID NO: 4)
        10         20         30         40         50         60
MAEPRQEFEV MEDHAGTYGL GDRKDQGGYT MHQDQEGDTD AGLKESPLQT PTEDGSEEPG

        70         80         90        100        110        120
SETSDAKSTP TAEDVTAPLV DEGAPGKQAA AQPHTEIPEG TTAEEAGIGD TPSLEDEAAG

       130        140        150        160        170        180
HVTQARMVSK SKDGTGSDDK KAKGADGKTK IATPRGAAPP GQKGQANATR IPAKTPPAPK

       190        200        210        220        230        240
TPPSSGEPPK SGDRSGYSSP GSPGTPGSRS RTPSLPTPPT REPKKVAVVR TPPKSPSSAK

       250        260        270        280        290        300
SRLQTAPVPM PDLKNVKSKI GSTENLKHQP GGGKVQIVYK PVDLSKVTSK CGSLGNIHHK

       310        320        330        340        350        360
PGGGQVEVKS EKLDFKDRVQ SKIGSLDNIT HVPGGGNKKI ETHKLTFREN AKAKTDHGAE

       370        380        390        400        410
IVYKSPVVSG DTSPRHLSNV SSTGSIDMVD SPQLATLADE VSASLAKQGL

P10636-4
                                                   (SEQ ID NO: 5)
        10         20         30         40         50         60
MAEPRQEFEV MEDHAGTYGL GDRKDQGGYT MHQDQEGDTD AGLKESPLQT PTEDGSEEPG

        70         80         90        100        110        120
SETSDAKSTP TAEAEEAGIG DTPSLEDEAA GHVTQARMVS KSKDGTGSDD KKAKGADGKT
```

-continued

```
       130        140        150        160        170        180
KIATPRGAAP PGQKGQANAT RIPAKTPPAP KTPPSSGEPP KSGDRSGYSS PGSPGTPGSR

       190        200        210        220        230        240
SRTPSLPTPP TREPKKVAVV RTPPKSPSSA KSRLQTAPVP MPDLKNVKSK IGSTENLKHQ

       250        260        270        280        290        300
PGGGKVQIVY KPVDLSKVTS KCGSLGNIHH KPGGGQVEVK SEKLDFKDRV QSKIGSLDNI

       310        320        330        340        350        360
THVPGGGNKK IETHKLTFRE NAKAKTDHGA EIVYKSPVVS GDTSPRHLSN VSSTGSIDMV

       370        380
DSPQLATLAD EVSASLAKQG L

P10636-2
                                                       (SEQ ID NO: 6)
        10         20         30         40         50         60
MAEPRQEFEV MEDHAGTYGL GDRKDQGGYT MHQDQEGDTD AGLKAEEAGI GDTPSLEDEA

        70         80         90        100        110        120
AGHVTQARMV SKSKDGTGSD DKKAKGADGK TKIATPRGAA PPGQKGQANA TRIPAKTPPA

       130        140        150        160        170        180
PKTPPSSGEP PKSGDRSGYS SPGSPGTPGS RSRTPSLPTP PTREPKKVAV VRTPPKSPSS

       190        200        210        220        230        240
AKSRLQTAPV PMPDLKNVKS KIGSTENLKH QPGGGKVQIV YKPVDLSKVT SKCGSLGNIH

       250        260        270        280        290        300
HKPGGGQVEV KSEKLDFKDR VQSKIGSLDN ITHVPGGGNK KIETHKLTFR ENAKAKTDHG

       310        320        330        340        350
AEIVYKSPVV SGDTSPRHLS NVSSTGSIDM VDSPQLATLA DEVSASLAKQ GL
```

Reference to tau includes known natural variations about 30 of which are listed in the Swiss-Prot database and permutations thereof, as well as mutations associated with tau pathologies, such as dementia, Pick's disease, supranuclear palsy, etc. (see, e.g., Swiss-Prot database and Poorkaj, et al. Ann Neurol. 43:815-825 (1998)). Some examples of tau mutations numbered by the 441 isoform are a lysine to threonine mutation at amino acid residue 257 (K257T), an isoleucine to valine mutation at amino acid position 260 (1260V); a glycine to valine mutation at amino acid position 272 (G272V); an asparagine to lysine mutation at amino acid position 279 (N279K); an asparagine to histidine mutation at amino acid position 296 (N296H); a proline to serine mutation at amino acid position 301 (P301S); a proline to leucine mutation at amino acid 301 (P301L); a glycine to valine mutation at amino acid position 303 (G303V); a serine to asparagine mutation at position 305 (S305N); a glycine to serine mutation at amino acid position 335 (G335S); a valine to methionine mutation at position 337 (V337M); a glutamic acid to valine mutation at position 342 (E342V); a lysine to isoleucine mutation at amino acid position 369 (K3691); a glycine to arginine mutation at amino acid position 389 (G389R); and an arginine to tryptophan mutation at amino acid position 406 (R406W).

Tau can be phosphorylated at one or more amino acid residues including tyrosine at amino acid positions 18, 29, 97, 310, and 394 serine at amino acid positions 184, 185, 198, 199, 202, 208, 214, 235, 237, 238, 262, 293, 324, 356, 396, 400, 404, 409, 412, 413, and 422; and threonine at amino acids positions 175, 181, 205, 212, 217, 231, and 403. Unless otherwise apparent from context, reference to tau, or their fragments includes the natural human amino acid sequences including isoforms, mutants, and allelic variants thereof.

III. Antibodies

A. Binding Specificity and Functional Properties

The invention provides antibodies that bind to tau. Some antibodies specifically bind to an epitope within KXXSXXNX(K/H)H (SEQ ID NO:191). Some antibodies bind to a peptide comprising, consisting essentially of, or consisting of amino acid residues 259-268 of 441 amino acid tau protein (SEQ ID NO:1). Some antibodies bind to a peptide comprising, consisting essentially of, or consisting of amino acid residues 290-299 of 441 amino acid tau protein (SEQ ID NO:1). Some antibodies bind to a peptide comprising, consisting essentially of, or consisting of amino acid residues 321-330 of 441 amino acid tau protein (SEQ ID NO:1). Some antibodies bind to a peptide comprising, consisting essentially of or consisting of amino acid residues 353-362 of 441 amino acid tau protein (SEQ ID NO:1). Some antibodies bind to two, three or all four of these peptides. Some antibodies specifically bind to an epitope within residues 199-213 of 383 amino acid 4R0N human tau protein (SEQ ID NO:3) (corresponding to residues 257-271 of SEQ ID NO:1). Some antibodies specifically bind to an epitope within residues 262-276 of 383 amino acid 4R0N human tau protein (SEQ ID NO:3) (corresponding to residues 320-334 of SEQ ID NO:1). Some antibodies of the invention specifically bind to a peptide consisting of residues 257-271 of 441 amino acid tau protein (SEQ ID NO:1). Some antibodies of the invention specifically bind to a peptide consisting of residues 320-334 of 441 amino acid tau protein (SEQ ID NO:1). Some antibodies of the invention specifically bind to a peptide consisting of residues 259-268 of 441 amino acid tau protein SEQ ID NO:1, namely KIGSTENLKH (SEQ ID NO:188). Some antibodies of the invention specifically bind to a peptide consisting of residues 290-299 of 441 amino acid tau protein SEQ ID NO:1, namely KCGSKDNIKH (SEQ ID NO:192). Some antibodies of the invention specifically bind to a peptide consisting of residues 321-330 of 441 amino acid tau protein SEQ ID NO:1, namely KCGSLGNIHH (SEQ ID NO:193). Some antibodies of the invention specifically bind to a peptide consisting of residues 353-362 of 441 amino acid tau protein SEQ ID NO:1, namely KIGSLDNITH (SEQ ID NO:194). Some antibodies of the invention specifically bind to a peptide consisting of the consensus motif KXXSXXNX(K/H)H (SEQ ID NO:191). Some antibodies bind to an epitope comprising residues 259, 262, 265, 267, 268, residues 290, 293, 296, 298, 299, residues 321, 324, 327, 329, 330, or residues 353, 356, 359, 362 of 441 amino acid tau protein SEQ ID NO:1. Some antibodies bind to tau irrespective of phosphorylation state. Some antibodies bind to an epitope not including a residue subject to phosphorylation. These antibodies can be obtained by immunizing with a tau polypeptide purified from a natural source or recombinantly expressed. Antibodies can be screened for binding tau in unphosphorylated form as well as a form in which one or more residues susceptible to phosphorylation are phosphorylated. Such antibodies preferably bind with indistinguishable affinities or at least within a factor of 1.5, 2 or 3-fold to phosphorylated tau compared to non-phosphorylated tau (i.e., are "pan-specific"). 3D6 is an example of a pan-specific monoclonal antibody. The invention also provides antibodies binding to the same epitope as any of the foregoing antibodies, such as, for example, the epitope of 3D6. Also included are antibodies competing for binding to tau with any of the foregoing antibodies, such as, for example, competing with 3D6.

The above-mentioned antibodies can be generated de novo by immunizing with a peptide including, consisting essentially of or consisting of residues 199-213 or 262-276 of SEQ ID NO:3 (corresponding to residues 257-271 or 320-334, respectively, of SEQ ID NO:1) or by immunizing with a peptide including, consisting essentially of or consisting of residues 259-268, 290-299, 321-330, or 353-362 of SEQ ID NO:1, or by immunizing with a full length tau polypeptide or fragment thereof comprising such residues and screening for specific binding to a peptide including such residues. Such peptides are preferably attached to a heterologous conjugate molecule that helps elicit an antibody response to the peptide. Attachment can be direct or via a spacer peptide or amino acid. Cysteine is used as a spacer amino acid because its free SH group facilitates attachment of a carrier molecule. A polyglycine linker (e.g., 2-6 glycines), with or without a cysteine residue between the glycines and the peptide can also be used. The carrier molecule serves to provide a T-cell epitope that helps elicit an antibody response against the peptide. Several carriers are commonly used particularly keyhole limpet hemocyanin (KLH), ovalbumin and bovine serum albumin (BSA). Peptide spacers can be added to peptide immunogen as part of solid phase peptide synthesis. Carriers are typically added by chemical cross-linking. Some examples of chemical crosslinkers that can be used include cross-N-maleimido-6-aminocaproyl ester or m-maleimidobenzoyl-N-hydroxysuccinimide ester (MBS) (see for example, Harlow, E. et al., Antibodies: A Laboratory Manual, Cold Spring Harbor Laboratory Press, Cold Spring Harbor, N.Y. 1988; Sinigaglia et al., Nature, 336:778-780 (1988); Chicz et al., J. Exp. Med., 178:27-47 (1993); Hammer et al., Cell 74:197-203 (1993); Falk K. et al., Immunogenetics, 39:230-242 (1994); WO 98/23635; and, Southwood et al. J. Immunology, 160: 3363-3373 (1998)). The carrier and spacer if present can be attached to either end of the immunogen.

A peptide with optional spacer and carrier can be used to immunize laboratory animals or B-cells as described in more detail below. Hybridoma supernatants can be tested for ability to bind one or more peptides including, consisting essentially of or consisting of residues 199-213 or 262-276 of SEQ ID NO:3 (corresponding to residues 257-271 or 320-334, respectively, of SEQ ID NO:1), or including, consisting essentially of or consisting of residues 259-268, 290-299, 321-330, or 353-362 of SEQ ID NO:1, and/or phosphorylated and non-phosphorylated forms of tau, such as, for example, a full-length isoform of tau with position 404 in phosphorylated form. The peptide can be attached to a carrier or other tag to facilitate the screening assay. In this case, the carrier or tag is preferentially different than the combination of spacer and carrier molecule used for immunization to eliminate antibodies specific for the spacer or carrier rather than the tau peptide. Any of the tau isoforms can be used.

The invention provides monoclonal antibodies binding to epitopes within tau. An antibody designated 3D6 is one such exemplary mouse antibody. Unless otherwise apparent from context, reference to 3D6 should be understood as referring to any of the mouse, chimeric, veneered, and humanized forms of this antibody. The antibody has been deposited as [DEPOSIT NUMBER]. This antibody specifically binds to an epitope of KXXSXXNX(K/H)H (SEQ ID NO:191). This antibody specifically binds within amino acid residues 199-213 and/or 262-276 of the 383 amino acid 4R0N human tau protein (SEQ ID NO:3) (corresponding to amino acid residues 257-271 and/or 320-334, respectively, of SEQ ID NO:1). The antibody specifically binds within amino acid residues 259-268 or 290-299 or 321-330 or 353-362 of SEQ ID NO:1, and combinations of any 2, 3 or all four thereof. This antibody is further characterized by its ability to bind both phosphorylated and unphosphorylated tau, both non-pathological and pathological forms and conformations of tau, and misfolded/aggregated forms of tau. An antibody designated 6A10 is one such exemplary mouse antibody. Unless otherwise apparent from context, reference to 6A10 should be understood as referring to any of the mouse, chimeric, veneered, and humanized forms of this antibody. Kabat/Chothia Composite CDRs of the heavy chain of 6A10 are designated SEQ ID NOs:67, 68, and 69, respectively, and Kabat CDRs of the light chain of 6A10 are designated SEQ ID NOs:12, 13, and 14, respectively. Mouse 6A10 shares 82.1% of VH sequence identity and 100% VL sequence identity with the VH chain and VL chain, respectively, of mouse 3D6.

Some antibodies of the invention bind to the same or overlapping epitope as an antibody designated 3D6. The sequences of the heavy and light chain mature variable regions of this antibody are designated SEQ ID NOs:7 and 11, respectively. Other antibodies having such a binding specificity can be produced by immunizing mice with tau or a portion thereof including, consisting essentially of or consisting of the desired epitope (e.g. 199-213 and/or 262-276 of SEQ ID NO:3, corresponding to residues 257-271 and/or 320-334, respectively, of SEQ ID NO:1; or e.g., 259-268 or 290-299 or 321-330 or 353-362 of SEQ ID NO: 1, any combination of 2, 3 or all 4 thereof) and screening resulting antibodies for binding to tau optionally in competition with an antibody having the variable regions of mouse 3D6 (IgG1 kappa). Fragments of tau including the desired epitope can be linked to a carrier that helps elicit an antibody response to the fragment and/or be combined with an adjuvant the helps elicit such a response. Such antibodies can be screened for differential binding to tau or a fragment thereof compared with mutants of specified residues. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 3D6) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for tau or a fragment thereof (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for tau or a fragment thereof are selected. The resulting antibodies usually have the same or similar epitope specificity as the murine starting material.

Kabat/Chothia Composite CDRs of the heavy chain of 3D6 are designated SEQ ID NOs:8, 9, and 10, respectively, and Kabat CDRs of the light chain of 3D6 are designated SEQ ID NOs:12, 13, and 14, respectively.

Table 2 indicates the 3D6 CDRs as defined by Kabat, Chothia, Composite of Chothia and Kabat (also referred to herein as "Kabat/Chothia Composite"), AbM, and Contact.

and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by any conventional definition, but preferably Kabat, that are 90%, 95%, 99% or 100% identical to corresponding CDRs of 3D6 are also included.

The invention also provides antibodies having some or all (e.g., 3, 4, 5, and 6) CDRs entirely or substantially from 3D6. Such antibodies can include a heavy chain variable region that has at least two, and usually all three, CDRs entirely or substantially from the heavy chain variable region of 3D6 and/or a light chain variable region having at least two, and usually all three, CDRs entirely or substantially from the light chain variable region of 3D6. The antibodies can include both heavy and light chains. A CDR is substantially from a corresponding 3D6 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 3D6 in the amino acid sequence of the mature heavy and/or light chain variable regions and maintain their functional properties, and/or differ from 3D6 by a small number of functionally inconsequential amino acid substitutions (e.g., conservative substitutions), deletions, or insertions.

Some antibodies identified by such assays can bind to monomeric, misfolded, aggregated, phosphorylated, or unphosphorylated forms of tau or otherwise. Likewise, some antibodies are immunoreactive on non-pathological and pathological forms and conformations of tau.

B. Non-Human Antibodies

The production of other non-human antibodies, e.g., murine, guinea pig, primate, rabbit or rat, against tau or a fragment thereof (e.g., amino acid residues 199-213 or 262-276 of SEQ ID NO:3, corresponding to amino acid residues 257-271 or 320-334, respectively, of SEQ ID NO:1; or amino acid residues 259-268 or 290-299 or 321-330 or 353-362 of SEQ ID NO:1) can be accomplished by, for example, immunizing the animal with tau or a fragment thereof. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered

TABLE 2

3D6 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34<br>SEQ ID NO: 12 | L24--L34<br>SEQ ID NO: 12 | L24--L34<br>SEQ ID NO: 12 | L24--L34<br>SEQ ID NO: 12 | L30--L36<br>SEQ ID NO :36 |
| L2 | L50--L56<br>SEQ ID NO: 13 | L50--L56<br>SEQ ID NO: 13 | L50--L56<br>SEQ ID NO: 13 | L50--L56<br>SEQ ID NO: 13 | L46--L55<br>SEQ ID NO: 37 |
| L3 | L89--L97<br>SEQ ID NO: 14 | L89--L97<br>SEQ ID NO: 14 | L89--L97<br>SEQ ID NO: 14 | L89--L97<br>SEQ ID NO: 14 | L89--L96<br>SEQ ID NO: 38 |
| H1 | H31--H35B<br>SEQ ID NO: 32 | H26--H32<br>SEQ ID NO: 33 | H26--H35B<br>SEQ ID NO: 8 | H26--H35B<br>SEQ ID NO: 8 | H30--H35B<br>SEQ ID NO: 39 |
| H2 | H50--H65<br>SEQ ID NO: 9 | H52--H56<br>SEQ ID NO: 34 | H50--H65<br>SEQ ID NO: 9 | H50--H58<br>SEQ ID NO: 35 | H47--H58<br>SEQ ID NO: 40 |
| H3 | H95--H102<br>SEQ ID NO: 10 | H95--H102<br>SEQ ID NO: 10 | H95--H102<br>SEQ ID NO: 10 | H95--H102<br>SEQ ID NO: 10 | H93--H101<br>SEQ ID NO: 41 |

Other antibodies can be obtained by mutagenesis of cDNA encoding the heavy and light chains of an exemplary antibody, such as 3D6. Monoclonal antibodies that are at least 70%, 80%, 90%, 95%, 96%, 97%, 98%, or 99% identical to 3D6 in amino acid sequence of the mature heavy fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to tau or an epitope within tau (e.g., an epitope comprising one or more of amino acid residues 199-213 or 262-276 of SEQ ID NO:3; corresponding to amino acid residues 257-271 or 320-334, respectively, of SEQ ID NO:1 or an epitope comprising one or more of amino acid residues 259-268 or 290-299 or 321-330 or 353-362 of SEQ ID NO:1). Such screening can be accomplished by determining binding of an antibody to a collection of tau variants, such as tau variants containing amino acid residues 199-213 or 262-276 of SEQ ID NO:3 (corresponding to amino acid residues 257-271 or 320-334, respectively, of SEQ ID NO:1) or tau variants containing amino acid residues 259-268 or 290-299 or 321-330 or 353-362 of SEQ ID NO:1, or mutations within these residues, and determining which tau variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical. To be classified as humanized under the 2014 World Health Organization (WHO) International non-proprietary names (INN) definition of humanized antibodies, an antibody must have at least 85% identity to human germline antibody sequences (i.e., prior to somatic hypermutation). Mixed antibodies are antibodies for which one antibody chain (e.g., heavy chain) meets the threshold but the other chain (e.g., light chain) does not meet the threshold. An antibody is classified as chimeric if neither chain meets the threshold, even though the variable framework regions for both chains were substantially human with some murine backmutations. See, Jones et al. (2016) The INNs and outs of antibody nonproprietary names, mAbs 8:1, 1-9, DOI: 10.1080/19420862.2015.1114320. See also "WHO-INN: International nonproprietary names (INN) for biological and biotechnological substances (a review)" (Internet) 2014. Available from: who.int/medicines/services/inn/BioRev2014.pdf, incorporated herein by reference. For the avoidance of doubt, the term "humanized" as used herein is not intended to be limited to the 2014 WHO INN definition of humanized antibodies. Some of the humanized antibodies provided herein have at least 85% sequence identity to human germline sequences and some of the humanized antibodies provided herein have less than 85% sequence identity to human germline sequences. Some of the heavy chains of the humanized antibodies provided herein have from about 60% to 100% sequence identity to human germ line sequences, such as, for example, in the range of about 60% to 69%, 70% to 79%, 80% to 84%, or 85% to 89%. Some heavy chains fall below the 2014 WHO INN definition and have, for example, about 64%, 65%, 66%, 67%, 68%, 69%, 70%, 71%, 72%, 73%, 74%, 75%, 76%, 77%, 78%, 79%, 80%, 81%, or 82%, 83%, or 84% sequence identity to human germ line sequences, while other heavy chains meet the 2014 WHO INN definition and have about 85%, 86%, 87%, 88%, 89% or greater sequence identity to human germ line sequences. Some of the light chains of the humanized antibodies provided herein have from about 60% to 100% sequence identity to human germ line sequences, such as, for example, in the range of about 80% to 84% or 85% to 89%. Some light chains fall below the 2014 WHO INN definition and have, for example, about 81%, 82%, 83% or 84% sequence identity to human germ line sequences, while other light chains meet the 2014 WHO INN definition and have about 85%, 86%, 87%, 88%, 89% or greater sequence identity to human germ line sequences. Some humanized antibodies provided herein that are "chimeric" under the 2014 WHO INN definition have heavy chains with less than 85% identity to human germ line sequences paired with light chains having less than 85% identity to human germ line sequences. Some humanized antibodies provided herein are "mixed" under the 2014 WHO INN definition, for example, having a heavy chain with at least 85% sequence identity to human germ line sequences paired with a light chain having less than 85% sequence identity to human germ line sequences, or vice versa. Some humanized antibodies provided herein meet the 2014 WHO INN definition of "humanized" and have a heavy chain with at least 85% sequence identity to human germ line sequences paired with a light chain having at least 85% sequence identity to human germ line sequences. Additional humanized antibodies of the invention meet the 2014 WHO INN definition of "mixed."

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.,* 320: 415-428, 2002; Iwahashi et al., *Mol. Immunol.* 36:1079-1091, 1999; Tamura et al, *J. Immunol.,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity and/or for meeting the WHO INN definition of "humanized". However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Some humanized and chimeric antibodies have the same (within experimental error) or improved functional properties, e.g., binding affinity for human tau, inhibition of tau internalization into neurons as described in the examples as a murine antibody from which they were derived. For example, some humanized and chimeric antibodies have a binding affinity within a factor of 3, 2 or 1 of the murine antibody from which they were derived or an affinity indistinguishable within experimental error. Some humanized and chimeric antibodies inhibit tau internalization into neurons as described in the examples within a factor of 3, 2 or 1 of the murine antibody from which they were derived or inhibit the same within experimental error as the mouse antibody from which they were derived. Some humanized antibodies exhibit reduced immunogenicity, increased affinity, increased thermostability and/or improved expression relative to previously described humanized forms of the 3D6 antibody (see WO 2017/191560) hu3D6VHv1bA11/L2-DIM4 demonstrated improved affinity, as evidenced by on-rate, off-rate, and Kd numbers, over parental hu3D6VHv1bA11/hu3D6VLv2. hu3D6VHv1bA11/L2-DIM4 demonstrated higher thermostability and titer over parental hu3D6VHv1bA11/hu3D6VLv2.

An example of an acceptor sequence for the heavy chain is the human mature heavy chain variable region of humanized 48G7 Fab with PDB accession code 2RCS-VH_huFrwk (SEQ ID NO:75). The variable domains of 3D6 and 48G7 Fab also share identical lengths for the CDR-H1, H2 loops. An example of an acceptor sequence for the heavy chain is the human mature heavy chain variable region IMGT #IGHV1-69-2*01 (SEQ ID NO:25). IMGT #IGHV1-69-2*01 (SEQ ID NO:25) shares the canonical form of mouse 3D6 heavy chain CDR-H1 and H2. IMGT #IGHV1-69-2*01 (SEQ ID NO:25) belongs to human heavy chain subgroup 1. An example of an acceptor sequence for the light chain is the human mature light chain variable region with PDB accession code human antibody ARX71335 VL (SEQ ID NO:82). The variable light domain of 3D6 and ARX71335 antibody also share identical lengths for the CDR-L1, L2 and L3 loops. An example of an acceptor sequence for the light chain is the human mature light chain variable region with IMGT #IGKV2-30*02 (SEQ ID NO:27). IMGT #IGKV2-30*02 (SEQ ID NO:27) has the same canonical classes for CDR-L1, CDR-L2 and L3 as mouse 3D6. IMGT #IGKV2-30*02 (SEQ ID NO:27) belongs to human kappa subgroup 2.

If more than one human acceptor antibody sequence is selected, a composite or hybrid of those acceptors can be used, and the amino acids used at different positions in the humanized light chain and heavy chain variable regions can be taken from any of the human acceptor antibody sequences used. For example, the human mature heavy chain variable regions of IMGT #IGHV1-69-2*01 (SEQ ID NO:25) and PDB accession code #2RCS-VH_huFrwk (SEQ ID NO:75) were used as acceptor sequences for humanization of the 3D6 mature heavy chain variable region. An example of a positions in which these two acceptors differ is position H17 (T or S). Humanized versions of the 3D6 heavy chain variable region can include either amino acid at this position. For example, the human mature light chain variable regions IMGT #IGKV2-30*02 (SEQ ID NO:27) and PDB code #ARX71335-VL_huFrwk (SEQ ID NO:82) were used as acceptor sequences for humanization of the 3D6 mature light chain variable region. An example of a position in which these two acceptors differ is position L100 (Q or A). Humanized versions of the 3D6 light chain variable region can include either amino acid at this position.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;

(2) is adjacent to a CDR region or within a CDR as defined by Chothia but not Kabat;

(3) otherwise interacts with a CDR region (e.g., is within about 6 Å of a CDR region), (e.g., identified by modeling the light or heavy chain on the solved structure of a homologous known immunoglobulin chain); or (4) is a residue participating in the VL-VH interface.

In an embodiment, humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682)].

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamine residues (Q) that may be replaced with glutamic acid (E) to minimize potential for pyroglutamate conversion [Y. Diana Liu, et al., 2011, J. Biol. Chem., 286: 11211-11217]. Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control.

Exemplary humanized antibodies are humanized forms of the mouse 3D6, designated Hu3D6.

The mouse antibody 3D6 comprises mature heavy and light chain variable regions having amino acid sequences comprising SEQ ID NO:7 and SEQ ID NO:11, respectively. The invention provides humanized forms of the murine 3D6 antibody including 10 exemplified humanized heavy chain mature variable regions (hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6VHvb5 (SEQ ID NO:80), hu3D6VHvb6 (SEQ ID NO:90), hu3D6VHvb7 (SEQ ID NO:91), hu3D6VHv1bA11 D60E (h3D6VHvb8, SEQ ID NO:146), hu3D6VHv1bA11 L82cV (SEQ ID NO:147), and hu3D6VHv1bA11 D60E_L80M_Q81E_L82cV_T83R (h3D6VHvb9, SEQ ID NO: 148)) and 56 exemplified humanized light chain mature variable regions (hu3D6VLvb1 (SEQ ID NO:83), hu3D6VLvb2 (SEQ ID NO:84), hu3D6VLvb3 (SEQ ID NO:85), hu3D6VLv2 L54D (SEQ ID NO:93), hu3D6VLv2 L54G (SEQ ID NO:94), hu3D6VLv2 L54N (SEQ ID NO:95), hu3D6VLv2 L54E (SEQ ID NO:96), hu3D6VLv2 L50E (SEQ ID NO:97), hu3D6VLv2 L54Q (SEQ ID NO:98), hu3D6VLv2 L50D (SEQ ID NO:99), hu3D6VLv2 L54K (SEQ ID NO:100), hu3D6VLv2 L54R (SEQ ID NO:101), hu3D6VLv2 L54T (SEQ ID NO:102), hu3D6VLv2 L50G (SEQ ID NO:103), hu3D6VLv2 I48G (SEQ ID NO:104), hu3D6VLv2 I48D (SEQ ID NO:105), hu3D6VLv2 L47G (SEQ ID NO:106), hu3D6VLv2 Y49E (SEQ ID NO:107), hu3D6VLv2 L54V (SEQ ID NO:108), hu3D6VLv2 L54S (SEQ ID NO:109), hu3D6VLv2 S52G (SEQ ID NO:110), hu3D6VLv2 L47N (SEQ ID NO:111), hu3D6VLv2 L47D (SEQ ID NO:112), hu3D6VLv2 L47E (SEQ ID NO:113), hu3D6VLv2 L47P (SEQ ID NO:114), hu3D6VLv2 L47T (SEQ ID NO:115), hu3D6VLv2 L47S (SEQ ID NO:116), hu3D6VLv2 L47A (SEQ ID NO:117), hu3D6VLv2 L50V (SEQ ID NO:118), hu3D6VLv2 L37Q_L50G_L54R (SEQ ID NO:119), hu3D6VLv2 L37Q_L50G_L54G (SEQ ID NO:120), hu3D6VLv2 L37Q_S52G_L54G (SEQ ID NO:121), hu3D6VLv2 L37Q_S52G_L54R (SEQ ID NO:122), hu3D6VLv2 L37Q_S52G_L54T (SEQ ID NO:123), hu3D6VLv2 L37Q_S52G_L54D (SEQ ID NO:124), hu3D6VLv2 L37Q_L54R (SEQ ID NO:125), hu3D6VLv2 L37Q_L54G (SEQ ID NO:126), hu3D6VLv2 L37Q_L54D (SEQ ID NO:127), hu3D6VLv2 L37Q_L50G (SEQ ID NO:128), hu3D6VLv2 L37Q_L50D (SEQ ID NO:129), hu3D6VLv2 L37Q_L54T (SEQ ID NO:130), hu3D6VLv2 L37Q_S52G (SEQ ID NO:131), hu3D6VLv2 L37Q_L54E (SEQ ID NO:145), hu3D6VLv2 L37Q_L50D_L54G (SEQ ID NO:132), hu3D6VLv2 L37Q_L50D_L54R (SEQ ID NO:133), hu3D6VLv2 L37Q_L50E_L54G (SEQ ID NO:134), hu3D6VLv2 L37Q_L50E_L54R (SEQ ID NO:135), hu3D6VLv2 L37Q_L50G_L54R_G100Q (SEQ ID NO:136), hu3D6VLv2 L37Q_L50G_L54G_G100Q (SEQ ID NO:137), hu3D6VLv2 L37Q_S52G_L54R_G100Q (SEQ ID NO:138), hu3D6VLv2 L37Q_S52G_L54D_G100Q (SEQ ID NO:139), hu3D6VLv2 L37Q_L50D_L54G_G100Q (SEQ ID NO:140), hu3D6VLv2 L37Q_L50D_L54R_G100Q (SEQ ID NO:141), hu3D6VLv2 L37Q_L50V_L54D_G100Q (SEQ ID NO:142), hu3D6VLv2 L37Q (SEQ ID NO:143), and hu3D6VLv2 G100Q (SEQ ID NO:144)).

FIGS. 2 and 3 show alignments of the heavy chain variable region and light chain variable region, respectively, of murine 3D6 and various humanized antibodies. FIGS. 9A and 9B show alignment of the heavy chain variable region of the murine 3D6 with the heavy chain variable region of various humanized antibodies. FIGS. 10A, 10B, 10C, and 10D show alignment of the light chain variable region of hu3D6VLv2 with the light chain variable region of various humanized antibodies.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 35 variable region framework positions were considered as candidates for substitutions in the 56 exemplified human mature light chain variable regions and the 10 exemplified human mature heavy chain variable regions, as further specified in the examples: L7 (T7S), L10 (T10S), L15 (I15L), L17 (Q17E), L37 (L37Q), L45 (K45R), L47 (L47G, L47N, L47D, L47E, L47P, L47T, L47S, or L47A), L48 (I48G or I48D), L49 (Y49E), L83 (L83V), L86 (H86Y), L100 (A100Q), L106 (L106I), H1 (Q1E), H5 (Q5V), H11 (L11V), H17 (S17T), H20 (L20I), H23 (T23K), H38 (K38R), H42 (E42G), H43 (Q43K), H66 (K66R), H67 (A67V), H75 (S75T), H76 (N76D), H80 (L80M), H81 (Q81E), H82c (L82cV), H83 (T83R), H91 (Y91F), H93 (A93S), H94 (S94T), H108 (T108L), and H109 (L109V). The following 9 variable region CDR positions were considered as candidates for substitutions in the 56 exemplified human mature light chain variable regions and 10 exemplified human mature heavy chain variable regions, as further specified in the examples: L24 (K24R), L50 (L50E, L50D, L50G, or L50V), L52 (S52G), L54 (L54D, L54G, L54N, L54E, L54Q, L54K, L54R, L54T, L54V, or L54S), H28 (N28T), H54 (N54D), H56 (D56E), H58 (V58I), and H60 (D60E). In some humanized 3D6 antibodies, Kabat CDR-H2 has an amino acid sequence comprising SEQ ID NO:87. In some humanized 3D6 antibodies, Kabat CDR-H2 has an amino acid sequence comprising SEQ ID NO:149. In some humanized 3D6 antibodies, Kabat-Chothia Composite CDR-H1 has an amino acid sequence comprising SEQ ID NO:86, and Kabat CDR-H2 has an amino acid sequence comprising SEQ ID NO:87. In some humanized 3D6 antibodies, Kabat-Chothia Composite CDR-H1 has an amino acid sequence comprising SEQ ID NO:86 and Kabat CDR-H2 has an amino acid sequence comprising SEQ ID NO:88. In some humanized 3D6 antibodies, Kabat-Chothia Composite CDR-H1 has an amino acid sequence comprising SEQ ID NO:86 and Kabat CDR-H2 has an amino acid sequence comprising SEQ ID NO:92. In some humanized 3D6 antibodies, Kabat CDR-L1 has an amino acid sequence comprising SEQ ID NO:89. In some humanized 3D6 antibodies, Kabat CDR-L2 comprises an amino acid sequence selected from the group consisting of SEQ ID NOs:150-175.

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions VHvb1/VLvb1, VHvb1/VLvb2, VHvb1/VLvb3, VHvb2/VLvb1, VHvb2/VLvb2, VHvb2/VLvb3, VHvb3/VLvb1, VHvb3/VLvb2, VHvb3/VLvb3, VHvb4/VLvb1, VHvb4/VLvb2, VHvb4/VLvb3, VHvb5/VLvb1, VHvb5/VLvb2, VHvb5/VLvb3, VHvb6/VLvb1, VHvb6/VLvb2, VHvb6/VLvb3, VHvb7/VLvb1, VHvb7/VLvb2, VHvb7/VLvb3. Exemplified antibodies include any permutations or combinations of the exemplified mature heavy chain variable regions hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6Hvb5 (SEQ ID NO:80), hu3D6VHvb6 (SEQ ID NO:90), hu3D6VHvb7 (SEQ ID NO:91), hu3D6VHvb7 (SEQ ID NO:91), hu3D6VHv1bA11 D60E (h3D6VHvb8, SEQ ID NO:146), hu3D6VHv1bA11 L82cV (SEQ ID NO:147), and hu3D6VHv1bA11 D60E_L80M_Q81E_L82cV_T83R (h3D6VHvb9, SEQ ID NO:148) with any of the humanized 3D6VL light chain variable regions hu3D6VLvb1 (SEQ ID NO:83), hu3D6VLvb2 (SEQ ID NO:84), hu3D6VLvb3 (SEQ ID NO:85), hu3D6VLv2 L54D (SEQ ID NO:93), hu3D6VLv2 L54G (SEQ ID NO:94), hu3D6VLv2 L54N (SEQ ID NO:95), hu3D6VLv2 L54E (SEQ ID NO:96), hu3D6VLv2 L50E (SEQ ID NO:97), hu3D6VLv2 L54Q (SEQ ID NO:98), hu3D6VLv2 L50D (SEQ ID NO:99), hu3D6VLv2 L54K (SEQ ID NO:100), hu3D6VLv2 L54R (SEQ ID NO:101), hu3D6VLv2 L54T (SEQ ID NO:102), hu3D6VLv2 L50G (SEQ ID NO:103), hu3D6VLv2 I48G (SEQ ID NO:104), hu3D6VLv2 I48D (SEQ ID NO:105), hu3D6VLv2 L47G (SEQ ID NO:106), hu3D6VLv2 Y49E (SEQ ID NO:107), hu3D6VLv2 L54V (SEQ ID NO:108), hu3D6VLv2 L54S (SEQ ID NO:109), hu3D6VLv2 S52G (SEQ ID NO:110), hu3D6VLv2 L47N (SEQ ID NO:111), hu3D6VLv2 L47D (SEQ ID NO:112), hu3D6VLv2 L47E (SEQ ID NO:113), hu3D6VLv2 L47P (SEQ ID NO:114), hu3D6VLv2 L47T (SEQ ID NO:115), hu3D6VLv2 L47S (SEQ ID NO:116), hu3D6VLv2 L47A (SEQ ID NO:117), hu3D6VLv2 L50V (SEQ ID NO:118), hu3D6VLv2 L37Q_L50G_L54R (SEQ ID NO:119), hu3D6VLv2 L37Q_L50G_L54G (SEQ ID NO:120), hu3D6VLv2 L37Q_S52G_L54G (SEQ ID NO:121), hu3D6VLv2 L37Q_S52G_L54R (SEQ ID NO:122), hu3D6VLv2 L37Q_S52G_L54T (SEQ ID NO:123), hu3D6VLv2 L37Q_S52G_L54D (SEQ ID NO:124), hu3D6VLv2 L37Q_L54R (SEQ ID NO:125), hu3D6VLv2 L37Q_L54G (SEQ ID NO:126), hu3D6VLv2 L37Q_L54D (SEQ ID NO:127), hu3D6VLv2 L37Q_L50G (SEQ ID NO:128), hu3D6VLv2 L37Q_L50D (SEQ ID NO:129), hu3D6VLv2 L37Q_L54T (SEQ ID NO:130), hu3D6VLv2 L37Q_S52G (SEQ ID NO:131), hu3D6VLv2 L37Q_L54E (SEQ ID NO:145), hu3D6VLv2 L37Q_L50D_L54G (SEQ ID NO:132), hu3D6VLv2 L37Q_L50D_L54R (SEQ ID NO:133), hu3D6VLv2 L37Q_L50E_L54G (SEQ ID NO:134), hu3D6VLv2 L37Q_L50E_L54R (SEQ ID NO:135), hu3D6VLv2 L37Q_L50G_L54R_G100Q (SEQ ID NO:136), hu3D6VLv2 L37Q_L50G_L54G_G100Q (SEQ ID NO:137), hu3D6VLv2 L37Q_S52G_L54R_G100Q (SEQ ID NO:138), hu3D6VLv2 L37Q_S52G_L54D_G100Q (SEQ ID NO:139), hu3D6VLv2 L37Q_L50D_L54G_G100Q (SEQ ID NO:140), hu3D6VLv2 L37Q_L50D_L54R_G100Q (SEQ ID NO:141), hu3D6VLv2 L37Q_L50V_L54D_G100Q (SEQ ID NO:142), hu3D6VLv2 L37Q (SEQ ID NO:143), and hu3D6VLv2 G100Q (SEQ ID NO:144).

Exemplified antibodies include any permutations or combinations of the exemplified mature heavy chain variable regions hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6Hvb5 (SEQ ID NO:80), hu3D6VHvb6 (SEQ ID NO:90), hu3D6VHvb7 (SEQ ID NO:91), hu3D6VHvb7 (SEQ ID NO:91), hu3D6VHv1bA11 D60E (h3D6VHvb8, SEQ ID NO:146), hu3D6VHv1bA11 L82cV (SEQ ID NO:147), and hu3D6VHv1bA11 D60E_L80M_Q81E_L82cV_T83R (h3D6VHvb9, SEQ ID NO: 148) with any of the humanized 3D6VL light chain variable regions hu3D6VLv1 (SEQ ID NO:20), hu3D6VLv2 (SEQ ID NO:21), hu3D6VLv3 (SEQ ID NO:22), and hu3D6VLv4 (SEQ ID NO:22). Exemplified antibodies include any permutations or combinations of the exemplified mature light chain variable regions hu3D6VLvb1 (SEQ ID NO:83), hu3D6VLvb2 (SEQ ID NO:84), hu3D6VLvb3 (SEQ ID NO:85), hu3D6VLv2 L54D (SEQ ID NO:93), hu3D6VLv2 L54G (SEQ ID NO:94), hu3D6VLv2 L54N (SEQ ID NO:95), hu3D6VLv2 L54E (SEQ ID NO:96), hu3D6VLv2 L50E (SEQ ID NO:97), hu3D6VLv2 L54Q (SEQ ID NO:98), hu3D6VLv2 L50D (SEQ ID NO:99), hu3D6VLv2 L54K (SEQ ID NO:100), hu3D6VLv2 L54R (SEQ ID NO:101), hu3D6VLv2 L54T (SEQ ID NO:102), hu3D6VLv2 L50G (SEQ ID NO:103), hu3D6VLv2 I48G (SEQ ID NO:104), hu3D6VLv2 I48D (SEQ ID NO:105), hu3D6VLv2 L47G (SEQ ID NO:106), hu3D6VLv2 Y49E (SEQ ID NO:107), hu3D6VLv2 L54V (SEQ ID NO:108), hu3D6VLv2 L54S (SEQ ID NO:109), hu3D6VLv2 S52G (SEQ ID NO:110), hu3D6VLv2 L47N (SEQ ID NO:111), hu3D6VLv2 L47D (SEQ ID NO:112), hu3D6VLv2 L47E (SEQ ID NO:113), hu3D6VLv2 L47P (SEQ ID NO:114), hu3D6VLv2 L47T (SEQ ID NO:115), hu3D6VLv2 L47S (SEQ ID NO:116), hu3D6VLv2 L47A (SEQ ID NO:117), hu3D6VLv2 L50V (SEQ ID NO:118), hu3D6VLv2 L37Q_L50G_L54R (SEQ ID NO:119), hu3D6VLv2 L37Q_L50G_L54G (SEQ ID NO:120), hu3D6VLv2 L37Q_S52G_L54G (SEQ ID NO:121), hu3D6VLv2 L37Q_S52G_L54R (SEQ ID NO:122), hu3D6VLv2 L37Q_S52G_L54T (SEQ ID NO:123), hu3D6VLv2 L37Q_S52G_L54D (SEQ ID NO:124), hu3D6VLv2 L37Q_L54R (SEQ ID NO:125), hu3D6VLv2 L37Q_L54G (SEQ ID NO:126), hu3D6VLv2 L37Q_L54D (SEQ ID NO:127), hu3D6VLv2 L37Q_L50G (SEQ ID NO:128), hu3D6VLv2 L37Q_L50D (SEQ ID NO:129), hu3D6VLv2 L37Q_L54T (SEQ ID NO:130), hu3D6VLv2 L37Q_S52G (SEQ ID NO:131), hu3D6VLv2 L37Q_L54E (SEQ ID NO:145), hu3D6VLv2 L37Q_L50D_L54G (SEQ ID NO:132), hu3D6VLv2

L37Q_L50D_L54R (SEQ ID NO:133), hu3D6VLv2 L37Q_L50E_L54G (SEQ ID NO:134), hu3D6VLv2 L37Q_L50E_L54R (SEQ ID NO:135), hu3D6VLv2 L37Q_L50G_L54R_G100Q (SEQ ID NO:136), hu3D6VLv2 L37Q_L50G_L54G_G100Q (SEQ ID NO:137), hu3D6VLv2 L37Q_S52G_L54R_G100Q (SEQ ID NO:138), hu3D6VLv2 L37Q_S52G_L54D_G100Q (SEQ ID NO:139), hu3D6VLv2 L37Q_L50D_L54G_G100Q (SEQ ID NO:140), hu3D6VLv2 L37Q_L50D_L54R_G100Q (SEQ ID NO:141), hu3D6VLv2 L37Q_L50V_L54D_G100Q (SEQ ID NO:142), hu3D6VLv2 L37Q (SEQ ID NO:143), and hu3D6VLv2 G100Q (SEQ ID NO:144) with any of the humanized 3D6 heavy chain variable regions hu3D6VHv1 (SEQ ID NO:15); hu3D6VHv2 (SEQ ID NO:16); hu3D6VHv1b (SEQ ID NO:17); hu3D6VHv1bA11 (SEQ ID NO:18); hu3D6VHv5 (SEQ ID NO:19); hu3D6VHv1bA11B6G2 (SEQ ID NO:46); hu3D6VHv1bA11B6H3 (SEQ ID NO:47); hu3D6VHv1c (SEQ ID NO:48); hu3D6VHv1d (SEQ ID NO:49); hu3D6VHv1e (SEQ ID NO:50); hu3D6VHv1f (SEQ ID NO:51); hu3D6VHv3 (SEQ ID NO:52); hu3D6VHv3b (SEQ ID NO:53); hu3D6VHv3c (SEQ ID NO:54); hu3D6VHv4 (SEQ ID NO:55); hu3D6VHv4b (SEQ ID NO:56); and hu3D6VHv4c (SEQ ID NO:57).

The invention provides an antibody in which humanized heavy chain variable region hu3D6VHv1bA11, also known as h3D6Hu5, (SEQ ID NO:18) is combined with humanized light chain variable region hu3D6VLv2 L37Q_S52G_L54R (L2-DIM4, SEQ ID NO:122). The invention provides an antibody in which humanized heavy chain variable region hu3D6VHv1bA11, also known as h3D6Hu5, (SEQ ID NO:18) is combined with humanized light chain variable region hu3D6VLv2 L37Q_S52G_L54T (L2-DIM5, SEQ ID NO:123). The invention provides an antibody in which humanized heavy chain variable region h3D6VHvb8 (SEQ ID NO:146) is combined with humanized light chain variable region hu3D6VLv2 L37Q_S52G_L54R (L2-DIM4, SEQ ID NO:122). The invention provides an antibody in which humanized heavy chain variable region hu3D6VHv1bA11, also known as h3D6Hu5, (SEQ ID NO:18) is combined with humanized light chain variable region hu3D6VLv2 L37Q_S52G_L54G (L2-DIM3, SEQ ID NO:121). The invention provides an antibody in which humanized heavy chain variable region hu3D6VHv1bA11, also known as h3D6Hu5, (SEQ ID NO:18) is combined with humanized light chain variable region hu3D6VLv2 S52G (L2-DIM9, SEQ ID NO:110). The invention provides an antibody in which humanized heavy chain variable region h3D6VHvb8 (SEQ ID NO:146) is combined with humanized light chain variable region hu3D6VLv2 L54G (L2-DIM7, SEQ ID NO:94). The invention provides an antibody in which humanized heavy chain variable region hu3D6VHv1bA11, also known as h3D6Hu5, (SEQ ID NO:18) is combined with humanized light chain variable region hu3D6VLv2 L50G (L2-DIM22, SEQ ID NO:103).

The invention provides an antibody in which any one of the exemplified humanized heavy chain variable regions is combined with a human heavy chain constant region. An exemplary human heavy chain constant region is provided as SEQ ID NO:176 (IgG1: allotype G1m17,1). For example, SEQ ID NO:178 sets forth the amino acid sequence of a mature heavy chain of a 3D6 humanized variant (hu3D6VHv1bA11 IgG1 G1m17 allotype). For example, SEQ ID NO:180 sets forth the amino acid sequence of a heavy chain of a 3D6 humanized variant (hu3D6VHv1bA11 IgG1 G1m17 allotype) bovine alpha-lactalbumin signal peptide at the N-terminus. The invention provides an antibody in which any one of the exemplified humanized light chain variable regions is combined with a light chain constant region. An exemplary light chain constant region is provided as SEQ ID NO:177 (kappa). For example, SEQ ID NO:179 sets forth the amino acid sequence of a mature light chain of a 3D6 humanized variant (hu3D6VLv2 variant L37Q_S52G_L54R, L2-DIM4 kappa). For example, SEQ ID NO:181 sets forth the amino acid sequence of a light chain of a 3D6 humanized variant (hu3D6VLv2 variant L37Q_S52G_L54R, L2-DIM4 kappa) with bovine alpha-lactalbumin signal peptide at the N-terminus.

The invention provides variants of the 3D6 humanized antibody in which the humanized mature heavy chain variable region shows at least 90%, 95%, 96%, 97%, 98%, or 99% identity to hu3D6VHvb1 (SEQ ID NO:76), hu3D6VHvb2 (SEQ ID NO:77), hu3D6VHvb3 (SEQ ID NO:78), hu3D6VHvb4 (SEQ ID NO:79), hu3D6Hvb5 (SEQ ID NO:80), hu3D6VHvb6 (SEQ ID NO:90), hu3D6VHvb7 (SEQ ID NO:91), hu3D6VHvb7 (SEQ ID NO:91), hu3D6VHv1bA11 D60E (h3D6VHvb8, SEQ ID NO:146), hu3D6VHv1bA11 L82cV (SEQ ID NO:147), or hu3D6VHv1bA11 D60E_L80M_Q81E_L82cV_T83R (h3D6VHvb9, SEQ ID NO:148) and the humanized mature light chain variable region shows at least 90%, 95%, 96%, 97%, 98%, or 99% identity to hu3D6VLvb1 (SEQ ID NO:83), hu3D6VLvb2 (SEQ ID NO:84), hu3D6VLvb3 (SEQ ID NO:85), hu3D6VLv2 L54D (SEQ ID NO:93), hu3D6VLv2 L54G (SEQ ID NO:94), hu3D6VLv2 L54N (SEQ ID NO:95), hu3D6VLv2 L54E (SEQ ID NO:96), hu3D6VLv2 L50E (SEQ ID NO:97), hu3D6VLv2 L54Q (SEQ ID NO:98), hu3D6VLv2 L50D (SEQ ID NO:99), hu3D6VLv2 L54K (SEQ ID NO:100), hu3D6VLv2 L54R (SEQ ID NO:101), hu3D6VLv2 L54T (SEQ ID NO:102), hu3D6VLv2 L50G (SEQ ID NO:103), hu3D6VLv2 I48G (SEQ ID NO:104), hu3D6VLv2 I48D (SEQ ID NO:105), hu3D6VLv2 L47G (SEQ ID NO:106), hu3D6VLv2 Y49E (SEQ ID NO:107), hu3D6VLv2 L54V (SEQ ID NO:108), hu3D6VLv2 L54S (SEQ ID NO:109), hu3D6VLv2 S52G (SEQ ID NO:110), hu3D6VLv2 L47N (SEQ ID NO:111), hu3D6VLv2 L47D (SEQ ID NO:112), hu3D6VLv2 L47E (SEQ ID NO: 113), hu3D6VLv2 L47P (SEQ ID NO:114), hu3D6VLv2 L47T (SEQ ID NO:115), hu3D6VLv2 L47S (SEQ ID NO:116), hu3D6VLv2 L47A (SEQ ID NO:117), hu3D6VLv2 L50V (SEQ ID NO:118), hu3D6VLv2 L37Q_L50G_L54R (SEQ ID NO: 119), hu3D6VLv2 L37Q_L50G_L54G (SEQ ID NO:120), hu3D6VLv2 L37Q_S52G_L54G (SEQ ID NO:121), hu3D6VLv2 L37Q_S52G_L54R (SEQ ID NO:122), hu3D6VLv2 L37Q_S52G_L54T (SEQ ID NO:123), hu3D6VLv2 L37Q_S52G_L54D (SEQ ID NO:124), hu3D6VLv2 L37Q_L54R (SEQ ID NO:125), hu3D6VLv2 L37Q_L54G (SEQ ID NO:126), hu3D6VLv2 L37Q_L54D (SEQ ID NO:127), hu3D6VLv2 L37Q_L50G (SEQ ID NO:128), hu3D6VLv2 L37Q_L50D (SEQ ID NO:129), hu3D6VLv2 L37Q_L54T (SEQ ID NO:130), hu3D6VLv2 L37Q_S52G (SEQ ID NO:131), hu3D6VLv2 L37Q_L54E (SEQ ID NO:145), hu3D6VLv2 L37Q_L50D_L54G (SEQ ID NO:132), hu3D6VLv2 L37Q_L50D_L54R (SEQ ID NO:133), hu3D6VLv2 L37Q_L50E_L54G (SEQ ID NO:134), hu3D6VLv2 L37Q_L50E_L54R (SEQ ID NO:135), hu3D6VLv2 L37Q_L50G_L54R_G100Q (SEQ ID NO:136), hu3D6VLv2 L37Q_L50G_L54G_G100Q (SEQ ID NO:137), hu3D6VLv2 L37Q_S52G_L54R_G100Q (SEQ ID NO:138), hu3D6VLv2 L37Q_S52G_L54D_G100Q (SEQ ID NO:139), hu3D6VLv2 L37Q_L50D_L54G_G100Q (SEQ ID NO:140), hu3D6VLv2 L37Q_L50D_L54R_G100Q (SEQ ID NO:141), hu3D6VLv2 L37Q_L50V_L54D_G100Q (SEQ ID NO:142), hu3D6VLv2 L37Q (SEQ ID NO:143), or hu3D6VLv2 G100Q (SEQ ID NO:144). In some such antibodies at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or all 44 of the backmutations or other mutations in SEQ ID NOs:76-80, SEQ ID NOs:90-91, SEQ ID NOs:146-148, SEQ ID NOs:83-85, and SEQ ID NOs:93-145 are retained.

In some humanized 3D6 antibodies, at least one of the following positions in the VH region is occupied by the amino acid as specified: H93 is occupied by S and H94 is occupied by T. In some humanized 3D6 antibodies, positions H93 and H94 are occupied by S and T, respectively.

In some humanized 3D6 antibodies, position H91 in the VH region is occupied by F.

In some humanized 3D6 antibodies, at least one of the following positions in the VH region is occupied by the amino acid as specified: H1 is occupied by E, H5 is occupied by V, H11 is occupied by V, H20 is occupied I, H23 is occupied by K, H38 is occupied by R, H42 is occupied by G, H43 is occupied by K, H66 is occupied by R, H75 is occupied by T, H76 is occupied by D, H81 is occupied by E, H108 is occupied by L, H109 is occupied by V. In some humanized 3D6 antibodies, positions H1, H5, H11, H20, H23, H38, H42, H43, H66, H75, H76, H81, H108, and H109 in the VH region are occupied by E, V, V, I, K, R, G, K, R, T, D, E, L, and V, respectively.

In some humanized 3D6 antibodies, at least one of the following positions in the VH region is occupied by the amino acid as specified: H17 is occupied by T, H80 is occupied by M, H83 is occupied by R. In some humanized 3D6 antibodies, positions H17, H80, and H83 in the VH region are occupied by T, M, and R, respectively.

In some humanized 3D6 antibodies, position H58 in the VH region is occupied by I.

In some humanized 3D6 antibodies, at least one of the following positions in the VH region is occupied by the amino acid as specified: H28 is occupied by T, H67 is occupied by V. In some humanized 3D6 antibodies, positions H28 and H67 in the VH region are occupied by T and V, respectively.

In some humanized 3D6 antibodies, at least one of the following positions in the VH region is occupied by the amino acid as specified: H54 is occupied by D, H56 is occupied by E. In some humanized 3D6 antibodies, positions H54 and H56 in the VH region are occupied by D and E, respectively.

In some humanized 3D6 antibodies, at least one of the following positions in the VH region is occupied by the amino acid as specified: H1 is occupied by Q or E, H5 is occupied by Q or V, H11 is occupied by L or V, H17 is occupied by S or T, H20 is occupied by L or I, H23 is occupied by T or K, H28 is occupied by N or T, H38 is occupied by K or R, H42 is occupied by E or G, H43 is occupied by Q or K, H54 is occupied by N or D, H56 is occupied by D or E, H58 is occupied by V or I, H66 is occupied by K or R, H67 is occupied by A or V, H75 is occupied by S or T, H76 is occupied by N or D, H80 is occupied by L or M, H81 is occupied by Q or E, H83 is occupied by T or R, H91 is occupied by F or Y, H93 is occupied by S, H94 is occupied by T, H108 is occupied by T or L, H109 is occupied by L or V.

In some humanized 3D6 antibodies, positions H91, H93, and H94 in the VH region are occupied by F, S, and T, respectively, as in huVHvb1. In some humanized 3D6 antibodies, positions H1, H5, H11, H20, H23, H38, H42, H43, H66, H75, H76, H81, H91, H93, H94, H108, and H109 in the VH region are occupied by E, V, V, I, K, R, G, K, R, T, D, E, F, S, T, L, and V, respectively, as in huVHvb2. In some humanized 3D6 antibodies, positions H1, H5, H11, H17, H20, H23, H38, H42, H43, H58, H66, H75, H76, H80, H81, H83, H93, H94, H108, and H109 in the VH region are occupied by E, V, V, T, I, K, R, G, K, I, R, T, D, M, E, R, S, T, L, and V, respectively, as in huVHvb3. In some humanized 3D6 antibodies, positions H1, H5, H11, H17, H20, H23, H28, H38, H42, H43, H58, H66, H67, H75, H76, H80, H81, H83, H93, H94, H108, and H109 in the VH region are occupied by E, V, V, T, I, K, T, R, G, K, I, R, V, T, D, M, E, R, S, T, L, and V, respectively, as in huVHvb4. In some humanized 3D6 antibodies, positions H1, H5, H11, H17, H20, H23, H28, H38, H42, H43, H54, H56, H58, H66, H67, H75, H76, H80, H81, H83, H93, H94, H108, and H109 in the VH region are occupied by E, V, V, T, I, K, T, R, G, K, D, E, I, R, V, T, D, M, E, R, S, T, L, and V, respectively, as in huVHvb5. In some humanized 3D6 antibodies, positions H1, H5, H11, H17, H20, H23, H28, H38, H42, H43, H54, H56, H66, H67, H75, H76, H80, H81, H83, H91, H93, H94, H108, and H109 in the VH region are occupied by E, V, V, T, I, K, T, R, G, K, D, E, R, V, T, D, M, E, R, F, S, T, L, and V, respectively, as in huVHvb6. In some humanized 3D6 antibodies, positions H1, H5, H11, H17, H20, H23, H28, H38, H42, H43, H54, H56, H66, H67, H75, H76, H80, H81, H83, H93, H94, H108, and H109 in the VH region are occupied by E, V, V, T, I, K, T, R, G, K, D, E, R, V, T, D, M, E, R, S, T, L, and V, respectively, as in huVHvb7.

In some humanized 3D6 antibodies, position H60 is occupied by E, as in hu3D6VHv1bA11 D60E (h3D6VHvb8). In some humanized 3D6 antibodies, position H82C is occupied by V, as in hu3D6VHv1bA11 L82cV. In some humanized 3D6 antibodies, positions H60, H80, H81, H82c, and H83 are occupied by E, M, E, V, and R, as in hu3D6VHv1bA11 D60E_L80M_Q81E_L82cV_T83R (h3D6VHvb9).

The heavy chain variable region of any of the above-referenced antibodies can be modified to further reduce immunogenicity. For example, in some of the humanized antibodies position H80 is occupied by M and/or position H82c is occupied by V.

In some humanized 3D6 antibodies, at least one of the following positions in the VL region is occupied by the amino acid as specified: L7 is occupied by S, L10 is occupied by S, L15 is occupied by L, L83 is occupied by V, L86 is occupied by Y, and L106 is occupied by I. In some humanized 3D6 antibodies, positions L7, L10, L15, L83, L86, and L106 are occupied by S, S, L, V, Y, and Y, respectively.

In some humanized 3D6 antibodies, at least one of the following positions in the VL region is occupied by the amino acid as specified: L7 is T or S, L10 is T or S, L15 is I or L, L17 is Q or E, L24 is K or R, L37 is L or Q, L45 is K or R, L83 is L or V, L86 is H or Y, L100 is A or Q, L106 is L or I.

In some humanized 3D6 antibodies, positions L7, L10, L15, L83, L86, and L106 in the VL region are occupied by S, S, L, V, Y, and I, respectively, as in huVLvb2. In some humanized 3D6 antibodies, positions L7, L10, L15, L17, L24, L37, L45, L83, L86, L100, and L106 in the VL region are occupied by S, S, L, E, R, Q, R, V, Y, Q, and I, respectively, as in huVLvb3.

The light chain variable region of any of the above referenced antibodies can be modified to further reduce immunogenicity. For example, in some of the humanized antibodies position L47 is occupied by G, N, D, E, P, T, S or A; position L48 is occupied by G or D; position L49 is occupied by E; position L50 is occupied by E, D, G, or V; position L52 is occupied by G; and/or position L54 is occupied by D, G, N, E, Q, K, R, T, V or S. The heavy chain variable region of any of the above-referenced antibodies can be modified to further reduce immunogenicity. For example, in some of the humanized antibodies position H80 is occupied by M and/or position H82c is occupied by V.

In some humanized 3D6 antibodies, position L54 is occupied by D, as in hu3D6VLv2 L54D. In some humanized 3D6 antibodies, position L54 is occupied by G, as in hu3D6VLv2 L54G. In some humanized 3D6 antibodies, position L54 is occupied by N, as in hu3D6VLv2 L54N, In some humanized 3D6 antibodies, position L54 is occupied by E, as in hu3D6VLv2 L54E. In some humanized 3D6 antibodies, position L50 is occupied by E, as in hu3D6VLv2 L50E. In some humanized 3D6 antibodies, position L54 is occupied by Q, as in hu3D6VLv2 L54Q. In some humanized 3D6 antibodies, position L50 is occupied by D, as in hu3D6VLv2 L50D. In some humanized 3D6 antibodies, position L54 is occupied by K, as in hu3D6VLv2 L54K. In some humanized 3D6 antibodies, position L54 is occupied by R, as in hu3D6VLv2 L54R. In some humanized 3D6 antibodies, position L54 is occupied by T, as in hu3D6VLv2 L54T. In some humanized 3D6 antibodies, position L50 is occupied by G, as in hu3D6VLv2 L50G. In some humanized 3D6 antibodies, position L48 is occupied by G, as in hu3D6VLv2 I48G. In some humanized 3D6 antibodies, position L48 is occupied by D, as in hu3D6VLv2 I48D. In some humanized 3D6 antibodies, position L47 is occupied by G, as in hu3D6VLv2 L47G. In some humanized 3D6 antibodies, position L49 is occupied by E, as in hu3D6VLv2 Y49E. In some humanized 3D6 antibodies, position L54 is occupied by V, as in hu3D6VLv2 L54V. In some humanized 3D6 antibodies, position L54 is occupied by S, as in hu3D6VLv2 L54S. In some humanized 3D6 antibodies, position L52 is occupied by G, as in hu3D6VLv2 S52G. In some humanized 3D6 antibodies, position L47 is occupied by N, as in hu3D6VLv2 L47N. In some humanized 3D6 antibodies, position L47 is occupied by D, as in hu3D6VLv2 L47D. In some humanized 3D6 antibodies, position L47 is occupied by E, as in hu3D6VLv2 L47E. In some humanized 3D6 antibodies, position L47 is occupied by P, as in hu3D6VLv2 L47P. In some humanized 3D6 antibodies, position L47 is occupied by T, as in hu3D6VLv2 L47T. In some humanized 3D6 antibodies, position L47 is occupied by S, as in hu3D6VLv2 L47S. In some humanized 3D6 antibodies, position L47 is occupied by A, as in hu3D6VLv2 L47A. In some humanized 3D6 antibodies, position L50 is occupied by V, as in hu3D6VLv2 L50V.

In some humanized 3D6 antibodies, positions L37, L50, and L54 are occupied by Q, G, and R, respectively, as in hu3D6VLv2 L37Q_L50G_L54R. In some humanized 3D6 antibodies, positions L37, L50, and L54 are occupied by Q, G, and G, respectively, as in hu3D6VLv2 L37Q_L50G_L54G. In some humanized 3D6 antibodies, positions L37, L52, and L54 are occupied by Q, G, and G, respectively, as in hu3D6VLv2 L37Q_S52G_L54G. In some humanized 3D6 antibodies, positions L37, L52, and L54 are occupied by Q, G, and R, respectively, as in hu3D6VLv2 L37Q_S52G_L54R. In some humanized 3D6 antibodies, positions L37, L52, and L54 are occupied by Q, G, and T, respectively, as in hu3D6VLv2 L37Q_S52G_L54T. In some humanized 3D6 antibodies, positions L37, L52, and L54 are occupied by Q, G, and D, respectively, as in hu3D6VLv2 L37Q_S52G_L54D.

In some humanized 3D6 antibodies, positions L37 and L54 are occupied Q and R, respectively, as in hu3D6VLv2 L37Q_L54R. In some humanized 3D6 antibodies, positions L37 and L54 are occupied by Q and G, respectively, as in hu3D6VLv2 L37Q_L54G. In some humanized 3D6 antibodies, positions L37 and L54 are occupied by Q and D, respectively, as in hu3D6VLv2 L37Q_L54D. In some humanized 3D6 antibodies, positions L37 and L50 are occupied by Q and G, respectively, as in hu3D6VLv2 L37Q_L50G. In some humanized 3D6 antibodies, positions L37 and L50 are occupied by Q and D, respectively, as in hu3D6VLv2 L37Q_L50D. In some humanized 3D6 antibodies, positions L37 and L54 are occupied by Q and T, respectively, as in hu3D6VLv2 L37Q_L54T. In some humanized 3D6 antibodies, positions L37 and L52 are occupied by Q and G, respectively, as in hu3D6VLv2 L37Q_S52G. In some humanized 3D6 antibodies, positions L37 and L54 are occupied by Q and E, respectively, as in hu3D6VLv2 L37Q_L54E.

In some humanized 3D6 antibodies, positions L37, L50, and L54 are occupied by Q, D, and G, respectively, as in hu3D6VLv2 L37Q_L50D_L54G. In some humanized 3D6 antibodies, positions L37, L50, and L54 are occupied by Q, D, and R, respectively, as in hu3D6VLv2 L37Q_L50D_L54R. In some humanized 3D6 antibodies, positions L37, L50, and L54 are occupied by Q, E, and G, respectively, as in hu3D6VLv2 L37Q_L50E_L54G. In some humanized 3D6 antibodies, positions L37, L50, and L54 are occupied by Q, E, and R, respectively, as in hu3D6VLv2 L37Q_L50E_L54R.

In some humanized 3D6 antibodies, positions L37, L50, L54, and L100 are occupied by Q, G, R, and Q, respectively, as in hu3D6VLv2 L37Q_L50G_L54R_G100Q. In some humanized 3D6 antibodies, positions L37, L50, L54, and L100 are occupied by Q, G, G, and Q, respectively, as in hu3D6VLv2 L37Q_L50G_L54G_G100Q. In some humanized 3D6 antibodies, positions L37, L52, L54, and L100 are occupied by Q, G, R, and Q, respectively, as in hu3D6VLv2 L37Q_S52G_L54R_G100Q. In some humanized 3D6 antibodies, positions L37, L52, L54, and L100 are occupied by Q, G, D, and Q, respectively, as in hu3D6VLv2 L37Q_S52G_L54D_G100Q. In some humanized 3D6 antibodies, positions L37, L50, L54, and L100 are occupied by Q, D, G, and Q, respectively, as in hu3D6VLv2 L37Q_L50D_L54G_G100Q. In some humanized 3D6 antibodies, positions L37, L50, L54, and L100 are occupied by Q, D, R, and Q, respectively, as in hu3D6VLv2 L37Q_L50D_L54R_G100Q. In some humanized 3D6 antibodies, positions L37, L50, L54, and L100 are occupied by Q, V, D, and Q, respectively, as in hu3D6VLv2 L37Q_L50V_L54D_G100Q.

In some humanized 3D6 antibodies, position L37 is occupied by Q, as in hu3D6VLv2 L37Q. In some humanized 3D6 antibodies, position L100 is occupied by Q as in hu3D6VLv2 G100Q.

Some humanized 3D6 antibodies comprise a mature heavy chain variable region comprising CDRs H1, H2 and H3 comprising SEQ ID NOs:8, 9, and 10, respectively except that position H28 can be occupied by N or T, H54 can be occupied by N or D, H56 can be occupied by D or E, position H58 occupied by V or I, and position H60 can be occupied by D or E, and a mature light chain variable region comprising CDRs L1, L2 and L3 comprising SEQ ID NOs.: 12, 13, and 14 respectively, except that position L24 can be occupied by K or R, position L50 can be occupied by L, E.

D, G, or V, position L52 can be occupied by S or G, and position L54 can be occupied by L, D, G, N, E, Q, K, R, T, V, or S, wherein at least one of the following positions is occupied by the amino acid as specified: H1 is occupied by Q, H5 is occupied by Q, H11 is occupied by L, H20 is occupied by L, H23 is occupied by T, H38 is occupied by K, H75 is occupied by S, H56 is occupied by E, H58 is occupied by I, H60 is occupied by E, H82c is occupied by V, L10 is occupied by T, L17 is occupied by E, L24 is occupied by R, L37 is occupied by Q, L47 is occupied by G, N, D, E, P, T, S, or A, L48 is occupied by G or D, L49 is occupied by E, L50 is occupied by E, D, G, or V, L52 is occupied by G, L54 is occupied by D, G, N. E, Q, K, R, T, V, or S, L83 is occupied by L, L86 is occupied by H, L100 is occupied by Q, L106 is occupied by L.

Some humanized 3D6 antibodies comprise three light chain CDRs and three heavy chain CDRs of monoclonal antibody 3D6, wherein 3D6 is a mouse antibody characterized by a heavy chain variable region having an amino acid sequence comprising SEQ ID NO:7 and a light chain variable region having an amino acid sequence comprising SEQ ID NO:11, except that position H27 can be occupied by F or Y, position H28 can be occupied by N or T, position H29 can be occupied by I or F, position H30 can be occupied by K or T, position H51 can be occupied by I or V, position H54 can be occupied by N or D, position H60 can be occupied by D, A, or E, position H61 can be occupied by P or E, position H102 can be occupied by F or Y, position L50 can be occupied by L, E. D, G, or V, position L52 can be occupied by S or G, and position L54 can be occupied by L, D, G, N, E, Q, K, R, T, V, or S, wherein at least one of the following positions is occupied by the amino acid as specified: L37 is occupied by Q, L47 is occupied by G, N, D, E, P, T, S, or A, L48 is occupied by G or D, L49 is occupied by E, L50 is occupied by E, D, G, or V, L52 is occupied by G, L54 is occupied by D, G, N. E, Q, K, R, T, V, or S, L100 is occupied by Q, H60 is occupied by E, H82c is occupied by V.

In some humanized 3D6 antibodies, the variable heavy chain has ≥85% identity to human sequence. In some humanized 3D6 antibodies, the variable light chain has ≥85% identity to human sequence. In some humanized 3D6 antibodies, each of the variable heavy chain and variable light chain has ≥85% identity to human germline sequence. In some humanized 3D6 antibodies, the three heavy chain CDRs are as defined by Kabat/Chothia Composite (SEQ ID NOs:8, 9, and 10) and the three light chain CDRs are as defined by Kabat/Chothia Composite (SEQ ID NOs:12, 13, and 14); provided that position H28 is occupied by N or T, position H54 is occupied by N or D, position H56 is occupied by D or E, position H58 is occupied by V or I, position H60 is occupied by D or E, position L24 is occupied by K or R, position L50 is occupied by L, E, D, G, or V, position L52 is occupied by S or G, and position L54 is occupied by L, D, G, N, E, Q, K, R, T, V, or S. In some humanized 3D6 antibodies, Kabat/Chothia Composite CDR-H1 has an amino acid sequence comprising SEQ ID NO:86. In some humanized 3D6 antibodies, Kabat CDR-H2 has an amino acid sequence comprising SEQ ID NO:87, SEQ ID NO:88, SEQ ID NO:92, or SEQ ID NO:149. In some humanized 3D6 antibodies, Kabat CDR-L1 has an amino acid sequence comprising SEQ ID NO:89. In some humanized 3D6 antibodies, Kabat CDR-L2 comprises an amino acid sequence selected from the group consisting of SEQ ID NOs:150-175.

The CDR regions of such humanized antibodies can be identical or substantially identical to the CDR regions of 3D6, The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu3D6 heavy and light chains by a small number (e.g., typically no more than 1, 2, 3, 5, 10, or 15) of replacements, deletions or insertions. Such differences are usually in the framework but can also occur in the CDRs.

A possibility for additional variation in humanized 3D6 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 3D6 variants (whether or not conservative) have no substantial effect on the binding affinity or potency of the humanized mAb, that is, its ability to bind to tau.

The humanized 3D6 antibodies are further characterized by their ability to bind both phosphorylated and unphosphorylated tau and misfolded/aggregated forms of tau.

D. Chimeric and Veneered Antibodies

The invention further provides chimeric and veneered forms of non-human antibodies, particularly the 3D6 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence. In an embodiment, a chimeric 3D6 antibody has a heavy chain amino acid sequence of SEQ ID NO:72 and a light chain amino acid sequence of SEQ ID NO:73.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 3D6 antibody are included in the invention.

E. Human Antibodies

Human antibodies against tau or a fragment thereof (e.g., amino acid residues 199-213 and/or 262-276 of SEQ ID NO:3, corresponding to amino acid residues 257-271 and/or 320-334, respectively, of SEQ ID NO:1 or amino acid residues 259-268 or 290-299 or 321-330 or 353-362 of SEQ ID NO:1 or any combination of 2, 3 or all 4 thereof) are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of tau, such as a tau fragment containing only amino acid residues 199-213 or 262-276 of SEQ ID NO:3 (corresponding to amino acid residues 257-271 or 320-334, respectively, of SEQ ID NO:1) or containing only amino acid residues 259-268 or 290-299 or 321-330 or 353-362 of SEQ ID NO:1, as the target antigen, and/or by screening antibodies against a collection of tau variants, such as tau variants containing various mutations within amino acid residues 199-213 or 262-276 of SEQ ID NO:3 (corresponding to amino acid residues 257-271 or 320-334, respectively, of SEQ ID NO:1), or within amino acid residues 259-268 or 290-299 or 321-330 or 353-362 of SEQ ID NO:1.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; 5,814,318; 5,789,650; 5,770,429; 5,661,016; 5,633,425; 5,625,126; 5,569,825; 5,545,806; Neuberger, *Nat. Biotechnol.* 14:826 (1996); and Kucherlapati, WO 91/10741 (1991)) phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332); and methods described in WO 2008/081008 (e.g., immortalizing memory B cells isolated from humans, e.g., with EBV, screening for desired properties, and cloning and expressing recombinant forms).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., Proc. Natl. Acad. USA, 63, 78-85 (1969)), Kabat numbering (Kabat, *Sequences of Proteins of Immunological Interest* (National Institutes of Health, Bethesda, M D, 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra).

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 with or without the C-terminal lysine. Reference to a human constant region includes a constant region with any natural allotype or any permutation of residues occupying positions in natural allotypes. An exemplary heavy chain constant region is SEQ ID NO:176, with or without the C-terminal lysine, and an exemplary light chain constant region is SEQ ID NO:177.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions.

In one approach, the heavy and light chain variable regions are re-engineered to encode splice donor sequences downstream of the respective VDJ or VJ junctions and are cloned into a mammalian expression vector, such as pCMV-h□1 for the heavy chain and pCMV-Mcl for the light chain. These vectors encode human □1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells or induced pluripotent stem cells (iPSCs), and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

IV. Active Immunogens

An agent used for active immunization serves to induce in a patient the same types of antibody described in connection with passive immunization above. Agents used for active immunization can be the same types of immunogens used for generating monoclonal antibodies in laboratory animals, e.g., a peptide of 3-15 or 3-12 or 5-12, or 5-8 contiguous amino acids from a region of tau corresponding to residues 199-213 or 262-276 of SEQ ID NO:3 (corresponding to residues 257-271 or 320-334, respectively, of SEQ ID NO:1), such as, for example, a peptide including residues 199-213 or 262-276 of SEQ ID NO:3 (corresponding to residues 257-271 or 320-334, respectively, of SEQ ID NO:1) or from a region of tau corresponding to residues 259-268 or 290-299 or 321-330 or 353-362 of SEQ ID NO:1, such as for example, a peptide including residues 259-268 or 290-299 or 321-330 or 353-362 of SEQ ID NO:1. For inducing antibodies binding to the same or overlapping epitope as 3D6, the epitope specificity of these antibodies can be mapped (e.g., by testing binding to a series of overlapping peptides spanning tau). A fragment of tau consisting of or including or overlapping the epitope can then be used as an immunogen. Such fragments are typically used in unphosphorylated form.

The heterologous carrier and adjuvant, if used may be the same as used for generating monoclonal antibody, but may also be selected for better pharmaceutical suitability for use in humans. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam3Cys), mannan (a mannose polymer), or glucan (a β1→2 polymer)), cytokines (e.g., IL-1, IL-1 alpha and β peptides, IL-2, γ-INF, IL-10, GM-CSF), and chemokines (e.g., MIP1-α and β, and RANTES). Immunogens may be linked to the carriers with or without spacers amino acids (e.g., gly-gly). Additional carriers include virus-like particles. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) PLoS ONE 2(5):e415.) Alternatively, peptide immunogens can be linked to at least one artificial T-cell epitope capable of binding a large proportion of MHC Class II molecules, such as the pan DR epitope ("PADRE"). PADRE is described in U.S. Pat. No. 5,736,142, WO 95/07707, and Alexander J et al, Immunity, 1:751-761 (1994). Active immunogens can be presented in multimeric form in which multiple copies of an immunogen and/or its carrier are presented as a single covalent molecule.

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of tau to elicit an immune response. Preferred adjuvants augment the intrinsic response to an immunogen without causing conformational changes in the immunogen that affect the qualitative form of the response. Preferred adjuvants include aluminum salts, such as aluminum hydroxide and aluminum phosphate, 3 De-O-acylated monophosphoryl lipid A (MPL™) (see GB 2220211 (RIBI ImmunoChem Research Inc., Hamilton, Montana, now part of Corixa). Stimulon™ QS-21 is a triterpene glycoside or saponin isolated from the bark of the *Quillaja Saponaria* Molina tree found in South America (see Kensil et al., in Vaccine Design: The Subunit and Adjuvant Approach (eds. Powell & Newman, Plenum Press, NY, 1995); U.S. Pat. No. 5,057,540), (Aquila BioPharmaceuticals, Framingham, MA; now Antigenics, Inc., New York, NY). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Another adjuvant is CpG (WO 98/40100). Adjuvants can be administered as a component of a therapeutic composition with an active agent or can be administered separately, before, concurrently with, or after administration of the therapeutic agent.

Analogs of natural fragments of tau that induce antibodies against tau can also be used. For example, one or more or all L-amino acids can be substituted with D amino acids in such peptides. Also the order of amino acids can be reversed (retro peptide). Optionally a peptide includes all D-amino acids in reverse order (retro-inverso peptide). Peptides and other compounds that do not necessarily have a significant amino acid sequence similarity with tau peptides but nevertheless serve as mimetics of tau peptides and induce a similar immune response. Anti-idiotypic antibodies against monoclonal antibodies to tau as described above can also be used. Such anti-Id antibodies mimic the antigen and generate an immune response to it (see Essential Immunology, Roit ed., Blackwell Scientific Publications, Palo Alto, CA 6th ed., p. 181).

Peptides (and optionally a carrier fused to the peptide) can also be administered in the form of a nucleic acid encoding the peptide and expressed in situ in a patient. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. Antibodies can also be administered in the form of nucleic acids encoding the antibody heavy and/or light chains. If both heavy and light chains are present, the chains are preferably linked as a single chain antibody. Antibodies for passive administration can also be prepared e.g., by affinity chromatography from sera of patients treated with peptide immunogens.

The DNA can be delivered in naked form (i.e., without colloidal or encapsulating materials). Alternatively, a number of viral vector systems can be used including retroviral systems (see, e.g., Lawrie and Tumin, Cur. Opin. Genet. Develop. 3, 102-109 (1993)); adenoviral vectors {see, e.g., Bett et al, J. Virol. 67, 591 1 (1993)) including retrovirus derived vectors such MMLV, HIV-1, and ALV; adeno-associated virus vectors {see, e.g., Zhou et al., J. Exp. Med. 179, 1867 (1994)), lentiviral vectors such as those based on HIV or FIV gag sequences, viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or encoding the antibody heavy and/or light chains, or a vector containing the same, can be packaged into liposomes. Suitable lipids and related analogs are described by U.S. Pat. Nos. 5,208,036, 5,264,618, 5,279,833, and 5,283,185. Vectors and DNA encoding an immunogen or encoding the antibody heavy and/or light chains, can also be adsorbed to or associated with particulate carriers, examples of which include polymethyl methacrylate polymers and polylactides and poly(lactide-co-glycolides), (see, e.g., McGee et al., J. Micro Encap. 1996).

Vectors or segments therefrom encoding the antibody heavy and/or light chains can be incorporated in cells ex vivo, for example to cells explanted from an individual patient (e.g., lymphocytes, bone marrow aspirates, tissue biopsy) or universal donor hematopoietic stem cells, followed by reimplantation of the cells into a patient, usually after selection for cells which have incorporated the transgenes. (see, e.g., WO 2017/091512). Exemplary patient-derived cells include patient derived induced pluripotent stem cells (iPSCs) or other types of stem cells (embryonic, hematopoietic, neural, or mesenchymal).

A vector or segment therefrom encoding the antibody heavy and/or light chains can be introduced into any region of interest in cells ex vivo, such as an albumin gene or other safe harbor gene. Cells incorporating the vector can be implanted with or without prior differentiation. Cells can be implanted into a specific tissue, such as a secretory tissue or a location of pathology, or systemically, such as by infusion into the blood. For example, cells can be implanted into a secretory tissue of a patient, such as the liver, optionally with prior differentiation to cells present in that tissue, such as hepatocytes in the case of a liver. Expression of the antibody in the liver results in secretion of the antibody to the blood.

H. Antibody Screening Assays

Antibodies can be initially screened for the intended binding specificity as described above. Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. The cells used for such screening are preferentially neuronal cells. A cellular model of tau pathology has been reported in which neuroblastoma cells are transfected with a four-repeat domain of tau, optionally with a mutation associated with tau pathology (e.g., delta K280, see Khlistunova, Current Alzheimer Research 4, 544-546 (2007)). In another model, tau is induced in the neuroblastoma N2a cell line by the addition of doxycyclin. The cell models enable one to study the toxicity of tau to cells in the soluble or aggregated state, the appearance of tau aggregates after switching on tau gene expression, the dissolution of tau aggregates after switching the gene expression off again, and the efficiency of antibodies in inhibiting formation of tau aggregates or disaggregating them.

Antibodies or active immunogens can also be screened in transgenic animal models of diseases associated with tau. Such transgenic animals can include a tau transgene (e.g., any of the human isoforms) and optionally a human APP transgene among others, such as a kinase that phosphorylates tau, ApoE, presenilin or alpha synuclein. Such transgenic animals are disposed to develop at least one sign or symptom of a disease associated with tau.

An exemplary transgenic animal is the K3 line of mice (Itner et al., Proc. Natl. Acad. Sci. USA 105(41):15997-6002 (2008)). These mice have a human tau transgene with a K 369 I mutation (the mutation is associated with Pick's disease) and a Thy 1.2 promoter. This model shows a rapid course of neurodegeneration, motor deficit and degeneration of afferent fibers and cerebellar granule cells. Another exemplary animal is the JNPL3 line of mice. These mice have a human tau transgene with a P301L mutation (the mutation is associated with frontotemporal dementia) and a Thy 1.2 promoter (Taconic, Germantown, N.Y., Lewis, et al., Nat Genet. 25:402-405 (2000)). These mice have a more gradual course of neurodegeneration. The mice develop neurofibrillary tangles in several brain regions and spinal cord, which is hereby incorporated by reference in its entirety). This is an excellent model to study the consequences of tangle development and for screening therapy that may inhibit the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored. Active immunization of these mice for 6-13 months with—AI wI KLH-PHF-1 generated titers of about 1,000 and showed fewer neurofibrillary tangles, less pSer422, and reduced weight loss relative to untreated control ice.

The activity of antibodies or active agents can be assessed by various criteria including reduction in amount of total tau or phosphorylated tau, reduction in other pathological characteristics, such as amyloid deposits of Aβ, and inhibition or delay or behavioral deficits. Active immunogens can also be tested for induction of antibodies in the sera. Both passive and active immunogens can be tested for passage of antibodies across the blood brain barrier into the brain of a transgenic animal. Antibodies or fragments inducing an antibody can also be tested in non-human primates that naturally or through induction develop symptoms of diseases characterized by tau. Tests on an antibody or active agent are usually performed in conjunction with a control in which a parallel experiment is conduct except that the antibody or active agent is absent (e.g., replaced by vehicle). Reduction, delay or inhibition of signs or symptoms disease attributable to an antibody or active agent under test can then be assessed relative to the control.

V. Patients Amenable to Treatment

The presence of neurofibrillary tangles has been found in several diseases including Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), and progressive supranuclear palsy (PSP). The present regimes can also be used in treatment or prophylaxis of any of these diseases. Because of the widespread association between neurological diseases and conditions and tau, the present regimes can be used in treatment or prophylaxis of any subject showing elevated levels of tau or phosphorylated tau (e.g., in the CSF) compared with a mean value in individuals without neurological disease. The present regimes can also be used in treatment or prophylaxis of neurological disease in individuals having a mutation in tau associated with neurological disease. The present methods are particularly suitable for treatment or prophylaxis of Alzheimer's disease, and especially in patients.

Patients amenable to treatment include individuals at risk of disease but not showing symptoms, as well as patients presently showing symptoms. Patients at risk of disease include those having a known genetic risk of disease. Such individuals include those having relatives who have experienced this disease, and those whose risk is determined by analysis of genetic or biochemical markers. Genetic markers of risk include mutations in tau, such as those discussed above, as well as mutations in other genes associated with neurological disease. For example, the ApoE4 allele in heterozygous and even more so in homozygous form is associated with risk of Alzheimer's disease. Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF tau or phospho-tau and Aβ42 levels. Elevated tau or phospho-tau and decreased Aβ42 levels signify the presence of AD. Some mutations associated with Parkinson's disease. Ala30Pro or Ala53, or mutations in other genes associated with Parkinson's disease such as leucine-rich repeat kinase, PARK8. Individuals can also be diagnosed with any of the neurological diseases mentioned above by the criteria of the DSM IV TR.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

I. Nucleic Acids

The invention further provides nucleic acids encoding any of the heavy and light chains described above (e.g., SEQ ID NO:7, SEQ ID NO:11, SEQ ID NOs:76-80, SEQ ID NOs: 90-91, SEQ ID NOs:146-148, SEQ ID NOs:83-85, SEQ ID NOs:93-145, and SEQ ID NOs:178-181). An exemplary nucleic acid encoding a heavy chain of the invention is SEQ ID NO:182, and an exemplary nucleic acid encoding a light chain of the invention is SEQ ID NO: 183. Optionally, such nucleic acids further encode a signal peptide and can be expressed with the signal peptide linked to the variable region. Coding sequences of nucleic acids can be operably linked with regulatory sequences to ensure expression of the coding sequences, such as a promoter, enhancer, ribosome binding site, transcription termination signal, and the like. The regulatory sequences can include a promoter, for example, a prokaryotic promoter or a eukaryotic promoter. The nucleic acids encoding heavy or light chains can be codon-optimized for expression in a host cell. The nucleic acids encoding heavy and light chains can encode a selectable gene. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens, such as tau, are useful in detecting the presence of tau; monitoring and evaluating the efficacy of therapeutic agents being used to treat patients diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP); inhibiting or reducing aggregation of tau; inhibiting or reducing tau fibril formation; reducing or clearing tau deposits; stabilizing non-toxic conformations of tau; or treating or effecting prophylaxis of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) in a patient. For example, such antibodies can be conjugated with other therapeutic moieties, other proteins, other antibodies, and/or detectable labels. See WO 03/057838; U.S. Pat. No. 8,455,622. Such therapeutic moieties can be any agent that can be used to treat, combat, ameliorate, prevent, or improve an unwanted condition or disease in a patient, such as Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

Conjugated therapeutic moieties can include cytotoxic agents, cytostatic agents, neurotrophic agents, neuroprotective agents, radiotherapeutic agents, immunomodulators, or any biologically active agents that facilitate or enhance the activity of the antibody. A cytotoxic agent can be any agent that is toxic to a cell. A cytostatic agent can be any agent that inhibits cell proliferation. A neurotrophic agent can be any agent, including chemical or proteinaceous agents, that promotes neuron maintenance, growth, or differentiation. A neuroprotective agent can be agent, including chemical or proteinaceous agents, that protects neurons from acute insult or degenerative processes. An immunomodulator can be any agent that stimulates or inhibits the development or maintenance of an immunologic response. A radiotherapeutic agent can be any molecule or compound that emits radiation. If such therapeutic moieties are coupled to a tau-specific antibody, such as the antibodies described herein, the coupled therapeutic moieties will have a specific affinity for tau-related disease-affected cells over normal cells. Consequently, administration of the conjugated antibodies directly targets cancer cells with minimal damage to surrounding normal, healthy tissue. This can be particularly useful for therapeutic moieties that are too toxic to be administered on their own. In addition, smaller quantities of the therapeutic moieties can be used.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio) propionate for ricin. See Pietersz et al., *Cancer Res.* 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., *Leukemia* 18:1215-1222 (2004).

Some such antibodies can be linked to radioisotopes. Examples of radioisotopes include, for example, yttrium$^{90}$ (90Y), indium$^{111}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Some such antibodies can be linked to other therapeutic moieties. Such therapeutic moieties can be, for example, cytotoxic, cytostatic, neurotrophic, or neuroprotective. For example, antibodies can be conjugated with toxic chemotherapeutic drugs such as maytansine, geldanamycin, tubulin inhibitors such as tubulin binding agents (e.g., auristatins), or minor groove binding agents such as calicheamicin. Other representative therapeutic moieties include agents known to be useful for treatment, management, or amelioration of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within tau or can bind to a different target antigen.

Antibodies can also be coupled with a detectable label. Such antibodies can be used, for example, for diagnosing Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP), and/or for assessing efficacy of treatment. Such antibodies are particularly useful for performing such determinations in subjects having or being susceptible to Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP), or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I) carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Ph, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.,* 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.,* 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

VI. Pharmaceutical Compositions and Methods of Use

In prophylactic applications, an antibody or agent for inducing an antibody or a pharmaceutical composition the same is administered to a patient susceptible to, or otherwise at risk of a disease (e.g., Alzheimer's disease) in regime (dose, frequency and route of administration) effective to reduce the risk, lessen the severity, or delay the onset of at least one sign or symptom of the disease. In particular, the regime is preferably effective to inhibit or delay tau or phospho-tau and paired filaments formed from it in the brain, and/or inhibit or delay its toxic effects and/or inhibit/ or delay development of behavioral deficits. In therapeutic applications, an antibody or agent to induce an antibody is administered to a patient suspected of, or already suffering from a disease (e.g., Alzheimer's disease) in a regime (dose, frequency and route of administration) effective to ameliorate or at least inhibit further deterioration of at least one sign or symptom of the disease. In particular, the regime is preferably effective to reduce or at least inhibit further increase of levels of tau, phosphor-tau, or paired filaments formed from it, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

Exemplary dosage ranges for antibodies are from about 0.01 to 60 mg/kg, or from about 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

The amount of an agent for active administration varies from 0.1-500 μg per patient and more usually from 1-100 or 1-10 μg per injection for human administration. The timing of injections can vary significantly from once a day, to once a year, to once a decade. A typical regimen consists of an immunization followed by booster injections at time intervals, such as 6 week intervals or two months. Another regimen consists of an immunization followed by booster injections 1, 2 and 12 months later. Another regimen entails an injection every two months for life. Alternatively, booster injections can be on an irregular basis as indicated by monitoring of immune response.

Antibodies or agents for inducing antibodies are preferably administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal, intraocular, or intramuscular. Preferred routes for administration of antibodies are intravenous and subcutaneous. Preferred routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Alzheimer's disease, the present regimes can be combined with immunotherapy against A3 (WO/2000/072880), cholinesterase inhibitors or memantine or in the case of Parkinson's disease immunotherapy against alpha synuclein WO/2008/103472, Levodopa, dopamine agonists, COMT inhibitors, MAO-B inhibitors, Amantadine, or anticholinergic agents.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-60 mg/kg (e.g., 0.5, 3, 10, 30, or 60 mg/kg), or 0.5-5 mg/kg body weight (e.g., 0.5, 1, 2, 3, 4 or 5 mg/kg) or 10-4000 mg or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

A. Diagnostics and Monitoring Methods

In Vivo Imaging, Diagnostic Methods, and Optimizing Immunotherapy

The invention provides methods of in vivo imaging tau protein deposits (e.g., neurofibrillary tangles and tau inclusions) in a patient. The methods work by administering a reagent, such as antibody that binds tau (e.g., a mouse, humanized, chimeric or veneered 3D6 antibody), to the patient and then detecting the agent after it has bound. Antibodies binding to an epitope of tau within amino acid residues 199-213 or 262-276 of SEQ ID NO:3 (corresponding to amino acid residues 257-271 or 320-334, respectively, of SEQ ID NO:1) or within amino acid residues 259-268 or 290-299 or 321-330 or 353-362 of SEQ ID NO:1, are preferred. In some methods, the antibody binds to an epitope within amino acid residues 199-213 of SEQ ID NO:3 (corresponding to amino acid residues 257-271 of SEQ ID NO:1), or within amino acids 262-276 of SEQ ID NO:3 (corresponding to amino acid residues 320-334 of SEQ ID NO:1). In some methods, the antibody binds to an epitope within amino acid residues 259-268 of SEQ ID NO:1, within amino acids 290-299 of SEQ ID NO:1, within amino acids 321-330 of SEQ ID NO1, or within amin acids 353-362 of SEQ ID NO:1. A clearing response to the administered antibodies can be avoided or reduced by using antibody fragments lacking a full-length constant region, such as Fabs. In some methods, the same antibody can serve as both a treatment and diagnostic reagent.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for tau is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using positron emission tomography (PET) or single-photon emission computed tomography (SPECT).

The methods of in vivo imaging of tau protein deposits are useful to diagnose or confirm diagnosis of a tauopathy, such as Alzheimer's disease, frontotemporal lobar degeneration, progressive supranuclear palsy and Pick's disease, or susceptibility to such a disease. For example, the methods can be used on a patient presenting with symptoms of dementia. If the patient has abnormal neurofibrillary tangles, then the patient is likely suffering from Alzheimer's disease. Alternatively, if the patient has abnormal tau inclusions, then depending on the location of the inclusions, the patient may be suffering from frontotemporal lobar degeneration. The methods can also be used on asymptomatic patients. Presence of abnormal tau protein deposits indicates susceptibility to future symptomatic disease. The methods are also useful for monitoring disease progression and/or response to treatment in patients who have been previously diagnosed with a tau-related disease.

Diagnosis can be performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning tau immunotherapy treatment, and measured values thereafter compared with the baseline values. A decrease in values relative to baseline signals a positive response to treatment.

In some patients, diagnosis of a tauopathy may be aided by performing a PET scan. A PET scan can be performed using, for example, a conventional PET imager and auxiliary equipment. The scan typically includes one or more regions of the brain known in general to be associated with tau protein deposits and one or more regions in which few if any deposits are generally present to serve as controls.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. A color scale can be used with different colors indicating different amounts of label and, inferentially, tau protein deposit detected. The results of the scan can also be presented numerically, with numbers relating to the amount of label detected and consequently amount of tau protein deposits. The label present in a region of the brain known to be associated with deposits for a particular tauopathy (e.g., Alzheimer's disease) can be compared with the label present in a region known not to be associated with deposits to provide a ratio indicative of the extent of deposits within the former region. For the same radiolabeled ligand, such ratios provide a comparable measure of tau protein deposits and changes thereof between different patients.

In some methods, a PET scan is performed concurrent with or in the same patient visit as an MRI or CAT scan. An MRI or CAT scan provides more anatomical detail of the brain than a PET scan. However, the image from a PET scan can be superimposed on an MRI or CAT scan image more precisely indicating the location of PET ligand and inferentially tau deposits relative to anatomical structures in the brain. Some machines can perform both PET scanning and MRI or CAT scanning without the patient changing positions between the scans facilitating superimposition of images.

Suitable PET ligands include radiolabeled antibodies of the invention (e.g., a mouse, humanized, chimeric or veneered 3D6 antibody). The radioisotope used can be, for example, $C^{11}$, $N^{13}$, $O^{15}$, $F^{18}$, or $I^{123}$. The interval between administering the PET ligand and performing the scan can depend on the PET ligand and particularly its rate of uptake and clearing into the brain, and the half-life of its radiolabel.

PET scans can also be performed as a prophylactic measure in asymptomatic patients or in patients who have symptoms of mild cognitive impairment but have not yet been diagnosed with a tauopathy but are at elevated risk of developing a tauopathy. For asymptomatic patients, scans are particularly useful for individuals considered at elevated risk of tauopathy because of a family history, genetic or biochemical risk factors, or mature age. Prophylactic scans can commence for example, at a patient age between 45 and 75 years. In some patients, a first scan is performed at age 50 years.

Prophylactic scans can be performed at intervals of for example, between six months and ten years, preferably between 1-5 years. In some patients, prophylactic scans are performed annually. If a PET scan performed as a prophylactic measure indicates abnormally high levels of tau protein deposits, immunotherapy can be commenced and subsequent PET scans performed as in patients diagnosed with a tauopathy. If a PET scanned performed as a prophylactic measure indicates levels of tau protein deposits within normal levels, further PET scans can be performed at intervals of between six months and 10 years, and preferably 1-5 years, as before, or in response to appearance of signs and symptoms of a tauopathy or mild cognitive impairment. By combining prophylactic scans with administration of tau-directed immunotherapy if and when an above normal level of tau protein deposits is detected, levels of tau protein deposits can be reduced to, or closer to, normal levels, or at least inhibited from increasing further, and the patient can remain free of the tauopathy for a longer period than if not receiving prophylactic scans and tau-directed immunotherapy (e.g., at least 5, 10, 15 or 20 years, or for the rest of the patient's life).

Normal levels of tau protein deposits can be determined by the amount of neurofibrillary tangles or tau inclusions in the brains of a representative sample of individuals in the general population who have not been diagnosed with a particular tauopathy (e.g., Alzheimer's disease) and are not considered at elevated risk of developing such disease (e.g., a representative sample of disease-free individuals under 50 years of age). Alternatively, a normal level can be recognized in an individual patient if the PET signal according to the present methods in a region of the brain in which tau protein deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with tau protein deposits compared with a region not known to be associated with deposits. For purposes of comparing the levels of tau protein deposits in an individual and population, the tau protein deposits should preferably be determined in the same region(s) of the brain, these regions including at least one region in which tau protein deposits associated with a particular tauopathy (e.g., Alzheimer's disease) are known to form. A patient having an elevated level of tau protein deposits is a candidate for commencing immunotherapy.

After commencing immunotherapy, a decrease in the level of tau protein deposits can be first seen as an indication that the treatment is having the desired effect. The observed decrease can be, for example, in the range of 1-100%, 1-50%, or 1-25% of the baseline value. Such effects can be measured in one or more regions of the brain in which deposits are known to form or can be measured from an average of such regions. The total effect of treatment can be approximated by adding the percentage reduction relative to baseline to the increase in tau protein deposits that would otherwise occur in an average untreated patient.

Maintenance of tau protein deposits at an approximately constant level or even a small increase in tau protein deposits can also be an indication of response to treatment albeit a suboptimal response. Such responses can be compared with a time course of levels of tau protein deposits in patients with a particular tauopathy (e.g., Alzheimer's disease) that did not receive treatment, to determine whether the immunotherapy is having an effect in inhibiting further increases of tau protein deposits.

Monitoring of changes in tau protein deposits allows adjustment of the immunotherapy or other treatment regime in response to the treatment. PET monitoring provides an indication of the nature and extent of response to treatment. Then a determination can be made whether to adjust treatment and if desired treatment can be adjusted in response to the PET monitoring. PET monitoring thus allows for tau-directed immunotherapy or other treatment regime to be adjusted before other biomarkers, MRI or cognitive measures have detectably responded. A significant change means that comparison of the value of a parameter after treatment relative to basement provides some evidence that treatment has or has not resulted in a beneficial effect. In some instances, a change of values of a parameter in a patient itself provides evidence that treatment has or has not resulted in a beneficial effect. In other instances, the change of values, if any, in a patient, is compared with the change of values, if any, in a representative control population of patients not undergoing immunotherapy. A difference in response in a particular patient from the normal response in the control patient (e.g., mean plus variance of a standard deviation) can also provide evidence that an immunotherapy regime is or is not achieving a beneficial effect in a patient.

In some patients, monitoring indicates a detectable decline in tau protein deposits but that the level of tau protein deposits remains above normal. In such patients, if there are no unacceptable side effects, the treatment regime can be continued as is or even increased in frequency of administration and/or dose if not already at the maximum recommended dose.

If the monitoring indicates levels of tau protein deposits in a patient have already been reduced to normal, or near-normal, levels of tau protein deposits, the immunotherapy regime can be adjusted from one of induction (i.e., that reduces the level of tau protein deposits) to one of maintenance (i.e. that maintains tau protein deposits at an approximately constant level). Such a regime can be affected by reducing the dose and or frequency of administering immunotherapy.

In other patients, monitoring can indicate that immunotherapy is having some beneficial effect but a suboptimal effect. An optimal effect can be defined as a percentage reduction in the level of tau protein deposits within the top half or quartile of the change in tau protein deposits (measured or calculated over the whole brain or representative region(s) thereof in which tau protein deposits are known to form) experienced by a representative sample of tauopathy patients undergoing immunotherapy at a given time point after commencing therapy. A patient experiencing a smaller decline or a patient whose tau protein deposits remains constant or even increases, but to a lesser extent than expected in the absence of immunotherapy (e.g., as inferred from a control group of patients not administered immunotherapy) can be classified as experiencing a positive but suboptimal response. Such patients can optionally be subject to an adjustment of regime in which the dose and or frequency of administration of an agent is increased.

In some patients, tau protein deposits may increase in similar or greater fashion to tau deposits in patients not receiving immunotherapy. If such increases persist over a period of time, such as 18 months or 2 years, even after any increase in the frequency or dose of agents, immunotherapy can if desired be discontinued in favor of other treatments.

The foregoing description of diagnosing, monitoring, and adjusting treatment for tauopathies has been largely focused on using PET scans. However, any other technique for visualizing and/or measuring tau protein deposits that is amenable to the use of tau antibodies of the invention (e.g., a mouse, humanized, chimeric or veneered 3D6 antibody) can be used in place of PET scans to perform such methods.

Also provided are methods of detecting an immune response against tau in a patient suffering from or susceptible to diseases associated with tau. The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to tau in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting tau in a subject, for example, by measuring tau in a sample from a subject or by in vivo imaging of tau in a subject. Such methods are useful to diagnose or confirm diagnosis of diseases associated with tau, or susceptibility thereto. The methods can also be used on asymptomatic subjects. The presence of tau indicates susceptibility to future symptomatic disease. The methods are also useful for monitoring disease progression and/or response to treatment in subjects who have been previously diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

Biological samples obtained from a subject having, suspected of having, or at risk of having Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) can be contacted with the antibodies disclosed herein to assess the presence of tau. For example, levels of tau in such subjects may be compared to those present in healthy subjects. Alternatively, levels of tau in such subjects receiving treatment for the disease may be compared to those of subjects who have not been treated for Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). Some such tests involve a biopsy of tissue obtained from such subjects. ELISA assays may also be useful methods, for example, for assessing tau in fluid samples.

VII. Kits

The invention further provides kits (e.g., containers) comprising an antibody disclosed herein and related materials, such as instructions for use (e.g., package insert). The instructions for use may contain, for example, instructions for administration of the antibody and optionally one or more additional agents. The containers of antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

VIII. Other Applications

The antibodies can be used for detecting tau, or fragments thereof, in the context of clinical diagnosis or treatment or in research. For example, the antibodies can be used to detect the presence of tau in a biological sample as an indication that the biological sample comprises tau deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of tau) to the biological sample(s) is increased, decreased, or the same relative to antibody binding to the control sample(s). Increased binding of the antibody to the biological sample(s) relative to the control sample(s) indicates the presence of tau in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the tau in a biological sample to monitor and evaluate the efficacy of a therapeutic agent being used to treat a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP). A biological sample from a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) is evaluated to establish a baseline for the binding of the antibodies to the sample (i.e., a baseline for the presence of the tau in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of tau) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of tau) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of tau), it can be concluded that the therapeutic agent was effective in treating the Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP) in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), chronic traumatic encephalopathy (CTE), globular glial tauopathy (GGT), or progressive supranuclear palsy (PSP).

The antibodies can also be used as research reagents for laboratory research in detecting tau, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify tau, or binding partners of tau, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of tau Monoclonal Antibodies

Monoclonal antibodies against tau were generated as follows. Immunizations were performed with either recombinant N-terminally His-tagged 383 a.a. human tau (4R0N), containing a P301S mutation [immunogen A] or recombinant 383 a.a. human tau (4R0N), containing a P301S mutation, lacking an N-terminal His-tag [immunogen B]. Immunogens were emulsified in RIBI adjuvant.

Five week old female Balb/c mice were intraperitoneally immunized with 25 μg of immunogen A on day 0, and 10 μg of immunogen A each on days 7, 14, 21, 27, 34, 48, 55, and 62. Mice were immunized with 10 μg of immunogen B on days 76 and 90. On days 43 and 98, mice were bled and titered against immunogen A; on day 101 the animals with highest titers were boosted with a terminal immunization of 50 μg immunogen B, which was delivered ½ intraperitoneally and 12 intravenously. Fused hybridomas were screened via ELISA against both immunogens, and positives with the highest signal were epitope mapped (see Example 2). 3D6 reacted to peptides corresponding to amino acid residues 199-213 of SEQ ID NO:3 and to amino acid residues. 262-276 of SEQ ID NO:3 (following numbering of the longest CNS isoform of tau, this corresponds to amino acid residues 257-271 of SEQ ID NO:1 and to amino acid residues 320-334 of SEQ ID NO:1).

Example 2. Epitope Mapping of Antibody 3D6

A range of overlapping biotinylated peptides spanning the entire 383aa 4R0N human tau protein were used for mapping the murine 3D6 antibody. Additional peptides were used to model potential post-translational modifications of the C- and N-terminal ends of the protein.

Biotinylated peptides were bound to separate wells of a streptavidin-coated ELISA plate. The plate was blocked and treated with murine 3D6, followed by incubation with a horseradish peroxidase-conjugated anti-mouse antibody. After thorough washing, OPD was applied to the plate and allowed to develop. The plate was read at 450 nm absorbance. Background subtraction was performed with absorbance values from wells containing no primary antibody, and a threshold for positive binding was set to 0.2 absorbance units. Positive binding was detected for the peptide spanning amino acid residues 199-213 (of SEQ ID NO:3), and amino acid residues 262-276 (of SEQ ID NO:3). Using the numbering of the full-length 4R2N human tau protein (441 amino acids) these peptides correspond to amino acid residues 257-271 (of SEQ ID NO:1) and 320-334 (of SEQ ID NO:1). (FIG. 1)

Example 3. Design of Humanized 3D6 Antibodies

The starting point or donor antibody for humanization was the mouse antibody 3D6. The heavy chain variable amino acid sequence of mature m3D6 is provided as SEQ ID NO:7. The light chain variable amino acid sequence of mature m3D6 is provided as SEQ ID NO:11. The heavy chain Kabat/Chothia Composite CDR1, CDR2, and CDR3 amino acid sequences are provided as SEQ ID NOs:8-10, respectively. The light chain Kabat CDR1, CDR2, and CDR3 amino acid sequences are provided as SEQ ID NOs12-14 respectively. Kabat numbering is used throughout.

The variable kappa (Vk) of 3D6 belongs to mouse Kabat subgroup 2 which corresponds to human Kabat subgroup 2 and the variable heavy (Vh) to mouse Kabat subgroup 2c which corresponds to human Kabat subgroup 1 [Kabat E. A., et al., (1991), Sequences of Proteins of Immunological Interest, Fifth Edition. NIH Publication No. 91-3242]. 16 residue Chothia CDR-L1 belongs to canonical class 4, 7 residue Chothia CDR-L2 to class 1, 9 residue Chothia CDR-L3 to class 1 in Vk [Martin A. C, and Thornton J. M. (1996) J. Mol. Biol. 263:800-15. [Martin & Thornton, 1996]. 10 residue Chothia CDR-H1 belongs to class 1, 17 residue Chothia CDR-H2 to class 2 [Martin & Thornton, 1996]]. CDR-H3 has no canonical classes. A search was made over the protein sequences in the PDB database [Deshpande N, et al., (2005) Nucleic Acids Res. 33: D233-7.] to find structures which would provide a rough structural model of 3D6. To build up a Fv model of 3D6, a .structure of murine anti-pyroglutamate-Abeta antibody Fab c #24 (pdb code 5MYX) [Piechotta, A. et al., 2017, J Biol Chem. 292: 12713-12724] with a resolution of 1.4 A was used. It retained the same canonical structure for the loops as 3D6.

The frameworks of 3D6 VH share a high degree of sequence similarity with the corresponding regions of humanized 48G7 Fab PDB: 2RCS, designed by Wedemayer, G. J., et al. (1997; Science 276: 1665-1669). The variable domains of 3D6 and 48G7 fab also share identical lengths for the CDR-H1, H2 loops. Similarly, the frameworks of 3D6 VL share a high degree of sequence similarity with the corresponding regions of human antibody ARX71335 VL, cloned by Dafferner, A. J., et al. (2017; Direct Submission). The variable light domain of 3D6 and ARX71335 antibody also share identical lengths for the CDR-L1, L2 and L3 loops. Accordingly, the framework regions of 48G7 VH (2RCS-VH) and ARX71335 VL were chosen as the acceptor sequences for the CDRs of 3D6. A model of the 3D6 CDRs grafted onto the respective human frame-works for VH and VL was built and used as a guidance for further backmutations.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: world wide web. who.int/medicines/services/inn/BioRev2014.pdf) Residues were changed to align with corresponding human germ line sequence, where possible, to enhance humanness and to reduce potential immunogenicity. For humanized VLvb2 and VLvb3 variants, mutations were introduced to render the sequences more similar to human germ line gene IGKV2-30*02 (SEQ ID NO:27). For humanized VHvb2, VHvb3, VHvb4, VHvb5, VHvb6, and VHvb6 variants, mutations were introduced to render the sequences more similar to human germ line gene IGHV1-69-2*01 (SEQ ID NO:25)

Versions of hu3D6-VH and hu3D6-VL were designed to enable assessment of various framework residues for their contributions to antigen binding, thermostability, and immunogenicity, and for optimization of glycosylation, aggregation, N-term heterogeneity, thermostability, surface exposed charged patches, surface exposed charge patches, deamination, and proteinase susceptibility. The positions considered for mutation include those that:

- define the canonical CDR conformations (summarized in Martin, A. C. R. (2010) Protein sequence and structure analysis of antibody variable domains. In: Kontermann R and Dübel S (eds). *Antibody Engineering*. Heidelberg, Germany: Springer International Publishing AG),
- are within the Vernier zone (Foote J and Winter G. (1992) Antibody framework residues affecting the conformation of the hypervariable loops. *J Mol Biol.* 224(2): 487-99),
- localize to the VH/VL domain interface (summarized in Leger O J P and Saldanha J. (2000) Preparation of recombinant antibodies from immune rodent spleens and the design of their humanisation by CDR grafting. In: Shepherd P and Dean C (eds). *Monoclonal Antibodies: a Practical Approach*. Oxford, UK: Oxford University Press.),
- are susceptible to post-translational modifications, such as glycosylation or pyroglutamination,
- are occupied by residues that are predicted to clash with CDRs, according to the model of 3D6 CDRs grafted onto VH and VL frameworks, or
- are occupied by residues that are rare among sequenced human antibodies, where either the parental mouse 3D6 residue or some other residue is much more prevalent within human antibody repertoire.

Alignments of the murine 3D6 and various humanized antibodies are shown for the light chain variable regions (Table 4 and FIG. 3), and heavy chain variable regions (Table 3 and FIG. 2).

7 humanized heavy chain variable region variants and 3 humanized light chain variable region variants were constructed containing different permutations of substitutions: hu3D6VHvb1, hu3D6VHvb2, hu3D6VHvb3, hu3D6VHvb4, hu3D6Hvb5, hu3D6VHvb6, or hu3D6VHvb7 (SEQ ID NOs:76-80 and 90-91, respectively); and hu3D6VLvb1, hu3D6VLvb2, or hu3D6VLvb3 (SEQ ID NOs:83-85, respectively) (Tables 3 and 4). The exemplary humanized Vk and Vh designs, with backmutations and other mutations based on selected human frameworks, are shown in Tables 3 and 4, respectively. The bolded areas in Tables 3 and 4 indicate the CDRs as defined by Kabat/Chothia Composite. SEQ ID NOs:76-80 and SEQ ID NOs:90-91 contain backmutations and other mutations as shown in Table 5. The amino acids at positions in hu3D6VHvb1, hu3D6VHvb2, hu3D6VHvb3, hu3D6VHvb4, hu3D6VHvb5, hu3D6VHvb6, and hu3D6VHvb7 are listed in Table 6. The amino acids at positions in hu3D6VLvb1, hu3D6VLvb2, and hu3D6VLvb3 are listed in Table 7.

TABLE 3

| Kabat residue # | Linear residue # | FR or CDR | Mouse 3D6 VH (SEQ ID NO: 7) | IMGT# IGHV1-69-2*01 (SEQ ID NO: 25) | 2RCS-VH_huFrwk (SEQ ID NO: 75) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|---|---|
| 1 | 1 | Fr1 | E | E | Q | Q | E | E | E | E | E | E |
| 2 | 2 | Fr1 | V | V | V | V | V | V | V | V | V | V |
| 3 | 3 | Fr1 | Q | Q | Q | Q | Q | Q | Q | Q | Q | Q |
| 4 | 4 | Fr1 | L | L | L | L | L | L | L | L | L | L |
| 5 | 5 | Fr1 | Q | V | Q | Q | V | V | V | V | V | V |
| 6 | 6 | Fr1 | Q | Q | Q | Q | Q | Q | Q | Q | Q | Q |
| 7 | 7 | Fr1 | S | S | S | S | S | S | S | S | S | S |
| 8 | 8 | Fr1 | G | G | G | G | G | G | G | G | G | G |
| 9 | 9 | Fr1 | A | A | A | A | A | A | A | A | A | A |
| 10 | 10 | Fr1 | D | E | E | E | E | E | E | E | E | E |
| 11 | 11 | Fr1 | L | V | L | L | V | V | V | V | V | V |
| 12 | 12 | Fr1 | V | K | V | V | V | V | V | V | V | V |
| 13 | 13 | Fr1 | R | K | K | K | K | K | K | K | K | K |
| 14 | 14 | Fr1 | P | P | P | P | P | P | P | P | P | P |
| 15 | 15 | Fr1 | G | G | G | G | G | G | G | G | G | G |
| 16 | 16 | Fr1 | A | A | A | A | A | A | A | A | A | A |
| 17 | 17 | Fr1 | L | T | S | S | S | T | T | T | T | T |
| 18 | 18 | Fr1 | V | V | V | V | V | V | V | V | V | V |
| 19 | 19 | Fr1 | K | K | K | K | K | K | K | K | K | K |
| 20 | 20 | Fr1 | L | I | L | L | I | I | I | I | I | I |
| 21 | 21 | Fr1 | S | S | S | S | S | S | S | S | S | S |
| 22 | 22 | Fr1 | C | C | C | C | C | C | C | C | C | C |
| 23 | 23 | Fr1 | K | K | T | T | K | K | K | K | K | K |
| 24 | 24 | Fr1 | A | A | A | A | A | A | A | A | A | A |
| 25 | 25 | Fr1 | S | S | S | S | S | S | S | S | S | S |
| **26** | **26** | **CDR-H1** | **G** | **G** | **G** | **G** | **G** | **G** | **G** | **G** | **G** | **G** |
| **27** | **27** | **CDR-H1** | **F** | **Y** | **F** | **F** | **F** | **F** | **F** | **F** | **F** | **F** |

TABLE 3-continued

| Kabat residue # | Linear residue # | FR or CDR | Mouse 3D6 VH (SEQ ID NO: 7) | IMGT# IGHV1-69-2*01 (SEQ ID NO: 25) | 2RCS-VH_huFrwk (SEQ ID NO: 75) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|---|---|
| **28** | **28** | **CDR-H1** | **N** | **T** | **N** | **N** | **N** | **N** | **T** | **T** | **T** | **T** |
| **29** | **29** | **CDR-H1** | **I** | **F** | **I** | **I** | **I** | **I** | **I** | **I** | **I** | **I** |
| **30** | **30** | **CDR-H1** | **K** | **T** | **K** | **K** | **K** | **K** | **K** | **K** | **K** | **K** |
| **31** | **31** | **CDR-H1** | **D** | **D** | **D** | **D** | **D** | **D** | **D** | **D** | **D** | **D** |
| **32** | **32** | **CDR-H1** | **Y** | **Y** | **T** | **Y** | **Y** | **Y** | **Y** | **Y** | **Y** | **Y** |
| **33** | **33** | **CDR-H1** | **Y** | **Y** | **Y** | **Y** | **Y** | **Y** | **Y** | **K** | **Y** | **Y** |
| **34** | **34** | **CDR-H1** | **L** | **M** | **M** | **L** | **L** | **L** | **L** | **L** | **L** | **L** |
| **35** | **35** | **CDR-H1** | **H** | **H** | **H** | **H** | **H** | **H** | **H** | **H** | **H** | **H** |
| **35A** | | **CDR-H1** | — | | — | — | — | — | — | — | — | — |
| **35B** | | **CDR-H1** | — | | — | — | — | — | — | — | — | — |
| 36 | 36 | Fr2 | W | W | W | W | W | W | W | W | W | W |
| 37 | 37 | Fr2 | V | V | V | V | V | V | V | V | V | V |
| 38 | 38 | Fr2 | R | Q | K | K | R | R | R | R | R | R |
| 39 | 39 | Fr2 | Q | Q | Q | Q | Q | Q | Q | Q | Q | Q |
| 40 | 40 | Fr2 | R | A | R | R | R | R | R | R | R | R |
| 41 | 41 | Fr2 | P | P | P | P | P | P | P | P | P | P |
| 42 | 42 | Fr2 | E | G | E | E | G | G | G | G | G | G |
| 43 | 43 | Fr2 | Q | K | Q | Q | K | K | K | Q | K | K |
| 44 | 44 | Fr2 | G | G | G | G | G | G | G | G | G | G |
| 45 | 45 | Fr2 | L | L | L | L | L | L | L | L | L | L |
| 46 | 46 | Fr2 | E | E | E | E | E | E | E | E | E | E |
| 47 | 47 | Fr2 | W | W | W | W | W | W | W | W | W | W |
| 48 | 48 | Fr2 | I | M | I | I | I | I | I | I | I | I |
| 49 | 49 | Fr2 | G | G | G | G | G | G | G | G | G | G |
| **50** | **50** | **CDR-H2** | **W** | **L** | **R** | **W** | **W** | **W** | **W** | **W** | **W** | **W** |
| **51** | **51** | **CDR-H2** | **I** | **V** | **I** | **I** | **I** | **I** | **I** | **I** | **I** | **I** |
| **52** | **52** | **CDR-H2** | **D** | **D** | **D** | **D** | **D** | **D** | **D** | **D** | **D** | **D** |
| **52A** | **53** | **CDR-H2** | **P** | **P** | **P** | **P** | **P** | **P** | **P** | **P** | **P** | **P** |
| **52B** | | **CDR-H2** | — | — | — | — | — | — | — | — | — | — |
| **52C** | | **CDR-H2** | — | — | — | — | — | — | — | — | — | — |
| **53** | **54** | **CDR-H2** | **E** | **E** | **A** | **E** | **E** | **E** | **E** | **E** | **E** | **E** |
| **54** | **55** | **CDR-H2** | **N** | **D** | **N** | **N** | **N** | **N** | **N** | **D** | **D** | **D** |
| **55** | **56** | **CDR-H2** | **G** | **G** | **G** | **G** | **G** | **G** | **G** | **G** | **G** | **G** |
| **56** | **57** | **CDR-H2** | **D** | **E** | **N** | **D** | **D** | **D** | **D** | **E** | **E** | **E** |
| **57** | **58** | **CDR-H2** | **T** | **T** | **T** | **T** | **T** | **T** | **T** | **T** | **T** | **T** |
| **58** | **59** | **CDR-H2** | **V** | **I** | **K** | **V** | **V** | **I** | **I** | **I** | **V** | **V** |
| **59** | **60** | **CDR-H2** | **Y** | **Y** | **Y** | **Y** | **Y** | **Y** | **Y** | **Y** | **Y** | **Y** |
| **60** | **61** | **CDR-H2** | **D** | **A** | **D** | **D** | **D** | **D** | **D** | **D** | **D** | **D** |
| **61** | **62** | **CDR-H2** | **P** | **E** | **P** | **P** | **P** | **P** | **P** | **P** | **P** | **P** |
| **62** | **63** | **CDR-H2** | **K** | **K** | **K** | **K** | **K** | **K** | **K** | **K** | **K** | **K** |
| **63** | **64** | **CDR-H2** | **F** | **F** | **F** | **F** | **F** | **F** | **F** | **F** | **F** | **F** |
| **64** | **65** | **CDR-H2** | **Q** | **Q** | **Q** | **Q** | **Q** | **Q** | **Q** | **Q** | **Q** | **Q** |
| **65** | **66** | **CDR-H2** | **G** | **G** | **G** | **G** | **G** | **G** | **G** | **G** | **G** | **G** |
| 66 | 67 | Fr3 | K | R | K | K | R | R | R | R | R | R |
| 67 | 68 | Fr3 | A | V | A | A | A | A | V | V | V | V |
| 68 | 69 | Fr3 | T | T | T | T | T | T | T | T | T | T |
| 69 | 70 | Fr3 | I | I | I | I | I | I | I | I | I | I |
| 70 | 71 | Fr3 | T | T | T | T | T | T | T | T | T | T |
| 71 | 72 | Fr3 | A | A | A | A | A | A | A | A | A | A |
| 72 | 73 | Fr3 | D | D | D | D | D | D | D | D | D | D |
| 73 | 74 | Fr3 | T | T | T | T | T | T | T | T | T | T |
| 74 | 75 | Fr3 | S | S | S | S | S | S | S | S | S | S |
| 75 | 76 | Fr3 | S | T | S | S | T | T | T | T | T | T |
| 76 | 77 | Fr3 | N | D | N | N | D | D | D | D | D | D |
| 77 | 78 | Fr3 | T | T | T | T | T | T | T | T | T | T |
| 78 | 79 | Fr3 | A | A | A | A | A | A | A | A | A | A |
| 79 | 80 | Fr3 | Y | Y | Y | Y | Y | Y | Y | Y | Y | Y |
| 80 | 81 | Fr3 | L | M | L | L | L | M | M | M | M | M |
| 81 | 82 | Fr3 | Q | E | Q | Q | E | E | E | E | E | E |
| 82 | 83 | Fr3 | L | L | L | L | L | L | L | L | L | L |
| 82A | 84 | Fr3 | G | S | S | S | S | S | S | S | S | S |
| 82B | 85 | Fr3 | S | S | S | S | S | S | S | S | S | S |
| 82C | 86 | Fr3 | L | L | L | L | L | L | L | L | L | L |
| 83 | 87 | Fr3 | T | R | T | T | T | R | R | R | R | R |
| 84 | 88 | Fr3 | S | S | S | S | S | S | S | S | S | S |
| 85 | 89 | Fr3 | E | E | E | E | E | E | E | E | E | E |
| 86 | 90 | Fr3 | D | D | D | D | D | D | D | D | D | D |
| 87 | 91 | Fr3 | T | T | T | T | T | T | T | T | T | T |
| 88 | 92 | Fr3 | A | A | A | A | A | A | A | A | A | A |
| 89 | 93 | Fr3 | V | V | V | V | V | V | V | V | V | V |
| 90 | 94 | Fr3 | Y | Y | Y | Y | Y | Y | Y | Y | Y | Y |
| 91 | 95 | Fr3 | F | Y | Y | F | F | Y | Y | Y | F | Y |
| 92 | 96 | Fr3 | C | C | C | C | C | C | C | C | C | C |

TABLE 3-continued

| Kabat residue # | Linear residue # | FR or CDR | Mouse 3D6 VH (SEQ ID NO: 7) | IMGT# IGHV1-69-2*01 (SEQ ID NO: 25) | 2RCS-VH_ huFrwk (SEQ ID NO: 75) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|---|---|
| 93 | 97 | Fr3 | S | A | A | S | S | S | S | S | S | S |
| 94 | 98 | Fr3 | T | T | S | T | T | T | T | T | T | T |
| **95** | **99** | **CDR-H3** | **L** | | **Y** | **L** | **L** | **L** | **L** | **L** | **L** | **L** |
| **96** | | **CDR-H3** | — | | **Y** | — | — | — | — | — | — | — |
| **97** | | **CDR-H3** | — | | **G** | — | — | — | — | — | — | — |
| **98** | | **CDR-H3** | — | | — | — | — | — | — | — | — | — |
| **99** | | **CDR-H3** | — | | — | — | — | — | — | — | — | — |
| **100** | | **CDR-H3** | — | | — | — | — | — | — | — | — | — |
| **100A** | | **CDR-H3** | — | | — | — | — | — | — | — | — | — |
| **100B** | | **CDR-H3** | — | | — | — | — | — | — | — | — | — |
| **100C** | | **CDR-H3** | — | | — | — | — | — | — | — | — | — |
| **100D** | | **CDR-H3** | — | | — | — | — | — | — | — | — | — |
| **100E** | | **CDR-H3** | — | | — | — | — | — | — | — | — | — |
| **100F** | | **CDR-H3** | — | | — | — | — | — | — | — | — | — |
| **100G** | | **CDR-H3** | — | | — | — | — | — | — | — | — | — |
| **100H** | | **CDR-H3** | — | | | — | — | — | — | — | — | — |
| **100I** | | **CDR-H3** | — | | | — | — | — | — | — | — | — |
| **100J** | | **CDR-H3** | — | | | — | — | — | — | — | — | — |
| **100K** | | **CDR-H3** | — | | | — | — | — | — | — | — | — |
| **101** | **100** | **CDR-H3** | **D** | **W** | **I** | **D** | **D** | **D** | **D** | **D** | **D** | **D** |
| **102** | **101** | **CDR-H3** | **F** | **H** | **Y** | **F** | **F** | **F** | **F** | **F** | **F** | **F** |
| 103 | 102 | Fr4 | W | W | W | W | W | W | W | W | € | W |
| 104 | 103 | Fr4 | G | G | G | G | G | G | G | G | G | G |
| 105 | 104 | Fr4 | Q | Q | Q | Q | Q | Q | Q | Q | Q | Q |
| 106 | 105 | Fr4 | G | G | G | G | G | G | G | G | G | G |
| 107 | 106 | Fr4 | T | T | T | T | T | T | T | T | T | T |
| 108 | 107 | Fr4 | T | L | T | T | L | L | L | L | L | L |
| 109 | 108 | Fr4 | L | V | L | L | V | V | V | V | V | V |
| 110 | 109 | Fr4 | T | T | T | T | T | T | T | T | T | T |
| 111 | 110 | Fr4 | V | V | V | V | V | V | V | V | V | V |
| 112 | 111 | Fr4 | S | S | S | S | S | S | S | S | S | S |
| 113 | 112 | Fr4 | S | S | S | S | S | S | S | S | S | S |

TABLE 4

| Kabat residue # | Linear residue # | FR or CDR | Mouse VL 3D6 (SEQ ID NO: 11) | ARX71335-VL_huFrwk (SEQ ID NO: 82) | IMGT#IGKV2-30*02 (SEQ ID NO: 27) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|---|---|
| 1 | 1 | Fr1 | D | D | D | D | D | D |
| 2 | 2 | Fr1 | V | V | V | V | V | V |
| 3 | 3 | Fr1 | V | V | V | V | V | V |
| 4 | 4 | Fr1 | M | M | M | M | M | M |
| 5 | 5 | Fr1 | T | T | T | T | T | T |
| 6 | 6 | Fr1 | Q | Q | Q | Q | Q | Q |
| 7 | 7 | Fr1 | T | T | S | T | S | S |
| 8 | 8 | Fr1 | P | P | P | P | P | P |
| 9 | 9 | Fr1 | L | L | L | L | L | L |
| 10 | 10 | Fr1 | T | T | S | T | S | S |
| 11 | 11 | Fr1 | L | L | L | L | L | L |
| 12 | 12 | Fr1 | S | S | P | S | S | S |
| 13 | 13 | Fr1 | V | V | V | V | V | V |
| 14 | 14 | Fr1 | T | T | T | T | T | T |
| 15 | 15 | Fr1 | I | I | L | I | L | L |
| 16 | 16 | Fr1 | G | G | G | G | G | G |
| 17 | 17 | Fr1 | Q | Q | Q | Q | Q | E |
| 18 | 18 | Fr1 | P | P | P | P | P | P |
| 19 | 19 | Fr1 | A | A | A | A | A | A |
| 20 | 20 | Fr1 | S | S | S | S | S | S |
| 21 | 21 | Fr1 | I | I | I | I | I | I |
| 22 | 22 | Fr1 | S | S | S | S | S | S |
| 23 | 23 | Fr1 | C | C | C | C | C | C |
| **24** | **24** | **CDR-L1** | **K** | **K** | **R** | **K** | **K** | **R** |
| **25** | **25** | **CDR-L1** | **S** | **S** | **S** | **S** | **S** | **S** |
| **26** | **26** | **CDR-L1** | **S** | **S** | **S** | **S** | **S** | **S** |
| **27** | **27** | **CDR-L1** | **Q** | **Q** | **Q** | **Q** | **Q** | **Q** |
| **27A** | **28** | **CDR-L1** | **S** | **S** | **S** | **S** | **S** | **S** |
| **27B** | **29** | **CDR-L1** | **L** | **L** | **L** | **L** | **L** | **L** |

TABLE 4-continued

| Kabat residue # | Linear residue # | FR or CDR | Mouse VL 3D6 (SEQ ID NO: 11) | ARX71335-VL_huFrwk (SEQ ID NO: 82) | IMGT#IGKV2-30*02 (SEQ ID NO: 27) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|---|---|
| **27C** | **30** | **CDR-L1** | **L** | **L** | **V** | **L** | **L** | **L** |
| **27D** | **31** | **CDR-L1** | **D** | **Y** | **H** | **D** | **D** | **D** |
| **27E** | **32** | **CDR-L1** | **S** | **S** | **S** | **S** | **S** | **S** |
| **27F** | | **CDR-L1** | — | | | | | |
| **28** | **33** | **CDR-L1** | **D** | **N** | **D** | **D** | **D** | **D** |
| **29** | **34** | **CDR-L1** | **G** | **G** | **G** | **G** | **G** | **G** |
| **30** | **35** | **CDR-L1** | **K** | **K** | **N** | **K** | **K** | **K** |
| **31** | **36** | **CDR-L1** | **T** | **T** | **T** | **T** | **T** | **T** |
| **32** | **37** | **CDR-L1** | **Y** | **Y** | **Y** | **Y** | **Y** | **Y** |
| **33** | **38** | **CDR-L1** | **L** | **L** | **L** | **L** | **L** | **L** |
| **34** | **39** | **CDR-L1** | **N** | **N** | **N** | **N** | **N** | **N** |
| 35 | 40 | Fr2 | W | W | W | W | W | W |
| 36 | 41 | Fr2 | L | L | F | L | L | L |
| 37 | 42 | Fr2 | L | L | Q | L | L | Q |
| 38 | 43 | Fr2 | Q | Q | Q | Q | Q | Q |
| 39 | 44 | Fr2 | R | R | R | R | R | R |
| 40 | 45 | Fr2 | P | P | P | P | P | P |
| 41 | 46 | Fr2 | G | G | G | G | G | G |
| 42 | 47 | Fr2 | Q | Q | Q | Q | Q | Q |
| 43 | 48 | Fr2 | S | S | S | S | S | S |
| 44 | 49 | Fr2 | P | P | P | P | P | P |
| 45 | 50 | Fr2 | K | K | R | K | K | R |
| 46 | 51 | Fr2 | R | R | R | R | R | R |
| 47 | 52 | Fr2 | L | L | L | L | L | L |
| 48 | 53 | Fr2 | I | I | I | I | I | I |
| 49 | 54 | Fr2 | Y | Y | Y | Y | Y | Y |
| **50** | **55** | **CDR-L2** | **L** | **L** | **K** | **L** | **L** | **L** |
| **51** | **56** | **CDR-L2** | **V** | **V** | **V** | **V** | **V** | **V** |
| **52** | **57** | **CDR-L2** | **S** | **S** | **S** | **S** | **S** | **S** |
| **53** | **58** | **CDR-L2** | **K** | **K** | **N** | **K** | **K** | **K** |
| **54** | **59** | **CDR-L2** | **L** | **L** | **R** | **L** | **L** | **L** |
| **55** | **60** | **CDR-L2** | **D** | **D** | **D** | **D** | **D** | **D** |
| **56** | **61** | **CDR-L2** | **S** | **S** | **S** | **S** | **S** | **S** |
| 57 | 62 | Fr3 | G | G | G | G | G | G |
| 58 | 63 | Fr3 | V | V | V | V | V | V |
| 59 | 64 | Fr3 | P | P | P | P | P | P |
| 60 | 65 | Fr3 | D | D | D | D | D | D |
| 61 | 66 | Fr3 | R | R | R | R | R | R |
| 62 | 67 | Fr3 | F | F | F | F | F | F |
| 63 | 68 | Fr3 | T | S | S | S | S | S |
| 64 | 69 | Fr3 | G | G | G | G | G | G |
| 65 | 70 | Fr3 | S | S | S | S | S | S |
| 66 | 71 | Fr3 | G | G | G | G | G | G |
| 67 | 72 | Fr3 | S | S | S | S | S | S |
| 68 | 73 | Fr3 | G | G | G | G | G | G |
| 69 | 74 | Fr3 | T | T | T | T | T | T |
| 70 | 75 | Fr3 | D | D | D | D | D | D |
| 71 | 76 | Fr3 | F | F | F | F | F | F |
| 72 | 77 | Fr3 | T | T | T | T | T | T |
| 73 | 78 | Fr3 | L | L | L | L | L | L |
| 74 | 79 | Fr3 | K | K | K | K | K | K |
| 75 | 80 | Fr3 | I | I | I | I | I | I |
| 76 | 81 | Fr3 | S | S | S | S | S | S |
| 77 | 82 | Fr3 | R | R | R | R | R | R |
| 78 | 83 | Fr3 | V | V | V | V | V | V |
| 79 | 84 | Fr3 | E | E | E | E | E | E |
| 80 | 85 | Fr3 | A | A | A | A | A | A |
| 81 | 86 | Fr3 | E | E | E | E | E | E |
| 82 | 87 | Fr3 | D | D | D | D | D | D |
| 83 | 88 | Fr3 | L | L | V | L | V | V |
| 84 | 89 | Fr3 | G | G | G | G | G | G |
| 85 | 90 | Fr3 | V | V | V | V | V | V |
| 86 | 91 | Fr3 | Y | H | Y | H | Y | Y |
| 87 | 92 | Fr3 | Y | Y | Y | Y | Y | Y |
| 88 | 93 | Fr3 | C | C | C | C | C | C |
| **89** | **94** | **CDR-L3** | **W** | **E** | **M** | **W** | **W** | **W** |
| **90** | **95** | **CDR-L3** | **Q** | **Q** | **Q** | **Q** | **Q** | **Q** |
| **91** | **96** | **CDR-L3** | **G** | **G** | **G** | **G** | **G** | **G** |
| **92** | **97** | **CDR-L3** | **T** | **T** | **T** | **T** | **T** | **T** |
| **93** | **98** | **CDR-L3** | **H** | **H** | **H** | **H** | **H** | **H** |
| **94** | **99** | **CDR-L3** | **F** | **F** | **W** | **F** | **F** | **F** |
| **95** | **100** | **CDR-L3** | **P** | **P** | **P** | **P** | **P** | **P** |
| **95A** | | **CDR-L3** | — | — | — | — | — | — |
| **95B** | | **CDR-L3** | — | — | — | — | — | — |

TABLE 4-continued

| Kabat residue # | Linear residue # | FR or CDR | Mouse VL 3D6 (SEQ ID NO: 11) | ARX71335-VL_huFrwk (SEQ ID NO: 82) | IMGT#IGKV2-30*02 (SEQ ID NO: 27) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|---|---|
| **95C** | | **CDR-L3** | — | — | — | — | — | — |
| **95D** | | **CDR-L3** | — | — | — | — | — | — |
| **95E** | | **CDR-L3** | — | — | — | — | — | — |
| **95F** | | **CDR-L3** | — | — | — | — | — | — |
| **96** | **101** | **CDR-L3** | **Y** | **L** | **Y** | **Y** | **Y** | **Y** |
| **97** | **102** | **CDR-L3** | **T** | **T** | **T** | **T** | **T** | **T** |
| 98 | 103 | Fr4 | F | F | F | F | F | F |
| 99 | 104 | Fr4 | G | G | G | G | G | G |
| 100 | 105 | Fr4 | G | A | Q | A | A | Q |
| 101 | 106 | Fr4 | G | G | G | G | G | G |
| 102 | 107 | Fr4 | T | T | T | T | T | T |
| 103 | 108 | Fr4 | K | K | K | K | K | K |
| 104 | 109 | Fr4 | L | L | L | L | L | L |
| 105 | 110 | Fr4 | E | E | E | E | E | E |
| 106 | 111 | Fr4 | I | L | I | L | I | I |
| 106A | 112 | Fr4 | K | K | K | K | K | K |

TABLE 5

$V_H$, $V_L$ Backmutations and Other Mutations for Humanized 3D6

| $V_H$ or $V_L$ Variant | $V_H$ or $V_L$ Exon Acceptor Sequence | Changes from Acceptor Framework (or CDR) Residues (based on Kabat/Chothia Composite CDRs) |
|---|---|---|
| Hu3D6VHvb1 (SEQ ID NO: 76) | PDB ID 2RCS-VH_huFrwk (SEQ ID NO: 75) IMGT# IGHV1-69-2*01 (SEQ (ID NO: 25) | H91, H93, H94 |
| Hu3D6VHvb2 (SEQ ID NO: 77) | PDB ID 2RCS-VH_huFrwk (SEQ ID NO: 75) IMGT# IGHV1-69-2*01 (SEQ (ID NO: 25) | H1, H5, H11, H20, H23, H38, H42, H43, H66, H67, H75, H76, H81, H91, H93, H94 |
| Hu3D6VHvb3 (SEQ ID NO: 78) | PDB ID 2RCS-VH_huFrwk (SEQ ID NO: 75) IMGT# IGHV1-69-2*01 (SEQ (ID NO: 25) | H1, H5, H11, H17, H20, H23, H38, H42, H43, H58, H66, H67, H75, H76, H80, H81, H83, H93, H94, H108, H109 |
| Hu3D6VHvb4 (SEQ ID NO: 79) | PDB ID 2RCS-VH_huFrwk (SEQ ID NO: 75) IMGT# IGHV1-69-2*01 (SEQ (ID NO: 25) | H1, H5, H11, H17, H20, H23, H28, H38, H42, H43, H58, H66, H67, H75, H76, H80, H81, H83, H93, H94, H108, H109 |
| Hu3D6VHvb5 (SEQ ID NO: 80) | PDB ID 2RCS-VH_huFrwk (SEQ ID NO: 75) IMGT# IGHV1-69-2*01 (SEQ (ID NO: 25) | H1, H5, H11, H17, H20, H23, H28, H38, H42, H43, H54, H56, H58, H66, H67, H75, H76, H80, H81, H83, H93, H94, H108, H109 |
| Hu3D6 VHvb6 (SEQ ID NO: 90) | PDB ID 2RCS-VH_huFrwk (SEQ ID NO: 75) IMGT# IGHV1-69-2*01 (SEQ (ID NO: 25) | H1, H5, H11, H17, H20, H23, H28, H38, H42, H43, H54, H56, H66, H67, H75, H76, H80, H81, H83, H91, H93, H94, H108, H109 |
| Hu3D6 VHvb7 (SEQ ID NO: 91) | PDB ID 2RCS-VH_huFrwk (SEQ ID NO: 75) IMGT# IGHV1-69-2*01 (SEQ (ID NO: 25) | H1, H5, H11, H17, H20, H23, H28, H38, H42, H43, H54, H56, H66, H67, H75, H76, H80, H81, H83, H93, H94, H108, H109 |
| Hu3D6VLvb1 (SEQ ID NO: 83) | PDB ID ARX71335-VL_huFrwk (SEQ ID NO: 82); IMGT#IGKV2-30*02 (SEQ (ID NO: 27) | |
| Hu3D6VLvb2 (SEQ ID NO: 84) | PDB ID ARX71335-VL_huFrwk (SEQ ID NO: 82); IMGT#IGKV2-30*02 (SEQ (ID NO: 27) | L7, L10, L15, L83, L86, L106 |
| Hu3D6VLvb3 (SEQ ID NO: 85) | PDB ID ARX71335-VL_huFrwk (SEQ ID NO: 82); IMGT#IGKV2-30*02 (SEQ (ID NO: 27) | L7, L10, L15, L17, L24, L37, L45, L83, L86, L100, L106 |

TABLE 6

Kabat Numbering of Framework (or CDR) Residues (based on Kabat/Chothia Composite CDRs) for Backmutations and Other Mutations in Heavy Chains of Humanized 3D6 Antibodies

| Residue | 2RCS-VH_ huFrwk (SEQ ID NO: 75) | (Heavy Chain) IMGT# IGHV1-69-2*01 (SEQ ID NO: 25) | Mouse 3D6 (SEQ ID NO: 7) | Hu3D6 VHvb1 (SEQ ID NO: 76) | Hu3D6 VHvb2 (SEQ ID NO: 77) | Hu3D6 VHvb3 (SEQ ID NO: 78) | Hu3D6 VHvvb4 (SEQ ID NO: 79) | Hu3D6 VHvb5 (SEQ ID NO: 80) | Hu3D6 VHvb6 (SEQ ID NO: 90) | Hu3D6 VHvb7 (SEQ ID NO: 91) |
|---|---|---|---|---|---|---|---|---|---|---|
| H1 | Q | E | E | Q | E | E | E | E | E | E |
| H5 | Q | V | Q | Q | V | V | V | V | V | V |
| H11 | L | V | L | L | V | V | V | V | V | V |
| H17 | S | T | L | S | S | T | T | T | T | T |
| H20 | L | I | L | L | I | I | I | I | I | I |
| H23 | T | K | K | T | K | K | K | K | K | K |
| H28 | N | T | N | N | N | N | T | T | T | T |
| H38 | K | Q | R | K | R | R | R | R | R | R |
| H42 | E | G | E | E | G | G | G | G | G | G |
| H43 | Q | K | Q | Q | K | K | K | K | K | K |
| H54 | N | D | N | N | N | N | N | D | D | D |
| H56 | N | E | D | D | D | D | D | E | E | E |
| H58 | K | I | V | V | V | I | I | I | V | V |
| H66 | K | R | K | K | R | R | R | R | R | R |
| H67 | A | V | A | A | A | A | V | V | V | V |
| H75 | S | T | S | S | T | T | T | T | T | T |
| H76 | N | D | N | N | D | D | D | D | D | D |
| H80 | L | M | L | L | L | M | M | M | M | M |
| H81 | Q | E | Q | Q | E | E | E | E | E | E |
| H83 | T | R | T | T | T | R | R | R | R | R |
| H91 | Y | Y | F | F | F | Y | Y | Y | F | Y |
| H93 | A | A | S | S | S | S | S | S | S | S |
| H94 | S | T | T | T | T | T | T | T | T | T |
| H108 | T | L | T | T | L | L | L | L | L | L |
| H109 | L | V | L | L | V | V | V | V | V | V |

TABLE 7

Kabat Numbering of Framework Residues (based on Kabat/Chothia Composite CDRs) for Backmutations and Other Mutations in Light Chains of Humanized 3D6 Antibodies

| Residue | ARX71335-VL huFrwk (SEQ ID NO: 82) | (Light Chain) IMGT#IGKV2-30*02 (SEQ ID NO: 27) | Mouse 3D6 (SEQ ID NO: 11) | Hu3D6VLvb1 (SEQ ID NO: 83) | Hu3D6VLvb2 (SEQ ID NO: 84) | Hu3D6VLvb3 (SEQ ID NO: 85) |
|---|---|---|---|---|---|---|
| L7 | T | S | T | T | S | S |
| L10 | T | S | T | T | S | S |
| L15 | I | L | I | I | L | L |
| L17 | Q | Q | Q | Q | Q | E |
| L24 | K | R | K | K | K | R |
| L37 | L | Q | L | L | L | Q |
| L45 | K | R | K | K | K | R |
| L83 | L | V | L | L | V | V |
| L86 | H | Y | Y | H | Y | Y |
| L100 | A | Q | G | A | A | Q |
| L106 | L | I | I | L | I | I |

Positions at which canonical, vernier, or interface residues differ between mouse and human acceptor sequences are candidates for substitution. Examples of canonical/CDR interacting residues include Kabat residues H54 and H94 in Table 3. Examples of vernier residues include Kabat residues H28, H67, H93, and H94 in Table 3. Examples of interface/packing (VH+VL) residues include Kabat residues H91 and H93 in Table 3.

The rationales for selection of the positions indicated in Table 3 in the heavy chain variable region as candidates for substitution are as follows.

Heavy Chain Variable Regions hu3D6VHvb1 consists of the CDR-H1, H2, and H3 loops of 3D6-VH grafted onto the framework of 48G7-VH (RCS-VH), with backmutations at positions H91 (Y91F), H93 (A93S), and H94 (S94T).

hu3D6VHvb2 reverts all framework substitutions at positions that are key for defining the Chothia canonical classes, are part of the Vernier zone, or localize to the VH/VL domain interface or contribute to structural stability. 3D6-VH_vb2 incorporates backmutations or substitutions Q1E, Q5V, L11V, L20I, T23K, K38R, E42G, Q43K, K66R, S75T, N76D, Q81E, Y91F, A93S, S94T T108L, and L109V, to enable assessment of these positions' contributions to antigen-binding affinity and immunogenicity.

hu3D6VHvb3, hu3D6VHvb4, hu3D6VHvb5, hu3D6VHvb6, and hu3D6VHvb7 consists of further substitutions and either add to antibody stability and/or for optimization of glycosylation, aggregation, N-term heterogeneity, thermostability, surface exposed charged patches, surface exposed charge patches, deamination, and proteinase susceptibility.

Q1E: is a stability enhancing mutation to mitigate pyroglutamate formation potential (Liu, supra.)

Q5V: is a frequency-based and germ line-aligning mutation. Val is most frequent in human sequences at this position. Val is in human germ line gene IMGT #IGHV1-69-2*01 (SEQ (ID NO: 25) at this position.

L11V: is a germ line-aligning mutation. Val is in human germ line gene IMGT #IGHV1-69-2*01 (SEQ (ID NO: 25) at this position.

S17T: is a germ line-aligning mutation. Thr is in human germ line gene IMGT #IGHV1-69-2*01 (SEQ (ID NO: 25) at this position.

L20I: is a germ line-aligning mutation. Ile is in human germ line gene IMGT #IGHV1-69-2*01 (SEQ (ID NO: 25) at this position.

T23K: is a frequency-based and germ line-aligning mutation. Lys is more frequent at this position. Lys is in human germ line gene IMGT #IGHV1-69-2*01 (SEQ (ID NO: 25) at this position.

N28T: This is a CDR-H1 residue substitution to Thr.

K38R: is a frequency-based back-mutation. Arg is most frequent at this position. Arg at this position is predicted to make two H-bonds with Glu 46 in addition to one H-bond each with Asp86 and Tyr 90 in heavy chain; therefore, Arg substitution may enhance stability over Lys at this position.

E42G: is a frequency-based and germ line-aligning mutation. Gly is in human germ line gene IMGT #IGHV1-69-2*01 (SEQ (ID NO: 25) at this position. Gly is most frequent at this position. Gly substitution is predicted not to affect stability.

Q43K: Lys side chain at this position is predicted to make H-bond with G42 besides main chain making H-bonds with Gln 39 and Arg 40, thereby Lys substitution may enhance stability over Q at this position.

N54D and D56E are substitutions of CDR residues and are predicted to be non-antigen contact positions as per homology model. N54D and D56E substitutions are predicted to stabilize antibody structure.

V58I: is a substitution of a CDR-H2 residue. Germline gene IMGT #IGHV1-69-2*01 (SEQ (ID NO: 25) has Ile at this position. This residue is predicted not to contact antigen.

K66R: Arg at this position is predicted to make H-bonds with Ser 82a and Thr 83 in addition to making H-bond and salt-bridge with Asp 86.

A67V: is a substitution of a Vernier zone residue. Germ line gene IMGT #IGHV1-69-2*01 (SEQ (ID NO: 25) has Val at this position.

S75T: Ser at this position is predicted to make H-bond with Asp 72 and Tyr 76. Thr at this position is predicted to also make these contacts but being surface exposed residue Thr may enhance antibody stability.

N76D: Asp is a germ line-aligning mutation. Asp is in human germ line gene IMGT #IGHV1-69-2*01 (SEQ (ID NO: 25) at this position.

L80M: Met is a germ line-aligning mutation. Met is in human germ line gene IMGT #IGHV1-69-2*01 (SEQ (ID NO: 25) at this position.

Q81E: Glu is predicted to make H-bond plus salt-bridge with K19 hence Glu at this position make enhance antibody stability.

T83R to enhance thermostability and to increase humanness. Arg is a germ-line aligning mutation. Arg is in human germ line gene IMGT #IGHV1-69-2*01 (SEQ (ID NO: 25) at this position. Arg is most frequent at this position.

F91Y: is mutation of an interface residue, and is a frequency-based back-mutation. Tyr is typically at this position, and may enhance antibody stability.

A93S: is a back-mutation of a Vernier zone and interface zone residue.

S94T: is a back-mutation of a Chothia defined canonical structural residue and vernier residue.

T108L: Leu is a germ line-aligning mutation. Leu is in human germ line gene IMGT #IGHV1-69-2*01 (SEQ (ID NO: 25) at this position. Leu at this position is predicted to make the antibody less immunogenic and to have no impact on antibody stability.

L109V: is a frequency-based mutation. Val is most frequent at this position.

The rationales for selection of the positions indicated in Table 4 in the light chain variable region as candidates for substitution are as follows.

Kappa Light Chain Variable Regions hu3D6VLvb1 consists of the CDR-L1, L2, and L3 loops of 3D6-VL grafted onto the framework of ARX71335 VL.

hu3D6VLvb2 and hu3D6VLvb3 reverts all framework substitutions at positions that are key for defining the Chothia canonical classes, are part of the Vernier zone, or locate to the VH/VL domain interface. Hu3D6-VLvb2 & Hu3D6-VLvb3 also include substitutions that contribute to structural stability hu3D6-VL_vb2 incorporates backmutations T7S, I15L, L83V, H86Y and L106I, to enable assessment of these positions' contributions to antigen-binding affinity and immunogenicity.

Hu3D6-VL_vb3 all substitutions mentioned for vb2 along with additional changes at Q17E, K24R, L37Q, K45R, and L106I T7S: is a germ line-aligning mutation. Ser is in human germ line gene IGKV2-30*02 (SEQ (ID NO: 27) at this position.

T10S: is a frequency-based and germ line-aligning mutation. Ser is frequent at this position. Ser is in human germ line gene IGKV2-30*02 (SEQ (ID NO: 27) at this position.

I15L: is a germline-aligning mutation. Leu is in human germ line gene IGKV2-30*02 (SEQ (ID NO: 27) at this position.

Q17E: Glu at this position is predicted to make H-bond with T14 and salt-bridge with Lys 107, both light chain residues, and to enhance antibody stability.

K24R: is a mutation of a CDR residue. Both Lys and Arg are predicted to make H-bond and salt-bridge with Asp 70 in the light chain. Arg is predicted to fit better in the conformation. Arg is also a germ line-aligning mutation. Arg is in human germ line gene IGKV2-30*02 (SEQ (ID NO: 27) at this position.

L37Q: This is predicted to be a deep buried residue, Leu is not predicted to interact with surrounding residues, whereas, Gln is predicted to make H-bonds with Q38 and Asp 82 in the light chain. Gln is also a germ line-aligning mutation. Gln is in human germ line gene IGKV2-30*02 (SEQ (ID NO: 27) at this position.

K45R: Although, Lys is predicted to make H-bonds with S56 and Gly 57; Arg's predicted interaction with neighboring residues is much more extensive as it is predicted to form salt-bridges with D55, H-bond with Arg46 and double H-bonds with S56. Arg is also a germ line-aligning mutation. Arg is in human germ line gene IGKV2-30*02 (SEQ (ID NO: 27) at this position.

L83V: This is a frequency-based mutation of a residue predicted to be surface exposed. Val is also a germ line-aligning mutation. Val is in human germ line gene IGKV2-30*02 (SEQ (ID NO: 27) at this position.

H86Y: Murine 3D6 VL has Tyr at this position. Tyr is also the most frequent residue at this position.

A100Q: Ala is rare at this position. Ala is predicted to be surface-exposed residue and is not predicted to interact surrounding residues. Gln is most frequent at this position. and is also a germline-aligning mutation. Gln is in human germ line gene IGKV2-30*02 (SEQ (ID NO: 27) at this position. Gln is predicted to make H-bond with Ser 7 stabilizing intra-chain.

L106I: is a frequency-based and germ line-aligning mutation. Ile is most frequent at this position. Ile is in human germ line gene IGKV2-30*02 (SEQ (ID NO: 27) at this position.

The designs based on these human frameworks were:

| heavy chain variable regions |
|---|
| >hu3D6VHvb1<br>(SEQ ID NO: 76)<br>QVQLQQSGAELVKPGASVKLSCTASGFNIKDYYLHWVKQRPEQGLEWIGWID<br>PENGDTVYDPKFQGKATITADTSSNTAYLQLSSLTSEDTAVYFCSTLDFWGQ<br>GTTLTVSS |
| >hu3D6VHvb2<br>(SEQ ID NO: 77)<br>EVQLVQSGAEVVKPGASVKISCKASGFNIKDYYLHWVRQRPGKGLEWIGWID<br>PENGDTVYDPKFQGRATITADTSTDTAYLELSSLTSEDTAVYFCSTLDFWGQ<br>GTLVTVSS |
| >hu3D6VHvb3<br>(SEQ ID NO: 78)<br>EVQLVQSGAEVVKPGATVKISCKASGFNIKDYYLHWVRQRPGKGLEWIGWID<br>PENGDTIYDPKFQGRATITADTSTDTAYMELSSLRSEDTAVYYCSTLDFWGQ<br>GTLVTVSS |
| hu3D6VHvb4<br>(SEQ ID NO: 79)<br>EVQLVQSGAEVVKPGATVKISCKASGFTIKDYYLHWVRQRPGKGLEWIGWID<br>PENGDTIYDPKFQGRVTITADTSTDTAYMELSSLRSEDTAVYYCSTLDFWGQ<br>GTLVTVSS |
| >hu3D6VHvb5<br>(SEQ ID NO: 80)<br>EVQLVQSGAEVVKPGATVKISCKASGFTIKDYYLHWVRQRPGKGLEWIGWID<br>PEDGETIYDPKFQGRVTITADTSTDTAYMELSSLRSEDTAVYYCSTLDFWGQ<br>GTLVTVSS |
| >hu3D6VHvb6<br>(SEQ ID NO: 90)<br>EVQLVQSGAEVVKPGATVKISCKASGFTIKDYYLHWVRQRPGKGLEWIGWID<br>PEDGETVYDPKFQGRVTITADTSTDTAYMELSSLRSEDTAVYFCSTLDFWGQ<br>GTLVTVSS |
| >hu3D6VHvb7<br>(SEQ ID NO: 91)<br>EVQLVQSGAEVVKPGATVKISCKASGFTIKDYYLHWVRQRPGKGLEWIGWID<br>PEDGETVYDPKFQGRVTITADTSTDTAYMELSSLRSEDTAVYYCSTLDFWGQ<br>GTLVTVSS |

-continued

| kappa light chain variable regions |
|---|
| hu3D6VLvb1 (SEQ ID NO: 83) DVVMTQTPLTLSVTIGQPASISCKSSQSLLDSDGKTYLNWLLQRPGQSPKRL IYLVSKLDSGVPDRFSGSGSGTDFTLKISRVEAEDLGVHYCWQGTHEPYTFG AGTKLELK |
| >hu3D6VLvb2 (SEQ ID NO: 84) DVVMTQSPLSLSVTLGQPASISCKSSQSLLDSDGKTYLNWLLQRPGQSPKRL IYLVSKLDSGVPDRFSGSGSGTDFTLKISRVEAEDVGVYYCWQGTHFPYTFG AGTKLEIK |
| >hu3D6VLvb3 (SEQ ID NO: 85) DVVMTQSPLSLSVTLGEPASISCRSSQSLLDSDGKTYLNWLQQRPGQSPRRL IYLVSKLDSGVPDRFSGSGSGTDFTLKISRVEAEDVGVYYCWQGTHEPYTFG QGTKLEIK |

Humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682).

Example 4. Mouse Monoclonal Antibodies Bind Tau in ELISA Assays

Methods: Indirect ELISA: 96-well polystyrene plates were coated with capture antibodies anti-6×His (FIG. 4A) or polyclonal anti-tau (Dako #A0024, FIG. 4B) suspended in 1×PBS for 2 hr at RT or 16 hr at 4° C. Coating was removed, and plates were blocked for 1 hr with 1% BSA in 1×PBS, followed by incubation with human recombinant tau, either with (FIG. 5A) or without (FIG. 4B) a polyhistidine tag at the N-terminus of the protein. After washing, plates were incubated with indicated antibodies, washed, and incubated with HRP-conjugated goat anti-mouse secondary antibody. Plates were developed with TMB, and $A_{450}$ was measured with a plate reader.

Sandwich ELISA: 96-well polystyrene plates were coated with anti-mouse antibodies in 1×PBS for 2 hr at RT or 16 hr at 4° C. Coating was removed, and plates were blocked for 1 hr with 1% BSA in 1×PBS. The plate was next incubated with the Indicated antibodies at identical concentrations, diluted in 0.1% BSA in 1×PBS. Plates were successively treated with human tau, polyclonal rabbit anti-tau (Dako #A0024), and HRP-conjugated goat anti-rabbit antibody, all diluted in 0.1% BSA in PBS with washes occurring between each step. Streptavidin-HRP was added, plates were developed with TMB, and $A_{450}$ was measured with a plate reader. See FIG. 4C.

Figure 4C:
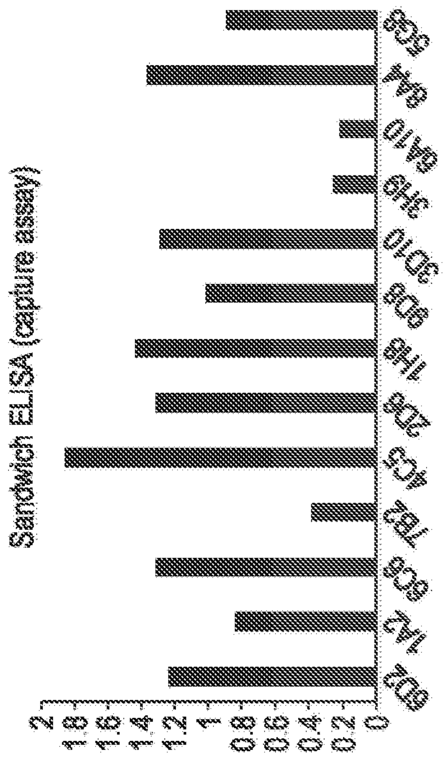

Results: A panel of hybridoma-produced antibodies were assayed for binding to tau via a number of different ELISA formats. Detection of tau was confirmed using an indirect format, using tau protein immobilized by its N-terminally fused polyhistidine tag (FIG. 4A). Binding to the native, untagged protein was also confirmed (FIG. 4B). To assess the solution affinity of the various antibodies, a sandwich ELISA format was used in which tested hybridoma antibodies were used as capture reagents (FIG. 4C).

Example 5. Affinity of Mouse Monoclonal Antibodies to Tau

Methods: SPR analysis was performed using a Biacore T200 to determine the binding kinetics of murine antibodies to recombinant human tau. To prepare a sensor surface, anti-mouse antibody (GE Life Sciences) was immobilized on sensor chip CM5 via amine coupling, and antibody was captured at a level to ensure maximum binding of 50 RU. Various concentrations of recombinant tau ranging from 10-0.14 nM were passed over the captured ligand at a flow rate of 50 μL/min in running buffer (HBS+0.05% P-20, 1 mg/mL BSA), for 180 sec association and 900 sec dissociation. Data were double-referenced to both an irrelevant sensor not containing antibody ligand, and 0 nM analyte concentration to account for the dissociation of ligand from the capture moiety. Data was then analyzed using a global 1:1 fit.

Figures 5, 6:
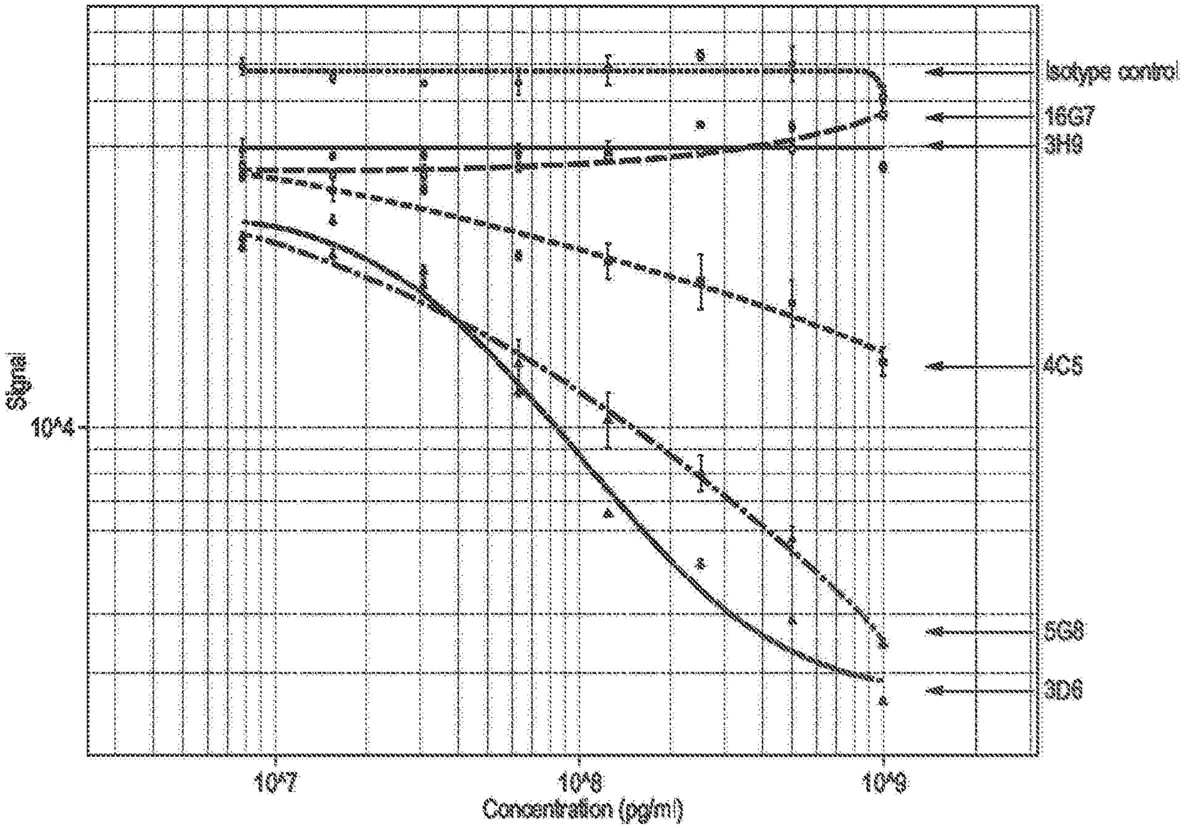
FIG. 5 depicts binding kinetics for selected mouse monoclonal anti-tau antibodies to recombinant human tau.
FIG. 6 depicts results of functional blocking assays for selected mouse monoclonal anti-tau antibodies.

Results: Multiple murine antibodies were selected based on their performance in a battery of ELISA assays, and their binding affinities were assessed via SPR. Antibodies were tested in parallel sets, and their binding association and dissociation rates were compared to select the highest binder to recombinant human tau. The highest binding affinity was observed with antibody clone 3D6. Binding affinities are shown in FIG. 5.

Example 6. Mouse Monoclonal Antibodies Prevent Binding of Human Tau to the Surface of Immortalized Neuronal Cells Methods: Inhibition_of Tau Binding to B103 Neuroblastoma Cells with Anti-Tau Monoclonal Antibodies 1. Resuspend B103 cells in PBS at $5\times10^5$ cells/mL. Plate 50 μL of cell suspension per well in a MSD High Bind plate. This results in 25K cells/well. Cover the plate and allow cells to attach at 37° C., 5% CO2, for 2 hrs.
2. Following cell attachment, remove PBS from wells by inverting plate and gently tapping to remove excess buffer. Add 50 μL of 3% MSD Blocker A in PBS or other suitable blocking buffer to each well and incubate plate at RT for 1 hr without shaking.
3. During the plate blocking step co-incubate Tau and anti-Tau antibodies as follows:
    - a. Start with anti-Tau antibody at 2 mg/mL and serial dilute in PBS, 1:2, for 7 additional dilutions.
    - b. Dilute Tau to 20 nM in PBS. The Tau concentration will be constant in each well.
    - c. Mix the Tau and anti-Tau antibody, 1:1, for a final Tau concentration of 10 nM and a starting concentration of anti-Tau of 1 mg/mL.

d. Incubate the mixture for approximately 1 hr at RT with shaking (600 rpm).

4. After plate blocking, step 2, remove blocking buffer from wells by inverting plate and gently tapping and wash plate 2× with PBS using a multichannel pipette. Ensure excess buffer is completely removed. Cool the plated cells to 4° C. prior to adding the Tau: anti-Tau complexes.

5. Add 50 µL of cooled complex, step 3, to the plated cells and incubate on ice for 30 minutes.

6. Wash plate 2× with chilled PBS as previously described.

7. Add 50 µL per well of the 16B5.SULFO-TAG for detection of cell surface bound Tau. Incubate for 30 minutes on ice.

8. Wash plate 2× with chilled PBS again as previously described.

9. Add 150 µL per well of 1× Read Buffer T Without Surfactant (diluted in H20) and read immediately on the MSD SECTOR™ 600 instrument. Avoid introducing bubbles when adding read buffer.

10. Report the MSD signals vs. concentration of anti-Tau.

Antibodies tested were anti-tau antibodies 3D6, 16G7, 3H9, 4C5, and 5G8, and isotype control.

Results:

Decreasing SulfoTag anti-tau signal occurring with increasing test antibody indicates functional blocking of the binding of tau to neuronal cell surfaces. No blocking was observed with isotype control, 16G7, or 3H9. Increasing amounts of functional blocking activity were observed with 4C5, 5G8, and 3D6. 3D6 demonstrated the deepest blocking activity of the antibodies tested. See FIG. 6.

Example 7. Disaggregation Activity

Methods: Aggregation of recombinant tau—Purified recombinant tau with an N-terminal 6×His tag was combined with equimolar amounts of low-molecular weight heparin in 1×PBS (pH 7.4), and incubated at 37° C. for 96 hr on a nutator. Aggregation of the sample was confirmed by binding to Thioflavin T.

Incubation with antibodies—Antibodies were incubated with aggregated, recombinant tau at the indicated molar ratios incubated at 37° C. for 96 hr without rotation or nutation. At the end of the experiment, aggregation was measured by incubating samples with 25 mM Thioflavin T, and measuring emitted fluorescence (450/482 ex/em). Signals were background subtracted to buffer samples.

Figure 7:
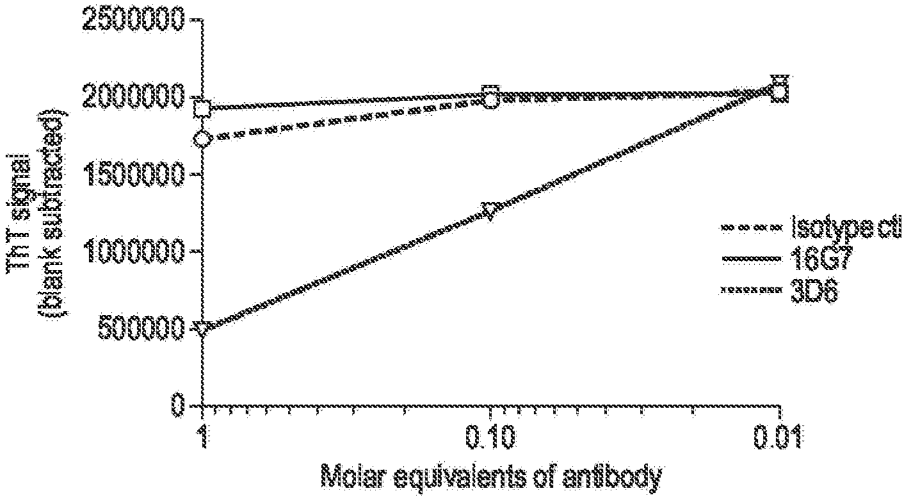
FIG. 7 depicts results of disaggregation assays for selected mouse monoclonal anti-tau antibodies.
Figure 8:
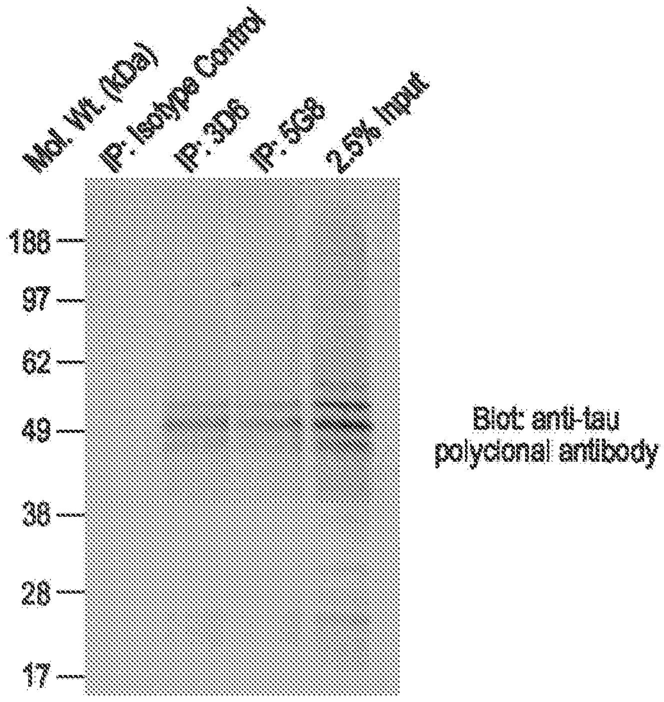
FIG. 8 depicts results of experiments showing that 3D6 and 5G8 immunocapture tau from human Alzheimer's disease tissue.

Results: As shown in FIG. 7, 3D6 preferentially disassembles intact tau fibrils. Varying molar ratios of 3D6 (triangles), isotype control (circles) and 16G7 (squares) were incubated with amyloid-containing tau fibrils for 96 hours. At the end of this period, the extent of aggregation was assessed by binding to Thioflavin T. 3D6 preferentially decreases the Thioflavin T signal present in the sample, compared to both an isotype control antibody as well as to 16G7, an anti-tau antibody that binds to a different region of tau.

Example 8. 3D6 and 5G8 Immunocapture Tau from Human Disease Tissue

Methods: High-salt soluble protein fractions were prepared to 1 mg/ml. For each immunoprecipitation, 200 µg of sample was used. 10 µg of the indicated antibody (either an isotype control, 3D6, or anti-tau antibody 5G8) was added to the high-salt sample preparations, and incubated for 2 hr. Protein G magnetic beads were then added to the mixtures, and incubated for a further hour to capture antibody/antigen complexes. Samples were thoroughly washed with 1×PBS, and beads were boiled in reducing/denaturing sample buffer to release captured proteins. Resulting samples were resolved by SDS-PAGE and Western blotting was performed using a polyclonal anti-tau antibody (Dako, #A0024).

Results: As shown in FIG. 8, 3D6 and 5G8 immunoprecipitated tau from Alzheimer disease tissue. High-salt soluble fractions were immunoprecipitated with the indicated antibody, and detected with a polyclonal anti-tau antibody directed towards a separate region of the tau molecule from the binding sites for 3D6 and tau antibody A. 3D6 robustly captured tau from this fraction. The input (high-salt soluble sample) is shown at right.

Example 9. Immunohistochemistry Immunoreactivity of 3D6

Frontotemporal cortices were obtained from patients without neurodegenerative disease or with Alzheimer disease, which was confirmed upon post-mortem assessment. Immunohistochemistry was performed on lightly acetone-fixed, 10 um slide-mounted cryosections. All staining steps were performed using a Leica BOND Rx autostainer, using Leica consumables. Either murine or a human form of 3D6 was incubated with tissue sections followed by addition of species-appropriate secondary antibodies conjugated to an HRP polymer. To prevent non-specific binding of endogenous immunoglobulin when using humanized antibodies on human tissue, the antibodies were non-covalently labeled with a biotin-conjugated anti-human monovalent Fab fragment in vitro before incubation on tissue. Tissue labeled with the primary antibody-biotin Fab fragment complex was further amplified using an avidin-biotin amplification system (Vector Laboratories, Burlingame, CA). The staining was visualized with a DAB chromogen, which produced a brown deposit. Negative control consisted of performing the entire immunohistochemical procedure on adjacent sections with an IgG isotype control antibody.

Antibodies tested were murine CD6, chimeric 3D6 (which contained VH and VL from the murine antibody with human constant regions, heavy chain SEQ ID NO:72 and light chain SEQ ID NO:73), and humanized variant hu3D6VHv5/hu3D6VLv2.

Staining performed with murine, chimeric, and humanized forms of 3D6 were qualitatively compared and assessed for the strength and intensity of staining, as well as localization of immunoreactivity. Intensity of staining was similar for chimeric and humanized forms of 3D6, and displayed similar localization patterns compared with the murine form of the antibody. Tau was detected in neurofibrillary tangles, fibrils, neuropil threads, and in degenerating axons. There was also notable somal staining detected.

Example 10. Affinity of Humanized Variants Towards Tau

Methods; Indirect ELISA 96-well polystyrene plates are coated with human recombinant tau suspended in 1×PBS for 2 h at RT or 16 h at 4° C. Coating is removed, and plates are blocked for 1 h with 1% BSA in 1×PBS. Humanized variant antibodies at 1 µg/mL in 0.1% BSA in 1×PBS are added to plates for 1 hour followed by washing, and HRP-conjugated goat anti-human antibody are added. Plates are developed with TMB, and $A_{450}$ is measured with a plate reader.

Sandwich ELISA 96-well polystyrene plates are coated with anti-human antibodies in 1×PBS for 2 hr at RT or 16 hr at 4° C. Coating is removed, and plates are blocked for 1 hr with 1% BSA in 1×PBS. Humanized variant antibodies at varying concentrations diluted in 0.1% BSA in 1×PBS are added to plates for 1 hour followed by washing, and biotinylated recombinant human tau diluted in 0.1% BSA in 1×PBS is added. After washing, Streptavidin-HRP is added, plates are developed with TMB, and $A_{450}$ is measured with a plate reader.

SPR analysis is performed using a Biacore T200 to determine the binding kinetics of h3D6-VHv5-L2 to recombinant human tau. To prepare a sensor surface, anti-human antibody (GE Life Sciences) is immobilized on sensor chip CM5 via amine coupling, and humanized variant antibody is captured at a level to ensure maximum binding of 50 RU. Various concentrations of recombinant tau ranging from 10-0.14 nM are passed over the captured ligand at a flow rate of 50 µL/min in running buffer (HBS+0.05% P-20, 1 mg/mL BSA), for 180 s association and 900 s dissociation. Data are double-referenced to both an irrelevant sensor not containing antibody ligand, and 0 nM analyte concentration to account for the dissociation of ligand from the capture moiety. Data is then analyzed using a global 1:1 fit.

Example 11 Immunogenicity of hu3D6VLv2 Light Chain Variable Region

The amino acid sequences of the hu3D6VLv2 light chain variable region (SEQ ID NO:21) of were analyzed using iedb.org Deimmunization Tool (Dhanda et al, Immunology. 2018 January; 153(1):118-132). Table 9 shows the peptides that may be selected for deimmunization of hu3D6VLv2, i.e., suggesting areas where further substitutions could be made to reduce potential immunogenicity.

TABLE 9

Results of immunogenicity analysis identifying potential peptides for deimmunization

| Start position (linear) | Stop position (linear) | Median percentile rank | Peptide |
|---|---|---|---|
| 1 | 15 | 14.845 | DVVMTQSPLSLPVTL (SEQ ID NO: 195) |
| 51 | 65 | 15.745 | RLIYLVSKLDSGVPD (SEQ ID NO: 196) |
| 46 | 60 | 18.58 | GQSPRRLIYL VSKLD (SEQ ID NO: 197) |

Based on the results of the analysis shown in Table 9, variants of hu3D6VLv2 light chain variable region were designed, targeting the amino acid residues bolded in Table 10. Each variant incorporates one of the following amino acid substitutions, as shown in Table 11.

TABLE 10

Amino acid residues in hu3D6VLv2 targeted for substitution.

| Targeted residues of hu3D6VLv2 light chain variable region | Original SEQ ID NO |
|---|---|
| DVVMTQSPLSLPVTLGQPASISCKSSQSLL<br>DSDGKTYLNWLLQRPGQSPRR**LIYL**V**S**K**L**D<br>SGVPDRFSGSGSGTDFTLKISR VEAEDVGV<br>YYCWQGTHFPYTFGGGTKLEIK | 21 |

TABLE 11

| Amino acid substitutions in hu3D6VLv2 designed to reduce immunogenicity | | | |
|---|---|---|---|
| Linear Number | Kabat Number | Variant Name | SEQ ID NO of resulting light chain variable region |
| L59D | L54D | hu3D6VLv2 L54D (also known as L2-DIM21) | SEQ ID NO: 93 |
| L59G | L54G | hu3D6VLv2 L54G (also known as L2-DIM7) | SEQ ID NO: 94 |
| L59N | L54N | hu3D6VLv2 L54N | SEQ ID NO: 95 |
| L59E | L54E | hu3D6VLv2 L54E | SEQ ID NO: 96 |
| L55E | L50E | hu3D6VLv2 L50E | SEQ ID NO: 97 |
| L59Q | L54Q | hu3D6VLv2 L54Q | SEQ ID NO: 98 |
| L55D | L50D | hu3D6VLv2 L50D | SEQ ID NO: 99 |
| L59K | L54K | hu3D6VLv2 L54K | SEQ ID NO: 100 |
| L59R | L54R | hu3D6VLv2 L54R | SEQ ID NO: 101 |
| L59T | L54T | hu3D6VLv2 L54T | SEQ ID NO: 102 |
| L55G | L50G | hu3D6VLv2 L50G (also known as L2-DIM22) | SEQ ID NO: 103 |
| I53G | I48G | hu3D6VLv2 I48G | SEQ ID NO: 104 |
| I53D | I48D | hu3D6VLv2 I48D | SEQ ID NO: 105 |
| L52G | L47G | hu3D6VLv2 L47G | SEQ ID NO: 106 |
| Y54E | Y49E | hu3D6VLv2 Y49E | SEQ ID NO: 107 |
| L59V | L54V | hu3D6VLv2 L54V | SEQ ID NO: 108 |
| L59S | L54S | hu3D6VLv2 L54S | SEQ ID NO: 109 |
| S57G | S52G | hu3D6VLv2 S52G (also known as L2-DIM9) | SEQ ID NO: 110 |
| L52N | L47N | hu3D6VLv2 L47N | SEQ ID NO: 111 |
| L52D | L47D | hu3D6VLv2 L47D | SEQ ID NO: 112 |
| L52E | L47E | hu3D6VLv2 L47E | SEQ ID NO: 113 |
| L52P | L47P | hu3D6VLv2 L47P | SEQ ID NO: 114 |
| L52T | L47T | hu3D6VLv2 L47T | SEQ ID NO: 115 |

TABLE 11-continued

| Amino acid substitutions in hu3D6VLv2 designed to reduce immunogenicity | | | |
|---|---|---|---|
| Linear Number | Kabat Number | Variant Name | SEQ ID NO of resulting light chain variable region |
| L52S | L47S | hu3D6VLv2 L47S | SEQ ID NO: 116 |
| L52A | L47A | hu3D6VLv2 L47A | SEQ ID NO: 117 |
| L55V | L50V | hu3D6VLv2 L50V | SEQ ID NO: 118 |

Additional variants of hu3D6VLv2 light chain variable region were designed, as shown in Table 12, which incorporate substitutions at one or two of the amino acid residues highlighted in Table 10. Some variants in Table 12 also incorporate the substitution L37Q (SEQ ID NOs: 119-135, and 145), or both the substitution L37Q and the substitution G100Q (SEQ ID NOs: 136-142).

The rationales for selection of the positions L37Q and G100Q as indicated in Table 12 and Table 13 in the light chain variable region as candidates for substitution are as follows.

L37Q is a mutation to increase humanness of the sequence. Gln is a germline-aligning mutation. Gln is in human germline gene IGKV2-30*02 (SEQ (ID NO: 27) at this position.

G100Q is a mutation to increase humanness of the sequence. Gln is a germline-aligning mutation. Gln is in human germline gene IGKV2-30*02 (SEQ (TD NO: 27) at this position.

TABLE 12

| Amino acid substitutions in hu3D6VLv2 designed to reduce immunogenicity | | |
|---|---|---|
| Substitutions in Additional Variants in hu3D6VLv2 designed to reduce immunogenicity (Kabat number of mutation(s) indicated) | Variant Name | SEQ ID NO: of resulting light chain variable region |
| L37Q_L50G_L54R | hu3D6VLv2 L37Q_L50G_L54R (also known as L2-DIM1) | SEQ ID NO: 119 |
| L37Q_L50G_L54G | hu3D6VLv2 L37Q_L50G_L54G (also known as L2-DIM2) | SEQ ID NO: 120 |
| L37Q_S52G_L54G | hu3D6VLv2 L37Q_S52G_L54G (also known as L2-DIM3) | SEQ ID NO: 121 |
| L37Q_S52G_L54R | hu3D6VLv2 L37Q_S52G_L54R (also known as L2-DIM4) | SEQ ID NO: 122 |
| L37Q_S52G_L54T | hu3D6VLv2 L37Q_S52G_L54T (also known as L2-DIM5) | SEQ ID NO: 123 |
| L37Q_S52G_L54D | hu3D6VLv2 L37Q_S52G_L54D (also known as L2-DIM6) | SEQ ID NO: 124 |
| L37Q_L54R | hu3D6VLv2 L37Q_L54R | SEQ ID NO: 125 |
| L37Q_L54G | hu3D6VLv2 L37Q_L54G | SEQ ID NO: 126 |
| L37Q_L54D | hu3D6VLv2 L37Q_L54D (also known as L2-DIM12) | SEQ ID NO: 127 |
| L37Q_L50G | hu3D6VLv2 L37Q_L50G (also known as L2-DIM13) | SEQ ID NO: 128 |
| L37Q_L50D | hu3D6VLv2 L37Q_L50D (also known as L2-DIM14) | SEQ ID NO: 129 |
| L37Q_L54T | hu3D6VLv2 L37Q_L54T | SEQ ID NO: 130 |
| L37Q_S52G | hu3D6VLv2 L37Q_S52G | SEQ ID NO: 131 |
| L37Q_L54E | hu3D6VLv2 L37Q_L54E | SEQ ID NO: 145 |
| L37Q_L50D_L54G | hu3D6VLv2 L37Q_L50D_L54G (also known as L2-DIM17) | SEQ ID NO: 132 |
| L37Q_L50D_L54R | hu3D6VLv2 L37Q_L50D_L54R (also known as L2-DIM18) | SEQ ID NO: 133 |
| L37Q_L50E_L54G | hu3D6VLv2 L37Q_L50E_L54G (also known as L2-DIM19) | SEQ ID NO: 134 |
| L37Q_L50E_L54R | hu3D6VLv2 L37Q_L50E_L54R (also known as L2-DIM20) | SEQ ID NO: 135 |

TABLE 12-continued

Amino acid substitutions in hu3D6VLv2 designed to reduce immunogenicity

| Substitutions in Additional Variants in hu3D6VLv2 designed to reduce immunogenicity (Kabat number of mutation(s) indicated) | Variant Name | SEQ ID NO: of resulting light chain variable region |
|---|---|---|
| L37Q_L50G_L54R_G100Q | hu3D6VLv2 L37Q_L50G_L54R_G100Q | SEQ ID NO: 136 |
| L37Q_L50G_L54G_G100Q | hu3D6VLv2 L37Q_L50G_L54G_G100Q | SEQ ID NO: 137 |
| L37Q_S52G_L54R_G100Q | hu3D6VLv2 L37Q_S52G_L54R_G100Q | SEQ ID NO: 138 |
| L37Q_S52G_L54D_G100Q | hu3D6VLv2 L37Q_S52G_L54D_G100Q | SEQ ID NO: 139 |
| L37Q_L50D_L54G_G100Q | hu3D6VLv2 L37Q_L50D_L54G_G100Q | SEQ ID NO: 140 |
| L37Q_L50D_L54R_G100Q | hu3D6VLv2 L37Q_L50D_L54R_G100Q | SEQ ID NO: 141 |
| L37Q_L50V_L54D_G100Q | hu3D6VLv2 L37Q_L50V_L54D_G100Q | SEQ ID NO: 142 |

Additional variants of hu3D6VLv2 light chain variable region were designed to incorporate L37Q (SEQ ID NO:143) or to incorporate G100Q (SEQ ID NO:144), as shown in Table 13.

TABLE 13

Additional Amino acid substitutions in hu3D6VLv2

| Substitutions in Additional Variants in hu3D6VLv2 (Kabat number of mutation(s) indicated) | Variant Name | SEQ ID NO: of resulting light chain variable region |
|---|---|---|
| L37Q | hu3D6VLv2 L37Q (also known as L2-DIM8) | SEQ ID NO: 143 |
| G100Q | hu3D6VLv2 G100Q | SEQ ID NO: 144 |

FIGS. 10A, 10B, 10C, and 10D show alignments of the light chain variable region of humanized versions of the 3D6 antibody: hu3D6VLv2 (SEQ ID NO:21), hu3D6VLv2 L37Q (SEQ ID NO:143), hu3D6VLv2 L50G (SEQ ID NO:103), hu3D6VLv2 S52G (SEQ ID NO:110), hu3D6VLv2 L54G (SEQ ID NO:94), hu3D6VLv2 L54D (SEQ ID NO:93), hu3D6VLv2 L54K (SEQ ID NO:100), hu3D6VLv2 L54R (SEQ ID NO:101), hu3D6VLv2 L54T (SEQ ID NO:102), hu3D6VLv2 L37Q_L50G (SEQ ID NO:128), hu3D6VLv2 L37Q_L50D (SEQ ID NO:129), hu3D6VLv2 L37Q_S52G (SEQ ID NO:131), hu3D6VLv2 L37Q_L54G (SEQ ID NO:126), hu3D6VLv2 L37Q_L54R (SEQ ID NO:125), hu3D6VLv2 L37Q_L54T (SEQ ID NO:130), hu3D6VLv2 L37Q_L54D (SEQ ID NO:127), hu3D6VLv2 L37Q_L54E (SEQ ID NO:145), hu3D6VLv2 L37Q_L50G_L54R (SEQ ID NO:119), hu3D6VLv2 L37Q_L50G_L54G (SEQ ID NO:120), hu3D6VLv2 L37Q_L50D_L54R (SEQ ID NO:133), hu3D6VLv2 L37Q_L50D_L54G (SEQ ID NO:132), hu3D6VLv2 L37Q_S52G_L54D (SEQ ID NO:124), hu3D6VLv2 L37Q_S52G_L54G (SEQ ID NO:121), hu3D6VLv2 L37Q_S52G_L54T (SEQ ID NO:123), hu3D6VLv2 L37Q_S52G_L54R (SEQ ID NO:122), hu3D6VLv2 L37Q_L50D_L54G_G100Q (SEQ ID NO:140), hu3D6VLv2 L37Q_L50D_L54R_G100Q (SEQ ID NO:141), hu3D6VLv2 L37Q_L50G_L54R_G100Q (SEQ ID NO:136), hu3D6VLv2 L37Q_L50G_L54G_G100Q (SEQ ID NO:137), hu3D6VLv2 L37Q_L50V_L54D_G100Q (SEQ ID NO:142), hu3D6VLv2 L37Q_S52G_L54D_G100Q (SEQ ID NO:139), and hu3D6VLv2 L37Q_S52G_L54R_G100Q (SEQ ID NO:138).

Example 12 Immunogenicity of hu3D6VHv1bA11 (Heavy Chain Variable Region)

Additional heavy chain variable region variants of hu3D6VHv1bA11 (also known as h3D6Hu5) (SEQ ID NO: 18) were designed, as shown in Table 14.

FIGS. 9A and 9B show alignments of the heavy chain variable region of murine 3D6 (SEQ ID NO:7) and of humanized versions of the 3D6 antibody (hu3D6VHvb1, hu3D6VHvb2, hu3D6VHvb3, hu3D6VHvb4, hu3D6VHvb5, hu3D6VHvb6, hu3D6VHvb7, hu3D6VHv1bA11, h3D6VHvb8, and h3D6VHvb9) with human germline heavy chain variable region sequence IGHV1-69-2*01 (SEQ ID NO:25) and with human acceptor heavy chain variable region sequence 2RCS VH hFrwk (SEQ ID NO:75). hu3D6VHvb1 is SEQ ID NO:76, hu3D6VHvb2 is SEQ ID NO:77, hu3D6VHvb3 is SEQ ID NO:78, hu3D6VHvb4 is SEQ ID NO:79, hu3D6VHvb5 is SEQ ID NO:80, hu3D6VHvb6 is SEQ ID NO:90, hu3D6VHvb7 is SEQ ID NO:91, hu3D6VHv1bA11 is SEQ ID NO:18, h3D6VHvb8 is SEQ ID NO:146, and h3D6VHvb9 is SEQ ID NO:148.

TABLE 14

Additional Amino acid substitutions in hu3D6VHv1bA11 (also known as h3D6Hu5)

| Substitutions in Additional Variants in hu3D6VHv1bA11 (Kabat number of mutation(s) indicated | Variant Name | SEQ ID NO of resulting heavy chain variable region |
|---|---|---|
| D60E | hu3D6VHv1bA11 D60E (also known as h3D6VHvb8) | SEQ ID NO: 146 |
| L82cV | hu3D6VHv1bA11 L82cV | SEQ ID NO: 147 |
| D60E_L80M_Q81E_L82cV_T83R | hu3D6VHv1bA11 D60E_L80M_Q81E_L82cV_T83R (also known as h3D6VHvb9) | SEQ ID NO: 148 |

The rationales for selection of the positions indicated in Table 14 in the heavy chain variable region as candidates for substitution are as follows.

D60E: to reduce potential proteolysis. Asp-Pro motifs are known to be potential proteolytic cleavage sites. There is an Asp-Pro motif in hu3D6VHv1bA11 (h3D6Hu5) VH at Kabat position 60-61. Based upon homology model, Glu substitution at position 60 is considered as conformation conserving. Therefore, D60E substitution is made to reduce potential proteolysis.

Q81E, to enhance thermostability and to increase humanness. Glu is predicted to make H-bond plus salt-bridge with K19 hence Glu at this position make enhance antibody stability. Glu is a germ-line aligning mutation. Glu is in human germline gene IMGT #IGHV1-69-2*01 (SEQ (ID NO: 25) at this position.

L82cV to reduce immunogenicity. In silico analysis of humanized hu3D6VHv1bA11 (h3D6Hu5) immunogenicity using IEDB (immune epitope database) immunogenicity analysis tool predicted a potential immunogenic peptide that included L82c. L82cV substitution is designed to reduce immunogenicity. Valine substitution at this position conserves loop conformation.

L80M, to reduce immunogenicity; and to increase humanness. Met is a germline-aligning mutation. Met is in human germ line gene IMGT #IGHV1-69-2*01 (SEQ (ID NO: 25) at this position.

T83R to enhance thermostability and to increase humanness. Arg is a germline aligning mutation. Arg is in human germ line gene IMGT #IGHV1-69-2*01 (SEQ (ID NO: 25) at this position. Arg is most frequent at this position.

Example 13 Analysis of Humanized 3D6 Variants

Humanized 3D6 variants with predicted deimmunizing substitutions were analyzed for several characteristics, including target binding affinity, activity in cell-based assays, thermostability, expression characteristics, and number of substitutions. In all cases, results were compared with the parental sequence, hu3D6VHv1bA11/hu3D6VLv2 to determine if any loss of activity or stability was noted.

Target binding analysis was performed using a Biacore T200 to compare the binding affinity of humanized 3D6 variants to recombinant human 4R0N tau. Anti-Human Fc antibody was immobilized on sensor chip CM3 via amine coupling, and humanized 3D6 variants were captured to equivalent levels. Various concentrations of recombinant 4R0N human tau (ranging from 0.02 nM to 12.5 nM) were passed over the captured ligand at 50 μL/min in running buffer (HBS+0.05% P-20, 1 mg/mL BSA) for 180 seconds association/420 seconds dissociation as a single cycle. Data was blank subtracted to both an irrelevant sensor not containing antibody and 0 nM analyte concentration. Analysis was performed using a global 1:1 fit with Biacore Evaluation software.

Affinity determination revealed a number of deimmunized variants that retained the affinity of the parental hu3D6VHv1bA11/hu3D6VLv2, which was determined by comparison of the $K_D$ of each antibody to that of parental hu3D6VHv1bA11/hu3D6VLv2. Antibodies determined to have $K_D$ comparable within 4-fold of hu3D6VHv1bA11/hu3D6VLv2 (Table 15) include hu3D6VHv1bA11/L2-DIM4, hu3D6VHv1bA11/L2-DIM9, hu3D6VHv1bA11/L2-DIM5, hu3D6VHv1bA11/L2-DIM3, h3D6VHvb8/L2-DIM4, hu3D6VHv1bA11/L2-DIM7, h3D6VHvb8/L2-DIM7, h3D6VHvb8/L2-DIM8, hu3D6VHv1bA11/L2-DIM12, hu3D6VHv1bA11/L2-DIM21, and hu3D6VHv1bA11/L2-DIM22. hu3D6VHv1bA11/L2-DIM4 demonstrated improved affinity, as evidenced by on-rate, off-rate, and Kd numbers, over parental hu3D6VHv1bA11/hu3D6VLv2.

TABLE 15

Affinity of 3D6 Humanized Variants

| 3D6 Humanized Variant | $K_a$ (1/M s) | $K_d$ (1/s) | $K_D$ (M) |
|---|---|---|---|
| hu3D6VHv1bA11/hu3D6VLv2 | 4.17E+06 | 7.40E−04 | 1.81E−10 |
| hu3D6VHv1bA11/L2-DIM4 | 5.65E+06 | 5.35E−04 | 9.48E−11 |
| hu3D6VHv1bA11/L2-DIM9 | 4.63E+06 | 7.40E−04 | 1.60E−10 |
| hu3D6VHv1bA11/L2-DIM5 | 4.02E+06 | 7.35E−04 | 1.83E−10 |
| hu3D6VHv1bA11/L2-DIM3 | 3.93E+06 | 7.81E−04 | 1.99E−10 |
| h3D6VHvb8/L2-DIM4 | 4.51E+06 | 1.02E−03 | 2.26E−10 |
| h3D6VHvb8/L2-DIM7 | 4.31E+06 | 1.19E−03 | 2.75E−10 |
| hu3D6VHv1bA11/L2-DIM7 | 3.46E+06 | 9.71E−04 | 2.81E−10 |
| h3D6VHvb8/L2-DIM8 | 3.28E+06 | 1.40E−03 | 4.27E−10 |
| hu3D6VHv1bA11/L2-DIM12 | 2.74E+06 | 1.33E−03 | 4.85E−10 |
| hu3D6VHv1bA11L2-DIM21 | 2.15E+06 | 1.49E−03 | 6.96E−10 |
| hu3D6VHv1bA11/L2-DIM22 | 3.54E+06 | 2.51E−03 | 7.08E−10 |
| hu3D6VHv1bA11/L2-DIM1 | 3.02E+06 | 2.60E−03 | 8.59E−10 |
| hu3D6VHv1bA11/L2-DIM13 | 3.15E+06 | 2.85E−03 | 9.04E−10 |
| hu3D6VHv1bA11/L2-DIM-17 | 5.24E+10 | 5.42E+01 | 1.03E−09 |
| h3D6VHvb8/L2-DIM1 | 6.19E+06 | 6.41E−03 | 1.04E−09 |
| h3D6VHvb8/L2-DIM2 | 1.03E+10 | 1.46E+01 | 1.42E−09 |
| hu3D6VHv1bA11/L2-DIM6 | 3.08E+06 | 4.61E−03 | 1.49E−09 |
| h3D6VHvb8/L2-DIM6 | 3.79E+09 | 5.67E+00 | 1.50E−09 |
| hu3D6VHv1bA11/L2-DIM14 | 7.69E+10 | 1.18E+02 | 1.53E−09 |
| hu3D6VHv1bA11/L2-DIM2 | 5.73E+06 | 9.33E−03 | 1.63E−09 |
| hu3D6VHv1bA11/L2-DIM19 | 3.28E+09 | 5.88E+00 | 1.79E−09 |
| hu3D6VHv1bA11/L2-DIM-18 | 1.51E+06 | 3.78E−03 | 2.51E−09 |
| hu3D6VHv1bA11/L2-DIM20 | 2.60E+05 | 9.35E−03 | 3.60E−08 |

In addition, as a secondary characteristic, thermostability and titer were analyzed for all deimmunized variants. Thermostability and titer levels were compared for antibodies that were comparable to hu3D6VHv1bA11/hu3D6VLv2 based on affinity measurements, and antibodies in Table 16 are listed in order based on variance from $T_m$ of hu3D6VHv1bA11/hu3D6VLv2.

Thermostability values were determined using differential scanning calorimetry (DSC). All DSC scans were performed using a VP-Capillary DSC system (Malvern). All samples were prepared to 0.5 mg/mL in 1×PBS, and referenced to 1×PBS. Approximately 0.5 mL of protein solution and buffer were introduced into the sample and reference cell. Calorimetric scan rates were carried out at scan rates of 60° C./hour, from 25° C. to 110° C. under constant pressure. Analysis was performed using origin software. Reported values are the temperature at which the maximal heat capacity of the Fab peak is recorded.

Titer was determined as follows. After expression in 293 suspension cells, antibodies were purified using Protein A chromatography utilizing standard methods. Following purification, the antibodies were exchanged into 1×PBS and protein concentrations were determined by absorbance at 280 nm. Titers were calculated by dividing the final yield of purified protein by the starting volume of the expression culture, and reported in milligrams per liter. hu3D6VHv1bA11/L2-DIM4 demonstrated higher thermostability and titer over parental hu3D6VHv1bA11/hu3D6VLv2. Thermostability and transient expression levels (titer) are both important considerations for drug development.

TABLE 16

Thermostability and Titer of 3D6 Humanized Variants

| 3D6 Humanized Variant | $T_m$ (° C.)-variance from hu3D6VHv1bA11/hu3D6VLv2 | titer (mg/L) |
|---|---|---|
| hu3D6VHv1bA11/hu3D6VLv2 | 0.00 | 456.00 |
| hu3D6VHv1bA11/L2-DIM4 | 0.08 | 467.00 |
| h3D6VHvb8/L2-DIM8 | −0.38 | 301.00 |
| h3D6VHvb8/L2-DIM4 | −0.78 | 445.00 |
| hu3D6VHv1bA11/L2-DIM22 | −1.23 | 570.00 |
| hu3D6VHv1bA11/L2-DIM9 | −2.19 | 290.00 |
| hu3D6VHv1bA11/L2-DIM5 | −3.34 | 383.00 |
| hu3D6VHv1bA11/L2-DIM7 | −4.24 | 231.00 |
| h3D6VHvb8/L2-DIM7 | −4.83 | 271.00 |
| hu3D6VHv1bA11/L2-DIM3 | −5.01 | 283.00 |
| hu3D6VHv1bA11/L2-DIM21 | −5.17 | 81.00 |
| hu3D6VHv1bA11/L2-DIM12 | −5.47 | 94.00 |

Based on analysis of the above-listed findings, the neutralization activity of seven antibodies in Table 16 were selected for further analysis in a cell based model of tau internalization: Substitutions in the heavy and light chains relative to parental hu3D6VHv1bA11/hu3D6VLv2 are noted.

An internalization assay employing fluorescence activated cell sorting (FACS) was performed to evaluate the ability of various antibodies to block neuronal internalization of tau. Antibodies that block internalization will likely block transmission of tau.

Soluble tau aggregates were generated by incubation of recombinant full length tau with equimolar amounts of low molecular weight heparin for 3d at 37° C. After incubation, insoluble and soluble tau was separated by centrifugation at 10,000×g for 15 minutes. The supernatant was then resolved by preparative size exclusion chromatography, and aggregate peaks (greater than 100 kDa) were collected and concentrated. To measure internalization, the soluble aggregate fraction was labeled with pHrodo Red succinimidyl ester, which fluoresces when internalized into the endolysosomal pathway.

pHrodo-labeled 4R0N human tau P301L soluble oligomer (1.5 μg/ml final concentration) was preincubated with anti-tau antibodies (dose titration: 80 μg/ml starting concentration followed by 4-fold serial dilutions) for 30 min at room temperature in cell culture media. Tau/antibody mixture was then added to B103 neuroblastoma cell lines at 500,000 cells/ml final concentration and incubated for 3-4 hrs at 37° C. in a tissue culture incubator (5% $CO_2$). Cells were then washed 3× with culture media, followed by 10 minutes culture media incubation, and washed 2× with FACS buffer (1% FBS in PBS). Cells were resuspended in 100 μl FACS buffer and Texas Red mean fluorescence intensity measured by FACS LSR II. Texas red fluorescence from pHrodo is activated by low pH associated with endolysosomal compartments upon internalization. Because FACS detects cells and pHrodo only fluoresces upon internalization, only tau internalized by the cells will be detected. The lower the mean fluorescence intensity, the lower the amount of internalized tau, which suggests a higher blocking activity of the antibody tested.

Figure 11:
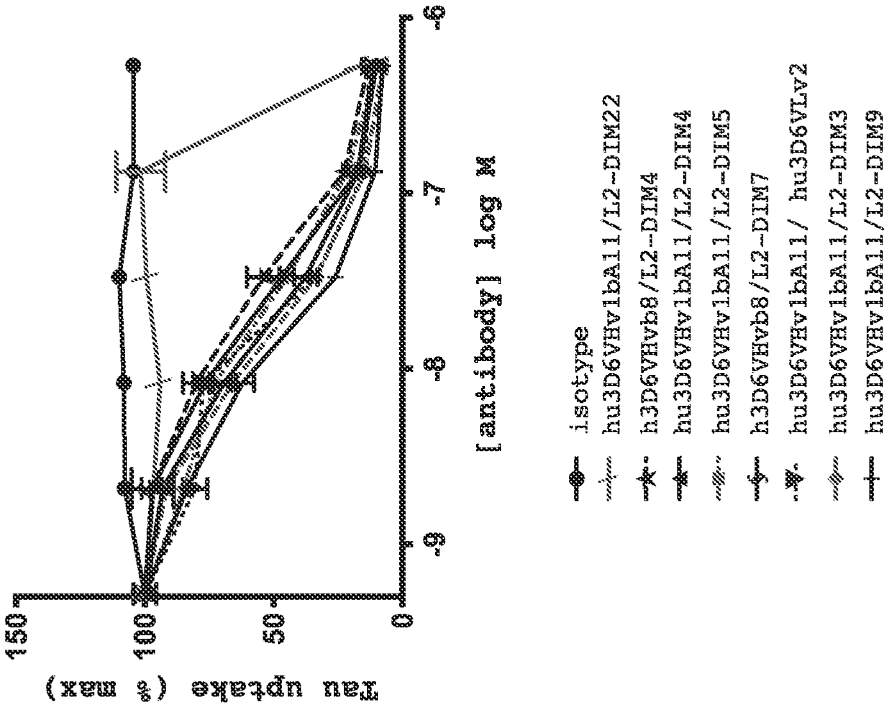
FIG. 11 shows results of tau internalization assay for selected humanized 3D6 variants.

With the exception of hu3D6VHv1bA11/L2-DIM22, all tested variants displayed a high degree of inhibitory activity in the model of tau internalization at an equivalent concentration (FIG. 11 and Table 17).

TABLE 17

Humanized 3D6 Variants Tested in Cell-Based Assay of Tau Internalization

| 3D6 Humanized Variant | Heavy Chain Substitutions Relative to Parent hu3D6VHv1bA11 | Light Chain Substitutions Relative to Parent hu3D6VLv2 | Inhibition of cell based internalization (at 133 nM antibody concentration, % of inhibition of maximal fluorescent signal ± standard deviation) |
|---|---|---|---|
| hu3D6VHv1bA11/hu3D6VLv2 | | | 87.2 ⌋ 1.6 |
| hu3D6VHv1bA11/L2-DIM4 | | L37Q_S52G_L54R | 92.2 ± 2.4 |
| hu3D6VHv1bA11/L2-DIM5 | | L37Q_S52G_L54T | 92.7 ± 3.6 |
| h3D6VHvb8/L2-DIM4 | D60E | L37Q_S52G_L54R | 89.4 ± 2.6 |
| hu3D6VHv1bA11/L2-DIM3 | | L37Q_S52G_L54G | 87.4 ± 3.6 |
| hu3D6VHv1bA11/L2-DIM9 | | S52G | 96 ± 3.5 |

TABLE 17-continued

Humanized 3D6 Variants Tested in Cell-Based Assay of Tau Internalization

| 3D6 Humanized Variant | Heavy Chain Substitutions Relative to Parent hu3D6VHv1bA11 | Light Chain Substitutions Relative to Parent hu3D6VLv2 | Inhibition of cell based internalization (at 133 nM antibody concentration, % of inhibition of maximal fluorescent signal ± standard deviation) |
|---|---|---|---|
| h3D6VHvb8/L2-DIM7 | D60E | L54G | 93.2 ± 1.3 |
| hu3D6VHv1bA11/ L2-DIM22 | | L50G | 8.7 ± 8.6 |

Example 14 Refinement of Epitope Mapping of 3D6

Initial peptide mapping indicated that the epitope for 3D36 is in the microtubule binding repeat region (MTBR, FIG. 1). Furthermore, peptide mapping indicated that 3D36 binds to multiple sites within the MTBR, suggesting a repeated and discontinuous epitope.

As the initial peptide map used for epitope studies utilized overlapping peptides overlaps that did not contain intact microtubule binding repeats, additional peptide mapping was carried out with the individual intact microtubule repeats. Biotinylated peptides corresponding to the amino acids for MTBR repeat 1-4 were added to a streptavidin-coated ELISA plate, washed, and blocked in 100 BSA/PBS. Varying amounts of 3D6 (ranging from 50 ug/ml-10 ng/ml) were then incubated on the plate. After washing, goat anti-mouse HRP was added to the ELISA plate, washed, and developed using OPD. Absorbance was detected at 490 nm, and binding curves were fitted using a 4-parameter log curve to determine EC50 values (Table 18). 3D6 bound MTBRs 1-3 relatively equivalently, with EC50 values of 72.5, 35.5 and 25.1 ng/ml respectively. However, binding to MTBR 4 was approximately 60-170 times lower, with an apparent EC50 of 4309 ng/ml. Sequence variations in the repeated epitope in MTBR 4 from MTBRs 1, 2, 3 and 4 may explain the weaker binding to MTBR 4.

TABLE 18

| Microtubule Repeat number | Amino acids (using the numbering of the full length tau isoform tau isoform SEQ ID NO: 1) | EC50 (ng/ml antibody) |
|---|---|---|
| 1 | 244-274 | 72.5 |
| 2 | 275-305 | 35.5 |
| 3 | 306-336 | 25.1 |
| 4 | 337-368 | 4309 |

In order to more closely elucidate the specific amino acids responsible for 3D6 binding, substitution mapping via microarray was performed using the peptide NVKSKIG-STENLKHQPG (SEQ ID NO:184), which is the sequence for residues 255-271 using the numbering of the full length tau isoform. The assay exchanged each of the amino acids in the peptide sequence with all 20 amino acids, to determine with a high degree of accuracy the core epitope for 3D6. The microarray was printed with all peptides in triplicate, along with HA control peptides to ensure assay performance. To perform the assay, the array was incubated with 3D6 (10 ug/ml) in blocking buffer, washed with PBS-T, followed by incubation with a goat anti-mouse secondary antibody conjugated to DyLight-680. In addition, the microarray was incubated with anti-HA antibody 12CA5 directly conjugated to DyLight-800. Microarrays were scanned using a LiCor scanner, and intensities of triplicates were averaged.

Figure 12A:
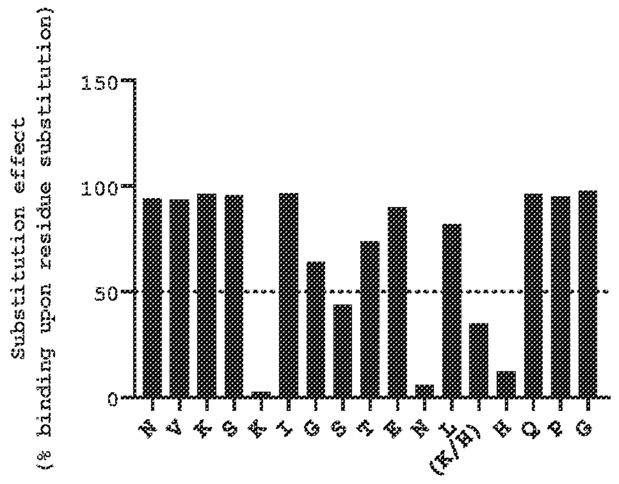
FIGS. 12A and 12B show results of substitution mapping microarray experiments.
Figure 12B:
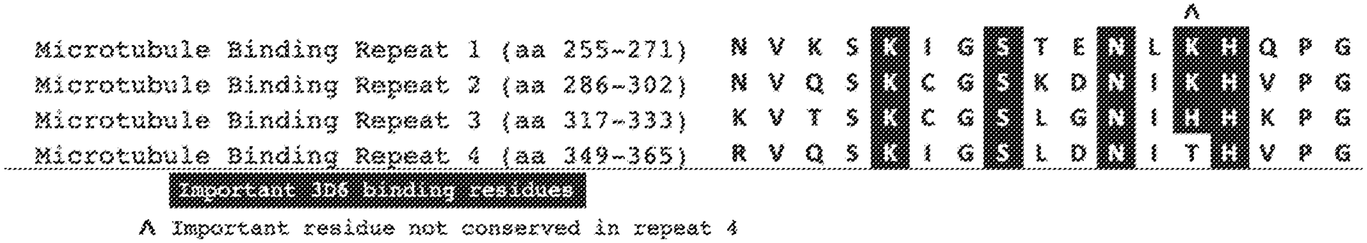

Substitution effects for each residue were calculated by determining the ratio of 3D6 binding lost when the native residue was mutated to the sum of all other 19 amino acids. Results are plotted in FIG. 12A. Loss of binding greater than 50% (dashed line) signifies an important residue for 3D6 binding. Binding of the probe peptide (residues 255-271 of the 441aa isoform) with 3D6 revealed an epitope substitution pattern with a conserved core motif KIGSTENLKH (SEQ ID NO:188), framed by variable N- and C-terminal stretches NVKS (SEQ ID NO:189) and QPG (SEQ ID NO:190), both of which are not important for binding. Within this core epitope, residues that do not permit substitution are $Lys^5$, $Asn^{11}$, and $His^{14}$; in addition, position 13 demonstrates reduced substitution tolerance for residues other than Lys and His. In addition to these important residues, $Ser^8$ only allows limited substitution. This results in a discontinuous epitope of KXXSXXNX(K/H)H (SEQ ID NO:191) as shown in FIG. 12B. Pertinent sections of the tau microtubule binding repeats are presented in alignment, with important 3D6 binding residues highlighted. When compared to the microtubule repeats in tau, the important residues are present in all repeats, with the exception of the penultimate position in the core epitope (K/H, indicated by ^). In this position, repeat 4 contains a threonine, which may be responsible for the lower 3D6 ELISA binding. The core epitope is defined at KIGSTENLKH (SEQ ID NO:188, residues 259-268 of SEQ ID NO:1, in MBTR repeat 1), KCGSKDNIKH (SEQ ID NO:192, residues 290-299 of SEQ ID NO:1, in MBTR repeat 2), KCGSLGNIHH (SEQ ID NO: 193, residues 321-330 of SEQ ID NO:1, in MBTR repeat 3), with lesser binding at KIGSLDNITH (SEQ ID NO:194, residues 353-362 of SEQ ID NO:1, in MBTR repeat 4).

Figure 13:
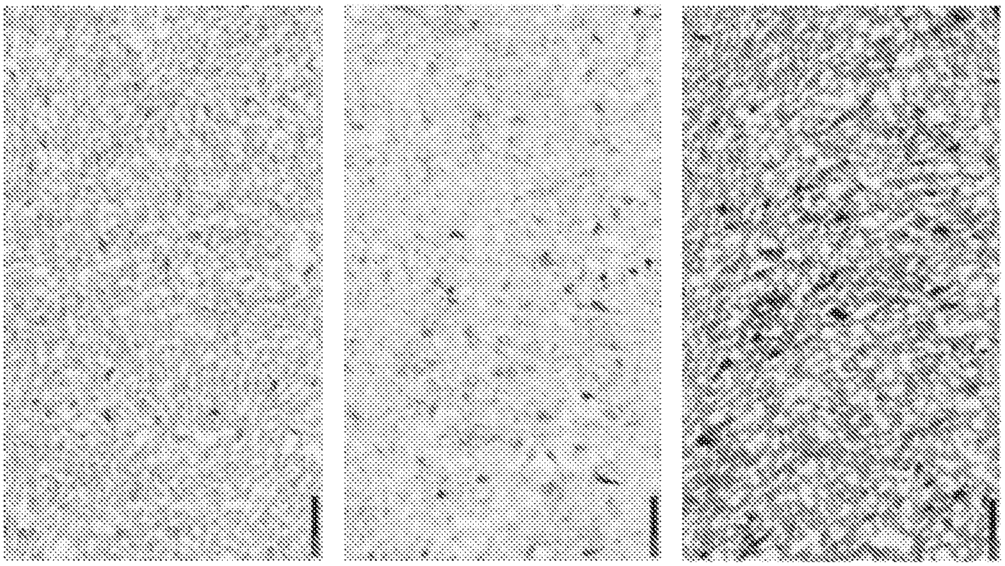
FIG. 13 depicts results of immunohistochemistry experiments showing 3D6 binds tau in normal (top panel) and Alzheimer's disease tissue (middle and bottom panels).

Example 15 Mouse 3D6 Binds Patient Samples from Alzheimer's Disease Patients, Immunohistochemistry Experiments Autopsy blocks of fresh frozen human brain samples (~0.5 g) were embedded in OCT, and cut using a cryostat to generate 10 m sections. Sections were placed into a solution of glucose oxidase and beta D-glucose, in the presence of sodium azide, to block endogenous peroxidase. Once tissue sections were prepared, they were stained with 3D6 at the indicated concentrations using an anti-mouse polymer and DAB-based detection Kit (Leica BOND refine detection kit) as per the manufacturer's instructions. Results are shown in FIG. 13.

In AD tissue, 3D6 binds hallmark pathological features of tau, including neurofibrillary tangles as well as dystrophic neurites. In addition, 3D6 binds soluble intracellular tau; this is evident by the staining present in normal healthy control tissue.

Example 16 Mouse 3D6 Binds Soluble Tau Aggregates, Cross-Linking High-Mass MALDI Mass Spectrometry Experiments In order to determine if 3D6 bound a single or multiple tau subunits, crosslinking high-mass MALDI mass spectrometry was utilized to assess the binding stoichiometry. Cross-linking allow the direct analysis of non-covalent interaction. By mixing a protein sample containing non-covalent interactions with a cross-linking mixture (Bich, C et al. Anal. Chem., 2010, 82 (1), pp 172-179), it is possible to specifically detect non-covalent complex with high-sensitivity. In this assay, the interaction of 3D6 with soluble tau aggregates were tested. Soluble tau aggregates were generated by incubation of recombinant full length tau with equimolar amounts of low molecular weight heparin for 3d at 37° C. After incubation, insoluble and soluble tau was separated by centrifugation at 10,000×g for 15 minutes. The supernatant was then resolved by preparative size exclusion chromatography, and aggregate peaks (greater than 100 kDa) were collected and concentrated.

3D6 was mixed with various ratios of soluble tau aggregate, and detected by high mass MALDI mass spectrometry. In addition, control experiments were performed of individual components to allow for correct labeling of detected peaks. Analysis was performed in linear positive mode with the HM4 interaction module (CovalX) with a standard nitrogen laser, focusing on the mass range of 0-1500 kDa.

Figure 14A:
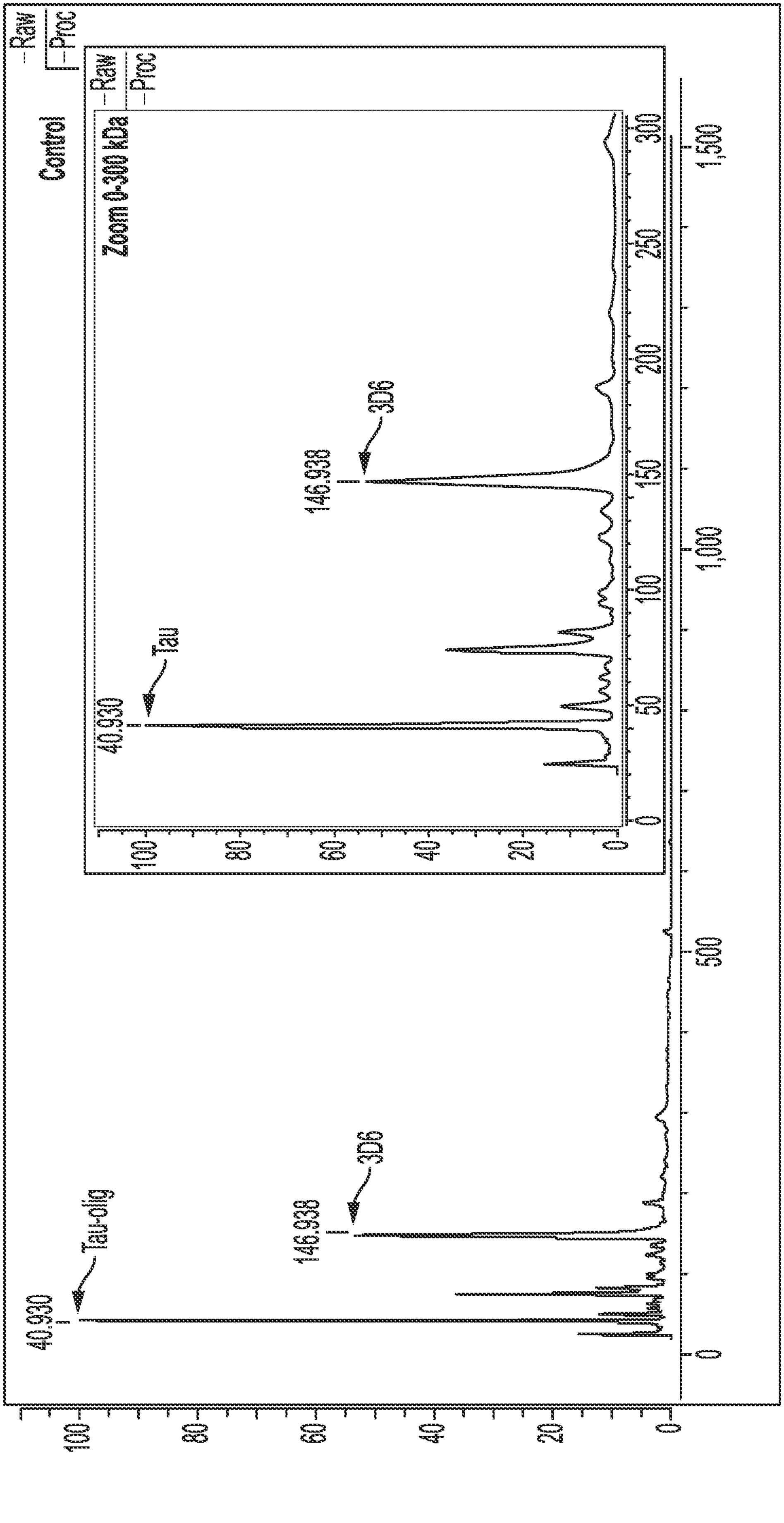
FIGS. 14A, 14B, and 14C shows results of mass spectrometry experiments to assess binding stoichiometry of 3D6.
Figure 14B:
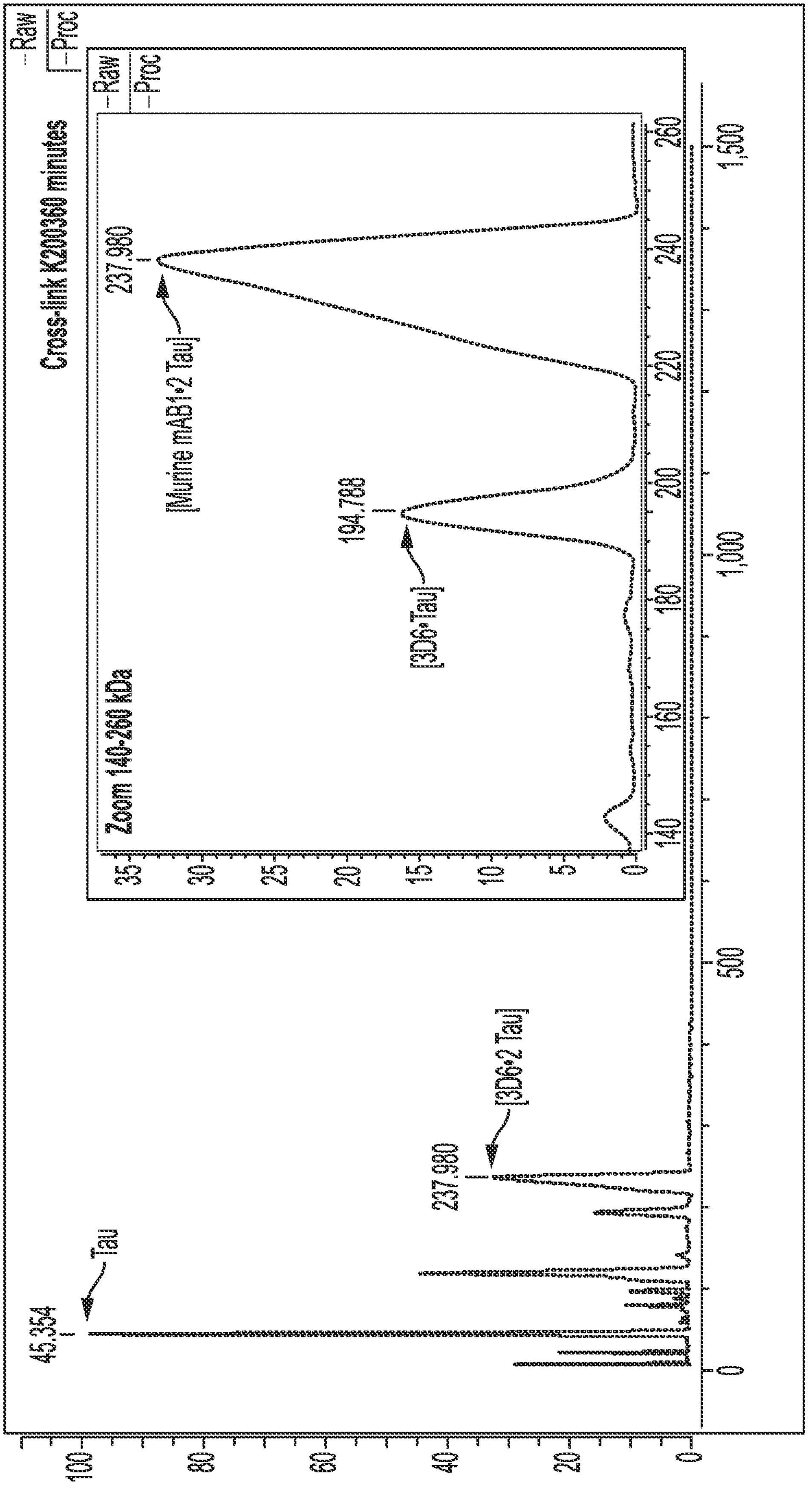
Figure 14C:
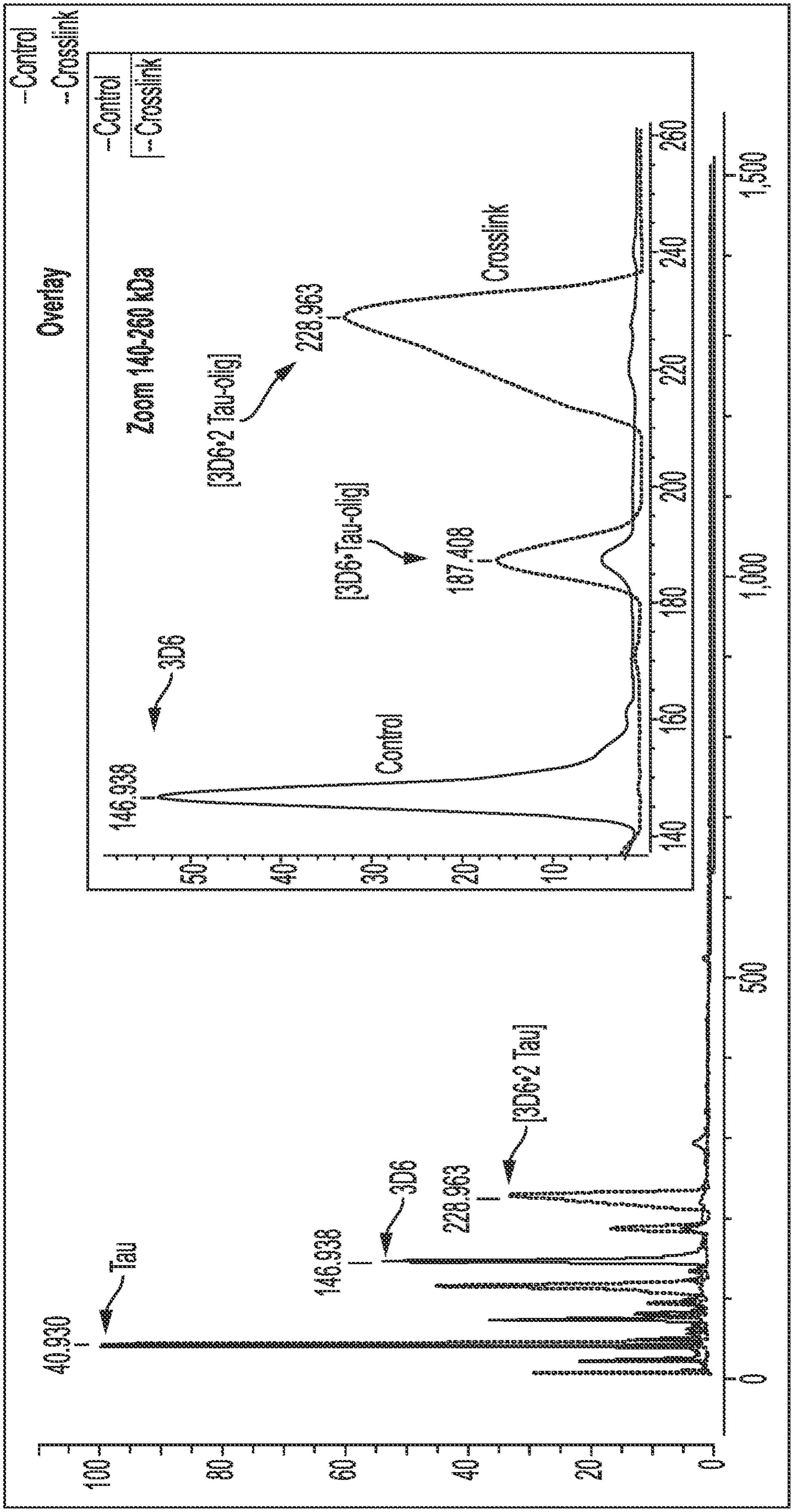

Results are shown in FIGS. 14A, 14B and 14C. In the control (uncrosslinked) results, both tau and 3D6 are detected as individual entities of 40.93 and 146.938 kDa, respectively. However, when crosslinked, the antibody peak for 3D6 disappears, whereas two new peaks appear representing 3D6 interacting with one and two antigens (at 194.788 and 228.963, respectively. As detected in the overlay inset, the 3D6 peak at 146.938 kDa is notably absent from the crosslinked samples. These data suggest that 3D6 very strongly binds soluble aggregates of tau, and carries this out either through binding of one or two complexes per antibody.

Example 17 Mouse 3D6 Interrupts Tau Seeding in an In Vivo Disease Model of Alzheimer's Disease Pathology The ability of 3D6 to interrupt tau seeding were investigated in an in vivo disease model of the propagation of AD pathology. Pathological seeds were generated using brainstem homogenates from end-stage hTauP301L mice, or wild type controls. To induce pathology, seeds were unilaterally injected in the hippocampus of 3.5 month old mice, well before the onset of the progression of natural pathology. In order to test the ability of antibodies to impact seeding of tau, antibodies were preincubated before injection. After one month, the amount of seeding in the ipsilateral side of the mice was assessed by AT8 immunoreactivity; the number of neurons per section within the hippocampus was determined.

Figure 15:
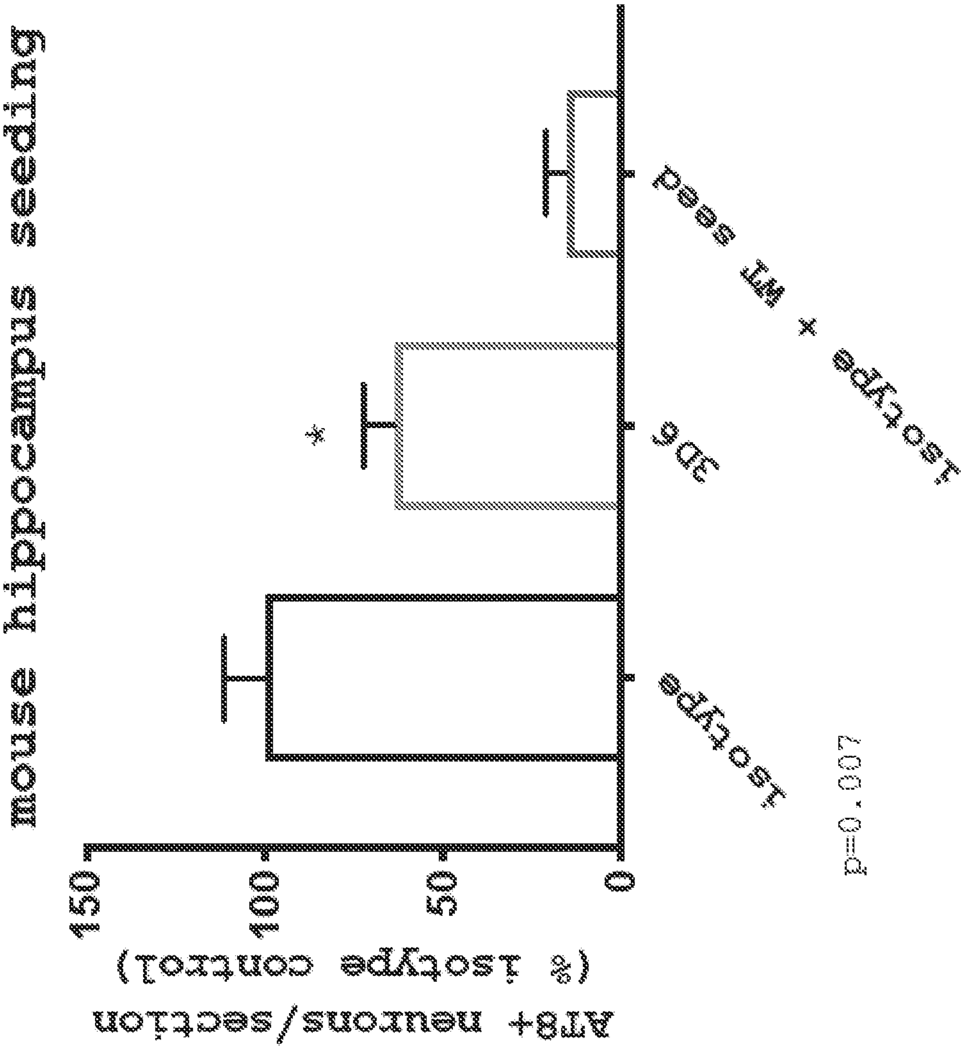
FIG. 15 shows that 3D6 interrupts tau seeding in an in vivo disease model of Alzheimer's disease.

Results are shown in FIG. 15. Compared to isotype control, preincubation of tau seeds with 3D6 was able to significantly decrease the amount of seeding detected in mice after one month, suggesting the interruption of tau internalization proximally to the injection site and suggesting that 3D6 can impair tau uptake and propagation.

Example 18 Mouse 3D6 and Humanized Variants Interrupt Tau Interaction with Heparin In Vitro Several studies indicate that tau internalization into cells is mediated via initial interaction of tau with surface-associated heparin sulfate proteoglycans (HSPGs), and that this interaction is an essential initial step leading to tau uptake, seeding, and propagation (Holmes et al., PNAS, 110(33), 2013; Katsinelos et al., Cell Rep, 23, 2018). Therefore, a favorable property of a therapeutic anti-tau antibody would be the ability to block the interaction between tau and heparin that would be present on the surface of cells.

To test the ability of murine and humanized 3D6 variants to interrupt tau interaction with heparin, ELISA plates coated with low molecular weight heparin were first blocked with 2% BSA in PBS for 2 h at room temperature. Plates were washed with TBST. After blocking, plates were incubated with biotinylated recombinant tau along with indicated concentrations of unlabeled antibody in 1% BSA/PBS for one hour at room temperature. Plates were again washed, and then incubated with streptavidin-HRP in 0.1% BSA/PBS for 45 min. Plates were then washed and developed with OPD, and absorbance was measured at 490 nm. Inhibition curves were analyzed using a 4-parameter log fit.

Figure 16:
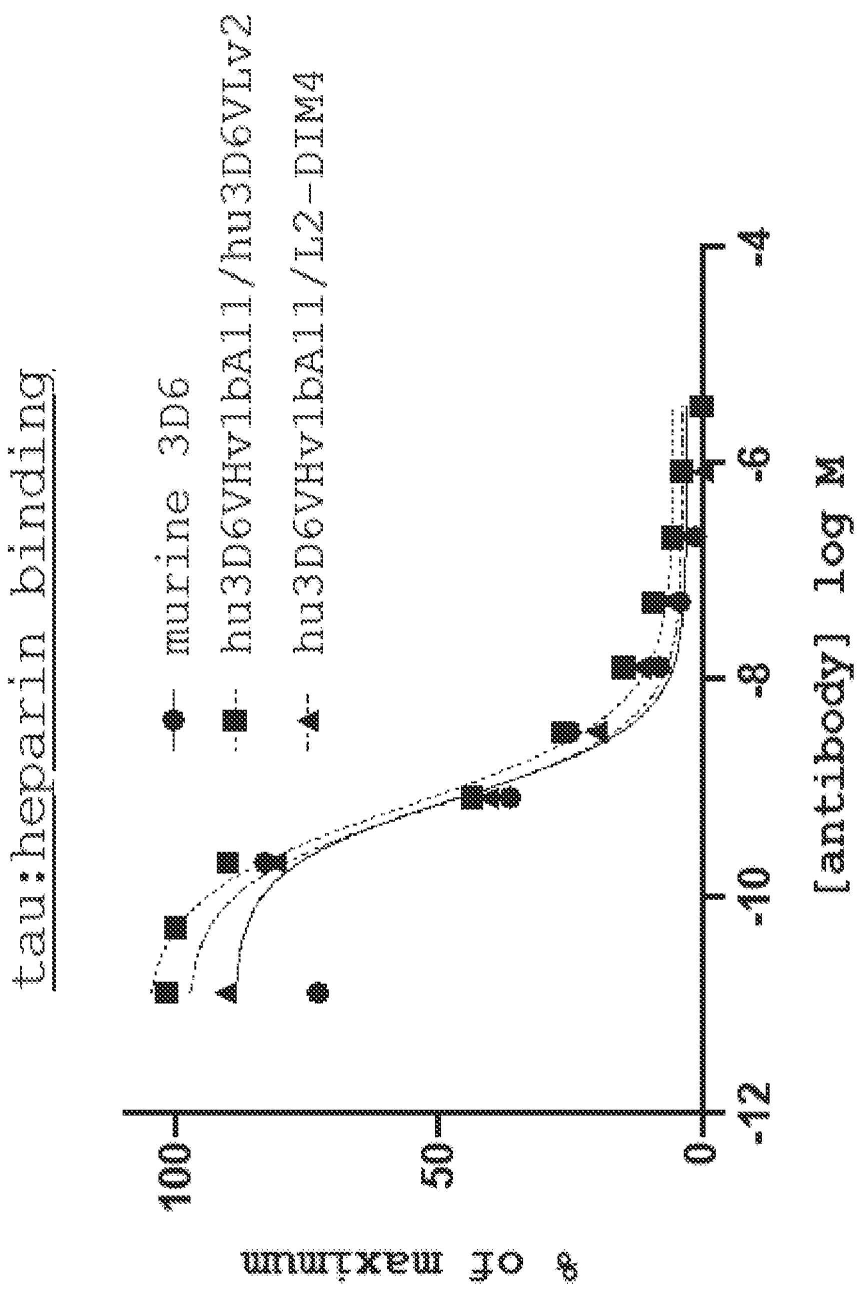
FIG. 16 shows that 3D6 humanized variants hu3D6VHv1bA11/hu3D6VLv2 and hu3D6VHv1bA11/L2-DIM4 block interaction between tau and heparin.

Results are shown in FIG. 16 and Table 19. Murine, as well as both humanized forms of 3D6 tested in the assay displayed the ability to block the tau/heparin interaction, indicating that the 3D6 epitope is important for this interaction, and that antibodies are able to inhibit the interaction. This suggests the ability to interrupt tau uptake into cells. Though all antibodies tested displayed inhibitory activity, the variant hu3D6VHv1bA11/L2-DIM4 retained activity closer to the murine form of the antibody (IC50=422.7 pM, compared to 409.2 pM for murine). In contrast, hu3D6VHv1bA11/hu3D6VLv2 demonstrated lower inhibitory activity (IC50=564.6 pM), compared to hu3D6VHv1bA11/L2-DIM4,_indicating hu3D6VHv1bA11/L2-DIM4 has a higher degree of retention of murine antibody properties and suggesting an improvement of inhibitory activity of hu3D6VHv1bA11/L2-DIM4 due to the amino acid variants in the CDR of the light chain.

TABLE 19

| Antibody | IC50 (pM) |
|---|---|
| murine 3D6 | 409.2 |
| hu3D6VHv1bA11/hu3D6VLv2 | 564.6 |
| hu3D6VHv1bA11/L2-DIM4 | 422.7 |

Example 19 3D6 Humanized Variants Bind Fibrillar Forms of Tau

Recombinant tau fibrils were generated by either incubation with equimolar amounts of low molecular weight heparin with either 4-repeat tau ("fibrillar tau") or seeding growth of 3-repeat and 4-repeat tau ("mixed fibrils"). Tau was incubated for 3-5d at 37° C. To isolate fibrils, prepared samples were ultracentrifuged at 100,000×g for 30 minutes. Pellets were resuspended in their original volume before storage at −80° C. before use.

ELISA plates were coated with preformed fibrils (overnight at 4° C. in 50 mM carbonate-bicarbonate buffer, pH 9.6), washed, and blocked with 1% BSA in PBS. After blocking, plates were incubated with the indicated concentrations of biotinylated primary antibody in 0.1% BSA/PBS for 1 h at room temperature. Plates were washed, and then incubated with streptavidin-TRP in 0.1% BSA/PBS for 45 min. Plates were then washed and developed with OPD, and absorbance was measured at 490 nm. Binding curves were analyzed using a 4-parameter log fit.

Figure 17:
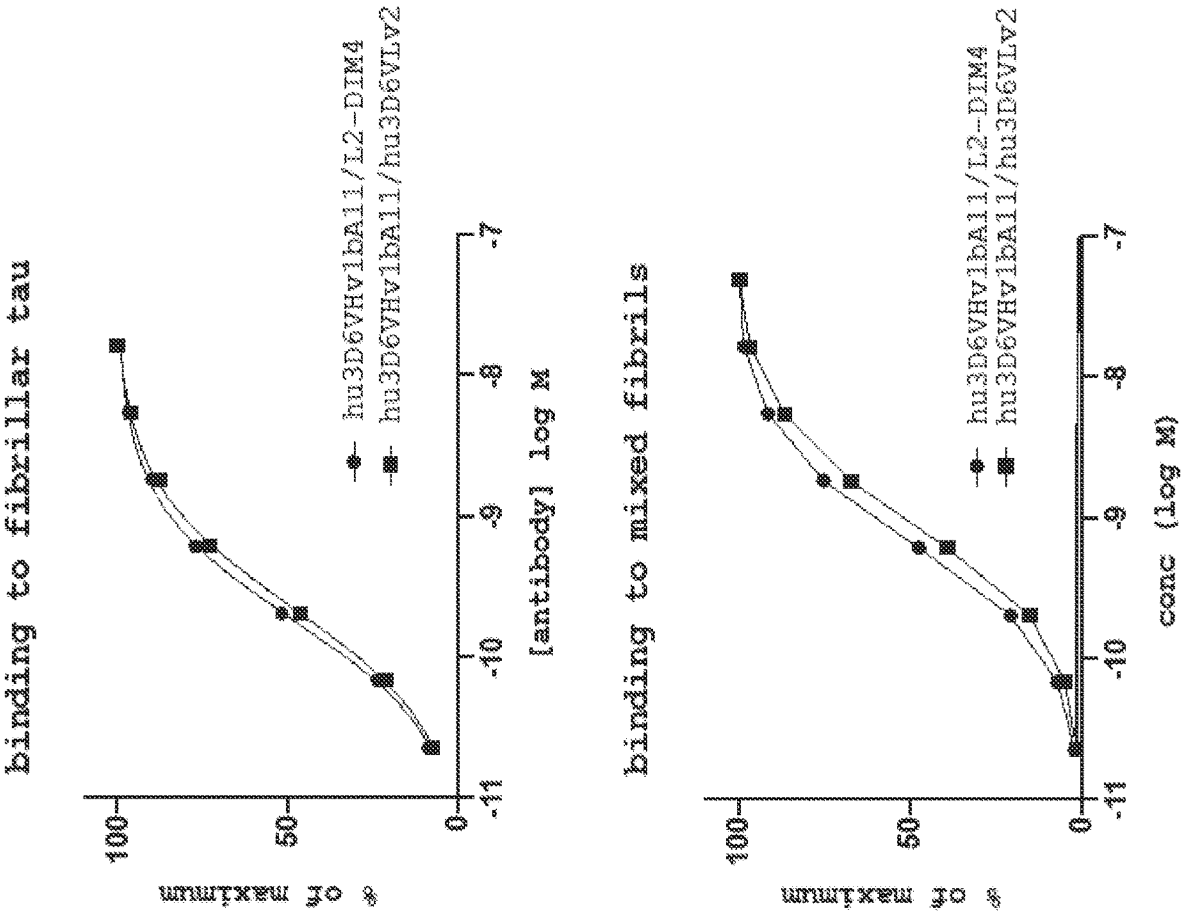
FIG. 17 shows that 3D6 humanized variants hu3D6VHv1bA11/hu3D6VLv2 and hu3D6VHv1bA11/L2-DIM4 bind fibrillar forms of tau.

Results are shown in FIG. 17 and Table 20. Both humanized forms of 3D6 tested in the assay displayed strong binding to fibrillar forms of tau, whether fibrils contained 4R tau only or both 3R and 4R tau. The variant hu3D6VH1v1bA11/L2-DIM4 displayed a preference for binding to both species (EC50=191.8 pM) compared to hu3D6VH1v1bA11/hu3D6VLv2 (EC50=236.7 pM), indicating an improvement in binding capacity of hu3D6VHv1bA11/L2-DIM4 due to the amino acid variants in the CDR of the light chain.

TABLE 20

| Antibody | Binding to 4R tau fibrils: EC50 (pM) |
|---|---|
| hu3D6VHv1bA11/L2-DIM4 | 191.8 |
| hu3D6VHv1bA11/hu3D6VLv2 | 236.7 |

Example 20 Exemplary CDRs

Exemplary CDRs of antibodies of the invention are in Table 21.

TABLE 21

Exemplary CDRs

| CDR and Definition | CDR Amino Acid Sequence | SEQ ID NO: | Exemplary VH or VL that CDR is present in |
|---|---|---|---|
| Kabat/Chothia HCDR1 | GFNIKDYYLH | 8 | Mouse 3D6 VH |
| Kabat HCDR2 | WIDPENGDTVYDPKFQG | 9 | Mouse 3D6 VH |
| Kabat HCDR3: | LDF | 10 | Mouse 3D6 VH |
| Kabat LCDR1 | KSSQSLLDSDGKTYLN | 12 | Mouse 3D6 VL |
| Kabat LCDR2 | LVSKLDS | 13 | Mouse 3D6 VL |
| Kabat LCDR3: | WQGTHFPYT | 14 | Mouse 3D6 VL |
| CDR-H1 Kabat | DYYLH | 32 | Mouse 3D6 VH |
| CDR-H1 Chothia | GFNIKDY | 33 | Mouse 3D6 VH |
| CDR-H2 Chothia | DPENGD | 34 | Mouse 3D6 VH |
| CDR-H2 AbM | WIDPENGDTV | 35 | Mouse 3D6 VH |
| CDR-L1 Contact | KTYLNWL | 36 | Mouse 3D6 VL |
| CDR-L2 Contact | RLIYL VSKLD | 37 | Mouse 3D6 VL |
| CDR-L3 Contact | WQGTHFPY | 38 | Mouse 3D6 VL |
| CDR-H1 Contact | KDYYLH | 39 | Mouse 3D6 VH |
| CDR-H2 Contact | WIGWIDPENGDTV | 40 | Mouse 3D6 VH |
| CDR-H3 Contact | STLD | 41 | Mouse 3D6 VH |
| Kabat-Chothia CDR-H1 | GFTIKDYYLH | 42 | hu3D6VHv5, hu3D6VHv1bA11B6G2, hu3D6VHv1bA11B6H3, hu3D6VHv1e, and hu3D6VHv1f |
| Kabat CDR-H2 | WIDPEDGDTVYAPKFQG | 43 | hu3D6VHv5 and hu3D6VHv1bA11B6H3 |
| Kabat-Chothia CDR-H1 | GFNFKDYYLH | 58 | hu3D6VH1c |
| Kabat-Chothia CDR-H1 | GYTFTDYYLH | 59 | hu3D6VHv1d, hu3D6VHv3c, and hu3D6VHv4c |
| Kabat-Chothia CDR-H1 | GYNFKDYYLH | 60 | hu3D6VHv3b and hu3D6VHv4b |

TABLE 21-continued

| Exemplary CDRs | | | |
|---|---|---|---|
| CDR and Definition | CDR Amino Acid Sequence | SEQ ID NO: | Exemplary VH or VL that CDR is present in |
| Kabat CDR-H2 | WVDPEDGDTVYAPKFQG | 61 | hu3D6VHv1bA11B6G2 |
| Kabat CDR-H2 | WIDPENGDTVYDEKFQG | 62 | hu3D6VHv1c, hu3D6VHv3b, and hu3D6VHv4b |
| Kabat CDR-H2 | WVDPEDGDTVYAEKFQG | 63 | hu3D6VHv1d, hu3D6VHv1f, hu3D6VHv3c, and hu3D6VHv4c |
| Kabat CDR-H2 | WIDPENGDTVYAEKFQG | 64 | hu3D6VHv1e |
| Kabat CDR-H3 | LDY | 65 | hu3D6VHv1f |
| Kabat/Chothia composite CDR-H1 | GLNIKDYYIH | 67 | Mouse 6A10 VH |
| Kabat CDR-H2 | WIDPENDDTEYAPKFQG | 68 | Mouse 6A10 VH |
| Kabat CDR-H3 | LDY | 69 | Mouse 6A10 VH |
| Kabat-Chothia Composite CDR-H1 | GFTIKDYYLH | 86 | hu3D6VHvb4 and hu3D6VHvb5 |
| Kabat CDR-H2 | WIDPENGDTIYDPKFQG | 87 | hu3D6VHvb3 and hu3D6VHvb4 |
| Kabat CDR-H2 | WIDPEDGETIYDPKFQG | 88 | hu3D6VHvb5 |
| Kabat CDR-L1 | RSSQSLLDSDGKTYLN | 89 | hu3D6VLvb3 |
| Kabat CDR-H2 | WIDPEDGETVYDPKFQG | 92 | hu3D6VHvb6 and hu3D6VHvb7 |
| Kabat CDR-H2 | WIDPENGDTVYEPKFQG | 149 | h3D6VHvb8 and h3D6VHvb9 |
| Kabat CDR-L2 | LVSKDDS | 150 | hu3D6VLv2 L54D and hu3D6VLv2 L37Q_L54D |
| Kabat CDR-L2 | LVSKGDS | 151 | hu3D6VLv2 L54G and hu3D6VLv2 L37Q L54G |
| Kabat CDR-L2 | LVSKNDS | 152 | hu3D6VLv2 L54N |
| Kabat CDR-L2 | LVSKEDS | 153 | hu3D6VLv2 L54E and hu3D6VLv2 L37Q L54E |
| Kabat CDR-L2 | EVSKLDS | 154 | hu3D6VLv2 L50E |
| Kabat CDR-L2 | LVSKQDS | 155 | hu3D6VLv2 L54Q |
| Kabat CDR-L2 | DVSKLDS | 156 | hu3D6VLv2 L50D and hu3D6VLv2 L37Q L50D |
| Kabat CDR-L2 | LVSKKDS | 157 | hu3D6VLv2 L54K |
| Kabat CDR-L2 | LVSKRDS | 158 | hu3D6VLv2 L54R and hu3D6VLv2 L37Q_L54R |
| Kabat CDR-L2 | LVSKTDS | 159 | hu3D6VLv2 L54T and hu3D6VLv2 L37Q L54T |
| Kabat CDR-L2 | GVSKLDS | 160 | hu3D6VLv2 L50G and hu3D6VLv2 L37Q L50G |
| Kabat CDR-L2 | LVSKVDS | 161 | hu3D6VLv2 L54V |
| Kabat CDR-L2 | LVSKSDS | 162 | hu3D6VLv2 L54S |
| Kabat CDR-L2 | LVGKLDS | 163 | hu3D6VLv2 S52G and hu3D6VLv2 L37Q S52G |
| Kabat CDR-L2 | VVSKLDS | 164 | hu3D6VLv2 L50V |

TABLE 21-continued

Exemplary CDRs

| CDR and Definition | CDR Amino Acid Sequence | SEQ ID NO: | Exemplary VH or VL that CDR is present in |
|---|---|---|---|
| Kabat CDR-L2 | GVSKRDS | 165 | hu3D6VLv2 L37Q_L50G_L54R and hu3D6VLv2 L37Q_L50G_L54R_G100Q |
| Kabat CDR-L2 | GVSKGDS | 166 | hu3D6VLv2 L37Q_L50G_L54G and hu3D6VLv2 L37Q_L50G_L54G_G100Q |
| Kabat CDR-L2 | LVGKGDS | 167 | hu3D6VLv2 L37Q_S52G_L54G |
| Kabat CDR-L2 | LVGKRDS | 168 | hu3D6VLv2 L37Q_S52G_L54R and hu3D6VLv2 L37Q_S52G_L54R_G100Q |
| Kabat CDR-L2 | LVGKTDS | 169 | hu3D6VLv2 L37Q_S52G_L54T |
| Kabat CDR-L2 | LVGKDDS | 170 | hu3D6VLv2 L37Q_S52G_L54D and hu3D6VLv2 L37Q_S52G_L54D_G100Q |
| Kabat CDR-L2 | DVSKGDS | 171 | in hu3D6VLv2 L37Q_L50D_L54G and hu3D6VLv2 L37Q_L50D_L54G_G100Q |
| Kabat CDR-L2 | DVSKRDS | 172 | hu3D6VLv2 L37Q_L50D_L54R and hu3D6VLv2 L37Q_L50D_L54R_G100Q |
| Kabat CDR-L2 | EVSKGDS | 173 | hu3D6VLv2 L37Q_L50E_L54G |
| Kabat CDR-L2 | EVSKRDS | 174 | hu3D6VLv2 L37Q_L50E_L54R |
| Kabat CDR-L2 | VVSKDDS | 175 | hu3D6VLv2 L37Q_L50V_L54D_G100Q |

Listing of Sequences

P10636-8 (SEQ ID NO: 1)
MAEPRQEFEVMEDHAGTYGLGDRKDQGGYTMHQDQEGDTDAGLKESPLQTPTEDGSE
EPGSETSDAKSTPTAEDVTAPLVDEGAPGKQAAAQPHTEIPEGTTAEEAGIGDTPSLEDE
AAGHVTQARMVSKSKDGTGSDDKKAKGADGKTKIATPRGAAPPGQKGQANATRIPAK
TPPAPKTPPSSGEPPKSGDRSGYSSPGSPGTPGSRSRTPSLPTPPTREPKKVAVVRTPPKSP
SSAKSRLQTAPVPMPDLKNVKSKIGSTENLKHQPGGGKVQIINKKLDLSNVQSKCGSKD
NIKHVPGGGSVQIVYKPVDLSKVTSKCGSLGNIHHKPGGGQVEVKSEKLDFKDRVQSKI
GSLDNITHVPGGGNKKIETHKLTFRENAKAKTDHGAEIVYKSPVVSGDTSPRHLSNVSST
GSIDMVDSPQLATLADEVSASLAKQGL

P10636-7 (SEQ ID NO: 2)
MAEPRQEFEVMEDHAGTYGLGDRKDQGGYTMHQDQEGDTDAGLKESPLQTPTEDGSE
EPGSETSDAKSTPTAEAEEAGIGDTPSLEDEAAGHVTQARMVSKSKDGTGSDDKKAKG
ADGKTKIATPRGAAPPGQKGQANATRIPAKTPPAPKTPPSSGEPPKSGDRSGYSSPGSPG
TPGSRSRTPSLPTPPTREPKKVAVVRTPPKSPSSAKSRLQTAPVPMPDLKNVKSKIGSTEN
LKHQPGGGKVQIINKKLDLSNVQSKCGSKDNIKHVPGGGSVQIVYKPVDLSKVTSKCGS
LGNIHHKPGGGQVEVKSEKLDFKDRVQSKIGSLDNITHVPGGGNKKIETHKLTFRENAK
AKTDHGAEIVYKSPVVSGDTSPRHLSNVSSTGSIDMVDSPQLATLADEVSASLAKQGL

P10636-6 (4RON human tau)(SEQ ID NO: 3)
MAEPRQEFEVMEDHAGTYGLGDRKDQGGYTMHQDQEGDTDAGLKAEEAGIGDTPSLE
DEAAGHVTQARMVSKSKDGTGSDDKKAKGADGKTKIATPRGAAPPGQKGQANATRIP
AKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIINKKLDLSNVQSKCGS
KDNIKHVPGGGSVQIVYKPVDLSKVTSKCGSLGNIHHKPGGGQVEVKSEKLDFKDRVQ
SKIGSLDNITHVPGGGNKKIETHKLTFRENAKAKTDHGAEIVYKSPVVSGDTSPRHLSNV
SSTGSIDMVDSPQLATLADEVSASLAKQGL P10636-5 (SEQ ID NO: 4)
MAEPRQEFEVMEDHAGTYGLGDRKDQGGYTMHQDQEGDTDAGLKESPLQTPTEDGSE
EPGSETSDAKSTPTAEDVTAPLVDEGAPGKQAAAQPHTEIPEGTTAEEAGIGDTPSLEDE
AAGHVTQARMVSKSKDGTGSDDKKAKGADGKTKIATPRGAAPPGQKGQANATRIPAK -continued

| Listing of Sequences |
|---|

TPPAPKTPPSSGEPPKSGDRSGYSSPGSPGTPGSRSRTPSLPTPPTREPKKVAVVRTPPKSP
SSAKSRLQTAPVPMPDLKNVKSKIGSTENLKHQPGGGKVQIVYKPVDLSKVTSKCGSLG
NIHHKPGGGQVEVKSEKLDFKDRVQSKIGSLDNITHVPGGGNKKIETHKLTFRENAKAK
TDHGAEIVYKSPVVSGDTSPRHLSNVSSTGSIDMVDSPQLATLADEVSASLAKQGL

P10636-4 (SEQ ID NO: 5)
MAEPRQEFEVMEDHAGTYGLGDRKDQGGYTMHQDQEGDTDAGLKESPLQTPTEDGSE
EPGSETSDAKSTPTAEAEEAGIGDTPSLEDEAAGHVTQARMVSKSKDGTGSDDKKAKG
ADGKTKIATPRGAAPPGQKGQANATRIPAKTPPAPKTPPSSGEPPKSGDRSGYSSPGSPG
TPGSRSRTPSLPTPPTREPKKVAVVRTPPKSPSSAKSRLQTAPVPMPDLKNVKSKIGSTEN
LKHQPGGGKVQIVYKPVDLSKVTSKCGSLGNIHHKPGGGQVEVKSEKLDFKDRVQSKI
GSLDNITHVPGGGNKKIETHKLTFRENAKAKTDHGAEIVYKSPVVSGDTSPRHLSNVSST
GSIDMVDSPQLATLADEVSASLAKQGL

P10636-2 (SEQ ID NO: 6)
MAEPRQEFEVMEDHAGTYGLGDRKDQGGYTMHQDQEGDTDAGLKAEEAGIGDTPSLE
DEAAGHVTQARMVSKSKDGTGSDDKKAKGADGKTKIATPRGAAPPGQKGQANATRIP
AKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIVYKPVDLSKVTSKCGS
LGNIHHKPGGGQVEVKSEKLDFKDRVQSKIGSLDNITHVPGGGNKKIETHKLTFRENAK
AKTDHGAEIVYKSPVVSGDTSPRHLSNVSSTGSIDMVDSPQLATLADEVSASLAKQGL

SEQ ID NO: 7; Murine 3D6 VH amino acid sequence:
EVQLQQSGADLVRPGALVKLSCKASGFNIKDYYLHWVRQRPEQGLEWIGWIDPENGDT
VYDPKFQGKATITADTSSNTAYLQLGSLTSEDTAVYFCSTLDFWGQGTTLTVSS SEQ ID NO: 8; Kabat/Chothia HCDR1:
GFNIKDYYLH SEQ ID NO: 9; Kabat HCDR2:
WIDPENGDTVYDPKFQG SEQ ID NO: 10; Kabat HCDR3:
LDF SEQ ID NO: 11; Murine 3D6 VL amino acid sequence:
DVVMTQTPLTLSVTIGQPASISCKSSQSLLDSDGKTYLNWLLQRPGQSPKRLIYLVSKLD
SGVPDRFTGSGSGTDFTLKISRVEAEDLGVYYCWQGTHFPYTFGGGTKLEIK SEQ ID NO: 12; Murine Kabat LCDR1:
KSSQSLLDSDGKTYLN SEQ ID NO: 13; Murine Kabat LCDR2:
LVSKLDS SEQ ID NO: 14; Murine Kabat LCDR3:
WQGTHFPYT SEQ ID NO: 15; hu3D6VHv1:
EVQLVQSGAEVVRPGALVKVSCKASGFNIKDYYLHWVRQAPEQGLEWIGWIDPENGDT
VYDPKFQGKATITADTSTNTAYLQLSSLTSEDTAVYFCSTLDFWGQGTLVTVSS SEQ ID NO: 16; hu3D6VHv2:
EVQLVQSGAEVKKPGASVKVSCKVSGFNIKDYYLHWVRQAPEQGLEWMGWIDPENGD
TVYDPKFQGRVTITADTSTNTAYMELSSLTSEDTAVYYCSTLDFWGQGTLVTVSS SEQ ID NO: 17; hu3D6VHv1b:
EVQLVQSGAEVVRPGALVKISCKASGFNIKDYYLHWVRQRPEQGLEWIGWIDPENGDT
VYDPKFQGKATITADTSTNTAYLQLGSLTSEDTAVYFCSTLDFWGQGTLVTVSS SEQ ID NO: 18; hu3D6VHv1bA11:
EVQLVQSGAEVVKPGATVKISCKASGFNIKDYYLHWVRQRPGQGLEWIGWIDPENGDT
VYDPKFQGRATITADTSTDTAYLQLGSLTSEDTAVYFCSTLDFWGQGTLVTVSS SEQ ID NO: 19; hu3D6VHv5:
EVQLVQSGAEVVKPGATVKISCKASGFTIKDYYLHWVRQRPGQGLEWIGWIDPEDGDT
VYAPKFQGRATITADTSTDTAYLQLGSLTSEDTAVYFCSTLDFWGQGTLVTVSS SEQ ID NO: 20; hu3D6VLv1:
DVVMTQSPLSLSVTLGQPASISCKSSQSLLDSDGKTYLNWLLQRPGQSPKRLIYLVSKLD
SGVPDRFSGSGSGTDFTLKISRVEAEDVGVYYCWQGTHFPYTFGGGTKLEIK SEQ ID NO: 21; hu3D6VLv2:
DVVMTQSPLSLPVTLGQPASISCKSSQSLLDSDGKTYLNWLLQRPGQSPRRLIYLVSKLD
SGVPDRFSGSGSGTDFTLKISRVEAEDVGVYYCWQGTHFPYTFGGGTKLEIK -continued

| Listing of Sequences |
| --- |

SEQ ID NO: 22; hu3D6VLv3:
DVVMTQSPLSLPVTLGQPASISCKSSQSLLDSDGKTYLNWLLQRPGQSPRRLIYLVSKLD
SGVPSRFSGSGSGTDFTLKISRVEAEDVGVYYCWQGTHFPYTFGGGTKLEIK

SEQ ID NO: 23; hu3D6VLv4:
DIVMTQTPLSLSVTIGQPASISCKSSQSLLDSDGKTYLNWLLQKPGQSPKRLIYLVSKLDS
GVPDRFSGSGSGTDFTLKISRVEAEDVGVYYCWQGTHFPYTFGGGTKLEIK

SEQ ID NO: 24; heavy chain variable acceptor Acc.# BAC01986.1
QVQLQQSGAEVKKPGSSVKVSCKASGGTFGSYAISWVRQAPGQGLEWMGRIIPILGIAT
YAQKFQGRVTITADKSTSTAYMDLSSLRSEDTAVYYCARGKGEFEGMDVWGQGTTVT
VSS SEQ ID NO: 25; heavy chain variable acceptor Acc.# IMGT# IGHV1-69-2*01
EVQLVQSGAEVKKPGATVKISCKVSGYTFTDYYMHWVQQAPGKGLEWMGLVDPEDG
ETIYAEKFQGRVTITADTSTDTAYMELSSLRSEDTAVYYCAT SEQ ID NO: 26; heavy chain variable acceptor Acc.# IMGT#IGKJ1*01
QHWGQGTLVTVSS SEQ ID NO: 27; light chain variable acceptor Acc. # IMGT#IGKV2-30*02
Acc. # IMGT#IGKV2-30*02
DVVMTQSPLSLPVTLGQPASISCRSSQSLVHSDGNTYLNWFQQRPGQSPRRLIYKVSNRD
SGVPDRFSGSGSGTDFTLKISRVEAEDVGVYYCMQGTHWP SEQ ID NO: 28; light chain variable acceptor Acc. # IMGT#IGKJ2*01
YTFGQGTKLEIK SEQ ID NO: 29; Light chain variable acceptor Acc. # AAZ09048.1
DVVMTQSPLSLTVTLGQPASISCRSSQSLVYSDGNTYLNWFQQRPGQSPRRLIYRVSHW
DSGVPDRFSGSGSGTDFTLKISRVEAEDVGVYYCMQGTYWPLTFGQGTKLEIK SEQ ID NO: 30; Murine 3D6 VH nucleic acid sequence:
GAGGTTCAGCTGCAGCAGTCTGGGGCTGACCTTGTGAGGCCAGGGGCCTTAGTCAA
GTTGTCCTGCAAAGCTTCTGGCTTCAACATTAAAGACTACTATTTGCACTGGGTGAG
GCAGAGGCCTGAACAGGGCCTGGAGTGGATTGGATGGATTGATCCTGAGAATGGTG
ATACTGTATATGACCCGAAGTTCCAGGGCAAGGCCACTATAACAGCAGACACATCC
TCCAATACAGCCTACCTGCAGCTCGGCAGCCTGACATCTGAGGACACTGCCGTCTAT
TTCTGTTCTACCCTTGACTTCTGGGGCCAAGGCACCACTCTCACAGTCTCCTCA SEQ ID NO: 31; Murine 3D6 VL nucleic acid sequence:
GATGTTGTGATGACCCAGACTCCACTCACTTTGTCGGTTACCATTGGACAACCAGCC
TCCATCTCTTGCAAGTCAAGTCAGAGCCTCTTAGATAGTGATGGAAAGACATATTTG
AATTGGTTGTTACAGAGGCCAGGCCAGTCTCCAAAGCGCCTAATCTATCTGGTGTCT
AAACTGGACTCTGGAGTCCCTGACAGGTTCACTGGCAGTGGATCAGGGACAGATTTC
ACACTGAAAATCAGCAGAGTGGAGGCTGAGGATTTGGGAGTTTATTATTGCTGGCA
AGGTACACATTTTCCGTACACGTTCGGAGGGGGGACCAAGCTGGAAATAAAACGT SEQ ID NO: 32; Murine CDR-H1 Kabat
DYYLH SEQ ID NO: 33; Murine CDR-H1 Chothia
GFNIKDY SEQ ID NO: 34; Murine CDR-H2 Chothia
DPENGD SEQ ID NO: 35; Murine CDR-H2 AbM
WIDPENGDTV SEQ ID NO: 36; Murine CDR-L1 Contact
KTYLNWL SEQ ID NO: 37; Murine CDR-L2 Contact
RLIYLVSKLD SEQ ID NO: 38; Murine CDR-L3 Contact
WQGTHFPY SEQ ID NO: 39; Murine CDR-H1 Contact
KDYYLH SEQ ID NO: 40; Murine CDR-H2 Contact
WIGWIDPENGDTV -continued

| Listing of Sequences |
| --- |

SEQ ID NO: 41; Murine CDR-H3 Contact
STLD

SEQ ID NO: 42; Alternate Kabat-Chothia CDR-H1
GFTIKDYYLH

SEQ ID NO: 43; Alternate Kabat CDR-H2
WIDPEDGDTVYAPKFQG

SEQ ID NO: 44; consensus VH amino acid sequence from FIG. 2 of PCT/IB2017/052544
EVQLVQSGAEVVXPGALVKISCKASGFNIKDYYLHWVRQRPEQGLEWIGWIDPENGDT
VYDPKFQGXATITADTSTNTAYLQLGSLTSEDTAVYFCSTLDFWGQGTLVTVSS SEQ ID NO: 45; consensus VL amino acid sequence of FIG. 3 of PCT/IB2017/052544
DVVMTQSPLSLSVTLGQPASISCKSSQSLLDSDGKTYLNWLLQRPGQSPKRLIYLVSKLD
SGVPDRFSGSGSGTDFTLKISRVEAEDVGVYYCWQGTHFPYTFGGGTKLEIKR SEQ ID NO: 46; hu3D6VHv1bA11B6G2:
EVQLVQSGAEVVKPGATVKISCKASGFTIKDYYLHWVRQRPGKGLEWIGWVDPEDGDT
VYAPKFQGRATITADTSTDTAYLELGSLTSEDTAVYFCSTLDFWGQGTLVTVSS SEQ ID NO: 47; hu3D6VHv1bA11B6H3:
EVQLVQSGAEVVKPGATVKISCKASGFTIKDYYLHWVRQRPGKGLEWIGWIDPEDGDT
VYAPKFQGRATITADTSTDTAYLELGSLTSEDTAVYFCSTLDFWGQGTLVTVSS SEQ ID NO: 48; hu3D6VHv1c:
EVQLVQSGAEVKRPGALVKISCKASGFNFKDYYLHWVRQRPEQGLEWMGWIDPENGD
TVYDEKFQGRVTITADTSTNTAYLQLGSLTSEDTAVYFCSTLDFWGQGTLVTVSS SEQ ID NO: 49; hu3D6VHv1d:
EVQLVQSGAEVKRPGALVKISCKASGYTFTDYYLHWVRQRPEQGLEWMGWVDPEDGD
TVYAEKFQGRVTITADTSTNTAYLQLGSLTSEDTAVYFCSTLDFWGQGTLVTVSS SEQ ID NO: 50; hu3D6VHv1e:
EVQLVQSGADVvkPGALVKISCKASGFTIKDYYLHWVRQRPEQGLEWIGWIDPENGDTV
YAEKFQGRVTITADTSTNTAYLeLGSLTSEDTAVYFCSTLDFWGQGTTLTVSS SEQ ID NO: 51; hu3D6VHv1f:
EVQLVQSGADVVKPGALVKISCKASGFTIKDYYLHWVRQRPGQGLEWIGWVDPEDGD
TVYAEKFQGRVTITADTSTDTAYMELGSLTSEDTAVYFCSTLDYWGQGTTLTVSS SEQ ID NO: 52; hu3D6VHv3:
EVQLVQSGAEVKKPGATVKISCKVSGFNIKDYYLHWVRQAPGKGLEWMGWIDPENGD
TVYDPKFQGRVTITADTSTDTAYMELSSLRSEDTAVYYCSTLDFWGQGTLVTVSS SEQ ID NO: 53; hu3D6VHv3b:
EVQLVQSGAEVKKPGALVKISCKVSGYNFKDYYLHWVRQAPGKGLEWMGWIDPENG
DTVYDEKFQGRVTITADTSTNTAYMELGSLRSEDTAVYYCSTLDFWGQGTLVTVSS SEQ ID NO: 54; hu3D6VHv3c:
EVQLVQSGAEVKKPGALVKISCKVSGYTFTDYYLHWVRQAPGKGLEWMGWVDPEDG
DTVYAEKFQGRVTITADTSTNTAYMELGSLRSEDTAVYYCSTLDFWGQGTLVTVSS SEQ ID NO: 55; hu3D6VHv4:
EVQLVQSGAEVVKPGATVKISCKVSGFNIKDYYLHWVRQRPGKGLEWIGWIDPENGDT
VYDPKFQGKATITADTSTNTAYLELGSLTSEDTAVYYCSTLDFWGQGTLVTVSS SEQ ID NO: 56; hu3D6VHv4b:
EVQLVQSGAEVVKPGALVKISCKVSGYNFKDYYLHWVRQRPGKGLEWMGWIDPENGD
TVYDEKFQGRVTITADTSTDTAYLELGSLTSEDTAVYYCSTLDFWGQGTLVTVSS SEQ ID NO: 57; hu3D6VHv4c:
EVQLVQSGAEVVKPGALVKISCKVSGYTFTDYYLHWVRQRPGKGLEWMGWVDPEDG
DTVYAEKFQGRVTITADTSTDTAYLELGSLTSEDTAVYYCSTLDFWGQGTLVTVSS SEQ ID NO: 58; Alternate Kabat-Chothia CDR-H1 (as in hu3D6VH1c).
GFNFKDYYLH SEQ ID NO: 59; Alternate Kabat-Chothia CDR-H1, (as in hu3D6VHv1d, hu3D6VHv3c, and hu3D6VHv4c).
GYTFTDYYLH -continued

| Listing of Sequences |
|---|

SEQ ID NO: 60; Alternate Kabat-Chothia CDR-H1 (as in hu3D6VHv3b and hu3D6VHv4b)
GYNFKDYYLH SEQ ID NO: 61; Alternate Kabat CDR-H2 (as in hu3D6VHv1bA11B6G2).
WVDPEDGDTVYAPKFQG SEQ ID NO: 62, Alternate Kabat CDR-H2 (as in hu3D6VHv1c, hu3D6VHv3b, AND hu3D6VHv4b.
WIDPENGDTVYDEKFQG SEQ ID NO: 63; Alternate Kabat CDR-H2 as in hu3D6VHv1d, hu3D6VHv1f, hu3D6VHv3c, and hu3D6VHv4c).
WVDPEDGDTVYAEKFQG SEQ ID NO: 64; Alternate Kabat CDR-H2 (as in hu3D6VHv1e).
WIDPENGDTVYAEKFQG SEQ ID NO: 65; Alternate Kabat CDR-H3 (as in hu3D6VHv1f)
LDY SEQ ID NO: 66; heavy chain variable region of the mouse 6A10 antibody.
EVQLQQSGAELVRSGASVKLSCTASGLNIKDYYIHWVKQRPEQGLEWIGWIDPENDDTE
YAPKFQGRATLTTDTSSNTAYLQLSSLTSEDTAVYYCTPLDYWGQGTSVTVSS SEQ ID NO: 67; Kabat/Chothia composite CDR-H1 of the mouse 6A10 antibody.
GLNIKDYYIH SEQ ID NO: 68; Kabat CDR-H2 of the mouse 6A10 antibody.
WIDPENDDTEYAPKFQG SEQ ID NO: 69; Kabat CDR-H3 of the mouse 6A10 antibody
LDY SEQ ID NO: 70; Mus VH structure template (PDB#1CR9_H)
KVKLQQSGAELVRSGASVKLSCTASGFNIKDYYIQWVKQRPEQGLEWIGWIDPENGNSEYAPRF
QGKATMTADTLSNTAYLQLSSLTSEDTAVYYCNADLHDYWGQGTTLTVSS SEQ ID NO: 71; consensus VH amino acid sequence from FIGS. 4A and 4B of PCT/IB2017/052544
EVQLVQSGAEVVKPGALVKISCKASGFNIKDYYLHWVRQRPGQGLEWIGWIDPENGDT
VYDPKFQGRVTITADTSTNTAYLELGSLTSEDTAVYFCSTLDFWGQGTLVTVSS SEQ ID NO: 72; heavy chain of chimeric 3D6 antibody
EVQLQQSGADLVRPGALVKLSCKASGFNIKDYYLHWVRQRPEQGLEWIGWIDPENGDT
VYDPKFQGKATITADTSSNTAYLQLGSLTSEDTAVYFCSTLDFWGQGTTLTVSSASTKG
PSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQ
QGNVFSCSVMHEALHNHYTQKSLSLSPGK SEQ ID NO: 73; light chain of chimeric 3D6 antibody
DVVMTQTPLTLSVTIGQPASISCKSSQSLLDSDGKTYLNWLLQRPGQSPKRLIYLVSKLD
SGVPDRFTGSGSGTDFTLKISRVEAEDLGVYYCWQGTHFPYTFGGGTKLEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 74; amino acid sequence of heavy chain variable structural model Acc.# 5MYX-VH_mSt
EVQLQQSGAELVRPGSSVKISCKASGYIFNNYWINWVKQRPGQGLEWIGQIYPGDGDTN
YNGKFKGKATLTADKSSSTAYMQLSSLTSEDSAVYFCAREGYIVYWGQGTLVTVSA SEQ ID NO: 75; amino acid sequence of heavy chain variable acceptor Acc.# 2RCS-VH_huFrwk
QVQLQQSGAELVKPGASVKLSCTASGFNIKDTYMHWVKQRPEQGLEWIGRIDPANGNT
KYDPKFQGKATITADTSSNTAYLQLSSLTSEDTAVYYCASYYGIYWGQGTTLTVSS SEQ ID NO: 76; amino acid sequence of heavy chain variable region of the humanized 3D6 antibody hu3D6VHvb1
QVQLQQSGAELVKPGASVKLSCTASGFNIKDYYLHWVKQRPEQGLEWIGWIDPENGDT
VYDPKFQGKATITADTSSNTAYLQLSSLTSEDTAVYFCSTLDFWGQGTTLTVSS -continued

| Listing of Sequences |
|---|

SEQ ID NO: 77; amino acid sequence of heavy chain variable region of the humanized 3D6 antibody hu3D6VHvb2
EVQLVQSGAEVVKPGASVKISCKASGFNIKDYYLHWVRQRPGKGLEWIGWIDPENGDT
VYDPKFQGRATITADTSTDTAYLELSSLTSEDTAVYFCSTLDFWGQGTLVTVSS SEQ ID NO: 78; amino acid sequence of heavy chain variable region of the humanized 3D6 antibody hu3D6VHvb3
EVQLVQSGAEVVKPGATVKISCKASGFNIKDYYLHWVRQRPGKGLEWIGWIDPENGDTI
YDPKFQGRATITADTSTDTAYMELSSLRSEDTAVYYCSTLDFWGQGTLVTVSS SEQ ID NO: 79; amino acid sequence of heavy chain variable region of the humanized 3D6 antibody hu3D6VHvb4
EVQLVQSGAEVVKPGATVKISCKASGFTIKDYYLHWVRQRPGKGLEWIGWIDPENGDTI
YDPKFQGRVTITADTSTDTAYMELSSLRSEDTAVYYCSTLDFWGQGTLVTVSS SEQ ID NO: 80; amino acid sequence of heavy chain variable region of the humanized 3D6 antibody hu3D6VHvb5
EVQLVQSGAEVVKPGATVKISCKASGFTIKDYYLHWVRQRPGKGLEWIGWIDPEDGETI
YDPKFQGRVTITADTSTDTAYMELSSLRSEDTAVYYCSTLDFWGQGTLVTVSS SEQ ID NO: 81; amino acid sequence of light chain variable structural model Acc.# 5MYX-VL_mSt
DVVLTQTPLTLSVTIGQPASISCKSSQSLLYSNGKTYLNWLLQRPGQSPKRLIYVVSKLDS
GVPDRFTGSGSGTDFTLKISRVEAEDLGVYYCVQGTHFPFTFGSGTKLEIK SEQ ID NO: 82; amino acid sequence of light chain variable acceptor Acc.# ARX71335-VL huFrwk
DVVMTQTPLTLSVTIGQPASISCKSSQSLLYSNGKTYLNWLLQRPGQSPKRLIYLVSKLD
SGVPDRFSGSGSGTDFTLKISRVEAEDLGVHYCEQGTHFPLTFGAGTKLELK SEQ ID NO: 83; amino acid sequence of light chain variable region of the humanized 3D6 antibody hu3D6VLvb1
DVVMTQTPLTLSVTIGQPASISCKSSQSLLDSDGKTYLNWLLQRPGQSPKRLIYLVSKLD
SGVPDRFSGSGSGTDFTLKISRVEAEDLGVHYCWQGTHFPYTFGAGTKLELK SEQ ID NO: 84; amino acid sequence of light chain variable region of the humanized 3D6 antibody hu3D6VLvb2
DVVMTQSPLSLSVTLGQPASISCKSSQSLLDSDGKTYLNWLLQRPGQSPKRLIYLVSKLD
SGVPDRFSGSGSGTDFTLKISRVEAEDVGVYYCWQGTHFPYTFGAGTKLEIK SEQ ID NO: 85; amino acid sequence of light chain variable region of the humanized 3D6 antibody hu3D6VLvb3
DVVMTQSPLSLSVTLGEPASISCRSSQSLLDSDGKTYLNWLQQRPGQSPRRLIYLVSKLD
SGVPDRFSGSGSGTDFTLKISRVEAEDVGVYYCWQGTHFPYTFGQGTKLEIK SEQ ID NO: 86; amino acid sequence of an alternate Kabat-Chothia Composite CDR-H1 of a humanized 3D6 antibody (as in hu3D6VHvb4 and hu3D6VHvb5)
GFTIKDYYLH SEQ ID NO: 87; amino acid sequence of an alternate Kabat CDR-H2 of a humanized 3D6 antibody (as in hu3D6VHvb3 and hu3D6VHvb4)
WIDPENGDTIYDPKFQG SEQ ID NO: 88; amino acid sequence of an alternate Kabat CDR-H2 of a humanized 3D6 antibody (as in hu3D6VHvb5)
WIDPEDGETIYDPKFQG SEQ ID NO: 89; amino acid sequence of an alternate Kabat CDR-L1 of a humanized 3D6 antibody (as in hu3D6VLvb3)
RSSQSLLDSDGKTYLN SEQ ID NO: 90; amino acid sequence of heavy chain variable region of the humanized 3D6 antibody hu3D6VHvb6
EVQLVQSGAEVVKPGATVKISCKASGFTIKDYYLHWVRQRPGKGLEWIGWIDPEDGET
VYDPKFQGRVTITADTSTDTAYMELSSLRSEDTAVYFCSTLDFWGQGTLVTVSS SEQ ID NO: 91; amino acid sequence of heavy chain variable region of the humanized 3D6 antibody hu3D6VHvb7
EVQLVQSGAEVVKPGATVKISCKASGFTIKDYYLHWVRQRPGKGLEWIGWIDPEDGET
VYDPKFQGRVTITADTSTDTAYMELSSLRSEDTAVYYCSTLDFWGQGTLVTVSS SEQ ID NO: 92; amino acid sequence of an alternate Kabat CDR-H2 of a humanized 3D6 antibody (as in hu3D6VHvb6 and hu3D6VHvb7)
WIDPEDGETVYDPKFQG -continued

| Listing of Sequences |
|---|
| SEQ ID NO: 93; light chain variable region of a hu3D6VLv2 variant L54D, also known as L2-DIM21<br>DVVMTQSPLSLPVTLGQPASISCKSSQSLLDSDGKTYLNWLLQRPGQSPRRLIYLVSKDDSGVP<br>DRFSGSGSGTDFTLKISRVEAEDVGVYYCWQGTHFPYTFGGGTKLEIK |
| SEQ ID NO: 94; light chain variable region of a hu3D6VLv2 variant L54G, also known as L2-DIM7<br>DVVMTQSPLSLPVTLGQPASISCKSSQSLLDSDGKTYLNWLLQRPGQSPRRLIYLVSKGDSGVP<br>DRFSGSGSGTDFTLKISRVEAEDVGVYYCWQGTHFPYTFGGGTKLEIK |
| SEQ ID NO: 95; light chain variable region of a hu3D6VLv2 variant L45N<br>DVVMTQSPLSLPVTLGQPASISCKSSQSLLDSDGKTYLNWLLQRPGQSPRRLIYLVSKNDSGVP<br>DRFSGSGSGTDFTLKISRVEAEDVGVYYCWQGTHFPYTFGGGTKLEIK |
| SEQ ID NO: 96; light chain variable region of a hu3D6VLv2 variant L54E<br>DVVMTQSPLSLPVTLGQPASISCKSSQSLLDSDGKTYLNWLLQRPGQSPRRLIYLVSKEDSGVP<br>DRFSGSGSGTDFTLKISRVEAEDVGVYYCWQGTHFPYTFGGGTKLEIK |
| SEQ ID NO: 97; light chain variable region of a hu3D6VLv2 variant L50E<br>DVVMTQSPLSLPVTLGQPASISCKSSQSLLDSDGKTYLNWLLQRPGQSPRRLIYEVSKLDSGVP<br>DRFSGSGSGTDFTLKISRVEAEDVGVYYCWQGTHFPYTFGGGTKLEIK |
| SEQ ID NO: 98; light chain variable region of a hu3D6VLv2 variant L54Q<br>DVVMTQSPLSLPVTLGQPASISCKSSQSLLDSDGKTYLNWLLQRPGQSPRRLIYLVSKQDSGVP<br>DRFSGSGSGTDFTLKISRVEAEDVGVYYCWQGTHFPYTFGGGTKLEIK |
| SEQ ID NO: 99; light chain variable region of a hu3D6VLv2 variant L50D<br>DVVMTQSPLSLPVTLGQPASISCKSSQSLLDSDGKTYLNWLLQRPGQSPRRLIYDVSKLDSGVP<br>DRFSGSGSGTDFTLKISRVEAEDVGVYYCWQGTHFPYTFGGGTKLEIK |
| SEQ ID NO: 100; light chain variable region of a hu3D6VLv2 variant L54K<br>DVVMTQSPLSLPVTLGQPASISCKSSQSLLDSDGKTYLNWLLQRPGQSPRRLIYLVSKKDSGVP<br>DRFSGSGSGTDFTLKISRVEAEDVGVYYCWQGTHFPYTFGGGTKLEIK |
| SEQ ID NO: 101; light chain variable region of a hu3D6VLv2 variant L54R<br>DVVMTQSPLSLPVTLGQPASISCKSSQSLLDSDGKTYLNWLLQRPGQSPRRLIYLVSKRDSGVP<br>DRFSGSGSGTDFTLKISRVEAEDVGVYYCWQGTHFPYTFGGGTKLEIK |
| SEQ ID NO: 102; light chain variable region of a hu3D6VLv2 variant L54T<br>DVVMTQSPLSLPVTLGQPASISCKSSQSLLDSDGKTYLNWLLQRPGQSPRRLIYLVSKTDSGVP<br>DRFSGSGSGTDFTLKISRVEAEDVGVYYCWQGTHFPYTFGGGTKLEIK |
| SEQ ID NO: 103; light chain variable region of a hu3D6VLv2 variant L50G, also known as L2-DIM22<br>DVVMTQSPLSLPVTLGQPASISCKSSQSLLDSDGKTYLNWLLQRPGQSPRRLIYGVSKLDSGVP<br>DRFSGSGSGTDFTLKISRVEAEDVGVYYCWQGTHFPYTFGGGTKLEIK |
| SEQ ID NO: 104; light chain variable region of a hu3D6VLv2 variant I48G<br>DVVMTQSPLSLPVTLGQPASISCKSSQSLLDSDGKTYLNWLLQRPGQSPRRLGYLVSKLDSGVP<br>DRFSGSGSGTDFTLKISRVEAEDVGVYYCWQGTHFPYTFGGGTKLEIK |
| SEQ ID NO: 105; light chain variable region of a hu3D6VLv2 variant I48D<br>DVVMTQSPLSLPVTLGQPASISCKSSQSLLDSDGKTYLNWLLQRPGQSPRRLDYLVSKLDSGVP<br>DRFSGSGSGTDFTLKISRVEAEDVGVYYCWQGTHFPYTFGGGTKLEIK |
| SEQ ID NO: 106; light chain variable region of a hu3D6VLv2 variant L47G<br>DVVMTQSPLSLPVTLGQPASISCKSSQSLLDSDGKTYLNWLLQRPGQSPRRGIYLVSKLDSGVP<br>DRFSGSGSGTDFTLKISRVEAEDVGVYYCWQGTHFPYTFGGGTKLEIK |
| SEQ ID NO: 107; light chain variable region of a hu3D6VLv2 variant Y49E<br>DVVMTQSPLSLPVTLGQPASISCKSSQSLLDSDGKTYLNWLLQRPGQSPRRLIELVSKLDSGVP<br>DRFSGSGSGTDFTLKISRVEAEDVGVYYCWQGTHFPYTFGGGTKLEIK |
| SEQ ID NO: 108; light chain variable region of a hu3D6VLv2 variant L54V<br>DVVMTQSPLSLPVTLGQPASISCKSSQSLLDSDGKTYLNWLLQRPGQSPRRLIYLVSKVDSGVP<br>DRFSGSGSGTDFTLKISRVEAEDVGVYYCWQGTHFPYTFGGGTKLEIK |
| SEQ ID NO: 109; light chain variable region of a hu3D6VLv2 variant L54S<br>DVVMTQSPLSLPVTLGQPASISCKSSQSLLDSDGKTYLNWLLQRPGQSPRRLIYLVSKSDSGVP<br>DRFSGSGSGTDFTLKISRVEAEDVGVYYCWQGTHFPYTFGGGTKLEIK |
| SEQ ID NO: 110; light chain variable region of a hu3D6VLv2 variant S52G, also known as L2-DIM9<br>DVVMTQSPLSLPVTLGQPASISCKSSQSLLDSDGKTYLNWLLQRPGQSPRRLIYLVGKLDSGVP<br>DRFSGSGSGTDFTLKISRVEAEDVGVYYCWQGTHFPYTFGGGTKLEIK |

-continued

| Listing of Sequences |
| --- |

SEQ ID NO: 111; light chain variable region of a hu3D6VLv2 variant L47N
DVVMTQSPLSLPVTLGQPASISCKSSQSLLDSDGKTYLNWLLQRPGQSPRRNIYLVSKLDSGVP
DRFSGSGSGTDFTLKISRVEAEDVGVYYCWQGTHFPYTFGGGTKLEIK SEQ ID NO: 112; light chain variable region of a hu3D6VLv2 variant L47D
DVVMTQSPLSLPVTLGQPASISCKSSQSLLDSDGKTYLNWLLQRPGQSPRRDIYLVSKLDSGVP
DRFSGSGSGTDFTLKISRVEAEDVGVYYCWQGTHFPYTFGGGTKLEIK SEQ ID NO: 113; light chain variable region of a hu3D6VLv2 variant L47E
DVVMTQSPLSLPVTLGQPASISCKSSQSLLDSDGKTYLNWLLQRPGQSPRREIYLVSKLDSGVP
DRFSGSGSGTDFTLKISRVEAEDVGVYYCWQGTHFPYTFGGGTKLEIK SEQ ID NO: 114; light chain variable region of a hu3D6VLv2 variant L47P
DVVMTQSPLSLPVTLGQPASISCKSSQSLLDSDGKTYLNWLLQRPGQSPRRPIYLVSKLDSGVP
DRFSGSGSGTDFTLKISRVEAEDVGVYYCWQGTHFPYTFGGGTKLEIK SEQ ID NO: 115; light chain variable region of a hu3D6VLv2 variant L47T
DVVMTQSPLSLPVTLGQPASISCKSSQSLLDSDGKTYLNWLLQRPGQSPRRTIYLVSKLDSGVP
DRFSGSGSGTDFTLKISRVEAEDVGVYYCWQGTHFPYTFGGGTKLEIK SEQ ID NO: 116; light chain variable region of a hu3D6VLv2 variant L47S
DVVMTQSPLSLPVTLGQPASISCKSSQSLLDSDGKTYLNWLLQRPGQSPRRSIYLVSKLDSGVP
DRFSGSGSGTDFTLKISRVEAEDVGVYYCWQGTHFPYTFGGGTKLEIK SEQ ID NO: 117; light chain variable region of a hu3D6VLv2 variant L47A
DVVMTQSPLSLPVTLGQPASISCKSSQSLLDSDGKTYLNWLLQRPGQSPRRAIYLVSKLDSGVP
DRFSGSGSGTDFTLKISRVEAEDVGVYYCWQGTHFPYTFGGGTKLEIK SEQ ID NO: 118, light chain variable region of a hu3D6VLv2 variant L50V
DVVMTQSPLSLPVTLGQPASISCKSSQSLLDSDGKTYLNWLLQRPGQSPRRLIYVVSKLDSGVP
DRFSGSGSGTDFTLKISRVEAEDVGVYYCWQGTHFPYTFGGGTKLEIK SEQ ID NO: 119; light chain variable region of a hu3D6VLv2 variant
L37Q_L50G_L54R, also known as L2-DIM1
DVVMTQSPLSLPVTLGQPASISCKSSQSLLDSDGKTYLNWLQQRPGQSPRRLIYGVSKGDSGVP
DRFSGSGSGTDFTLKISRVEAEDVGVYYCWQGTHFPYTFGGGTKLEIK SEQ ID NO: 120; light chain variable region of a hu3D6VLv2 variant
L37Q_L50G_L54G, also known as L2-DIM2
DVVMTQSPLSLPVTLGQPASISCKSSQSLLDSDGKTYLNWLQQRPGQSPRRLIYEVSKGDSGVP
DRFSGSGSGTDFTLKISRVEAEDVGVYYCWQGTHFPYTFGGGTKLEIK SEQ ID NO: 121; light chain variable region of a hu3D6VLv2 variant
L37Q_S52G_L54G, also known as L2-DIM3
DVVMTQSPLSLPVTLGQPASISCKSSQSLLDSDGKTYLNWLQQRPGQSPRRLIYLVGKGDSGVP
DRFSGSGSGTDFTLKISRVEAEDVGVYYCWQGTHFPYTFGGGTKLEIK SEQ ID NO: 122; light chain variable region of a hu3D6VLv2 variant
L37Q_S52G_L54R, also known as L2-DIM4
DVVMTQSPLSLPVTLGQPASISCKSSQSLLDSDGKTYLNWLQQRPGQSPRRLIYLVGKRDSGVP
DRFSGSGSGTDFTLKISRVEAEDVGVYYCWQGTHFPYTFGGGTKLEIK SEQ ID NO: 123; light chain variable region of a hu3D6VLv2 variant
L37Q_S52G_L54T, also known as L2-DIM5
DVVMTQSPLSLPVTLGQPASISCKSSQSLLDSDGKTYLNWLQQRPGQSPRRLIYLVGKTDSGVP
DRFSGSGSGTDFTLKISRVEAEDVGVYYCWQGTHFPYTFGGGTKLEIK SEQ ID NO: 124; light chain variable region of a hu3D6VLv2 variant
L37Q_S52G_L54D, also known as L2-DIM6
DVVMTQSPLSLPVTLGQPASISCKSSQSLLDSDGKTYLNWLQQRPGQSPRRLIYLVGKDDSGVP
DRFSGSGSGTDFTLKISRVEAEDVGVYYCWQGTHFPYTFGGGTKLEIK SEQ ID NO: 125; light chain variable region of a hu3D6VLv2 variant
L37Q_L54R
DVVMTQSPLSLPVTLGQPASISCKSSQSLLDSDGKTYLNWLQQRPGQSPRRLIYLVSKGDSGVP
DRFSGSGSGTDFTLKISRVEAEDVGVYYCWQGTHFPYTFGGGTKLEIK SEQ ID NO: 126; light chain variable region of a hu3D6VLv2 variant
L37Q_L54G
DVVMTQSPLSLPVILGQPASISCKSSQSLLDSDGKTYLNWLQQRPGQSPRRLIYLVSKGDSGVP
DRFSGSGSGTDFTLKISRVEAEDVGVYYCWQGTHFPYTFGGGTKLEIK SEQ ID NO: 127; light chain variable region of a hu3D6VLv2 variant
L37Q_L54D, also known as L2-DIM12
DVVMTQSPLSLPVILGQPASISCKSSQSLLDSDGKTYLNWLQQRPGQSPRRLIYLVSKDDSGVP
DRFSGSGSGTDFTLKISRVEAEDVGVYYCWQGTHFPYTFGGGTKLEIK -continued

| Listing of Sequences |
|---|

SEQ ID NO: 128; light chain variable region of a hu3D6VLv2 variant L37Q_L50G, also known as L2-DIM13
DVVMTQSPLSLPVTLGQPASISCKSSQSLLDSDGKTYLNWLQQRPGQSPRRLIYGVSKLDSGVP
DRFSGSGSGTDFTLKISRVEAEDVGVYYCWQGTHFPYTFGGGTKLEIK SEQ ID NO: 129; light chain variable region of a hu3D6VLv2 variant L37Q_L50D, also known as L2-DIM14
DVVMTQSPLSLPVTLGQPASISCKSSQSLLDSDGKTYLNWLQQRPGQSPRRLIYDVSKLDSGVP
DRFSGSGSGTDFTLKISRVEAEDVGVYYCWQGTHFPYTFGGGTKLEIK SEQ ID NO: 130; light chain variable region of a hu3D6VLv2 variant L37Q_L54T
DVVMTQSPLSLPVTLGQPASISCKSSQSLLDSDGKTYLNWLQQRPGQSPRRLIYDVSKLDSGVP
DRFSGSGSGTDFTLKISRVEAEDVGVYYCWQGTHFPYTFGGGTKLEIK SEQ ID NO: 131; light chain variable region of a hu3D6VLv2 variant L37Q_S52G
DVVMTQSPLSLPVTLGQPASISCKSSQSLLDSDGKTYLNWLQQRPGQSPRRLIYLVGKLDSGVP
DRFSGSGSGTDFTLKISRVEAEDVGVYYCWQGTHFPYTFGGGTKLEIK SEQ ID NO: 132; light chain variable region of a hu3D6VLv2 variant L37Q_L50D_L54G, also known as L2-DIM17
DVVMTQSPLSLPVILGQPASISCKSSQSLLDSDGKTYLNWLQQRPGQSPRRLIYDVSKGDSGVP
DRFSGSGSGTDFTLKISRVEAEDVGVYYCWQGTHFPYTFGGGTKLEIK SEQ ID NO: 133; light chain variable region of a hu3D6VLv2 variant L37Q_L50D_L54R, also known as L2-DIM18
DVVMTQSPLSLPVTLGQPASISCKSSQSLLDSDGKTYLNWLQQRPGQSPRRLIYDVSKRDSGVP
DRFSGSGSGTDFTLKISRVEAEDVGVYYCWQGTHFPYTFGGGTKLEIK SEQ ID NO: 134; light chain variable region of a hu3D6VLv2 variant L37Q_L50E_L54G, also known as L2-DIM19
DVVMTQSPLSLPVILGQPASISCKSSQSLLDSDGKTYLNWLQQRPGQSPRRLIYEVSKGDSGVP
DRFSGSGSGTDFTLKISRVEAEDVGVYYCWQGTHFPYTFGGGTKLEIK SEQ ID NO: 135; light chain variable region of a hu3D6VLv2 variant L37Q_L50E_L54R, also known as L2-DIM20
DVVMTQSPLSLPVTLGQPASISCKSSQSLLDSDGKTYLNWLQQRPGQSPRRLIYEVSKRDSGVP
DRFSGSGSGTDFTLKISRVEAEDVGVYYCWQGTHFPYTFGGGTKLEIK SEQ ID NO: 136; light chain variable region of a hu3D6VLv2 variant L37Q_L50G_L54R_G100Q
DVVMTQSPLSLPVTLGQPASISCKSSQSLLDSDGKTYLNWLQQRPGQSPRRLIYGVSKRDSGVP
DRFSGSGSGTDFTLKISRVEAEDVGVYYCWQGTHFPYTFGQGTKLEIK SEQ ID NO: 137; light chain variable region of a hu3D6VLv2 variant L37Q_L50G_L54G_G100Q
DVVMTQSPLSLPVTLGQPASISCKSSQSLLDSDGKTYLNWLQQRPGQSPRRLIYGVSKGDSGVP
DRFSGSGSGTDFTLKISRVEAEDVGVYYCWQGTHFPYTFGQGTKLEIK SEQ ID NO: 138; light chain variable region of a hu3D6VLv2 variant L37Q_S52G_L54R_G100Q
DVVMTQSPLSLPVTLGQPASISCKSSQSLLDSDGKTYLNWLQQRPGQSPRRLIYLVGKRDSGVP
DRFSGSGSGTDFTLKISRVEAEDVGVYYCWQGTHFPYTFGQGTKLEIK SEQ ID NO: 139; light chain variable region of a hu3D6VLv2 variant L37Q_S52G_L54D_G100Q
DVVMTQSPLSLPVTLGQPASISCKSSQSLLDSDGKTYLNWLQQRPGQSPRRLIYLVGKDDSGVP
DRFSGSGSGTDFTLKISRVEAEDVGVYYCWQGTHFPYTFGQGTKLEIK SEQ ID NO: 140; light chain variable region of a hu3D6VLv2 variant L37Q_L50D_L54G_G100Q
DVVMTQSPLSLPVTLGQPASISCKSSQSLLDSDGKTYLNWLQQRPGQSPRRLIYDVSKGDSGVP
DRFSGSGSGTDFTLKISRVEAEDVGVYYCWQGTHFPYTFGQGTKLEIK SEQ ID NO: 141; light chain variable region of a hu3D6VLv2 variant L37Q_L50D_L54R_G100Q
DVVMTQSPLSLPVTLGQPASISCKSSQSLLDSDGKTYLNWLQQRPGQSPRRLIYDVSKRDSGVP
DRFESGSGSGTDFTLKISRVEAEDVGVYYCWQGTHFPYTFGQGTKLEIK SEQ ID NO: 142; light chain variable region of a hu3D6VLv2 variant L37Q_L50V_L54D_G100Q
DVVMTQSPLSLPVTLGQPASISCKSSQSLLDSDGKTYLNWLQQRPGQSPRRLIYVVSKDDSGVP
DRFSGSGSGTDFTLKISRVEAEDVGVYYCWQGTHFPYTFGQGTKLEIK -continued

| Listing of Sequences |
|---|

SEQ ID NO: 143; light chain variable region of a hu3D6VLv2 variant L37Q, also known as L2-DIM8
DVVMTQSPLSLPVTLGQPASISCKSSQSLLDSDGKTYLNWLQQRPGQSPRRLIYLVSKLDSGVP
DRFSGSGSGTDFTLKISRVEAEDVGVYYCWQGTHFPYTFGGGTKLEIK SEQ ID NO: 144 light chain variable region of a hu3D6VLv2 variant G100Q
DVVMTQSPLSLPVTLGQPASISCKSSQSLLDSDGKTYLNWLLQRPGQSPRRLIYLVSKLDSGVP
DRFSGSGSGTDFTLKISRVEAEDVGVYYCWQGTHFPYTFGQGTKLEIK SEQ ID NO: 145 light chain variable region of a hu3D6VLv2 variant L37Q_L54E
DVVMTQSPLSLPVTLGQPASISCKSSQSLLDSDGKTYLNWLQQRPGQSPRRLIYLVSKEDSGVP
DRFSGSGSGTDFTLKISRVEAEDVGVYYCWQGTHFPYTFGGGTKLEIK SEQ ID NO: 146; heavy chain variable region of a hu3D6VHv1bA11 variant D60E, also known as h3D6VHvb8
EVQLVQSGAEVVKPGATVKISCKASGFNIKDYYLHWVRQRPGQGLEWIGWIDPENGDTVYEPKF
QGRATITADTSTDTAYLQLGSLTSEDTAVYFCSTLDFWGQGTLVTVSS SEQ ID NO: 147 heavy chain variable region of a hu3D6VHv1bA11 variant L82cV
EVQLVQSGAEVVKPGATVKISCKASGFNIKDYYLHWVRQRPGQGLEWIGWIDPENGDTVYDPKF
QGRATITADTSTDTAYLQLGSVTSEDTAVYFCSTLDFWGQGTLVTVSS SEQ ID NO: 148; heavy chain variable region of a hu3D6VHv1bA11 variant D60E_L80M_Q81E_L82cV_T83R, also known as h3D6VHvb9
EVQLVQSGAEVVKPGATVKISCKASGENIKDYYLHWVRQRPGQGLEWIGWIDPENGDTVYEPKF
QGRATITADTSTDTAYMELGSVRSEDTAVYFCSTLDFWGQGTLVTVSS SEQ ID NO: 149; amino acid sequence of an alternate Kabat CDR-H2 of a humanized 3D6 antibody (as in h3D6VHvb8 and in h3D6VHvb9)
WIDPENGDTVYEPKFQG SEQ ID NO: 150; amino acid sequence of an alternate Kabat CDR-L2 of a humanized 3D6 antibody (as in hu3D6VLv2 L54D and in hu3D6VLv2 L37Q_L54D):
LVSKDDS SEQ ID NO: 151; amino acid sequence of an alternate Kabat CDR-L2 of a humanized 3D6 antibody (as in hu3D6VLv2 L54G and in hu3D6VLv2 L37Q_L54G):
LVSKGDS SEQ ID NO: 152; amino acid sequence of an alternate Kabat CDR-L2 of a humanized 3D6 antibody (as in hu3D6VLv2 L54N):
LVSKNDS SEQ ID NO: 153; amino acid sequence of an alternate Kabat CDR-L2 of a humanized 3D6 antibody (as in hu3D6VLv2 L54E and in hu3D6VLv2 L37Q_L54E):
LVSKEDS SEQ ID NO: 154; amino acid sequence of an alternate Kabat CDR-L2 of a humanized 3D6 antibody (as in hu3D6VLv2 L50E):
EVSKLDS SEQ ID NO: 155; amino acid sequence of an alternate Kabat CDR-L2 of a humanized 3D6 antibody (as in hu3D6VLv2 L54Q):
LVSKQDS SEQ ID NO: 156; amino acid sequence of an alternate Kabat CDR-L2 of a humanized 3D6 antibody (as in hu3D6VLv2 L50D and in hu3D6VLv2 L37Q_L50D):
DVSKLDS SEQ ID NO: 157; amino acid sequence of an alternate Kabat CDR-L2 of a humanized 3D6 antibody (as in hu3D6VLv2 L54K):
LVSKKDS SEQ ID NO: 158; amino acid sequence of an alternate Kabat CDR-L2 of a humanized 3D6 antibody (as in hu3D6VLv2 L54R and in hu3D6VLv2 L37Q_L54R):
LVSKRDS SEQ ID NO: 159; amino acid sequence of an alternate Kabat CDR-L2 of a humanized 3D6 antibody (as in hu3D6VLv2 L54T and in hu3D6VLv2 L37Q_L54T):
LVSKTDS -continued

| Listing of Sequences |
|---|

SEQ ID NO: 160; amino acid sequence of an alternate Kabat CDR-L2 of a humanized 3D6 antibody (as in hu3D6VLv2 L50G and in hu3D6VLv2 L37Q_L50G):
GVSKLDS SEQ ID NO: 161; amino acid sequence of an alternate Kabat CDR-L2 of a humanized 3D6 antibody (as in hu3D6VLv2 L54V):
LVSKVDS SEQ ID NO: 162; amino acid sequence of an alternate Kabat CDR-L2 of a humanized 3D6 antibody (as in hu3D6VLv2 L54S):
LVSKSDS SEQ ID NO: 163; amino acid sequence of an alternate Kabat CDR-L2 of a humanized 3D6 antibody (as in hu3D6VLv2 S52G and in hu3D6VLv2 L37Q_S52G):
LVGKLDS SEQ ID NO: 164; amino acid sequence of an alternate Kabat CDR-L2 of a humanized 3D6 antibody (as in hu3D6VLv2 L50V):
VVSKLDS SEQ ID NO: 165; amino acid sequence of an alternate Kabat CDR-L2 of a humanized 3D6 antibody (as in hu3D6VLv2 L37Q_L50G_L54R and hu3D6VLv2 L37Q_L50G_L54R_G100Q):
GVSKRDS SEQ ID NO: 166; amino acid sequence of an alternate Kabat CDR-L2 of a humanized 3D6 antibody (as in hu3D6VLv2 L37Q_L50G_L54G and in hu3D6VLv2 L37Q_L50G_L54G_G100Q):
GVSKGDS SEQ ID NO: 167; amino acid sequence of an alternate Kabat CDR-L2 of a humanized 3D6 antibody (as in hu3D6VLv2 L37Q_S52G_L54G):
LVGKGDS SEQ ID NO: 168; amino acid sequence of an alternate Kabat CDR-L2 of a humanized 3D6 antibody (as in hu3D6VLv2 L37Q_S52G_L54R and in hu3D6VLv2 L37Q_S52G_L54R_G100Q):
LVGKRDS SEQ ID NO: 169; amino acid sequence of an alternate Kabat CDR-L2 of a humanized 3D6 antibody (as in hu3D6VLv2 L37Q_S52G_L54T):
LVGKTDS SEQ ID NO: 170; amino acid sequence of an alternate Kabat CDR-L2 of a humanized 3D6 antibody (as in hu3D6VLv2 L37Q_S52G_L54D and in hu3D6VLv2 L37Q_S52G_L54D_G100Q):
LVGKDDS SEQ ID NO: 171; amino acid sequence of an alternate Kabat CDR-L2 of a humanized 3D6 antibody (as in hu3D6VLv2 L37Q_L50D_L54G and in hu3D6VLv2 L37Q_L50D_L54G_G100Q):
DVSKGDS SEQ ID NO: 172; amino acid sequence of an alternate Kabat CDR-L2 of a humanized 3D6 antibody (as in hu3D6VLv2 L37Q_L50D_L54R and in hu3D6VLv2 L37Q_L50D_L54R_G100Q):
DVSKRDS SEQ ID NO: 173; amino acid sequence of an alternate Kabat CDR-L2 of a humanized 3D6 antibody (as in hu3D6VLv2 L37Q_L50E_L54G):
EVSKGDS SEQ ID NO: 174; amino acid sequence of an alternate Kabat CDR-L2 of a humanized 3D6 antibody (as in hu3D6VLv2 L37Q_L50E_L54R):
EVSKRDS SEQ ID NO: 175; amino acid sequence of an alternate Kabat CDR-L2 of a humanized 3D6 antibody (as in hu3D6VLv2 L37Q_L50V_L54D_G100Q):
VVSKDDS SEQ ID NO: 176; amino acid sequence of a heavy chain constant region (IgG1: allotype G1m17,1):
ASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFY -continued

| Listing of Sequences |
|---|
| PSDIAVEWESNGQPENNYKTTPPVLDSDGSFFLYSKLTVDKSRWQQGNVFSCSVMHEALHNHYT<br>QKSLSLSPGK<br><br>SEQ ID NO: 177; amino acid sequence of a light chain constant region (kappa):<br>RTVAAPSVFIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC<br><br>SEQ ID NO: 178; amino acid sequence of a mature heavy chain of a 3D6 humanized variant (hu3D6VHv1bA11 IgG1 G1m17 allotype)<br>EVQLVQSGAEVVKPGATVKISCKASGFNIKDYYLHWVRQRPGQGLEWIGWIDPENGDTVYDPKF<br>QGRATITADTSTDTAYLQLGSLTSEDTAVYFCSTLDFWGQGTLVTVSSASTKGPSVFPLAPSSK<br>STSGGTAALGCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLMISRTPEVTC<br>VVVDVSHEDPEVKENWYVDGVEVHNAKTKPREEQYNSTYRVVSVLTVLHQDWLNGKEYKCKVSN<br>KALPAPIEKTISKAKGQPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYTQKSLSLSPGK<br><br>SEQ ID NO: 179; amino acid sequence of a mature light chain of a 3D6 humanized variant (hu3D6VLv2 variant L37Q_S52G_L54R, L2-DIM4 kappa)<br>DVVMTQSPLSLPVTLGQPASISCKSSQSLLDSDGKTYLNWLQQRPGQSPRRLIYLVGKRDSGVP<br>DRFSGSGSGTDFTLKISRVEAEDVGVYYCWQGTHFPYTFGGGTKLEIKRTVAAPSVFIFPPSDE<br>QLKSGTASVVCLLNNFYPREAKVQWKVDNALQSGNSQESVTEQDSKDSTYSLSSTLTLSKADYE<br>KHKVYACEVTHQGLSSPVTKSFNRGEC<br><br>SEQ ID NO: 180; amino acid sequence of a heavy chain of a 3D6 humanized variant (hu3D6VHv1bA11 IgG1 G1m17 allotype) with bovine alpha-lactalbumin signal peptide at the N-terminus<br>MMSFVSLLLVGILFHATQAEVQLVQSGAEVVKPGATVKISCKASGFNIKDYYLHWVRQRPGQGL<br>EWIGWIDPENGDTVYDPKFQGRATITADTSTDTAYLQLGSLTSEDTAVYFCSTLDFWGQGTLVT<br>VSSASTKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPELLGGPSVFL<br>FPPKPKDTLMISRTPEVTCVVVDVSHEDPEVKENWYVDGVEVHNAKTKPREEQYNSTYRVVSVL<br>TVLHQDWLNGKEYKCKVSNKALPAPIEKTISKAKGQPREPQVYTLPPSREEMTKNQVSLTCLVK<br>GFYPSDIAVEWESNGQPENNYKTTPPVLDSDGSFFLYSKLTVDKSRWQQGNVFSCSVMHEALHN<br>HYTQKSLSLSPGK<br><br>SEQ ID NO: 181; amino acid sequence of a light chain of a 3D6 humanized variant (hu3D6VLv2 variant L37Q_S52G_L54R, L2-DIM4 kappa) with bovine alpha-lactalbumin signal peptide at the N-terminus.<br>MMSFVSLLLVGILFHATQADVVMTQSPLSLPVTLGQPASISCKSSQSLLDSDGKTYLNWLQQRP<br>GQSPRRLIYLVGKRDSGVPDRFSGSGSGTDFTLKISRVEAEDVGVYYCWQGTHFPYTFGGGTKL<br>EIKRTVAAPSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC<br><br>SEQ ID NO: 182; nucleotide sequence encoding a heavy chain of a 3D6 humanized variant (hu3D6VHv1bA11 IgG1 G1m17 allotype) with bovine alpha-lactalbumin signal peptide at the N-terminus<br>ATGATGTCCTTTGTCTCTCTGCTCCTGGTTGGCATCCTATTCCATGCCACCCAGGCCGAGGTGC<br>AGCTGGTGCAGTCTGGGGCAGAGGTTGTGAAGCCAGGGGCCACAGTCAAGATCTCCTGTAAGGC<br>TTCTGGCTTCAACATTAAAGACTACTATCTGCACTGGGTGCGGCAGAGGCCTGGACAGGGCCTG<br>GAGTGGATTGGATGGATTGATCCTGAGAATGGTGATACTGTGTATGACCCGAAGTTCCAGGGCA<br>GGGCCACTATAACAGCAGACACATCCACCGACACAGCCTACCTGCAGCTCGGCAGCCTGACATC<br>TGAGGACACTGCCGTCTATTTCTGTTCTACCCTGGACTTCTGGGGCCAAGGCACCCTTGTCACA<br>GTCTCCTCAGCCTCCACCAAGGGCCCATCGGTCTTCCCCCTGGCACCCTCTAGCAAGAGCACCT<br>CTGGGGGCACAGCGGCCCTGGGCTGCCTGGTCAAGGACTACTTCCCCGAACCGGTGACGGTGTC<br>GTGGAACTCAGGCGCCCTGACCAGCGGCGTGCACACCTTCCCGGCTGTCCTACAGTCCTCAGGA<br>CTCTACTCCCTCAGCAGCGTGGTGACCGTGCCCTCCAGCAGCTTGGGCACCCAGACCTACATCT<br>GCAACGTGAATCACAAGCCCAGCAACACCAAGGTGGACAAGAAGGTTGAGCCCAAATCTTGTGA<br>CAAAACTCACACATGCCCACCGTGCCCAGCACCTGAACTCCTGGGGGGACCGTCAGTCTTCCTC<br>TTCCCCCCAAAACCCAAGGACACCCTCATGATCTCCCGGACCCCTGAGGTCACATGCGTGGTGG<br>TGGACGTGAGCCACGAAGACCCTGAGGTCAAGTTCAACTGGTACGTGGACGGCGTGGAGGTGCA<br>TAATGCCAAGACAAAGCCGAGAGAGGAGCAGTACAACAGCACGTACCGTGTGGTCAGCGTCCTC<br>ACCGTCCTGCACCAGGACTGGCTGAATGGCAAGGAGTACAAGTGCAAGGTCTCCAACAAAGCCC<br>TCCCAGCCCCCATCGAGAAAACCATCTCCAAAGCCAAAGGGCAGCCCCGAGAACCACAGGTGTA<br>CACCCTGCCCCCATCCCGGGAGGAGATGACCAAGAACCAGGTCAGCCTGACCTGCCTGGTCAAA<br>GGCTTCTATCCCAGCGACATCGCCGTGGAGTGGGAGAGCAATGGGCAGCCGGAGAACAACTACA<br>AGACCACGCCTCCCGTGCTGGACTCCGACGGCTCCTTCTTCCTCTATTCCAAACTCACCGTGGA<br>CAAGAGCAGGTGGCAGCAGGGGAACGTCTTCTCATGCTCCGTGATGCATGAGGCTCTGCACAAC<br>CACTACACGCAGAAGAGCCTCTCCCTGTCTCCCGGGAAATGATGAGATCTCGAG |

-continued

| Listing of Sequences |
|---|
| SEQ ID NO: 183; nucleotide sequence encoding a light chain of a 3D6 humanized variant (hu3D6VLv2 variant L37Q_S52G_L54R, L2-DIM4 kappa) with bovine alpha-lactalbumin signal peptide at the N-terminus<br>ATGATGTCCTTTGTCTCTCTGCTCCTGGTTGGCATCCTATTCCATGCCACCCAGGCCGATGTTG<br>TGATGACCCAGTCTCCACTCTCTTTGCCCGTTACCCTTGGACAACCTGCCTCCATCTCTTGCAA<br>GTCAAGTCAGAGCCTCTTAGATAGTGATGGAAAGACATATTTGAATTGGTTGCAACAGAGGCCA<br>GGCCAGTCTCCACGGCGCCTAATCTATCTGGTGGGCAAACGGGACTCTGGAGTCCCTGACAGGT<br>TCAGTGGCAGTGGATCAGGGACAGATTTCACACTGAAAATCAGCAGAGTGGAGGCTGAGGATGT<br>GGGAGTTTATTATTGCTGGCAAGGCACACATTTTCCGTACACGTTCGGAGGGGGGACCAAGCTG<br>GAAATAAAACGAACTGTGGCTGCACCATCTGTCTTCATCTTCCCGCCATCTGATGAGCAGCTTA<br>AGTCCGGAACTGCTAGCGTTGTGTGCCTGCTGAATAACTTCTATCCCAGAGAGGCCAAAGTACA<br>GTGGAAGGTGGATAACGCCCTCCAATCGGGTAACTCCCAGGAGAGTGTCACAGAGCAGGACAGC<br>AAGGACAGCACCTACAGCCTCAGCAGCACCCTGACGCTGAGCAAAGCAGACTACGAGAAACACA<br>AAGTCTACGCCTGCGAAGTCACCCATCAGGGCCTGAGCTCGCCCGTCACAAAGAGCTTCAACAG<br>GGGAGAGTGTTAGTGAGATCTCGAG |
| SEQ ID NO: 184; amino acid sequence of a region of tau microtubule binding repeat 1 (amino acid residues 255-271 of SEQ ID NO: 1)<br>NVKSKIGSTENLKHQPG |
| SEQ ID NO: 185; amino acid sequence of of a region of tau microtubule binding repeat 2 (amino acid residues 286-302 of SEQ ID NO: 1)<br>NVQSKCGSKDNIKHVPG |
| SEQ ID NO: 186; amino acid sequence of of a region of tau microtubule binding repeat 3 (amino acid residues 317-333 of SEQ ID NO: 1)<br>KVTSKCGSLGNIHHKPG |
| SEQ ID NO: 187; amino acid sequence of of a region of tau microtubule binding repeat 4 (amino acid residues 349-365 of SEQ ID NO: 1)<br>RVQSKIGSLDNITHVPG |
| SEQ ID NO: 188; amino acid sequence of a core motif of tau bound by 3D6<br>KIGSTENLKH |
| SEQ ID NO: 189; amino acid sequence of tau sequence N-terminal to a core motif of tau bound by 3D6<br>NVKS |
| SEQ ID NO: 190; amino acid sequence of tau sequence C-terminal to core motif of tau bound by 3D6<br>QPG |
| SEQ ID NO: 191; amino acid sequence of epitope of 3D6<br>KXXSXXNX(K/H)H |
| SEQ ID NO: 192; amino acid sequence of a core motif of tau bound by 3D6<br>KCGSKDNIKH |
| SEQ ID NO: 193; amino acid sequence of a core motif of tau bound by 3D6<br>KCGSLGNIHH |
| SEQ ID NO: 194; amino acid sequence of a core motif of tau bound by 3D6<br>KIGSLDNITH |

What is claimed is:

1. An antibody specifically binding to human tau or an antigen-binding antibody fragment, comprising: (a) a mature heavy chain variable region comprising SEQ ID NO: 18 and a mature light chain variable region comprising SEQ ID NO: 110, 121, 122, or 124; or (b) a mature heavy light chain variable region comprising SEQ ID NO: 146 and a mature light chain variable region comprising SEQ ID NO: 94 or 122.

2. The antibody or antigen-binding antibody fragment of claim 1, wherein the antibody is a chimeric, veneered, or humanized antibody.

3. The antibody or antigen-binding antibody fragment of claim 1 that is an intact antibody.

4. The antibody or antigen-binding antibody fragment of claim 1 that is an antigen-binding antibody fragment.

5. The antibody or antigen-binding antibody fragment of claim 4, wherein the antigen-binding antibody fragment is a single-chain antibody, Fab, or Fab'2 fragment.

6. The antibody or antigen-binding antibody fragment of claim 1, wherein the antibody has an isotype of human IgG1, human IgG2, or human IgG4.

7. The antibody or antigen-binding antibody fragment of claim 1, wherein the mature light chain variable region is fused to a light chain constant region and the mature heavy chain variable region is fused to a heavy chain constant region.

8. The antibody or antigen-binding antibody fragment of claim 7, wherein the heavy chain constant region comprises the amino acid sequence of SEQ ID NO: 176, with or without C-terminal lysine.

9. The antibody or antigen-binding antibody fragment of claim 7, wherein the mature heavy chain variable region fused to the heavy chain constant region comprises the amino acid sequence of SEQ ID NO: 178, with or without C-terminal lysine.

10. The antibody or antigen-binding antibody fragment of claim 7, wherein the light chain constant region comprises the amino acid sequence of SEQ ID NO: 177.

11. The antibody or antigen-binding antibody fragment of claim 7, wherein the mature light chain variable region is fused to a light chain constant region comprising the amino acid sequence of SEQ ID NO: 179.

12. The antibody or antigen-binding antibody fragment of claim 1 comprising at least one mutation in the heavy chain constant region.

13. The antibody or antigen-binding antibody fragment of claim 12, wherein the at least one mutation in the heavy chain constant region reduces complement fixation or activation by the heavy chain constant region or reduces binding to a Fcγ receptor relative to a natural heavy chain constant region.

14. The antibody or antigen-binding antibody fragment of claim 13 comprising a mutation at one or more of positions 241, 264, 265, 270, 296, 297, 318, 320, 322, 329, and 331 by EU numbering or having alanine at positions 318, 320, and 322.

15. The antibody or antigen-binding antibody fragment of claim 1, wherein the antibody or antigen-binding antibody fragment is conjugated to a therapeutic, cytotoxic, cytostatic, neurotrophic, or neuroprotective agent.

16. A pharmaceutical composition comprising the antibody or antigen-binding antibody fragment of claim 1 and a pharmaceutically-acceptable carrier.

17. A nucleic acid encoding the heavy chain and light chain of the antibody or antigen-binding antibody fragment of claim 1.

18. A method of producing an antibody, the method comprising:

(a) culturing cells comprising transformed with nucleic acids encoding the heavy and light chains of the antibody or antigen-binding antibody fragment of claim 1, so that the cells secrete the antibody; and (b) purifying the antibody from cell culture media.

19. A method of producing a cell line producing an antibody, the method comprising:

(a) introducing a vector encoding heavy and light chains of the antibody or antigen-binding antibody fragment of claim 1 and a selectable marker into cells;

(b) propagating the cells under conditions to select for cells having increased copy number of the vector;

(c) isolating single cells from the selected cells; and (d) banking cells cloned from a single cell selected based on yield of the antibody.

20. A method of inhibiting or reducing aggregation of tau in a subject having or at risk of developing a tau-mediated amyloidosis, comprising administering to the subject an effective regime of the antibody or antigen-binding antibody fragment of claim 1, thereby inhibiting or reducing aggregation of tau in the subject.

21. A method of treating or effecting prophylaxis of a tau-related disease in a subject, comprising administering to the subject an effective regime of the antibody or antigen-binding antibody fragment of claim 1, thereby treating or effecting prophylaxis of the disease in the subject.

22. A method of claim 21, wherein the tau-related disease is Alzheimer's disease.

23. A method of reducing aberrant transmission of tau, inducing phagocytosis of tau, inhibiting tau deposition or aggregation, or inhibiting formation of tau tangles in a subject, comprising administering to the subject an effective regime of the antibody or antigen-binding antibody fragment of claim 1, thereby reducing transmission of tau, inducing phagocytosis of tau, inhibiting tau aggregation or deposition, or inhibiting formation of tau tangles in the subject.

24. A method of measuring efficacy of treatment in a subject being treated for a disease associated with tau aggregation or deposition, comprising:

(a) measuring a first level of tau protein deposits in the subject prior to treatment by administering to the subject the antibody or antigen-binding antibody fragment of claim 1, and detecting a first amount of the antibody or antigen-binding antibody fragment bound to tau in the subject;

(b) administering the treatment to the subject; and (c) measuring a second level of tau protein deposits in the subject after treatment by administering to the subject the antibody or antigen-binding antibody fragment, and detecting the antibody or antigen-binding antibody fragment bound to tau in the subject, wherein a decrease in the second level of tau protein deposits as compared to the first level of tau protein deposits indicates a positive response to the treatment.

25. A method of measuring efficacy of treatment in a subject being treated for a disease associated with tau aggregation or deposition, comprising:

(a) measuring a first level of tau protein deposits in the subject prior to treatment by administering to the subject the antibody or antigen-binding antibody fragment of claim 1, and detecting a first amount of the antibody or antigen-binding antibody fragment bound to tau in the subject;

(b) administering the treatment to the subject; and (c) measuring a second level of tau protein deposits in the subject after treatment by administering to the subject the antibody or antigen-binding antibody fragment, and detecting a second amount of the antibody or antigen-binding antibody fragment bound to tau in the subject, wherein no change or a small increase in the second level of tau protein deposits as compared to the first level of tau protein deposits indicates a positive response to treatment.

* * * * *

SEQUENCE LISTING

```
Sequence total quantity: 194
SEQ ID NO: 1            moltype = AA  length = 441
FEATURE                 Location/Qualifiers
source                  1..441
                        mol_type = protein
                        organism = Homo sapiens
SEQUENCE: 1
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGGKVQIINK KLDLSNVQSK CGSKDNIKHV  300
PGGGSVQIVY KPVDLSKVTS KCGSLGNIHH KPGGGQVEVK SEKLDFKDRV QSKIGSLDNI  360
THVPGGGNKK IETHKLTFRE NAKAKTDHGA EIVYKSPVVS GDTSPRHLSN VSSTGSIDMV  420
```

-continued

```
DSPQLATLAD EVSASLAKQG L                                         441

SEQ ID NO: 2           moltype = AA  length = 412
FEATURE                Location/Qualifiers
source                 1..412
                       mol_type = protein
                       organism = Homo sapiens
SEQUENCE: 2
MAEPRQEFEV MEDHAGTYGL GDRKDQGGYT MHQDQEGDTD AGLKESPLQT PTEDGSEEPG  60
SETSDAKSTP TAEAEEAGIG DTPSLEDEAA GHVTQARMVS KSKDGTGSDD KKAKGADGKT  120
KIATPRGAAP PGQKGQANAT RIPAKTPPAP KTPPSSGEPP KSGDRSGYSS PGSPGTPGSR  180
SRTPSLPTPP TREPKKVAVV RTPPKSPSSA KSRLQTAPVP MPDLKNVKSK IGSTENLKHQ  240
PGGGKVQIIN KKLDLSNVQS KCGSKDNIKH VPGGGSVQIV YKPVDLSKVT SKCGSLGNIH  300
HKPGGGQVEV KSEKLDFKDR VQSKIGSLDN ITHVPGGGNK KIETHKLTFR ENAKAKTDHG  360
AEIVYKSPVV SGDTSPRHLS NVSSTGSIDM VDSPQLATLA DEVSASLAKQ GL          412

SEQ ID NO: 3           moltype = AA  length = 383
FEATURE                Location/Qualifiers
source                 1..383
                       mol_type = protein
                       organism = Homo sapiens
SEQUENCE: 3
MAEPRQEFEV MEDHAGTYGL GDRKDQGGYT MHQDQEGDTD AGLKAEEAGI GDTPSLEDEA  60
AGHVTQARMV SKSKDGTGSD DKKAKGADGK TKIATPRGAA PPGQKGQANA TRIPAKTPPA  120
PKTPPSSGEP PKSGDRSGYS SPGSPGTPGS RSRTPSLPTP PTREPKKVAV VRTPPKSPSS  180
AKSRLQTAPV PMPDLKNVKS KIGSTENLKH QPGGGKVQII NKKLDLSNVQ SKCGSKDNIK  240
HVPGGGSVQI VYKPVDLSKV TSKCGSLGNI HHKPGGGQVE VKSEKLDFKD RVQSKIGSLD  300
NITHVPGGGN KKIETHKLTF RENAKAKTDH GAEIVYKSPV VSGDTSPRHL SNVSSTGSID  360
MVDSPQLATL ADEVSASLAK QGL                                       383

SEQ ID NO: 4           moltype = AA  length = 410
FEATURE                Location/Qualifiers
source                 1..410
                       mol_type = protein
                       organism = Homo sapiens
SEQUENCE: 4
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGGKVQIVYK PVDLSKVTSK CGSLGNIHHK  300
PGGGQVEVKS EKLDFKDRVQ SKIGSLDNIT HVPGGGNKKI ETHKLTFREN AKAKTDHGAE  360
IVYKSPVVSG DTSPRHLSNV SSTGSIDMVD SPQLATLADE VSASLAKQGL          410

SEQ ID NO: 5           moltype = AA  length = 381
FEATURE                Location/Qualifiers
source                 1..381
                       mol_type = protein
                       organism = Homo sapiens
SEQUENCE: 5
MAEPRQEFEV MEDHAGTYGL GDRKDQGGYT MHQDQEGDTD AGLKESPLQT PTEDGSEEPG  60
SETSDAKSTP TAEAEEAGIG DTPSLEDEAA GHVTQARMVS KSKDGTGSDD KKAKGADGKT  120
KIATPRGAAP PGQKGQANAT RIPAKTPPAP KTPPSSGEPP KSGDRSGYSS PGSPGTPGSR  180
SRTPSLPTPP TREPKKVAVV RTPPKSPSSA KSRLQTAPVP MPDLKNVKSK IGSTENLKHQ  240
PGGGKVQIVY KPVDLSKVTS KCGSLGNIHH KPGGGQVEVK SEKLDFKDRV QSKIGSLDNI  300
THVPGGGNKK IETHKLTFRE NAKAKTDHGA EIVYKSPVVS GDTSPRHLSN VSSTGSIDMV  360
DSPQLATLAD EVSASLAKQG L                                         381

SEQ ID NO: 6           moltype = AA  length = 352
FEATURE                Location/Qualifiers
source                 1..352
                       mol_type = protein
                       organism = Homo sapiens
SEQUENCE: 6
MAEPRQEFEV MEDHAGTYGL GDRKDQGGYT MHQDQEGDTD AGLKAEEAGI GDTPSLEDEA  60
AGHVTQARMV SKSKDGTGSD DKKAKGADGK TKIATPRGAA PPGQKGQANA TRIPAKTPPA  120
PKTPPSSGEP PKSGDRSGYS SPGSPGTPGS RSRTPSLPTP PTREPKKVAV VRTPPKSPSS  180
AKSRLQTAPV PMPDLKNVKS KIGSTENLKH QPGGGKVQIV YKPVDLSKVT SKCGSLGNIH  240
HKPGGGQVEV KSEKLDFKDR VQSKIGSLDN ITHVPGGGNK KIETHKLTFR ENAKAKTDHG  300
AEIVYKSPVV SGDTSPRHLS NVSSTGSIDM VDSPQLATLA DEVSASLAKQ GL          352

SEQ ID NO: 7           moltype = AA  length = 112
FEATURE                Location/Qualifiers
source                 1..112
                       mol_type = protein
                       organism = synthetic construct
SEQUENCE: 7
EVQLQQSGAD LVRPGALVKL SCKASGFNIK DYYLHWVRQR PEQGLEWIGW IDPENGDTVY  60
DPKFQGKATI TADTSSNTAY LQLGSLTSED TAVYFCSTLD FWGQGTTLTV SS          112
```

```
SEQ ID NO: 8            moltype = AA  length = 10
FEATURE                 Location/Qualifiers
source                  1..10
                        mol_type = protein
                        organism = synthetic construct
SEQUENCE: 8
GFNIKDYYLH                                                  10

SEQ ID NO: 9            moltype = AA  length = 17
FEATURE                 Location/Qualifiers
source                  1..17
                        mol_type = protein
                        organism = synthetic construct
SEQUENCE: 9
WIDPENGDTV YDPKFQG                                          17

SEQ ID NO: 10           moltype =   length =
SEQUENCE: 10
000

SEQ ID NO: 11           moltype = AA  length = 112
FEATURE                 Location/Qualifiers
source                  1..112
                        mol_type = protein
                        organism = synthetic construct
SEQUENCE: 11
DVVMTQTPLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQGTHFP YTFGGGTKLE IK          112

SEQ ID NO: 12           moltype = AA  length = 16
FEATURE                 Location/Qualifiers
source                  1..16
                        mol_type = protein
                        organism = synthetic construct
SEQUENCE: 12
KSSQSLLDSD GKTYLN                                           16

SEQ ID NO: 13           moltype = AA  length = 7
FEATURE                 Location/Qualifiers
source                  1..7
                        mol_type = protein
                        organism = synthetic construct
SEQUENCE: 13
LVSKLDS                                                     7

SEQ ID NO: 14           moltype = AA  length = 9
FEATURE                 Location/Qualifiers
source                  1..9
                        mol_type = protein
                        organism = synthetic construct
SEQUENCE: 14
WQGTHFPYT                                                   9

SEQ ID NO: 15           moltype = AA  length = 112
FEATURE                 Location/Qualifiers
source                  1..112
                        mol_type = protein
                        organism = synthetic construct
SEQUENCE: 15
EVQLVQSGAE VVRPGALVKV SCKASGFNIK DYYLHWVRQA PEQGLEWIGW IDPENGDTVY  60
DPKFQGKATI TADTSTNTAY LQLSSLTSED TAVYFCSTLD FWGQGTLVTV SS          112

SEQ ID NO: 16           moltype = AA  length = 112
FEATURE                 Location/Qualifiers
source                  1..112
                        mol_type = protein
                        organism = synthetic construct
SEQUENCE: 16
EVQLVQSGAE VKKPGASVKV SCKVSGFNIK DYYLHWVRQA PEQGLEWMGW IDPENGDTVY  60
DPKFQGRVTI TADTSTNTAY MELSSLTSED TAVYYCSTLD FWGQGTLVTV SS          112

SEQ ID NO: 17           moltype = AA  length = 112
FEATURE                 Location/Qualifiers
source                  1..112
                        mol_type = protein
                        organism = synthetic construct
SEQUENCE: 17
EVQLVQSGAE VVRPGALVKI SCKASGFNIK DYYLHWVRQR PEQGLEWIGW IDPENGDTVY  60
```

```
DPKFQGKATI TADTSTNTAY LQLGSLTSED TAVYFCSTLD FWGQGTLVTV SS          112

SEQ ID NO: 18           moltype = AA  length = 112
FEATURE                 Location/Qualifiers
source                  1..112
                        mol_type = protein
                        organism = synthetic construct
SEQUENCE: 18
EVQLVQSGAE VVKPGATVKI SCKASGFNIK DYYLHWVRQR PGQGLEWIGW IDPENGDTVY  60
DPKFQGRATI TADTSTDTAY LQLGSLTSED TAVYFCSTLD FWGQGTLVTV SS          112

SEQ ID NO: 19           moltype = AA  length = 112
FEATURE                 Location/Qualifiers
source                  1..112
                        mol_type = protein
                        organism = synthetic construct
SEQUENCE: 19
EVQLVQSGAE VVKPGATVKI SCKASGFTIK DYYLHWVRQR PGQGLEWIGW IDPEDGDTVY  60
APKFQGRATI TADTSTDTAY LQLGSLTSED TAVYFCSTLD FWGQGTLVTV SS          112

SEQ ID NO: 20           moltype = AA  length = 112
FEATURE                 Location/Qualifiers
source                  1..112
                        mol_type = protein
                        organism = synthetic construct
SEQUENCE: 20
DVVMTQSPLS LSVTLGQPAS ISCKSSQSLL DSDGKTYLNW LLQRPGQSPK RLIYLVSKLD  60
SGVPDRFSGS GSGTDFTLKI SRVEAEDVGV YYCWQGTHFP YTFGGGTKLE IK          112

SEQ ID NO: 21           moltype = AA  length = 112
FEATURE                 Location/Qualifiers
source                  1..112
                        mol_type = protein
                        organism = synthetic construct
SEQUENCE: 21
DVVMTQSPLS LPVTLGQPAS ISCKSSQSLL DSDGKTYLNW LLQRPGQSPR RLIYLVSKLD  60
SGVPDRFSGS GSGTDFTLKI SRVEAEDVGV YYCWQGTHFP YTFGGGTKLE IK          112

SEQ ID NO: 22           moltype = AA  length = 112
FEATURE                 Location/Qualifiers
source                  1..112
                        mol_type = protein
                        organism = synthetic construct
SEQUENCE: 22
DVVMTQSPLS LPVTLGQPAS ISCKSSQSLL DSDGKTYLNW LLQRPGQSPR RLIYLVSKLD  60
SGVPSRFSGS GSGTDFTLKI SRVEAEDVGV YYCWQGTHFP YTFGGGTKLE IK          112

SEQ ID NO: 23           moltype = AA  length = 112
FEATURE                 Location/Qualifiers
source                  1..112
                        mol_type = protein
                        organism = synthetic construct
SEQUENCE: 23
DIVMTQTPLS LSVTIGQPAS ISCKSSQSLL DSDGKTYLNW LLQKPGQSPK RLIYLVSKLD  60
SGVPDRFSGS GSGTDFTLKI SRVEAEDVGV YYCWQGTHFP YTFGGGTKLE IK          112

SEQ ID NO: 24           moltype = AA  length = 119
FEATURE                 Location/Qualifiers
source                  1..119
                        mol_type = protein
                        organism = Homo sapiens
SEQUENCE: 24
QVQLQQSGAE VKKPGSSVKV SCKASGGTFG SYAISWVRQA PGQGLEWMGR IIPILGIATY  60
AQKFQGRVTI TADKSTSTAY MDLSSLRSED TAVYYCARGK GEFEGMDVWG QGTTVTVSS   119

SEQ ID NO: 25           moltype = AA  length = 98
FEATURE                 Location/Qualifiers
source                  1..98
                        mol_type = protein
                        organism = Homo sapiens
SEQUENCE: 25
EVQLVQSGAE VKKPGATVKI SCKVSGYTFT DYYMHWVQQA PGKGLEWMGL VDPEDGETIY  60
AEKFQGRVTI TADTSTDTAY MELSSLRSED TAVYYCAT                          98

SEQ ID NO: 26           moltype = AA  length = 13
FEATURE                 Location/Qualifiers
source                  1..13
                        mol_type = protein
                        organism = Homo sapiens
```

```
SEQUENCE: 26
QHWGQGTLVT VSS                                                   13

SEQ ID NO: 27          moltype = AA  length = 100
FEATURE                Location/Qualifiers
source                 1..100
                       mol_type = protein
                       organism = Homo sapiens
SEQUENCE: 27
DVVMTQSPLS LPVTLGQPAS ISCRSSQSLV HSDGNTYLNW FQQRPGQSPR RLIYKVSNRD  60
SGVPDRFSGS GSGTDFTLKI SRVEAEDVGV YYCMQGTHWP                        100

SEQ ID NO: 28          moltype = AA  length = 12
FEATURE                Location/Qualifiers
source                 1..12
                       mol_type = protein
                       organism = Homo sapiens
SEQUENCE: 28
YTFGQGTKLE IK                                                    12

SEQ ID NO: 29          moltype = AA  length = 112
FEATURE                Location/Qualifiers
source                 1..112
                       mol_type = protein
                       organism = Homo sapiens
SEQUENCE: 29
DVVMTQSPLS LTVTLGQPAS ISCRSSQSLV YSDGNTYLNW FQQRPGQSPR RLIYRVSHWD  60
SGVPDRFSGS GSGTDFTLKI SRVEAEDVGV YYCMQGTYWP LTFGQGTKLE IK          112

SEQ ID NO: 30          moltype = DNA  length = 336
FEATURE                Location/Qualifiers
source                 1..336
                       mol_type = other DNA
                       organism = synthetic construct
SEQUENCE: 30
gaggttcagc tgcagcagtc tggggctgac cttgtgaggc caggggcctt agtcaagttg  60
tcctgcaaag cttctggctt caacattaaa gactactatt tgcactgggt gaggcagagg  120
cctgaacagg gcctggagtg gattggatgg attgatcctg agaatggtga tactgtatat  180
gacccgaagt tccagggcaa ggccactata acagcagaca catcctccaa tacagcctac  240
ctgcagctcg gcagcctgac atctgaggac actgccgtct atttctgttc taccettgac  300
ttctggggcc aaggcaccac tctcacagtc tcctca                          336

SEQ ID NO: 31          moltype = DNA  length = 339
FEATURE                Location/Qualifiers
source                 1..339
                       mol_type = other DNA
                       organism = synthetic construct
SEQUENCE: 31
gatgttgtga tgacccagac tccactcact ttgtcggtta ccattggaca accagcctcc  60
atctcttgca agtcaagtca gagcctctta gatagtgatg gaaagacata tttgaattgg  120
ttgttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttccg  300
tacacgttcg gaggggggac caagctggaa ataaaacgt                       339

SEQ ID NO: 32          moltype = AA  length = 5
FEATURE                Location/Qualifiers
source                 1..5
                       mol_type = protein
                       organism = synthetic construct
SEQUENCE: 32
DYYLH                                                            5

SEQ ID NO: 33          moltype = AA  length = 7
FEATURE                Location/Qualifiers
source                 1..7
                       mol_type = protein
                       organism = synthetic construct
SEQUENCE: 33
GFNIKDY                                                          7

SEQ ID NO: 34          moltype = AA  length = 6
FEATURE                Location/Qualifiers
source                 1..6
                       mol_type = protein
                       organism = synthetic construct
SEQUENCE: 34
DPENGD                                                           6
```

```
SEQ ID NO: 35           moltype = AA  length = 10
FEATURE                 Location/Qualifiers
source                  1..10
                        mol_type = protein
                        organism = synthetic construct
SEQUENCE: 35
WIDPENGDTV                                                  10

SEQ ID NO: 36           moltype = AA  length = 7
FEATURE                 Location/Qualifiers
source                  1..7
                        mol_type = protein
                        organism = synthetic construct
SEQUENCE: 36
KTYLNWL                                                     7

SEQ ID NO: 37           moltype = AA  length = 10
FEATURE                 Location/Qualifiers
source                  1..10
                        mol_type = protein
                        organism = synthetic construct
SEQUENCE: 37
RLIYLVSKLD                                                  10

SEQ ID NO: 38           moltype = AA  length = 8
FEATURE                 Location/Qualifiers
source                  1..8
                        mol_type = protein
                        organism = synthetic construct
SEQUENCE: 38
WQGTHFPY                                                    8

SEQ ID NO: 39           moltype = AA  length = 6
FEATURE                 Location/Qualifiers
source                  1..6
                        mol_type = protein
                        organism = synthetic construct
SEQUENCE: 39
KDYYLH                                                      6

SEQ ID NO: 40           moltype = AA  length = 13
FEATURE                 Location/Qualifiers
source                  1..13
                        mol_type = protein
                        organism = synthetic construct
SEQUENCE: 40
WIGWIDPENG DTV                                              13

SEQ ID NO: 41           moltype = AA  length = 4
FEATURE                 Location/Qualifiers
source                  1..4
                        mol_type = protein
                        organism = synthetic construct
SEQUENCE: 41
STLD                                                        4

SEQ ID NO: 42           moltype = AA  length = 10
FEATURE                 Location/Qualifiers
source                  1..10
                        mol_type = protein
                        organism = synthetic construct
SEQUENCE: 42
GFTIKDYYLH                                                  10

SEQ ID NO: 43           moltype = AA  length = 17
FEATURE                 Location/Qualifiers
source                  1..17
                        mol_type = protein
                        organism = synthetic construct
SEQUENCE: 43
WIDPEDGDTV YAPKFQG                                          17

SEQ ID NO: 44           moltype = AA  length = 112
FEATURE                 Location/Qualifiers
VARIANT                 13
                        note = Arg or Lys
VARIANT                 67
                        note = Lys or Arg
source                  1..112
```

```
                         mol_type = protein
                         organism = synthetic construct
SEQUENCE: 44
EVQLVQSGAE VVXPGALVKI SCKASGFNIK DYYLHWVRQR PEQGLEWIGW IDPENGDTVY  60
DPKFQGXATI TADTSTNTAY LQLGSLTSED TAVYFCSTLD FWGQGTLVTV SS          112

SEQ ID NO: 45            moltype = AA  length = 113
FEATURE                  Location/Qualifiers
source                   1..113
                         mol_type = protein
                         organism = synthetic construct
SEQUENCE: 45
DVVMTQSPLS LSVTLGQPAS ISCKSSQSLL DSDGKTYLNW LLQRPGQSPK RLIYLVSKLD  60
SGVPDRFSGS GSGTDFTLKI SRVEAEDVGV YYCWQGTHFP YTFGGGTKLE IKR         113

SEQ ID NO: 46            moltype = AA  length = 112
FEATURE                  Location/Qualifiers
source                   1..112
                         mol_type = protein
                         organism = synthetic construct
SEQUENCE: 46
EVQLVQSGAE VVKPGATVKI SCKASGFTIK DYYLHWVRQR PGKGLEWIGW VDPEDGDTVY  60
APKFQGRATI TADTSTDTAY LELGSLTSED TAVYFCSTLD FWGQGTLVTV SS          112

SEQ ID NO: 47            moltype = AA  length = 112
FEATURE                  Location/Qualifiers
source                   1..112
                         mol_type = protein
                         organism = synthetic construct
SEQUENCE: 47
EVQLVQSGAE VVKPGATVKI SCKASGFTIK DYYLHWVRQR PGKGLEWIGW IDPEDGDTVY  60
APKFQGRATI TADTSTDTAY LELGSLTSED TAVYFCSTLD FWGQGTLVTV SS          112

SEQ ID NO: 48            moltype = AA  length = 112
FEATURE                  Location/Qualifiers
source                   1..112
                         mol_type = protein
                         organism = synthetic construct
SEQUENCE: 48
EVQLVQSGAE VKRPGALVKI SCKASGFNFK DYYLHWVRQR PEQGLEWMGW IDPENGDTVY  60
DEKFQGRVTI TADTSTNTAY LQLGSLTSED TAVYFCSTLD FWGQGTLVTV SS          112

SEQ ID NO: 49            moltype = AA  length = 112
FEATURE                  Location/Qualifiers
source                   1..112
                         mol_type = protein
                         organism = synthetic construct
SEQUENCE: 49
EVQLVQSGAE VKRPGALVKI SCKASGYTFT DYYLHWVRQR PEQGLEWMGW VDPEDGDTVY  60
AEKFQGRVTI TADTSTNTAY LQLGSLTSED TAVYFCSTLD FWGQGTLVTV SS          112

SEQ ID NO: 50            moltype = AA  length = 112
FEATURE                  Location/Qualifiers
source                   1..112
                         mol_type = protein
                         organism = synthetic construct
SEQUENCE: 50
EVQLVQSGAD VVKPGALVKI SCKASGFTIK DYYLHWVRQR PEQGLEWIGW IDPENGDTVY  60
AEKFQGRVTI TADTSTNTAY LELGSLTSED TAVYFCSTLD FWGQGTTLTV SS          112

SEQ ID NO: 51            moltype = AA  length = 112
FEATURE                  Location/Qualifiers
source                   1..112
                         mol_type = protein
                         organism = synthetic construct
SEQUENCE: 51
EVQLVQSGAD VVKPGALVKI SCKASGFTIK DYYLHWVRQR PGQGLEWIGW VDPEDGDTVY  60
AEKFQGRVTI TADTSTDTAY MELGSLTSED TAVYFCSTLD YWGQGTTLTV SS          112

SEQ ID NO: 52            moltype = AA  length = 112
FEATURE                  Location/Qualifiers
source                   1..112
                         mol_type = protein
                         organism = synthetic construct
SEQUENCE: 52
EVQLVQSGAE VKKPGATVKI SCKVSGFNIK DYYLHWVRQA PGKGLEWMGW IDPENGDTVY  60
DPKFQGRVTI TADTSTDTAY MELSSLRSED TAVYYCSTLD FWGQGTLVTV SS          112

SEQ ID NO: 53            moltype = AA  length = 112
```

```
FEATURE                Location/Qualifiers
source                 1..112
                       mol_type = protein
                       organism = synthetic construct
SEQUENCE: 53
EVQLVQSGAE VKKPGALVKI SCKVSGYNFK DYYLHWVRQA PGKGLEWMGW IDPENGDTVY  60
DEKFQGRVTI TADTSTNTAY MELGSLRSED TAVYYCSTLD FWGQGTLVTV SS          112

SEQ ID NO: 54          moltype = AA  length = 112
FEATURE                Location/Qualifiers
source                 1..112
                       mol_type = protein
                       organism = synthetic construct
SEQUENCE: 54
EVQLVQSGAE VKKPGALVKI SCKVSGYTFT DYYLHWVRQA PGKGLEWMGW VDPEDGDTVY  60
AEKFQGRVTI TADTSTNTAY MELGSLRSED TAVYYCSTLD FWGQGTLVTV SS          112

SEQ ID NO: 55          moltype = AA  length = 112
FEATURE                Location/Qualifiers
source                 1..112
                       mol_type = protein
                       organism = synthetic construct
SEQUENCE: 55
EVQLVQSGAE VVKPGATVKI SCKVSGFNIK DYYLHWVRQR PGKGLEWIGW IDPENGDTVY  60
DPKFQGKATI TADTSTNTAY LELGSLTSED TAVYYCSTLD FWGQGTLVTV SS          112

SEQ ID NO: 56          moltype = AA  length = 112
FEATURE                Location/Qualifiers
source                 1..112
                       mol_type = protein
                       organism = synthetic construct
SEQUENCE: 56
EVQLVQSGAE VVKPGALVKI SCKVSGYNFK DYYLHWVRQR PGKGLEWMGW IDPENGDTVY  60
DEKFQGRVTI TADTSTDTAY LELGSLTSED TAVYYCSTLD FWGQGTLVTV SS          112

SEQ ID NO: 57          moltype = AA  length = 112
FEATURE                Location/Qualifiers
source                 1..112
                       mol_type = protein
                       organism = synthetic construct
SEQUENCE: 57
EVQLVQSGAE VVKPGALVKI SCKVSGYTFT DYYLHWVRQR PGKGLEWMGW VDPEDGDTVY  60
AEKFQGRVTI TADTSTDTAY LELGSLTSED TAVYYCSTLD FWGQGTLVTV SS          112

SEQ ID NO: 58          moltype = AA  length = 10
FEATURE                Location/Qualifiers
source                 1..10
                       mol_type = protein
                       organism = synthetic construct
SEQUENCE: 58
GFNFKDYYLH                                                         10

SEQ ID NO: 59          moltype = AA  length = 10
FEATURE                Location/Qualifiers
source                 1..10
                       mol_type = protein
                       organism = synthetic construct
SEQUENCE: 59
GYTFTDYYLH                                                         10

SEQ ID NO: 60          moltype = AA  length = 10
FEATURE                Location/Qualifiers
source                 1..10
                       mol_type = protein
                       organism = synthetic construct
SEQUENCE: 60
GYNFKDYYLH                                                         10

SEQ ID NO: 61          moltype = AA  length = 17
FEATURE                Location/Qualifiers
source                 1..17
                       mol_type = protein
                       organism = synthetic construct
SEQUENCE: 61
WVDPEDGDTV YAPKFQG                                                 17

SEQ ID NO: 62          moltype = AA  length = 17
FEATURE                Location/Qualifiers
source                 1..17
```

```
                        mol_type = protein
                        organism = synthetic construct
SEQUENCE: 62
WIDPENGDTV YDEKFQG                                                   17

SEQ ID NO: 63           moltype = AA  length = 17
FEATURE                 Location/Qualifiers
source                  1..17
                        mol_type = protein
                        organism = synthetic construct
SEQUENCE: 63
WVDPEDGDTV YAEKFQG                                                   17

SEQ ID NO: 64           moltype = AA  length = 17
FEATURE                 Location/Qualifiers
source                  1..17
                        mol_type = protein
                        organism = synthetic construct
SEQUENCE: 64
WIDPENGDTV YAEKFQG                                                   17

SEQ ID NO: 65           moltype =   length =
SEQUENCE: 65
000

SEQ ID NO: 66           moltype = AA  length = 112
FEATURE                 Location/Qualifiers
source                  1..112
                        mol_type = protein
                        organism = synthetic construct
SEQUENCE: 66
EVQLQQSGAE LVRSGASVKL SCTASGLNIK DYYIHWVKQR PEQGLEWIGW IDPENDDTEY  60
APKFQGRATL TTDTSSNTAY LQLSSLTSED TAVYYCTPLD YWGQGTSVTV SS          112

SEQ ID NO: 67           moltype = AA  length = 10
FEATURE                 Location/Qualifiers
source                  1..10
                        mol_type = protein
                        organism = synthetic construct
SEQUENCE: 67
GLNIKDYYIH                                                           10

SEQ ID NO: 68           moltype = AA  length = 17
FEATURE                 Location/Qualifiers
source                  1..17
                        mol_type = protein
                        organism = synthetic construct
SEQUENCE: 68
WIDPENDDTE YAPKFQG                                                   17

SEQ ID NO: 69           moltype =   length =
SEQUENCE: 69
000

SEQ ID NO: 70           moltype = AA  length = 114
FEATURE                 Location/Qualifiers
source                  1..114
                        mol_type = protein
                        organism = Mus musculus
SEQUENCE: 70
KVKLQQSGAE LVRSGASVKL SCTASGFNIK DYYIQWVKQR PEQGLEWIGW IDPENGNSEY  60
APRFQGKATM TADTLSNTAY LQLSSLTSED TAVYYCNADL HDYWGQGTTL TVSS        114

SEQ ID NO: 71           moltype = AA  length = 112
FEATURE                 Location/Qualifiers
source                  1..112
                        mol_type = protein
                        organism = synthetic construct
SEQUENCE: 71
EVQLVQSGAE VVKPGALVKI SCKASGFNIK DYYLHWVRQR PGQGLEWIGW IDPENGDTVY  60
DPKFQGRVTI TADTSTNTAY LELGSLTSED TAVYFCSTLD FWGQGTLVTV SS          112

SEQ ID NO: 72           moltype = AA  length = 442
FEATURE                 Location/Qualifiers
source                  1..442
                        mol_type = protein
                        organism = synthetic construct
SEQUENCE: 72
EVQLQQSGAD LVRPGALVKL SCKASGFNIK DYYLHWVRQR PEQGLEWIGW IDPENGDTVY  60
```

```
DPKFQGKATI TADTSSNTAY LQLGSLTSED TAVYFCSTLD FWGQGTTLTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YNSTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                           442

SEQ ID NO: 73          moltype = AA  length = 219
FEATURE                Location/Qualifiers
source                 1..219
                       mol_type = protein
                       organism = synthetic construct
SEQUENCE: 73
DVVMTQTPLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQGTHFP YTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 74          moltype = AA  length = 115
FEATURE                Location/Qualifiers
source                 1..115
                       mol_type = protein
                       organism = Homo sapiens
SEQUENCE: 74
EVQLQQSGAE LVRPGSSVKI SCKASGYIFN NYWINWVKQR PGQGLEWIGQ IYPGDGDTNY  60
NGKFKGKATL TADKSSSTAY MQLSSLTSED SAVYFCAREG YIVYWGQGTL VTVSA        115

SEQ ID NO: 75          moltype = AA  length = 114
FEATURE                Location/Qualifiers
source                 1..114
                       mol_type = protein
                       organism = Homo sapiens
SEQUENCE: 75
QVQLQQSGAE LVKPGASVKL SCTASGFNIK DTYMHWVKQR PEQGLEWIGR IDPANGNTKY  60
DPKFQGKATI TADTSSNTAY LQLSSLTSED TAVYYCASYY GIYWGQGTTL TVSS         114

SEQ ID NO: 76          moltype = AA  length = 112
FEATURE                Location/Qualifiers
source                 1..112
                       mol_type = protein
                       organism = synthetic construct
SEQUENCE: 76
QVQLQQSGAE LVKPGASVKL SCTASGFNIK DYYLHWVKQR PEQGLEWIGW IDPENGDTVY  60
DPKFQGKATI TADTSSNTAY LQLSSLTSED TAVYFCSTLD FWGQGTTLTV SS           112

SEQ ID NO: 77          moltype = AA  length = 112
FEATURE                Location/Qualifiers
source                 1..112
                       mol_type = protein
                       organism = synthetic construct
SEQUENCE: 77
EVQLVQSGAE VVKPGASVKI SCKASGFNIK DYYLHWVRQR PGKGLEWIGW IDPENGDTVY  60
DPKFQGRATI TADTSTDTAY LELSSLTSED TAVYFCSTLD FWGQGTLVTV SS           112

SEQ ID NO: 78          moltype = AA  length = 112
FEATURE                Location/Qualifiers
source                 1..112
                       mol_type = protein
                       organism = synthetic construct
SEQUENCE: 78
EVQLVQSGAE VVKPGATVKI SCKASGFNIK DYYLHWVRQR PGKGLEWIGW IDPENGDTIY  60
DPKFQGRATI TADTSTDTAY MELSSLRSED TAVYYCSTLD FWGQGTLVTV SS           112

SEQ ID NO: 79          moltype = AA  length = 112
FEATURE                Location/Qualifiers
source                 1..112
                       mol_type = protein
                       organism = synthetic construct
SEQUENCE: 79
EVQLVQSGAE VVKPGATVKI SCKASGFTIK DYYLHWVRQR PGKGLEWIGW IDPENGDTIY  60
DPKFQGRVTI TADTSTDTAY MELSSLRSED TAVYYCSTLD FWGQGTLVTV SS           112

SEQ ID NO: 80          moltype = AA  length = 112
FEATURE                Location/Qualifiers
source                 1..112
                       mol_type = protein
                       organism = synthetic construct
SEQUENCE: 80
```

```
EVQLVQSGAE VVKPGATVKI SCKASGFTIK DYYLHWVRQR PGKGLEWIGW IDPEDGETIY  60
DPKFQGRVTI TADTSTDTAY MELSSLRSED TAVYYCSTLD FWGQGTLVTV SS          112

SEQ ID NO: 81          moltype = AA  length = 112
FEATURE                Location/Qualifiers
source                 1..112
                       mol_type = protein
                       organism = Homo sapiens
SEQUENCE: 81
DVVLTQTPLT LSVTIGQPAS ISCKSSQSLL YSNGKTYLNW LLQRPGQSPK RLIYVVSKLD  60
SGVPDRFTGS GSGTDFTLKI SRVEAEDLGV YYCVQGTHFP FTFGSGTKLE IK          112

SEQ ID NO: 82          moltype = AA  length = 112
FEATURE                Location/Qualifiers
source                 1..112
                       mol_type = protein
                       organism = Homo sapiens
SEQUENCE: 82
DVVMTQTPLT LSVTIGQPAS ISCKSSQSLL YSNGKTYLNW LLQRPGQSPK RLIYLVSKLD  60
SGVPDRFSGS GSGTDFTLKI SRVEAEDLGV HYCEQGTHFP LTFGAGTKLE LK          112

SEQ ID NO: 83          moltype = AA  length = 112
FEATURE                Location/Qualifiers
source                 1..112
                       mol_type = protein
                       organism = synthetic construct
SEQUENCE: 83
DVVMTQTPLT LSVTIGQPAS ISCKSSQSLL DSDGKTYLNW LLQRPGQSPK RLIYLVSKLD  60
SGVPDRFSGS GSGTDFTLKI SRVEAEDLGV HYCWQGTHFP YTFGAGTKLE LK          112

SEQ ID NO: 84          moltype = AA  length = 112
FEATURE                Location/Qualifiers
source                 1..112
                       mol_type = protein
                       organism = synthetic construct
SEQUENCE: 84
DVVMTQSPLS LSVTLGQPAS ISCKSSQSLL DSDGKTYLNW LLQRPGQSPK RLIYLVSKLD  60
SGVPDRFSGS GSGTDFTLKI SRVEAEDVGV YYCWQGTHFP YTFGAGTKLE IK          112

SEQ ID NO: 85          moltype = AA  length = 112
FEATURE                Location/Qualifiers
source                 1..112
                       mol_type = protein
                       organism = synthetic construct
SEQUENCE: 85
DVVMTQSPLS LSVTLGEPAS ISCRSSQSLL DSDGKTYLNW LQQRPGQSPR RLIYLVSKLD  60
SGVPDRFSGS GSGTDFTLKI SRVEAEDVGV YYCWQGTHFP YTFGQGTKLE IK          112

SEQ ID NO: 86          moltype = AA  length = 10
FEATURE                Location/Qualifiers
source                 1..10
                       mol_type = protein
                       organism = synthetic construct
SEQUENCE: 86
GFTIKDYYLH                                                         10

SEQ ID NO: 87          moltype = AA  length = 17
FEATURE                Location/Qualifiers
source                 1..17
                       mol_type = protein
                       organism = synthetic construct
SEQUENCE: 87
WIDPENGDTI YDPKFQG                                                 17

SEQ ID NO: 88          moltype = AA  length = 17
FEATURE                Location/Qualifiers
source                 1..17
                       mol_type = protein
                       organism = synthetic construct
SEQUENCE: 88
WIDPEDGETI YDPKFQG                                                 17

SEQ ID NO: 89          moltype = AA  length = 16
FEATURE                Location/Qualifiers
source                 1..16
                       mol_type = protein
                       organism = synthetic construct
SEQUENCE: 89
RSSQSLLDSD GKTYLN                                                  16
```

```
SEQ ID NO: 90          moltype = AA  length = 112
FEATURE                Location/Qualifiers
source                 1..112
                       mol_type = protein
                       organism = synthetic construct
SEQUENCE: 90
EVQLVQSGAE VVKPGATVKI SCKASGFTIK DYYLHWVRQR PGKGLEWIGW IDPEDGETVY  60
DPKFQGRVTI TADTSTDTAY MELSSLRSED TAVYFCSTLD FWGQGTLVTV SS          112

SEQ ID NO: 91          moltype = AA  length = 112
FEATURE                Location/Qualifiers
source                 1..112
                       mol_type = protein
                       organism = synthetic construct
SEQUENCE: 91
EVQLVQSGAE VVKPGATVKI SCKASGFTIK DYYLHWVRQR PGKGLEWIGW IDPEDGETVY  60
DPKFQGRVTI TADTSTDTAY MELSSLRSED TAVYYCSTLD FWGQGTLVTV SS          112

SEQ ID NO: 92          moltype = AA  length = 17
FEATURE                Location/Qualifiers
source                 1..17
                       mol_type = protein
                       organism = synthetic construct
SEQUENCE: 92
WIDPEDGETV YDPKFQG                                                 17

SEQ ID NO: 93          moltype = AA  length = 112
FEATURE                Location/Qualifiers
source                 1..112
                       mol_type = protein
                       organism = synthetic construct
SEQUENCE: 93
DVVMTQSPLS LPVTLGQPAS ISCKSSQSLL DSDGKTYLNW LLQRPGQSPR RLIYLVSKDD  60
SGVPDRFSGS GSGTDFTLKI SRVEAEDVGV YYCWQGTHFP YTFGGGTKLE IK          112

SEQ ID NO: 94          moltype = AA  length = 112
FEATURE                Location/Qualifiers
source                 1..112
                       mol_type = protein
                       organism = synthetic construct
SEQUENCE: 94
DVVMTQSPLS LPVTLGQPAS ISCKSSQSLL DSDGKTYLNW LLQRPGQSPR RLIYLVSKGD  60
SGVPDRFSGS GSGTDFTLKI SRVEAEDVGV YYCWQGTHFP YTFGGGTKLE IK          112

SEQ ID NO: 95          moltype = AA  length = 112
FEATURE                Location/Qualifiers
source                 1..112
                       mol_type = protein
                       organism = synthetic construct
SEQUENCE: 95
DVVMTQSPLS LPVTLGQPAS ISCKSSQSLL DSDGKTYLNW LLQRPGQSPR RLIYLVSKND  60
SGVPDRFSGS GSGTDFTLKI SRVEAEDVGV YYCWQGTHFP YTFGGGTKLE IK          112

SEQ ID NO: 96          moltype = AA  length = 112
FEATURE                Location/Qualifiers
source                 1..112
                       mol_type = protein
                       organism = synthetic construct
SEQUENCE: 96
DVVMTQSPLS LPVTLGQPAS ISCKSSQSLL DSDGKTYLNW LLQRPGQSPR RLIYLVSKED  60
SGVPDRFSGS GSGTDFTLKI SRVEAEDVGV YYCWQGTHFP YTFGGGTKLE IK          112

SEQ ID NO: 97          moltype = AA  length = 112
FEATURE                Location/Qualifiers
source                 1..112
                       mol_type = protein
                       organism = synthetic construct
SEQUENCE: 97
DVVMTQSPLS LPVTLGQPAS ISCKSSQSLL DSDGKTYLNW LLQRPGQSPR RLIYEVSKLD  60
SGVPDRFSGS GSGTDFTLKI SRVEAEDVGV YYCWQGTHFP YTFGGGTKLE IK          112

SEQ ID NO: 98          moltype = AA  length = 112
FEATURE                Location/Qualifiers
source                 1..112
                       mol_type = protein
                       organism = synthetic construct
SEQUENCE: 98
DVVMTQSPLS LPVTLGQPAS ISCKSSQSLL DSDGKTYLNW LLQRPGQSPR RLIYLVSKQD  60
```

```
SGVPDRFSGS GSGTDFTLKI SRVEAEDVGV YYCWQGTHFP YTFGGGTKLE IK          112

SEQ ID NO: 99          moltype = AA  length = 112
FEATURE                Location/Qualifiers
source                 1..112
                       mol_type = protein
                       organism = synthetic construct
SEQUENCE: 99
DVVMTQSPLS LPVTLGQPAS ISCKSSQSLL DSDGKTYLNW LLQRPGQSPR RLIYDVSKLD  60
SGVPDRFSGS GSGTDFTLKI SRVEAEDVGV YYCWQGTHFP YTFGGGTKLE IK          112

SEQ ID NO: 100         moltype = AA  length = 112
FEATURE                Location/Qualifiers
source                 1..112
                       mol_type = protein
                       organism = synthetic construct
SEQUENCE: 100
DVVMTQSPLS LPVTLGQPAS ISCKSSQSLL DSDGKTYLNW LLQRPGQSPR RLIYLVSKKD  60
SGVPDRFSGS GSGTDFTLKI SRVEAEDVGV YYCWQGTHFP YTFGGGTKLE IK          112

SEQ ID NO: 101         moltype = AA  length = 112
FEATURE                Location/Qualifiers
source                 1..112
                       mol_type = protein
                       organism = synthetic construct
SEQUENCE: 101
DVVMTQSPLS LPVTLGQPAS ISCKSSQSLL DSDGKTYLNW LLQRPGQSPR RLIYLVSKRD  60
SGVPDRFSGS GSGTDFTLKI SRVEAEDVGV YYCWQGTHFP YTFGGGTKLE IK          112

SEQ ID NO: 102         moltype = AA  length = 112
FEATURE                Location/Qualifiers
source                 1..112
                       mol_type = protein
                       organism = synthetic construct
SEQUENCE: 102
DVVMTQSPLS LPVTLGQPAS ISCKSSQSLL DSDGKTYLNW LLQRPGQSPR RLIYLVSKTD  60
SGVPDRFSGS GSGTDFTLKI SRVEAEDVGV YYCWQGTHFP YTFGGGTKLE IK          112

SEQ ID NO: 103         moltype = AA  length = 112
FEATURE                Location/Qualifiers
source                 1..112
                       mol_type = protein
                       organism = synthetic construct
SEQUENCE: 103
DVVMTQSPLS LPVTLGQPAS ISCKSSQSLL DSDGKTYLNW LLQRPGQSPR RLIYGVSKLD  60
SGVPDRFSGS GSGTDFTLKI SRVEAEDVGV YYCWQGTHFP YTFGGGTKLE IK          112

SEQ ID NO: 104         moltype = AA  length = 112
FEATURE                Location/Qualifiers
source                 1..112
                       mol_type = protein
                       organism = synthetic construct
SEQUENCE: 104
DVVMTQSPLS LPVTLGQPAS ISCKSSQSLL DSDGKTYLNW LLQRPGQSPR RLGYLVSKLD  60
SGVPDRFSGS GSGTDFTLKI SRVEAEDVGV YYCWQGTHFP YTFGGGTKLE IK          112

SEQ ID NO: 105         moltype = AA  length = 112
FEATURE                Location/Qualifiers
source                 1..112
                       mol_type = protein
                       organism = synthetic construct
SEQUENCE: 105
DVVMTQSPLS LPVTLGQPAS ISCKSSQSLL DSDGKTYLNW LLQRPGQSPR RLDYLVSKLD  60
SGVPDRFSGS GSGTDFTLKI SRVEAEDVGV YYCWQGTHFP YTFGGGTKLE IK          112

SEQ ID NO: 106         moltype = AA  length = 112
FEATURE                Location/Qualifiers
source                 1..112
                       mol_type = protein
                       organism = synthetic construct
SEQUENCE: 106
DVVMTQSPLS LPVTLGQPAS ISCKSSQSLL DSDGKTYLNW LLQRPGQSPR RGIYLVSKLD  60
SGVPDRFSGS GSGTDFTLKI SRVEAEDVGV YYCWQGTHFP YTFGGGTKLE IK          112

SEQ ID NO: 107         moltype = AA  length = 112
FEATURE                Location/Qualifiers
source                 1..112
                       mol_type = protein
                       organism = synthetic construct
```

```
SEQUENCE: 107
DVVMTQSPLS LPVTLGQPAS ISCKSSQSLL DSDGKTYLNW LLQRPGQSPR RLIELVSKLD  60
SGVPDRFSGS GSGTDFTLKI SRVEAEDVGV YYCWQGTHFP YTFGGGTKLE IK          112

SEQ ID NO: 108         moltype = AA  length = 112
FEATURE                Location/Qualifiers
source                 1..112
                       mol_type = protein
                       organism = synthetic construct
SEQUENCE: 108
DVVMTQSPLS LPVTLGQPAS ISCKSSQSLL DSDGKTYLNW LLQRPGQSPR RLIYLVSKVD  60
SGVPDRFSGS GSGTDFTLKI SRVEAEDVGV YYCWQGTHFP YTFGGGTKLE IK          112

SEQ ID NO: 109         moltype = AA  length = 112
FEATURE                Location/Qualifiers
source                 1..112
                       mol_type = protein
                       organism = synthetic construct
SEQUENCE: 109
DVVMTQSPLS LPVTLGQPAS ISCKSSQSLL DSDGKTYLNW LLQRPGQSPR RLIYLVSKSD  60
SGVPDRFSGS GSGTDFTLKI SRVEAEDVGV YYCWQGTHFP YTFGGGTKLE IK          112

SEQ ID NO: 110         moltype = AA  length = 112
FEATURE                Location/Qualifiers
source                 1..112
                       mol_type = protein
                       organism = synthetic construct
SEQUENCE: 110
DVVMTQSPLS LPVTLGQPAS ISCKSSQSLL DSDGKTYLNW LLQRPGQSPR RLIYLVGKLD  60
SGVPDRFSGS GSGTDFTLKI SRVEAEDVGV YYCWQGTHFP YTFGGGTKLE IK          112

SEQ ID NO: 111         moltype = AA  length = 112
FEATURE                Location/Qualifiers
source                 1..112
                       mol_type = protein
                       organism = synthetic construct
SEQUENCE: 111
DVVMTQSPLS LPVTLGQPAS ISCKSSQSLL DSDGKTYLNW LLQRPGQSPR RNIYLVSKLD  60
SGVPDRFSGS GSGTDFTLKI SRVEAEDVGV YYCWQGTHFP YTFGGGTKLE IK          112

SEQ ID NO: 112         moltype = AA  length = 112
FEATURE                Location/Qualifiers
source                 1..112
                       mol_type = protein
                       organism = synthetic construct
SEQUENCE: 112
DVVMTQSPLS LPVTLGQPAS ISCKSSQSLL DSDGKTYLNW LLQRPGQSPR RDIYLVSKLD  60
SGVPDRFSGS GSGTDFTLKI SRVEAEDVGV YYCWQGTHFP YTFGGGTKLE IK          112

SEQ ID NO: 113         moltype = AA  length = 112
FEATURE                Location/Qualifiers
source                 1..112
                       mol_type = protein
                       organism = synthetic construct
SEQUENCE: 113
DVVMTQSPLS LPVTLGQPAS ISCKSSQSLL DSDGKTYLNW LLQRPGQSPR REIYLVSKLD  60
SGVPDRFSGS GSGTDFTLKI SRVEAEDVGV YYCWQGTHFP YTFGGGTKLE IK          112

SEQ ID NO: 114         moltype = AA  length = 112
FEATURE                Location/Qualifiers
source                 1..112
                       mol_type = protein
                       organism = synthetic construct
SEQUENCE: 114
DVVMTQSPLS LPVTLGQPAS ISCKSSQSLL DSDGKTYLNW LLQRPGQSPR RPIYLVSKLD  60
SGVPDRFSGS GSGTDFTLKI SRVEAEDVGV YYCWQGTHFP YTFGGGTKLE IK          112

SEQ ID NO: 115         moltype = AA  length = 112
FEATURE                Location/Qualifiers
source                 1..112
                       mol_type = protein
                       organism = synthetic construct
SEQUENCE: 115
DVVMTQSPLS LPVTLGQPAS ISCKSSQSLL DSDGKTYLNW LLQRPGQSPR RTIYLVSKLD  60
SGVPDRFSGS GSGTDFTLKI SRVEAEDVGV YYCWQGTHFP YTFGGGTKLE IK          112

SEQ ID NO: 116         moltype = AA  length = 112
FEATURE                Location/Qualifiers
source                 1..112
```

```
                        mol_type = protein
                        organism = synthetic construct
SEQUENCE: 116
DVVMTQSPLS LPVTLGQPAS ISCKSSQSLL DSDGKTYLNW LLQRPGQSPR RSIYLVSKLD  60
SGVPDRFSGS GSGTDFTLKI SRVEAEDVGV YYCWQGTHFP YTFGGGTKLE IK          112

SEQ ID NO: 117          moltype = AA  length = 112
FEATURE                 Location/Qualifiers
source                  1..112
                        mol_type = protein
                        organism = synthetic construct
SEQUENCE: 117
DVVMTQSPLS LPVTLGQPAS ISCKSSQSLL DSDGKTYLNW LLQRPGQSPR RAIYLVSKLD  60
SGVPDRFSGS GSGTDFTLKI SRVEAEDVGV YYCWQGTHFP YTFGGGTKLE IK          112

SEQ ID NO: 118          moltype = AA  length = 112
FEATURE                 Location/Qualifiers
source                  1..112
                        mol_type = protein
                        organism = synthetic construct
SEQUENCE: 118
DVVMTQSPLS LPVTLGQPAS ISCKSSQSLL DSDGKTYLNW LLQRPGQSPR RLIYVVSKLD  60
SGVPDRFSGS GSGTDFTLKI SRVEAEDVGV YYCWQGTHFP YTFGGGTKLE IK          112

SEQ ID NO: 119          moltype = AA  length = 112
FEATURE                 Location/Qualifiers
source                  1..112
                        mol_type = protein
                        organism = synthetic construct
SEQUENCE: 119
DVVMTQSPLS LPVTLGQPAS ISCKSSQSLL DSDGKTYLNW LQQRPGQSPR RLIYGVSKGD  60
SGVPDRFSGS GSGTDFTLKI SRVEAEDVGV YYCWQGTHFP YTFGGGTKLE IK          112

SEQ ID NO: 120          moltype = AA  length = 112
FEATURE                 Location/Qualifiers
source                  1..112
                        mol_type = protein
                        organism = synthetic construct
SEQUENCE: 120
DVVMTQSPLS LPVTLGQPAS ISCKSSQSLL DSDGKTYLNW LQQRPGQSPR RLIYEVSKGD  60
SGVPDRFSGS GSGTDFTLKI SRVEAEDVGV YYCWQGTHFP YTFGGGTKLE IK          112

SEQ ID NO: 121          moltype = AA  length = 112
FEATURE                 Location/Qualifiers
source                  1..112
                        mol_type = protein
                        organism = synthetic construct
SEQUENCE: 121
DVVMTQSPLS LPVTLGQPAS ISCKSSQSLL DSDGKTYLNW LQQRPGQSPR RLIYLVGKGD  60
SGVPDRFSGS GSGTDFTLKI SRVEAEDVGV YYCWQGTHFP YTFGGGTKLE IK          112

SEQ ID NO: 122          moltype = AA  length = 112
FEATURE                 Location/Qualifiers
source                  1..112
                        mol_type = protein
                        organism = synthetic construct
SEQUENCE: 122
DVVMTQSPLS LPVTLGQPAS ISCKSSQSLL DSDGKTYLNW LQQRPGQSPR RLIYLVGKRD  60
SGVPDRFSGS GSGTDFTLKI SRVEAEDVGV YYCWQGTHFP YTFGGGTKLE IK          112

SEQ ID NO: 123          moltype = AA  length = 112
FEATURE                 Location/Qualifiers
source                  1..112
                        mol_type = protein
                        organism = synthetic construct
SEQUENCE: 123
DVVMTQSPLS LPVTLGQPAS ISCKSSQSLL DSDGKTYLNW LQQRPGQSPR RLIYLVGKTD  60
SGVPDRFSGS GSGTDFTLKI SRVEAEDVGV YYCWQGTHFP YTFGGGTKLE IK          112

SEQ ID NO: 124          moltype = AA  length = 112
FEATURE                 Location/Qualifiers
source                  1..112
                        mol_type = protein
                        organism = synthetic construct
SEQUENCE: 124
DVVMTQSPLS LPVTLGQPAS ISCKSSQSLL DSDGKTYLNW LQQRPGQSPR RLIYLVGKDD  60
SGVPDRFSGS GSGTDFTLKI SRVEAEDVGV YYCWQGTHFP YTFGGGTKLE IK          112

SEQ ID NO: 125          moltype = AA  length = 112
```

```
FEATURE                Location/Qualifiers
source                 1..112
                       mol_type = protein
                       organism = synthetic construct
SEQUENCE: 125
DVVMTQSPLS LPVTLGQPAS ISCKSSQSLL DSDGKTYLNW LQQRPGQSPR RLIYLVSKGD  60
SGVPDRFSGS GSGTDFTLKI SRVEAEDVGV YYCWQGTHFP YTFGGGTKLE IK          112

SEQ ID NO: 126         moltype = AA  length = 112
FEATURE                Location/Qualifiers
source                 1..112
                       mol_type = protein
                       organism = synthetic construct
SEQUENCE: 126
DVVMTQSPLS LPVTLGQPAS ISCKSSQSLL DSDGKTYLNW LQQRPGQSPR RLIYLVSKGD  60
SGVPDRFSGS GSGTDFTLKI SRVEAEDVGV YYCWQGTHFP YTFGGGTKLE IK          112

SEQ ID NO: 127         moltype = AA  length = 112
FEATURE                Location/Qualifiers
source                 1..112
                       mol_type = protein
                       organism = synthetic construct
SEQUENCE: 127
DVVMTQSPLS LPVTLGQPAS ISCKSSQSLL DSDGKTYLNW LQQRPGQSPR RLIYLVSKDD  60
SGVPDRFSGS GSGTDFTLKI SRVEAEDVGV YYCWQGTHFP YTFGGGTKLE IK          112

SEQ ID NO: 128         moltype = AA  length = 112
FEATURE                Location/Qualifiers
source                 1..112
                       mol_type = protein
                       organism = synthetic construct
SEQUENCE: 128
DVVMTQSPLS LPVTLGQPAS ISCKSSQSLL DSDGKTYLNW LQQRPGQSPR RLIYGVSKLD  60
SGVPDRFSGS GSGTDFTLKI SRVEAEDVGV YYCWQGTHFP YTFGGGTKLE IK          112

SEQ ID NO: 129         moltype = AA  length = 112
FEATURE                Location/Qualifiers
source                 1..112
                       mol_type = protein
                       organism = synthetic construct
SEQUENCE: 129
DVVMTQSPLS LPVTLGQPAS ISCKSSQSLL DSDGKTYLNW LQQRPGQSPR RLIYDVSKLD  60
SGVPDRFSGS GSGTDFTLKI SRVEAEDVGV YYCWQGTHFP YTFGGGTKLE IK          112

SEQ ID NO: 130         moltype = AA  length = 112
FEATURE                Location/Qualifiers
source                 1..112
                       mol_type = protein
                       organism = synthetic construct
SEQUENCE: 130
DVVMTQSPLS LPVTLGQPAS ISCKSSQSLL DSDGKTYLNW LQQRPGQSPR RLIYDVSKLD  60
SGVPDRFSGS GSGTDFTLKI SRVEAEDVGV YYCWQGTHFP YTFGGGTKLE IK          112

SEQ ID NO: 131         moltype = AA  length = 112
FEATURE                Location/Qualifiers
source                 1..112
                       mol_type = protein
                       organism = synthetic construct
SEQUENCE: 131
DVVMTQSPLS LPVTLGQPAS ISCKSSQSLL DSDGKTYLNW LQQRPGQSPR RLIYLVGKLD  60
SGVPDRFSGS GSGTDFTLKI SRVEAEDVGV YYCWQGTHFP YTFGGGTKLE IK          112

SEQ ID NO: 132         moltype = AA  length = 112
FEATURE                Location/Qualifiers
source                 1..112
                       mol_type = protein
                       organism = synthetic construct
SEQUENCE: 132
DVVMTQSPLS LPVTLGQPAS ISCKSSQSLL DSDGKTYLNW LQQRPGQSPR RLIYDVSKGD  60
SGVPDRFSGS GSGTDFTLKI SRVEAEDVGV YYCWQGTHFP YTFGGGTKLE IK          112

SEQ ID NO: 133         moltype = AA  length = 112
FEATURE                Location/Qualifiers
source                 1..112
                       mol_type = protein
                       organism = synthetic construct
SEQUENCE: 133
DVVMTQSPLS LPVTLGQPAS ISCKSSQSLL DSDGKTYLNW LQQRPGQSPR RLIYDVSKRD  60
SGVPDRFSGS GSGTDFTLKI SRVEAEDVGV YYCWQGTHFP YTFGGGTKLE IK          112
```

```
SEQ ID NO: 134         moltype = AA  length = 112
FEATURE                Location/Qualifiers
source                 1..112
                       mol_type = protein
                       organism = synthetic construct
SEQUENCE: 134
DVVMTQSPLS LPVTLGQPAS ISCKSSQSLL DSDGKTYLNW LQQRPGQSPR RLIYEVSKGD  60
SGVPDRFSGS GSGTDFTLKI SRVEAEDVGV YYCWQGTHFP YTFGGGTKLE IK          112

SEQ ID NO: 135         moltype = AA  length = 112
FEATURE                Location/Qualifiers
source                 1..112
                       mol_type = protein
                       organism = synthetic construct
SEQUENCE: 135
DVVMTQSPLS LPVTLGQPAS ISCKSSQSLL DSDGKTYLNW LQQRPGQSPR RLIYEVSKRD  60
SGVPDRFSGS GSGTDFTLKI SRVEAEDVGV YYCWQGTHFP YTFGGGTKLE IK          112

SEQ ID NO: 136         moltype = AA  length = 112
FEATURE                Location/Qualifiers
source                 1..112
                       mol_type = protein
                       organism = synthetic construct
SEQUENCE: 136
DVVMTQSPLS LPVTLGQPAS ISCKSSQSLL DSDGKTYLNW LQQRPGQSPR RLIYGVSKRD  60
SGVPDRFSGS GSGTDFTLKI SRVEAEDVGV YYCWQGTHFP YTFGQGTKLE IK          112

SEQ ID NO: 137         moltype = AA  length = 112
FEATURE                Location/Qualifiers
source                 1..112
                       mol_type = protein
                       organism = synthetic construct
SEQUENCE: 137
DVVMTQSPLS LPVTLGQPAS ISCKSSQSLL DSDGKTYLNW LQQRPGQSPR RLIYGVSKGD  60
SGVPDRFSGS GSGTDFTLKI SRVEAEDVGV YYCWQGTHFP YTFGQGTKLE IK          112

SEQ ID NO: 138         moltype = AA  length = 112
FEATURE                Location/Qualifiers
source                 1..112
                       mol_type = protein
                       organism = synthetic construct
SEQUENCE: 138
DVVMTQSPLS LPVTLGQPAS ISCKSSQSLL DSDGKTYLNW LQQRPGQSPR RLIYLVGKRD  60
SGVPDRFSGS GSGTDFTLKI SRVEAEDVGV YYCWQGTHFP YTFGQGTKLE IK          112

SEQ ID NO: 139         moltype = AA  length = 112
FEATURE                Location/Qualifiers
source                 1..112
                       mol_type = protein
                       organism = synthetic construct
SEQUENCE: 139
DVVMTQSPLS LPVTLGQPAS ISCKSSQSLL DSDGKTYLNW LQQRPGQSPR RLIYLVGKDD  60
SGVPDRFSGS GSGTDFTLKI SRVEAEDVGV YYCWQGTHFP YTFGQGTKLE IK          112

SEQ ID NO: 140         moltype = AA  length = 112
FEATURE                Location/Qualifiers
source                 1..112
                       mol_type = protein
                       organism = synthetic construct
SEQUENCE: 140
DVVMTQSPLS LPVTLGQPAS ISCKSSQSLL DSDGKTYLNW LQQRPGQSPR RLIYDVSKGD  60
SGVPDRFSGS GSGTDFTLKI SRVEAEDVGV YYCWQGTHFP YTFGQGTKLE IK          112

SEQ ID NO: 141         moltype = AA  length = 112
FEATURE                Location/Qualifiers
source                 1..112
                       mol_type = protein
                       organism = synthetic construct
SEQUENCE: 141
DVVMTQSPLS LPVTLGQPAS ISCKSSQSLL DSDGKTYLNW LQQRPGQSPR RLIYDVSKRD  60
SGVPDRFSGS GSGTDFTLKI SRVEAEDVGV YYCWQGTHFP YTFGQGTKLE IK          112

SEQ ID NO: 142         moltype = AA  length = 112
FEATURE                Location/Qualifiers
source                 1..112
                       mol_type = protein
                       organism = synthetic construct
SEQUENCE: 142
```

```
DVVMTQSPLS LPVTLGQPAS ISCKSSQSLL DSDGKTYLNW LQQRPGQSPR RLIYVVSKDD  60
SGVPDRFSGS GSGTDFTLKI SRVEAEDVGV YYCWQGTHFP YTFGQGTKLE IK          112

SEQ ID NO: 143          moltype = AA  length = 112
FEATURE                 Location/Qualifiers
source                  1..112
                        mol_type = protein
                        organism = synthetic construct
SEQUENCE: 143
DVVMTQSPLS LPVTLGQPAS ISCKSSQSLL DSDGKTYLNW LQQRPGQSPR RLIYLVSKLD  60
SGVPDRFSGS GSGTDFTLKI SRVEAEDVGV YYCWQGTHFP YTFGGGTKLE IK          112

SEQ ID NO: 144          moltype = AA  length = 112
FEATURE                 Location/Qualifiers
source                  1..112
                        mol_type = protein
                        organism = synthetic construct
SEQUENCE: 144
DVVMTQSPLS LPVTLGQPAS ISCKSSQSLL DSDGKTYLNW LLQRPGQSPR RLIYLVSKLD  60
SGVPDRFSGS GSGTDFTLKI SRVEAEDVGV YYCWQGTHFP YTFGQGTKLE IK          112

SEQ ID NO: 145          moltype = AA  length = 112
FEATURE                 Location/Qualifiers
source                  1..112
                        mol_type = protein
                        organism = synthetic construct
SEQUENCE: 145
DVVMTQSPLS LPVTLGQPAS ISCKSSQSLL DSDGKTYLNW LQQRPGQSPR RLIYLVSKED  60
SGVPDRFSGS GSGTDFTLKI SRVEAEDVGV YYCWQGTHFP YTFGGGTKLE IK          112

SEQ ID NO: 146          moltype = AA  length = 112
FEATURE                 Location/Qualifiers
source                  1..112
                        mol_type = protein
                        organism = synthetic construct
SEQUENCE: 146
EVQLVQSGAE VVKPGATVKI SCKASGFNIK DYYLHWVRQR PGQGLEWIGW IDPENGDTVY  60
EPKFQGRATI TADTSTDTAY LQLGSLTSED TAVYFCSTLD FWGQGTLVTV SS          112

SEQ ID NO: 147          moltype = AA  length = 112
FEATURE                 Location/Qualifiers
source                  1..112
                        mol_type = protein
                        organism = synthetic construct
SEQUENCE: 147
EVQLVQSGAE VVKPGATVKI SCKASGFNIK DYYLHWVRQR PGQGLEWIGW IDPENGDTVY  60
DPKFQGRATI TADTSTDTAY LQLGSVTSED TAVYFCSTLD FWGQGTLVTV SS          112

SEQ ID NO: 148          moltype = AA  length = 112
FEATURE                 Location/Qualifiers
source                  1..112
                        mol_type = protein
                        organism = synthetic construct
SEQUENCE: 148
EVQLVQSGAE VVKPGATVKI SCKASGFNIK DYYLHWVRQR PGQGLEWIGW IDPENGDTVY  60
EPKFQGRATI TADTSTDTAY MELGSVRSED TAVYFCSTLD FWGQGTLVTV SS          112

SEQ ID NO: 149          moltype = AA  length = 17
FEATURE                 Location/Qualifiers
source                  1..17
                        mol_type = protein
                        organism = synthetic construct
SEQUENCE: 149
WIDPENGDTV YEPKFQG                                                 17

SEQ ID NO: 150          moltype = AA  length = 7
FEATURE                 Location/Qualifiers
source                  1..7
                        mol_type = protein
                        organism = synthetic construct
SEQUENCE: 150
LVSKDDS                                                            7

SEQ ID NO: 151          moltype = AA  length = 7
FEATURE                 Location/Qualifiers
source                  1..7
                        mol_type = protein
                        organism = synthetic construct
SEQUENCE: 151
```

```
LVSKGDS                                                    7

SEQ ID NO: 152         moltype = AA  length = 7
FEATURE                Location/Qualifiers
source                 1..7
                       mol_type = protein
                       organism = synthetic construct
SEQUENCE: 152
LVSKNDS                                                    7

SEQ ID NO: 153         moltype = AA  length = 7
FEATURE                Location/Qualifiers
source                 1..7
                       mol_type = protein
                       organism = synthetic construct
SEQUENCE: 153
LVSKEDS                                                    7

SEQ ID NO: 154         moltype = AA  length = 7
FEATURE                Location/Qualifiers
source                 1..7
                       mol_type = protein
                       organism = synthetic construct
SEQUENCE: 154
EVSKLDS                                                    7

SEQ ID NO: 155         moltype = AA  length = 7
FEATURE                Location/Qualifiers
source                 1..7
                       mol_type = protein
                       organism = synthetic construct
SEQUENCE: 155
LVSKQDS                                                    7

SEQ ID NO: 156         moltype = AA  length = 7
FEATURE                Location/Qualifiers
source                 1..7
                       mol_type = protein
                       organism = synthetic construct
SEQUENCE: 156
DVSKLDS                                                    7

SEQ ID NO: 157         moltype = AA  length = 7
FEATURE                Location/Qualifiers
source                 1..7
                       mol_type = protein
                       organism = synthetic construct
SEQUENCE: 157
LVSKKDS                                                    7

SEQ ID NO: 158         moltype = AA  length = 7
FEATURE                Location/Qualifiers
source                 1..7
                       mol_type = protein
                       organism = synthetic construct
SEQUENCE: 158
LVSKRDS                                                    7

SEQ ID NO: 159         moltype = AA  length = 7
FEATURE                Location/Qualifiers
source                 1..7
                       mol_type = protein
                       organism = synthetic construct
SEQUENCE: 159
LVSKTDS                                                    7

SEQ ID NO: 160         moltype = AA  length = 7
FEATURE                Location/Qualifiers
source                 1..7
                       mol_type = protein
                       organism = synthetic construct
SEQUENCE: 160
GVSKLDS                                                    7

SEQ ID NO: 161         moltype = AA  length = 7
FEATURE                Location/Qualifiers
source                 1..7
                       mol_type = protein
                       organism = synthetic construct
```

```
SEQUENCE: 161
LVSKVDS                                                        7

SEQ ID NO: 162          moltype = AA  length = 7
FEATURE                 Location/Qualifiers
source                  1..7
                        mol_type = protein
                        organism = synthetic construct
SEQUENCE: 162
LVSKSDS                                                        7

SEQ ID NO: 163          moltype = AA  length = 7
FEATURE                 Location/Qualifiers
source                  1..7
                        mol_type = protein
                        organism = synthetic construct
SEQUENCE: 163
LVGKLDS                                                        7

SEQ ID NO: 164          moltype = AA  length = 7
FEATURE                 Location/Qualifiers
source                  1..7
                        mol_type = protein
                        organism = synthetic construct
SEQUENCE: 164
VVSKLDS                                                        7

SEQ ID NO: 165          moltype = AA  length = 7
FEATURE                 Location/Qualifiers
source                  1..7
                        mol_type = protein
                        organism = synthetic construct
SEQUENCE: 165
GVSKRDS                                                        7

SEQ ID NO: 166          moltype = AA  length = 7
FEATURE                 Location/Qualifiers
source                  1..7
                        mol_type = protein
                        organism = synthetic construct
SEQUENCE: 166
GVSKGDS                                                        7

SEQ ID NO: 167          moltype = AA  length = 7
FEATURE                 Location/Qualifiers
source                  1..7
                        mol_type = protein
                        organism = synthetic construct
SEQUENCE: 167
LVGKGDS                                                        7

SEQ ID NO: 168          moltype = AA  length = 7
FEATURE                 Location/Qualifiers
source                  1..7
                        mol_type = protein
                        organism = synthetic construct
SEQUENCE: 168
LVGKRDS                                                        7

SEQ ID NO: 169          moltype = AA  length = 7
FEATURE                 Location/Qualifiers
source                  1..7
                        mol_type = protein
                        organism = synthetic construct
SEQUENCE: 169
LVGKTDS                                                        7

SEQ ID NO: 170          moltype = AA  length = 7
FEATURE                 Location/Qualifiers
source                  1..7
                        mol_type = protein
                        organism = synthetic construct
SEQUENCE: 170
LVGKDDS                                                        7

SEQ ID NO: 171          moltype = AA  length = 7
FEATURE                 Location/Qualifiers
source                  1..7
                        mol_type = protein
```

```
                        organism = synthetic construct
SEQUENCE: 171
DVSKGDS                                                              7

SEQ ID NO: 172          moltype = AA  length = 7
FEATURE                 Location/Qualifiers
source                  1..7
                        mol_type = protein
                        organism = synthetic construct
SEQUENCE: 172
DVSKRDS                                                              7

SEQ ID NO: 173          moltype = AA  length = 7
FEATURE                 Location/Qualifiers
source                  1..7
                        mol_type = protein
                        organism = synthetic construct
SEQUENCE: 173
EVSKGDS                                                              7

SEQ ID NO: 174          moltype = AA  length = 7
FEATURE                 Location/Qualifiers
source                  1..7
                        mol_type = protein
                        organism = synthetic construct
SEQUENCE: 174
EVSKRDS                                                              7

SEQ ID NO: 175          moltype = AA  length = 7
FEATURE                 Location/Qualifiers
source                  1..7
                        mol_type = protein
                        organism = synthetic construct
SEQUENCE: 175
VVSKDDS                                                              7

SEQ ID NO: 176          moltype = AA  length = 330
FEATURE                 Location/Qualifiers
source                  1..330
                        mol_type = protein
                        organism = Homo sapiens
SEQUENCE: 176
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 177          moltype = AA  length = 107
FEATURE                 Location/Qualifiers
source                  1..107
                        mol_type = protein
                        organism = Homo sapiens
SEQUENCE: 177
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 178          moltype = AA  length = 442
FEATURE                 Location/Qualifiers
source                  1..442
                        mol_type = protein
                        organism = synthetic construct
SEQUENCE: 178
EVQLVQSGAE VVKPGATVKI SCKASGFNIK DYYLHWVRQR PGQGLEWIGW IDPENGDTVY  60
DPKFQGRATI TADTSTDTAY LQLGSLTSED TAVYFCSTLD FWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKKV EPKSCDKTHT CPPCPAPELL GGPSVFLFPP  240
KPKDTLMISR TPEVTCVVVD VSHEDPEVKF NWYVDGVEVH NAKTKPREEQ YNSTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                          442

SEQ ID NO: 179          moltype = AA  length = 219
FEATURE                 Location/Qualifiers
source                  1..219
                        mol_type = protein
                        organism = synthetic construct
SEQUENCE: 179
```

```
DVVMTQSPLS LPVTLGQPAS ISCKSSQSLL DSDGKTYLNW LQQRPGQSPR RLIYLVGKRD  60
SGVPDRFSGS GSGTDFTLKI SRVEAEDVGV YYCWQGTHFP YTFGGGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 180          moltype = AA  length = 461
FEATURE                 Location/Qualifiers
source                  1..461
                        mol_type = protein
                        organism = synthetic construct
SEQUENCE: 180
MMSFVSLLLV GILFHATQAE VQLVQSGAEV VKPGATVKIS CKASGFNIKD YYLHWVRQRP  60
GQGLEWIGWI DPENGDTVYD PKFQGRATIT ADTSTDTAYL QLGSLTSEDT AVYFCSTLDF  120
WGQGTLVTVS SASTKGPSVF PLAPSSKSTS GGTAALGCLV KDYFPEPVTV SWNSGALTSG  180
VHTFPAVLQS SGLYSLSSVV TVPSSSLGTQ TYICNVNHKP SNTKVDKKVE PKSCDKTHTC  240
PPCPAPELLG GPSVFLFPPK PKDTLMISRT PEVTCVVVDV SHEDPEVKFN WYVDGVEVHN  300
AKTKPREEQY NSTYRVVSVL TVLHQDWLNG KEYKCKVSNK ALPAPIEKTI SKAKGQPREP  360
QVYTLPPSRE EMTKNQVSLT CLVKGFYPSD IAVEWESNGQ PENNYKTTPP VLDSDGSFFL  420
YSKLTVDKSR WQQGNVFSCS VMHEALHNHY TQKSLSLSPG K                       461

SEQ ID NO: 181          moltype = AA  length = 238
FEATURE                 Location/Qualifiers
source                  1..238
                        mol_type = protein
                        organism = synthetic construct
SEQUENCE: 181
MMSFVSLLLV GILFHATQAD VVMTQSPLSL PVTLGQPASI SCKSSQSLLD SDGKTYLNWL  60
QQRPGQSPRR LIYLVGKRDS GVPDRFSGSG SGTDFTLKIS RVEAEDVGVY YCWQGTHFPY  120
TFGGGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 182          moltype = DNA  length = 1398
FEATURE                 Location/Qualifiers
source                  1..1398
                        mol_type = other DNA
                        organism = synthetic construct
SEQUENCE: 182
atgatgtcct ttgtctctct gctcctggtt ggcatcctat tccatgccac ccaggccgag  60
gtgcagctgg tgcagtctgg ggcagaggtt gtgaagccag ggccacagt caagatctcc  120
tgtaaggctt ctggcttcaa cattaaagac tactatctgc actgggtgcg gcagaggcct  180
ggacagggcc tggagtggat tggatggatt gatcctgaga atggtgatac tgtgtatgac  240
ccgaagttcc agggcagggc cactataaca gcagacacat ccaccgacac agcctacctg  300
cagctcggca gcctgacatc tgaggacact gccgtctatt tctgttctac cctggacttc  360
tggggccaag gcacccttgt cacagtctcc tcagcctcca ccaagggccc atcggtcttc  420
cccctggcac cctctagcaa gagcacctct gggggcacag cggccctggg ctgcctggtc  480
aaggactact tccccgaacc ggtgacggtg tcgtggaact caggcgccct gaccagcggc  540
gtgcacacct tcccggctgt cctacagtcc tcaggactct actccctcag cagcgtggtg  600
accgtgccct ccagcagctt gggcacccag acctacatct gcaacgtgaa tcacaagccc  660
agcaacacca aggtggacaa gaaggttgag cccaaatctt gtgacaaaac tcacacatgc  720
ccaccgtgcc cagcacctga actcctgggg ggaccgtcag tcttcctctt ccccccaaaa  780
cccaaggaca ccctcatgat ctcccggacc cctgaggtca catgcgtggt ggtggacgtg  840
agccacgaag accctgaggt caagttcaac tggtacgtgg acggcgtgga ggtgcataat  900
gccaagacaa agccgagaga ggagcagtac aacagcacgt accgtgtggt cagcgtcctc  960
accgtcctgc accaggactg gctgaatggc aaggagtaca agtgcaaggt ctccaacaaa  1020
gccctcccag cccccatcga gaaaaccatc tccaaagcca aagggcagcc ccgagaacca  1080
caggtgtaca ccctgccccc atcccgggag gagatgacca agaaccaggt cagcctgacc  1140
tgcctggtca aaggcttcta tcccagcgac atcgccgtgg agtgggagag caatgggcag  1200
ccggagaaca actacaagac cacgcctccc gtgctggact ccgacggctc cttcttcctc  1260
tattccaaac tcaccgtgga caagagcagg tggcagcagg ggaacgtctt ctcatgctcc  1320
gtgatgcatg aggctctgca caaccactac acgcagaaga gcctctccct gtctcccggg  1380
aaatgatgag atctcgag                                                1398

SEQ ID NO: 183          moltype = DNA  length = 729
FEATURE                 Location/Qualifiers
source                  1..729
                        mol_type = other DNA
                        organism = synthetic construct
SEQUENCE: 183
atgatgtcct ttgtctctct gctcctggtt ggcatcctat tccatgccac ccaggccgat  60
gttgtgatga cccagtctcc actctctttg cccgttaccc ttggacaacc tgcctccatc  120
tcttgcaagt caagtcagag cctcttagat agtgatggaa agacatattt gaattggttg  180
caacagaggc caggccagtc tccacggcgc ctaatctatc tggtgggcaa acgggactct  240
ggagtccctg acaggttcag tggcagtgga tcagggacag atttcacact gaaaatcagc  300
agagtggagg ctgaggatgt gggagtttat tattgctggc aaggcacaca ttttccgtac  360
acgttcggag gggggaccaa gctggaaata aaacgaactg tggctgcacc atctgtcttc  420
atcttcccgc catctgatga gcagcttaag tccggaactg ctagcgttgt gtgcctgctg  480
aataacttct atcccagaga ggccaaagta cagtggaagg tggataacgc cctccaatcg  540
ggtaactccc aggagagtgt cacagagcag gacagcaagg acagcaccta cagcctcagc  600
agcaccctga cgctgagcaa agcagactac gagaaacaca aagtctacgc ctgcgaagtc  660
```

```
acccatcagg gcctgagctc gcccgtcaca aagagcttca acaggggaga gtgttagtga  720
gatctcgag                                                           729

SEQ ID NO: 184          moltype = AA  length = 17
FEATURE                 Location/Qualifiers
source                  1..17
                        mol_type = protein
                        organism = Homo sapiens
SEQUENCE: 184
NVKSKIGSTE NLKHQPG                                                  17

SEQ ID NO: 185          moltype = AA  length = 17
FEATURE                 Location/Qualifiers
source                  1..17
                        mol_type = protein
                        organism = Homo sapiens
SEQUENCE: 185
NVQSKCGSKD NIKHVPG                                                  17

SEQ ID NO: 186          moltype = AA  length = 17
FEATURE                 Location/Qualifiers
source                  1..17
                        mol_type = protein
                        organism = Homo sapiens
SEQUENCE: 186
KVTSKCGSLG NIHHKPG                                                  17

SEQ ID NO: 187          moltype = AA  length = 17
FEATURE                 Location/Qualifiers
source                  1..17
                        mol_type = protein
                        organism = Homo sapiens
SEQUENCE: 187
RVQSKIGSLD NITHVPG                                                  17

SEQ ID NO: 188          moltype = AA  length = 10
FEATURE                 Location/Qualifiers
source                  1..10
                        mol_type = protein
                        organism = Homo sapiens
SEQUENCE: 188
KIGSTENLKH                                                          10

SEQ ID NO: 189          moltype = AA  length = 4
FEATURE                 Location/Qualifiers
source                  1..4
                        mol_type = protein
                        organism = Homo sapiens
SEQUENCE: 189
NVKS                                                                4

SEQ ID NO: 190          moltype =   length =
SEQUENCE: 190
000

SEQ ID NO: 191          moltype = AA  length = 10
FEATURE                 Location/Qualifiers
VARIANT                 9
                        note = Xaa = Lys or His
source                  1..10
                        mol_type = protein
                        organism = synthetic construct
SEQUENCE: 191
KXXSXXNXXH                                                          10

SEQ ID NO: 192          moltype = AA  length = 10
FEATURE                 Location/Qualifiers
source                  1..10
                        mol_type = protein
                        organism = Homo sapiens
SEQUENCE: 192
KCGSKDNIKH                                                          10

SEQ ID NO: 193          moltype = AA  length = 10
FEATURE                 Location/Qualifiers
source                  1..10
                        mol_type = protein
                        organism = Homo sapiens
SEQUENCE: 193
```

-continued

```
KCGSLGNIHH                                                           10

SEQ ID NO: 194        moltype = AA  length = 10
FEATURE               Location/Qualifiers
source                1..10
                      mol_type = protein
                      organism = Homo sapiens
SEQUENCE: 194
KIGSLDNITH                                                           10
```